(12) United States Patent
Dietrich et al.

(10) Patent No.: US 11,597,951 B2
(45) Date of Patent: *Mar. 7, 2023

(54) METHOD FOR PREPARATION OF DIESTER DERIVATIVES OF MALONIC ACID

(71) Applicant: Lygos, Inc., Berkeley, CA (US)

(72) Inventors: Jeffrey A. Dietrich, Berkeley, CA (US); Eric Steen, Berkeley, CA (US); Johan van Walsem, Berkeley, CA (US)

(73) Assignee: LYGOS, INC., Berkeley, CA (US)

(*) Notice: Subject to any disclaimer, the term of this patent is extended or adjusted under 35 U.S.C. 154(b) by 30 days.

This patent is subject to a terminal disclaimer.

(21) Appl. No.: 16/969,517

(22) PCT Filed: Feb. 12, 2019

(86) PCT No.: PCT/US2019/017657
§ 371 (c)(1),
(2) Date: Aug. 12, 2020

(87) PCT Pub. No.: WO2019/160862
PCT Pub. Date: Aug. 22, 2019

(65) Prior Publication Data
US 2020/0399666 A1    Dec. 24, 2020

Related U.S. Application Data

(60) Provisional application No. 62/630,102, filed on Feb. 13, 2018.

(51) Int. Cl.
*C12P 7/46* (2006.01)
*C07C 67/58* (2006.01)
(52) U.S. Cl.
CPC ............... *C12P 7/46* (2013.01); *C07C 67/58* (2013.01)

(58) Field of Classification Search
CPC .................................. C07C 67/58; C12P 7/46
See application file for complete search history.

(56) References Cited

U.S. PATENT DOCUMENTS

| 4,894,471 A | 1/1990 | Angeletti et al. |
| 5,980,640 A | 11/1999 | Nurmi et al. |

(Continued)

FOREIGN PATENT DOCUMENTS

| WO | 2003050274 | 6/2003 |
| WO | 2018089971 | 5/2018 |

OTHER PUBLICATIONS

Rekha et al. (A Simple, Efficient, Green, Cost Effective and Chemoselective Process for the Esterification of Carboxylic Acids, Organic Process Research and Development, 13, 769-773, Published 2009) (Year: 2009).*

(Continued)

*Primary Examiner* — Yevgeny Valenrod
*Assistant Examiner* — Blaine G Doletski
(74) *Attorney, Agent, or Firm* — Faegre Drinker Biddle & Reath LLP

(57) ABSTRACT

Methods for the preparation of bio-based malonic acid and diester derivatives of malonic acid are provided. For example, a dialkyl malonate may be prepared by the steps of (i) separating calcium malonate crystals from a fermentation broth; (ii) obtaining dissolved malonic acid; (iii) crystallizing the dissolved malonic acid; and (iv) performing esterification to obtain the dialkyl malonate. The disclosed methods produce diester derivatives of malonic acid with fewer impurities, which is useful for many industrial processes. The diester derivatives of malonic acid can be purified from existing sources of malonic acid, or from malonic acid made from a renewable carbon source.

22 Claims, 6 Drawing Sheets
Specification includes a Sequence Listing.

(56) References Cited

U.S. PATENT DOCUMENTS

| | | |
|---|---|---|
| 7,019,170 B2 | 3/2006 | Eyal et al. |
| 2012/0225095 A1 | 9/2012 | Hanchar et al. |
| 2017/0362614 A1* | 12/2017 | Dietrich .................. C12N 9/16 |

OTHER PUBLICATIONS

International Search Report and Written Opinion, ISA/US, PCT/US2019/017657, dated Mar. 26, 2019, 7 pgs.

* cited by examiner

SEQUENCE LISTING

```
<160> NUMBER OF SEQ ID NOS: 44

<210> SEQ ID NO 1
<211> LENGTH: 500
<212> TYPE: PRT
<213> ORGANISM: Saccharomyces cerevisiae

<400> SEQUENCE: 1

Met Leu Arg Asn Thr Leu Lys Cys Ala Gln Leu Ser Ser Lys Tyr Gly
1               5                   10                  15

Phe Lys Thr Thr Thr Arg Thr Phe Met Thr Thr Gln Pro Gln Leu Asn
            20                  25                  30

Val Thr Asp Ala Pro Pro Val Leu Phe Thr Val Gln Asp Thr Ala Arg
        35                  40                  45
```

```
Val Ile Thr Leu Asn Arg Pro Lys Lys Leu Asn Ala Leu Asn Ala Glu
    50                  55                  60

Met Ser Glu Ser Met Phe Lys Thr Leu Asn Glu Tyr Ala Lys Ser Asp
 65              70                  75                      80

Thr Thr Asn Leu Val Ile Leu Lys Ser Ser Asn Arg Pro Arg Ser Phe
                85                  90                  95

Cys Ala Gly Gly Asp Val Ala Thr Val Ala Ile Phe Asn Phe Asn Lys
            100                 105                 110

Glu Phe Ala Lys Ser Ile Lys Phe Phe Thr Asp Glu Tyr Ser Leu Asn
            115                 120                 125

Phe Gln Ile Ala Thr Tyr Leu Lys Pro Ile Val Thr Phe Met Asp Gly
        130                 135                 140

Ile Thr Met Gly Gly Gly Val Gly Leu Ser Ile His Thr Pro Phe Arg
145                 150                 155                 160

Ile Ala Thr Glu Asn Thr Lys Trp Ala Met Pro Glu Met Asp Ile Gly
                165                 170                 175

Phe Phe Pro Asp Val Gly Ser Thr Phe Ala Leu Pro Arg Ile Val Thr
            180                 185                 190

Leu Ala Asn Ser Asn Ser Gln Met Ala Leu Tyr Leu Cys Leu Thr Gly
        195                 200                 205

Glu Val Val Thr Gly Ala Asp Ala Tyr Met Leu Gly Leu Ala Ser His
210                 215                 220

Tyr Val Ser Ser Glu Asn Leu Asp Ala Leu Gln Lys Arg Leu Gly Glu
225                 230                 235                 240

Ile Ser Pro Pro Phe Asn Asn Asp Pro Gln Ser Ala Tyr Phe Phe Gly
                245                 250                 255

Met Val Asn Glu Ser Ile Asp Glu Phe Val Ser Pro Leu Pro Lys Asp
            260                 265                 270

Tyr Val Phe Lys Tyr Ser Asn Glu Lys Leu Asn Val Ile Glu Ala Cys
            275                 280                 285

Phe Asn Leu Ser Lys Asn Gly Thr Ile Glu Asp Ile Met Asn Asn Leu
        290                 295                 300

Arg Gln Tyr Glu Gly Ser Ala Glu Gly Lys Ala Phe Ala Gln Glu Ile
305                 310                 315                 320

Lys Thr Lys Leu Leu Thr Lys Ser Pro Ser Ser Leu Gln Ile Ala Leu
                325                 330                 335

Arg Leu Val Gln Glu Asn Ser Arg Asp His Ile Glu Ser Ala Ile Lys
            340                 345                 350

Arg Asp Leu Tyr Thr Ala Ala Asn Met Cys Met Asn Gln Asp Ser Leu
            355                 360                 365

Val Glu Phe Ser Glu Ala Thr Lys His Lys Leu Ile Asp Lys Gln Arg
        370                 375                 380

Val Pro Tyr Pro Trp Thr Lys Glu Gln Leu Phe Val Ser Gln Leu
385                 390                 395                 400

Thr Ser Ile Thr Ser Pro Lys Pro Ser Leu Pro Met Ser Leu Leu Arg
                405                 410                 415

Asn Thr Ser Asn Val Thr Trp Thr Gln Tyr Pro Tyr His Ser Lys Tyr
            420                 425                 430

Gln Leu Pro Thr Glu Gln Glu Ile Ala Ala Tyr Ile Glu Lys Arg Thr
        435                 440                 445

Asn Asp Asp Thr Gly Ala Lys Val Thr Glu Arg Glu Val Leu Asn His
450                 455                 460

Phe Ala Asn Val Ile Pro Ser Arg Arg Gly Lys Leu Gly Ile Gln Ser
```

```
465                 470                 475                 480
Leu Cys Lys Ile Val Cys Glu Arg Lys Cys Glu Glu Val Asn Asp Gly
                485                 490                 495

Leu Arg Trp Lys
        500

<210> SEQ ID NO 2
<211> LENGTH: 1000
<212> TYPE: DNA
<213> ORGANISM: Haemophilus influenzae

<400> SEQUENCE: 2
atgttttaca ctgaaactta tgatgtgatt gtgatcggtg gtggtcatgc gggtacagaa     60
gccgcacttg caccagctcg tatgggattt aaaacccttt tattaacaca taatgtagat    120
actttagggc aaatgtcttg taaccctgca attggtggga tcggtaaagg tcatttagta    180
aaagaagtag atgcaatggg cggtttaatg gcgcatgctg cagataaagc agggatccaa    240
tttcgtactt taaatagcag taaaggccca gcagtgcgtg ctactcgagc tcaagctgac    300
agagttctat atcgtcaagc tgttcgtact gcattagaaa atcaacctaa tttagatatt    360
ttccaacaag aagcgaccga tattctgatt aagcaagatc gagttacagg cgttagcaca    420
aaaatgggat taacttttcg tgctaaatca gtggtattaa ctgcgggtac tttcttagct    480
ggtaaaattc atattggttt ggaaaattat gaaggtggcc gtgcagggga tcctgcttct    540
gtaaatcttt cacatcgatt aagagatctc ggattacgtg tagatcgcct taaaacaggt    600
acaccgccgc gtattgatgc acgtacgatc aattttgata ttttagctaa caacacggt    660 gatgctgttt tacctgtgtt ttcttttatg ggatcagttg atgatcaccc tcaacaaatt    720
ccttgttata taactcatac caatgaacaa acccatgaag tgatccgtaa taacttggat    780
cgcagtccaa tgtatactgg tgtgattgaa gggatcggtc acgttattg cccatccatt    840 gaagataaag tgatgcgttt ctcggatcgt aattcacatc aaatttattt agaaccagaa    900
ggcttaacca gtaatgaagt gtatccaaac gggatctcta ccagtttacc gtttgacgtg    960
caaatgggca ttgtgaattc tatgaaaggt ttagaaaacg                         1000

<210> SEQ ID NO 3
<211> LENGTH: 224
<212> TYPE: PRT
<213> ORGANISM: Acinetobacter calcoaceticus

<400> SEQUENCE: 3

Met Asn Ser Ile Ala Glu Leu Pro Leu Ser Ile Gln Ile Ser Lys Lys
1               5                   10                  15

Leu Glu Asp Asp Ile Ile Tyr Gly Phe Tyr Leu Pro Gly Thr Lys Leu
                20                  25                  30

Asp Glu Gln Glu Leu Cys Glu Arg Tyr Gly Ala Ser Arg Thr Pro Ile
            35                  40                  45

Arg Glu Ala Leu Lys Leu Leu Ala Ala Glu Gly Leu Val Glu Ile Arg
        50                  55                  60

Pro Arg Arg Gly Ala Ile Ile Pro Thr Ile Asn Pro Leu Thr Leu Cys
65                  70                  75                  80

Glu Met Phe Glu Val Met Ala Glu Leu Glu Ala Met Cys Gly Arg Leu
                85                  90                  95

Ala Ala Arg Arg Ile Gln Pro Glu Glu Lys Leu Glu Leu Gln Arg Leu
            100                 105                 110
```

```
His Gln Leu Cys Gln Asp Tyr Leu Asn Gln Asn Asp Ser Glu Asn Tyr
            115                 120                 125

Tyr Glu Ala Asn Arg Leu Phe His Phe Ala Ile Tyr Gln Ala Ser His
130                 135                 140

Asn Ala Phe Leu Ile Glu Gln Ala Cys Thr Leu His Lys Arg Leu His
145                 150                 155                 160

Pro Tyr Arg Arg Leu Gln Leu Arg Val Asn Asn Arg Met Asn Asn Ser
                165                 170                 175

Phe Thr Glu His Asn Glu Ile Leu Glu Ala Ile Phe Ala Gly Asn Glu
            180                 185                 190

Gln Gln Ala Glu Ala Leu Leu Lys Ala His Val Val Ile Gln Gly Gln
            195                 200                 205

Lys Phe Thr Asp Phe Ile Ser Thr Ile Glu Ser Leu Gln Pro Lys Ser
210                 215                 220
```

<210> SEQ ID NO 4
<211> LENGTH: 222
<212> TYPE: PRT
<213> ORGANISM: Rhizobium leguminosarum

<400> SEQUENCE: 4

```
Met Arg Lys Val Lys Arg Met Ser Glu Asn Val Gly Arg Trp Leu Arg
1               5                   10                  15

Asp Glu Ile Glu Asn Ser Ile Leu Ser Asn Glu Phe Ser Pro Gly Glu
            20                  25                  30

Arg Leu Asp Glu Thr Val Leu Ala Thr Arg Phe Gly Val Ser Arg Thr
        35                  40                  45

Pro Val Arg Glu Ala Leu Met Gln Leu Asp Ala Ile Gly Leu Ile Glu
    50                  55                  60

Ile Arg Pro Arg Arg Gly Ala Ile Val Ile Asp Pro Gly Pro His Arg
65                  70                  75                  80

Val Tyr Glu Met Phe Glu Val Met Ala Glu Leu Glu Gly Leu Ala Gly
                85                  90                  95

Ser Leu Ala Ala Arg Arg Leu Asp Lys Thr Ser Arg Glu Ala Ile Thr
            100                 105                 110

Ala Thr His Gly Arg Cys Glu Lys Ser Ala Ala Gly Asp Ser Asp
        115                 120                 125

Ala Tyr Tyr Tyr Asp Asn Glu Glu Phe His Lys Ala Ile Tyr Ala Ala
    130                 135                 140

Gly Arg Ser Asp Phe Leu Glu Glu Gln Cys Leu Gln Leu His Arg Arg
145                 150                 155                 160

Leu Arg Pro Asp Arg Arg Leu Gln Leu Arg Val Arg Asn Arg Leu Ser
                165                 170                 175

Thr Ser Phe Leu Glu His Cys Ala Ile Val Asp Ala Ile Phe Ala Gly
            180                 185                 190

Asp Gly Asp Glu Ala Arg Arg Leu Leu Arg Gly His Val Gly Ile Gln
        195                 200                 205

Gly Glu Arg Phe Ser Asp Leu Val Ala Ser Met Ala Ala Arg
    210                 215                 220
```

<210> SEQ ID NO 5
<211> LENGTH: 308
<212> TYPE: PRT
<213> ORGANISM: Klebsiella pneumoniae

<400> SEQUENCE: 5

```
Met Lys Asp Asp Ile Asn Gln Glu Ile Thr Phe Arg Lys Leu Ser Val
1               5                   10                  15

Phe Met Met Phe Met Ala Lys Gly Asn Ile Ala Arg Thr Ala Glu Ala
            20                  25                  30

Met Lys Leu Ser Ser Val Ser Val His Arg Ala Leu His Thr Leu Glu
        35                  40                  45

Glu Gly Val Gly Cys Pro Leu Phe Val His Lys Gly Arg Asn Leu Leu
    50                  55                  60

Pro Leu Gln Ala Ala Trp Thr Leu Leu Glu Tyr Cys Gln Asp Val Ile
65                  70                  75                  80

Ser Leu Met Asn Arg Gly Leu Glu Ala Thr Arg Lys Val Ala Gly Val
            85                  90                  95

Gly Gln Gly Arg Leu Arg Ile Gly Thr Leu Tyr Ser Leu Thr Leu Glu
            100                 105                 110

Thr Val Pro Arg Ile Ile Met Gly Met Lys Leu Arg Arg Pro Glu Leu
            115                 120                 125

Glu Leu Asp Leu Thr Met Gly Ser Asn Gln Met Leu Leu Asp Met Leu
            130                 135                 140

Glu Asp Asp Ala Leu Asp Ala Ile Leu Ile Ala Thr Asn Glu Gly Glu
145                 150                 155                 160

Phe Asn Asn Thr Ala Phe Asp Val Val Pro Leu Phe Glu Asp Asp Ile
                165                 170                 175

Phe Leu Ala Ala Pro Ala Thr Glu Arg Leu Asp Ala Ser Arg Leu Ala
            180                 185                 190

Asp Leu Arg Asp Tyr Ala Asp Arg Lys Phe Val Ser Leu Ala Glu Gly
            195                 200                 205

Phe Ala Thr Tyr Ala Gly Phe Arg Glu Ala Phe His Ile Ala Gly Phe
210                 215                 220

Glu Pro Glu Ile Val Thr Arg Val Asn Asp Ile Phe Ser Met Ile Ser
225                 230                 235                 240

Leu Val Gln Ala Gly Val Gly Phe Ala Leu Leu Pro Gly Arg Met Lys
                245                 250                 255

Lys Val Tyr Glu Lys Asp Val Gln Leu Leu Lys Leu Ala Glu Pro Tyr
            260                 265                 270

Gln Met Arg Gln Leu Ile Ser Ile Val Tyr Ser His His Arg Glu Arg
            275                 280                 285

Asp Ala Asp Leu Leu Ala Leu Ala Ala Glu Gly Arg Met Tyr Ala Arg
            290                 295                 300

Ser Ile Asn Arg
305

<210> SEQ ID NO 6
<211> LENGTH: 77
<212> TYPE: DNA
<213> ORGANISM: Acinetobacter calcoaceticus

<400> SEQUENCE: 6
aaaaaaattg tatacaattt atgtttattt gagtacaaag cattgtacac tgaatacaga    60
taggctataa ctatacc                                                  77

<210> SEQ ID NO 7
<211> LENGTH: 598
<212> TYPE: PRT
<213> ORGANISM: Artificial Sequence
<220> FEATURE:
<223> OTHER INFORMATION: EHD3 EC 3.1.2.4 malonyl-CoA hydrolase
``` consensus sequence
<220> FEATURE:
<221> NAME/KEY: VARIANT
<222> LOCATION: (1)..(16)
<223> OTHER INFORMATION: Xaa can be any naturally occurring amino acid
      or absent
<220> FEATURE:
<221> NAME/KEY: VARIANT
<222> LOCATION: (18)..(18)
<223> OTHER INFORMATION: Ile, Leu or Val
<220> FEATURE:
<221> NAME/KEY: VARIANT
<222> LOCATION: (19)..(19)
<223> OTHER INFORMATION: Arg, Lys or His
<220> FEATURE:
<221> NAME/KEY: VARIANT
<222> LOCATION: (20)..(21)
<223> OTHER INFORMATION: Ser or Thr
<220> FEATURE:
<221> NAME/KEY: VARIANT
<222> LOCATION: (22)..(22)
<223> OTHER INFORMATION: Ile, Leu or Val
<220> FEATURE:
<221> NAME/KEY: VARIANT
<222> LOCATION: (23)..(23)
<223> OTHER INFORMATION: Arg, Lys or His
<220> FEATURE:
<221> NAME/KEY: VARIANT
<222> LOCATION: (24)..(24)
<223> OTHER INFORMATION: Xaa can be any naturally occurring amino acid
<220> FEATURE:
<221> NAME/KEY: VARIANT
<222> LOCATION: (27)..(27)
<223> OTHER INFORMATION: Xaa can be any naturally occurring amino acid
<220> FEATURE:
<221> NAME/KEY: VARIANT
<222> LOCATION: (28)..(28)
<223> OTHER INFORMATION: Ser or Thr
<220> FEATURE:
<221> NAME/KEY: VARIANT
<222> LOCATION: (29)..(30)
<223> OTHER INFORMATION: Arg, Lys or His
<220> FEATURE:
<221> NAME/KEY: VARIANT
<222> LOCATION: (31)..(31)
<223> OTHER INFORMATION: Xaa can be any naturally occurring amino acid
<220> FEATURE:
<221> NAME/KEY: VARIANT
<222> LOCATION: (32)..(35)
<223> OTHER INFORMATION: Xaa can be any naturally occurring amino acid
      or absent
<220> FEATURE:
<221> NAME/KEY: VARIANT
<222> LOCATION: (36)..(36)
<223> OTHER INFORMATION: Xaa can be any naturally occurring amino acid
<220> FEATURE:
<221> NAME/KEY: VARIANT
<222> LOCATION: (37)..(40)
<223> OTHER INFORMATION: Xaa can be any naturally occurring amino acid
      or absent
<220> FEATURE:
<221> NAME/KEY: VARIANT
<222> LOCATION: (41)..(41)
<223> OTHER INFORMATION: Xaa can be any naturally occurring amino acid
<220> FEATURE:
<221> NAME/KEY: VARIANT
<222> LOCATION: (44)..(44)
<223> OTHER INFORMATION: Ile, Leu or Val
<220> FEATURE:
<221> NAME/KEY: VARIANT
<222> LOCATION: (45)..(46)
<223> OTHER INFORMATION: Arg, Lys or His
<220> FEATURE:
<221> NAME/KEY: VARIANT
<222> LOCATION: (47)..(47)
<223> OTHER INFORMATION: Ile, Leu or Val
<220> FEATURE:
<221> NAME/KEY: VARIANT
<222> LOCATION: (48)..(48)

```
<223> OTHER INFORMATION: Arg, Lys or His
<220> FEATURE:
<221> NAME/KEY: VARIANT
<222> LOCATION: (49)..(52)
<223> OTHER INFORMATION: Xaa can be any naturally occurring amino acid
      or absent
<220> FEATURE:
<221> NAME/KEY: VARIANT
<222> LOCATION: (53)..(53)
<223> OTHER INFORMATION: Xaa can be any naturally occurring amino acid
<220> FEATURE:
<221> NAME/KEY: VARIANT
<222> LOCATION: (54)..(58)
<223> OTHER INFORMATION: Xaa can be any naturally occurring amino acid
      or absent
<220> FEATURE:
<221> NAME/KEY: VARIANT
<222> LOCATION: (59)..(59)
<223> OTHER INFORMATION: Xaa can be any naturally occurring amino acid
<220> FEATURE:
<221> NAME/KEY: VARIANT
<222> LOCATION: (60)..(60)
<223> OTHER INFORMATION: Arg, Lys or His
<220> FEATURE:
<221> NAME/KEY: VARIANT
<222> LOCATION: (61)..(61)
<223> OTHER INFORMATION: Ser or Thr
<220> FEATURE:
<221> NAME/KEY: VARIANT
<222> LOCATION: (62)..(62)
<223> OTHER INFORMATION: Ile, Leu or Val
<220> FEATURE:
<221> NAME/KEY: VARIANT
<222> LOCATION: (63)..(65)
<223> OTHER INFORMATION: Ser or Thr
<220> FEATURE:
<221> NAME/KEY: VARIANT
<222> LOCATION: (66)..(90)
<223> OTHER INFORMATION: Xaa can be any naturally occurring amino acid
      or absent
<220> FEATURE:
<221> NAME/KEY: VARIANT
<222> LOCATION: (93)..(93)
<223> OTHER INFORMATION: Ile, Leu or Val
<220> FEATURE:
<221> NAME/KEY: VARIANT
<222> LOCATION: (95)..(97)
<223> OTHER INFORMATION: Xaa can be any naturally occurring amino acid
<220> FEATURE:
<221> NAME/KEY: VARIANT
<222> LOCATION: (98)..(100)
<223> OTHER INFORMATION: Ser or Thr
<220> FEATURE:
<221> NAME/KEY: VARIANT
<222> LOCATION: (102)..(102)
<223> OTHER INFORMATION: Ile, Leu or Val
<220> FEATURE:
<221> NAME/KEY: VARIANT
<222> LOCATION: (104)..(104)
<223> OTHER INFORMATION: Ser or Thr
<220> FEATURE:
<221> NAME/KEY: VARIANT
<222> LOCATION: (105)..(105)
<223> OTHER INFORMATION: Ile, Leu or Val
<220> FEATURE:
<221> NAME/KEY: VARIANT
<222> LOCATION: (107)..(107)
<223> OTHER INFORMATION: Asp or Glu
<220> FEATURE:
<221> NAME/KEY: VARIANT
<222> LOCATION: (108)..(108)
<223> OTHER INFORMATION: Ser or Thr
<220> FEATURE:
<221> NAME/KEY: VARIANT
<222> LOCATION: (111)..(112)
<223> OTHER INFORMATION: Ile, Leu or Val
<220> FEATURE:
<221> NAME/KEY: VARIANT
<222> LOCATION: (113)..(113)
```

```
<223> OTHER INFORMATION: Ser or Thr
<220> FEATURE:
<221> NAME/KEY: VARIANT
<222> LOCATION: (118)..(118)
<223> OTHER INFORMATION: Arg, Lys or His
<220> FEATURE:
<221> NAME/KEY: VARIANT
<222> LOCATION: (125)..(125)
<223> OTHER INFORMATION: Ser or Thr
<220> FEATURE:
<221> NAME/KEY: VARIANT
<222> LOCATION: (126)..(126)
<223> OTHER INFORMATION: Asp or Glu
<220> FEATURE:
<221> NAME/KEY: VARIANT
<222> LOCATION: (128)..(128)
<223> OTHER INFORMATION: Ser or Thr
<220> FEATURE:
<221> NAME/KEY: VARIANT
<222> LOCATION: (129)..(129)
<223> OTHER INFORMATION: Asp or Glu
<220> FEATURE:
<221> NAME/KEY: VARIANT
<222> LOCATION: (130)..(130)
<223> OTHER INFORMATION: Ser or Thr
<220> FEATURE:
<221> NAME/KEY: VARIANT
<222> LOCATION: (131)..(131)
<223> OTHER INFORMATION: Ile, Leu or Val
<220> FEATURE:
<221> NAME/KEY: VARIANT
<222> LOCATION: (133)..(133)
<223> OTHER INFORMATION: Arg, Lys or His
<220> FEATURE:
<221> NAME/KEY: VARIANT
<222> LOCATION: (134)..(134)
<223> OTHER INFORMATION: Ser or Thr
<220> FEATURE:
<221> NAME/KEY: VARIANT
<222> LOCATION: (139)..(139)
<223> OTHER INFORMATION: Ser or Thr
<220> FEATURE:
<221> NAME/KEY: VARIANT
<222> LOCATION: (142)..(142)
<223> OTHER INFORMATION: Asp or Glu
<220> FEATURE:
<221> NAME/KEY: VARIANT
<222> LOCATION: (143)..(144)
<223> OTHER INFORMATION: Ser or Thr
<220> FEATURE:
<221> NAME/KEY: VARIANT
<222> LOCATION: (146)..(149)
<223> OTHER INFORMATION: Ile, Leu or Val
<220> FEATURE:
<221> NAME/KEY: VARIANT
<222> LOCATION: (150)..(150)
<223> OTHER INFORMATION: Arg, Lys or His
<220> FEATURE:
<221> NAME/KEY: VARIANT
<222> LOCATION: (152)..(152)
<223> OTHER INFORMATION: Ser or Thr
<220> FEATURE:
<221> NAME/KEY: VARIANT
<222> LOCATION: (157)..(157)
<223> OTHER INFORMATION: Ser or Thr
<220> FEATURE:
<221> NAME/KEY: VARIANT
<222> LOCATION: (158)..(158)
<223> OTHER INFORMATION: Ile, Leu or Val
<220> FEATURE:
<221> NAME/KEY: VARIANT
<222> LOCATION: (166)..(166)
<223> OTHER INFORMATION: Ser or Thr
<220> FEATURE:
<221> NAME/KEY: VARIANT
<222> LOCATION: (167)..(167)
<223> OTHER INFORMATION: Ile, Leu or Val
<220> FEATURE:
<221> NAME/KEY: VARIANT
```

```
<222> LOCATION: (169)..(169)
<223> OTHER INFORMATION: Ile, Leu or Val
<220> FEATURE:
<221> NAME/KEY: VARIANT
<222> LOCATION: (170)..(170)
<223> OTHER INFORMATION: Xaa can be any naturally occurring amino acid
<220> FEATURE:
<221> NAME/KEY: VARIANT
<222> LOCATION: (172)..(172)
<223> OTHER INFORMATION: Ile, Leu or Val
<220> FEATURE:
<221> NAME/KEY: VARIANT
<222> LOCATION: (173)..(173)
<223> OTHER INFORMATION: Asp or Glu
<220> FEATURE:
<221> NAME/KEY: VARIANT
<222> LOCATION: (174)..(175)
<223> OTHER INFORMATION: Arg, Lys or His
<220> FEATURE:
<221> NAME/KEY: VARIANT
<222> LOCATION: (177)..(178)
<223> OTHER INFORMATION: Xaa can be any naturally occurring amino acid
      or absent
<220> FEATURE:
<221> NAME/KEY: VARIANT
<222> LOCATION: (179)..(180)
<223> OTHER INFORMATION: Arg, Lys or His
<220> FEATURE:
<221> NAME/KEY: VARIANT
<222> LOCATION: (181)..(181)
<223> OTHER INFORMATION: Ser or Thr
<220> FEATURE:
<221> NAME/KEY: VARIANT
<222> LOCATION: (182)..(182)
<223> OTHER INFORMATION: Ile, Leu or Val
<220> FEATURE:
<221> NAME/KEY: VARIANT
<222> LOCATION: (183)..(183)
<223> OTHER INFORMATION: Asp or Glu
<220> FEATURE:
<221> NAME/KEY: VARIANT
<222> LOCATION: (186)..(186)
<223> OTHER INFORMATION: Arg, Lys or His
<220> FEATURE:
<221> NAME/KEY: VARIANT
<222> LOCATION: (187)..(187)
<223> OTHER INFORMATION: Ser or Thr
<220> FEATURE:
<221> NAME/KEY: VARIANT
<222> LOCATION: (188)..(188)
<223> OTHER INFORMATION: Ala, Asp, Arg, His, Lys, Ser, Thr, Asn, Gln,
      Tyr
<220> FEATURE:
<221> NAME/KEY: VARIANT
<222> LOCATION: (191)..(191)
<223> OTHER INFORMATION: Ile, Leu or Val
<220> FEATURE:
<221> NAME/KEY: VARIANT
<222> LOCATION: (195)..(195)
<223> OTHER INFORMATION: Ile, Leu or Val
<220> FEATURE:
<221> NAME/KEY: VARIANT
<222> LOCATION: (199)..(199)
<223> OTHER INFORMATION: Ile, Leu or Val
<220> FEATURE:
<221> NAME/KEY: VARIANT
<222> LOCATION: (202)..(205)
<223> OTHER INFORMATION: Ile, Leu or Val
<220> FEATURE:
<221> NAME/KEY: VARIANT
<222> LOCATION: (207)..(207)
<223> OTHER INFORMATION: Asp or Glu
<220> FEATURE:
<221> NAME/KEY: VARIANT
<222> LOCATION: (217)..(217)
<223> OTHER INFORMATION: Ile, Leu or Val
<220> FEATURE:
<221> NAME/KEY: VARIANT
<222> LOCATION: (218)..(218)
```

```
<223> OTHER INFORMATION: Ser or Thr
<220> FEATURE:
<221> NAME/KEY: VARIANT
<222> LOCATION: (219)..(219)
<223> OTHER INFORMATION: Ile, Leu or Val
<220> FEATURE:
<221> NAME/KEY: VARIANT
<222> LOCATION: (221)..(221)
<223> OTHER INFORMATION: Ser or Thr
<220> FEATURE:
<221> NAME/KEY: VARIANT
<222> LOCATION: (225)..(225)
<223> OTHER INFORMATION: Ile, Leu or Val
<220> FEATURE:
<221> NAME/KEY: VARIANT
<222> LOCATION: (231)..(231)
<223> OTHER INFORMATION: Arg, Lys or His
<220> FEATURE:
<221> NAME/KEY: VARIANT
<222> LOCATION: (247)..(248)
<223> OTHER INFORMATION: Ser or Thr
<220> FEATURE:
<221> NAME/KEY: VARIANT
<222> LOCATION: (251)..(251)
<223> OTHER INFORMATION: Ile, Leu or Val
<220> FEATURE:
<221> NAME/KEY: VARIANT
<222> LOCATION: (253)..(253)
<223> OTHER INFORMATION: Arg, Lys or His
<220> FEATURE:
<221> NAME/KEY: VARIANT
<222> LOCATION: (254)..(255)
<223> OTHER INFORMATION: Ile, Leu or Val
<220> FEATURE:
<221> NAME/KEY: VARIANT
<222> LOCATION: (256)..(256)
<223> OTHER INFORMATION: Ser or Thr
<220> FEATURE:
<221> NAME/KEY: VARIANT
<222> LOCATION: (257)..(257)
<223> OTHER INFORMATION: Ile, Leu or Val
<220> FEATURE:
<221> NAME/KEY: VARIANT
<222> LOCATION: (260)..(260)
<223> OTHER INFORMATION: Ser or Thr
<220> FEATURE:
<221> NAME/KEY: VARIANT
<222> LOCATION: (261)..(261)
<223> OTHER INFORMATION: Arg, Lys or His
<220> FEATURE:
<221> NAME/KEY: VARIANT
<222> LOCATION: (262)..(262)
<223> OTHER INFORMATION: Ser or Thr
<220> FEATURE:
<221> NAME/KEY: VARIANT
<222> LOCATION: (264)..(264)
<223> OTHER INFORMATION: Ile, Leu or Val
<220> FEATURE:
<221> NAME/KEY: VARIANT
<222> LOCATION: (266)..(266)
<223> OTHER INFORMATION: Ile, Leu or Val
<220> FEATURE:
<221> NAME/KEY: VARIANT
<222> LOCATION: (270)..(270)
<223> OTHER INFORMATION: Ile, Leu or Val
<220> FEATURE:
<221> NAME/KEY: VARIANT
<222> LOCATION: (273)..(273)
<223> OTHER INFORMATION: Asp or Glu
<220> FEATURE:
<221> NAME/KEY: VARIANT
<222> LOCATION: (274)..(275)
<223> OTHER INFORMATION: Ile, Leu or Val
<220> FEATURE:
<221> NAME/KEY: VARIANT
<222> LOCATION: (276)..(276)
<223> OTHER INFORMATION: Ser or Thr
<220> FEATURE:
<221> NAME/KEY: VARIANT
```

```
<222> LOCATION: (278)..(279)
<223> OTHER INFORMATION: Asp or Glu
<220> FEATURE:
<221> NAME/KEY: VARIANT
<222> LOCATION: (282)..(283)
<223> OTHER INFORMATION: Ile, Leu or Val
<220> FEATURE:
<221> NAME/KEY: VARIANT
<222> LOCATION: (285)..(285)
<223> OTHER INFORMATION: Ile, Leu or Val
<220> FEATURE:
<221> NAME/KEY: VARIANT
<222> LOCATION: (290)..(290)
<223> OTHER INFORMATION: Ile, Leu or Val
<220> FEATURE:
<221> NAME/KEY: VARIANT
<222> LOCATION: (291)..(291)
<223> OTHER INFORMATION: Ser or Thr
<220> FEATURE:
<221> NAME/KEY: VARIANT
<222> LOCATION: (292)..(292)
<223> OTHER INFORMATION: Arg, Lys or His
<220> FEATURE:
<221> NAME/KEY: VARIANT
<222> LOCATION: (293)..(293)
<223> OTHER INFORMATION: Asp or Glu
<220> FEATURE:
<221> NAME/KEY: VARIANT
<222> LOCATION: (295)..(295)
<223> OTHER INFORMATION: Ile, Leu or Val
<220> FEATURE:
<221> NAME/KEY: VARIANT
<222> LOCATION: (296)..(297)
<223> OTHER INFORMATION: Asp or Glu
<220> FEATURE:
<221> NAME/KEY: VARIANT
<222> LOCATION: (299)..(299)
<223> OTHER INFORMATION: Asp or Glu
<220> FEATURE:
<221> NAME/KEY: VARIANT
<222> LOCATION: (300)..(300)
<223> OTHER INFORMATION: Arg, Lys or His
<220> FEATURE:
<221> NAME/KEY: VARIANT
<222> LOCATION: (305)..(305)
<223> OTHER INFORMATION: Ile, Leu or Val
<220> FEATURE:
<221> NAME/KEY: VARIANT
<222> LOCATION: (306)..(306)
<223> OTHER INFORMATION: Arg, Lys or His
<220> FEATURE:
<221> NAME/KEY: VARIANT
<222> LOCATION: (308)..(308)
<223> OTHER INFORMATION: Ser or Thr
<220> FEATURE:
<221> NAME/KEY: VARIANT
<222> LOCATION: (309)..(309)
<223> OTHER INFORMATION: Asp or Glu
<220> FEATURE:
<221> NAME/KEY: VARIANT
<222> LOCATION: (310)..(310)
<223> OTHER INFORMATION: Xaa can be any naturally occurring amino acid
<220> FEATURE:
<221> NAME/KEY: VARIANT
<222> LOCATION: (311)..(311)
<223> OTHER INFORMATION: Ile, Leu or Val
<220> FEATURE:
<221> NAME/KEY: VARIANT
<222> LOCATION: (312)..(312)
<223> OTHER INFORMATION: Asp or Glu
<220> FEATURE:
<221> NAME/KEY: VARIANT
<222> LOCATION: (313)..(313)
<223> OTHER INFORMATION: Xaa can be any naturally occurring amino acid
<220> FEATURE:
<221> NAME/KEY: VARIANT
<222> LOCATION: (314)..(314)
<223> OTHER INFORMATION: Xaa can be any naturally occurring amino acid
    or absent
```

```
<220> FEATURE:
<221> NAME/KEY: VARIANT
<222> LOCATION: (315)..(317)
<223> OTHER INFORMATION: Xaa can be any naturally occurring amino acid
<220> FEATURE:
<221> NAME/KEY: VARIANT
<222> LOCATION: (318)..(318)
<223> OTHER INFORMATION: Ser or Thr
<220> FEATURE:
<221> NAME/KEY: VARIANT
<222> LOCATION: (320)..(320)
<223> OTHER INFORMATION: Ser or Thr
<220> FEATURE:
<221> NAME/KEY: VARIANT
<222> LOCATION: (321)..(322)
<223> OTHER INFORMATION: Asp or Glu
<220> FEATURE:
<221> NAME/KEY: VARIANT
<222> LOCATION: (325)..(325)
<223> OTHER INFORMATION: Asp or Glu
<220> FEATURE:
<221> NAME/KEY: VARIANT
<222> LOCATION: (326)..(327)
<223> OTHER INFORMATION: Ile, Leu or Val
<220> FEATURE:
<221> NAME/KEY: VARIANT
<222> LOCATION: (329)..(329)
<223> OTHER INFORMATION: Asp or Glu
<220> FEATURE:
<221> NAME/KEY: VARIANT
<222> LOCATION: (330)..(330)
<223> OTHER INFORMATION: Ser or Thr
<220> FEATURE:
<221> NAME/KEY: VARIANT
<222> LOCATION: (331)..(331)
<223> OTHER INFORMATION: Ile, Leu or Val
<220> FEATURE:
<221> NAME/KEY: VARIANT
<222> LOCATION: (332)..(332)
<223> OTHER INFORMATION: Asp or Glu
<220> FEATURE:
<221> NAME/KEY: VARIANT
<222> LOCATION: (335)..(336)
<223> OTHER INFORMATION: Ser or Thr
<220> FEATURE:
<221> NAME/KEY: VARIANT
<222> LOCATION: (338)..(338)
<223> OTHER INFORMATION: Xaa can be any naturally occurring amino acid
    or absent
<220> FEATURE:
<221> NAME/KEY: VARIANT
<222> LOCATION: (339)..(339)
<223> OTHER INFORMATION: Ile, Leu or Val
<220> FEATURE:
<221> NAME/KEY: VARIANT
<222> LOCATION: (341)..(341)
<223> OTHER INFORMATION: Arg, Lys or His
<220> FEATURE:
<221> NAME/KEY: VARIANT
<222> LOCATION: (342)..(342)
<223> OTHER INFORMATION: Asp or Glu
<220> FEATURE:
<221> NAME/KEY: VARIANT
<222> LOCATION: (344)..(344)
<223> OTHER INFORMATION: Arg, Lys or His
<220> FEATURE:
<221> NAME/KEY: VARIANT
<222> LOCATION: (346)..(346)
<223> OTHER INFORMATION: Arg, Lys or His
<220> FEATURE:
<221> NAME/KEY: VARIANT
<222> LOCATION: (348)..(348)
<223> OTHER INFORMATION: Ser or Thr
<220> FEATURE:
<221> NAME/KEY: VARIANT
<222> LOCATION: (350)..(350)
<223> OTHER INFORMATION: Asp or Glu
<220> FEATURE:
<221> NAME/KEY: VARIANT
```

```
<222> LOCATION: (351)..(351)
<223> OTHER INFORMATION: Arg, Lys or His
<220> FEATURE:
<221> NAME/KEY: VARIANT
<222> LOCATION: (353)..(353)
<223> OTHER INFORMATION: Asp or Glu
<220> FEATURE:
<221> NAME/KEY: VARIANT
<222> LOCATION: (356)..(356)
<223> OTHER INFORMATION: Asp or Glu
<220> FEATURE:
<221> NAME/KEY: VARIANT
<222> LOCATION: (357)..(357)
<223> OTHER INFORMATION: Arg, Lys or His
<220> FEATURE:
<221> NAME/KEY: VARIANT
<222> LOCATION: (360)..(360)
<223> OTHER INFORMATION: Asp or Glu
<220> FEATURE:
<221> NAME/KEY: VARIANT
<222> LOCATION: (361)..(361)
<223> OTHER INFORMATION: Ile, Leu or Val
<220> FEATURE:
<221> NAME/KEY: VARIANT
<222> LOCATION: (362)..(362)
<223> OTHER INFORMATION: Ser or Thr
<220> FEATURE:
<221> NAME/KEY: VARIANT
<222> LOCATION: (363)..(363)
<223> OTHER INFORMATION: Arg, Lys or His
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (365)..(366)
<223> OTHER INFORMATION: Ser or Thr
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (368)..(368)
<223> OTHER INFORMATION: Arg, Lys or His
<220> FEATURE:
<221> NAME/KEY: VARIANT
<222> LOCATION: (369)..(369)
<223> OTHER INFORMATION: Asp or Glu
<220> FEATURE:
<221> NAME/KEY: VARIANT
<222> LOCATION: (370)..(371)
<223> OTHER INFORMATION: Ile, Leu or Val
<220> FEATURE:
<221> NAME/KEY: VARIANT
<222> LOCATION: (372)..(373)
<223> OTHER INFORMATION: Arg, Lys or His
<220> FEATURE:
<221> NAME/KEY: VARIANT
<222> LOCATION: (375)..(376)
<223> OTHER INFORMATION: Asp or Glu
<220> FEATURE:
<221> NAME/KEY: VARIANT
<222> LOCATION: (377)..(377)
<223> OTHER INFORMATION: Ile, Leu or Val
<220> FEATURE:
<221> NAME/KEY: VARIANT
<222> LOCATION: (378)..(378)
<223> OTHER INFORMATION: Xaa can be any naturally occurring amino acid
     or absent
<220> FEATURE:
<221> NAME/KEY: VARIANT
<222> LOCATION: (379)..(380)
<223> OTHER INFORMATION: Xaa can be any naturally occurring amino acid
<220> FEATURE:
<221> NAME/KEY: VARIANT
<222> LOCATION: (381)..(381)
```

```
<223> OTHER INFORMATION: Xaa can be any naturally occurring amino acid
      or absent
<220> FEATURE:
<221> NAME/KEY: VARIANT
<222> LOCATION: (383)..(383)
<223> OTHER INFORMATION: Asp or Glu
<220> FEATURE:
<221> NAME/KEY: VARIANT
<222> LOCATION: (385)..(385)
<223> OTHER INFORMATION: Ser or Thr
<220> FEATURE:
<221> NAME/KEY: VARIANT
<222> LOCATION: (386)..(387)
<223> OTHER INFORMATION: Asp or Glu
<220> FEATURE:
<221> NAME/KEY: VARIANT
<222> LOCATION: (389)..(389)
<223> OTHER INFORMATION: Arg, Lys or His
<220> FEATURE:
<221> NAME/KEY: VARIANT
<222> LOCATION: (390)..(390)
<223> OTHER INFORMATION: Asp or Glu
<220> FEATURE:
<221> NAME/KEY: VARIANT
<222> LOCATION: (393)..(393)
<223> OTHER INFORMATION: Arg, Lys or His
<220> FEATURE:
<221> NAME/KEY: VARIANT
<222> LOCATION: (394)..(394)
<223> OTHER INFORMATION: Asp or Glu
<220> FEATURE:
<221> NAME/KEY: VARIANT
<222> LOCATION: (395)..(395)
<223> OTHER INFORMATION: Ile, Leu or Val
<220> FEATURE:
<221> NAME/KEY: VARIANT
<222> LOCATION: (396)..(396)
<223> OTHER INFORMATION: Arg, Lys or His
<220> FEATURE:
<221> NAME/KEY: VARIANT
<222> LOCATION: (397)..(397)
<223> OTHER INFORMATION: Asp or Glu
<220> FEATURE:
<221> NAME/KEY: VARIANT
<222> LOCATION: (398)..(398)
<223> OTHER INFORMATION: Arg, Lys or His
<220> FEATURE:
<221> NAME/KEY: VARIANT
<222> LOCATION: (400)..(400)
<223> OTHER INFORMATION: Ile, Leu or Val
<220> FEATURE:
<221> NAME/KEY: VARIANT
<222> LOCATION: (401)..(401)
<223> OTHER INFORMATION: Ser or Thr
<220> FEATURE:
<221> NAME/KEY: VARIANT
<222> LOCATION: (405)..(405)
<223> OTHER INFORMATION: Ser or Thr
<220> FEATURE:
<221> NAME/KEY: VARIANT
<222> LOCATION: (407)..(407)
<223> OTHER INFORMATION: Ile, Leu or Val
<220> FEATURE:
<221> NAME/KEY: VARIANT
<222> LOCATION: (409)..(409)
<223> OTHER INFORMATION: Ile, Leu or Val
<220> FEATURE:
<221> NAME/KEY: VARIANT
<222> LOCATION: (411)..(411)
<223> OTHER INFORMATION: Ile, Leu or Val
<220> FEATURE:
<221> NAME/KEY: VARIANT
<222> LOCATION: (412)..(412)
<223> OTHER INFORMATION: Arg, Lys or His
<220> FEATURE:
<221> NAME/KEY: VARIANT
<222> LOCATION: (413)..(414)
<223> OTHER INFORMATION: Ile, Leu or Val
```

```
<220> FEATURE:
<221> NAME/KEY: VARIANT
<222> LOCATION: (415)..(415)
<223> OTHER INFORMATION: Arg, Lys or His
<220> FEATURE:
<221> NAME/KEY: VARIANT
<222> LOCATION: (416)..(416)
<223> OTHER INFORMATION: Asp or Glu
<220> FEATURE:
<221> NAME/KEY: VARIANT
<222> LOCATION: (418)..(418)
<223> OTHER INFORMATION: Ser or Thr
<220> FEATURE:
<221> NAME/KEY: VARIANT
<222> LOCATION: (419)..(419)
<223> OTHER INFORMATION: Arg, Lys or His
<220> FEATURE:
<221> NAME/KEY: VARIANT
<222> LOCATION: (420)..(420)
<223> OTHER INFORMATION: Asp or Glu
<220> FEATURE:
<221> NAME/KEY: VARIANT
<222> LOCATION: (421)..(421)
<223> OTHER INFORMATION: Arg, Lys or His
<220> FEATURE:
<221> NAME/KEY: VARIANT
<222> LOCATION: (422)..(422)
<223> OTHER INFORMATION: Ile, Leu or Val
<220> FEATURE:
<221> NAME/KEY: VARIANT
<222> LOCATION: (423)..(423)
<223> OTHER INFORMATION: Asp or Glu
<220> FEATURE:
<221> NAME/KEY: VARIANT
<222> LOCATION: (424)..(424)
<223> OTHER INFORMATION: Ser or Thr
<220> FEATURE:
<221> NAME/KEY: VARIANT
<222> LOCATION: (426)..(426)
<223> OTHER INFORMATION: Ile, Leu or Val
<220> FEATURE:
<221> NAME/KEY: VARIANT
<222> LOCATION: (427)..(428)
<223> OTHER INFORMATION: Arg, Lys or His
<220> FEATURE:
<221> NAME/KEY: VARIANT
<222> LOCATION: (431)..(431)
<223> OTHER INFORMATION: Ile, Leu or Val
<220> FEATURE:
<221> NAME/KEY: VARIANT
<222> LOCATION: (434)..(434)
<223> OTHER INFORMATION: Ser or Thr
<220> FEATURE:
<221> NAME/KEY: VARIANT
<222> LOCATION: (438)..(438)
<223> OTHER INFORMATION: Ile, Leu or Val
<220> FEATURE:
<221> NAME/KEY: VARIANT
<222> LOCATION: (440)..(440)
<223> OTHER INFORMATION: Xaa can be any naturally occurring amino acid
     or absent
<220> FEATURE:
<221> NAME/KEY: VARIANT
<222> LOCATION: (441)..(443)
<223> OTHER INFORMATION: Xaa can be any naturally occurring amino acid
<220> FEATURE:
<221> NAME/KEY: VARIANT
<222> LOCATION: (445)..(445)
<223> OTHER INFORMATION: Asp or Glu
<220> FEATURE:
<221> NAME/KEY: VARIANT
<222> LOCATION: (446)..(446)
<223> OTHER INFORMATION: Ser or Thr
<220> FEATURE:
<221> NAME/KEY: VARIANT
<222> LOCATION: (447)..(448)
<223> OTHER INFORMATION: Ile, Leu or Val
<220> FEATURE:
<221> NAME/KEY: VARIANT
```

```
<222> LOCATION: (451)..(451)
<223> OTHER INFORMATION: Ser or Thr
<220> FEATURE:
<221> NAME/KEY: VARIANT
<222> LOCATION: (452)..(452)
<223> OTHER INFORMATION: Asp or Glu
<220> FEATURE:
<221> NAME/KEY: VARIANT
<222> LOCATION: (454)..(454)
<223> OTHER INFORMATION: Ser or Thr
<220> FEATURE:
<221> NAME/KEY: VARIANT
<222> LOCATION: (455)..(456)
<223> OTHER INFORMATION: Arg, Lys or His
<220> FEATURE:
<221> NAME/KEY: VARIANT
<222> LOCATION: (459)..(459)
<223> OTHER INFORMATION: Ile, Leu or Val
<220> FEATURE:
<221> NAME/KEY: VARIANT
<222> LOCATION: (460)..(460)
<223> OTHER INFORMATION: Asp or Glu
<220> FEATURE:
<221> NAME/KEY: VARIANT
<222> LOCATION: (463)..(463)
<223> OTHER INFORMATION: Arg, Lys or His
<220> FEATURE:
<221> NAME/KEY: VARIANT
<222> LOCATION: (464)..(464)
<223> OTHER INFORMATION: Ile, Leu or Val
<220> FEATURE:
<221> NAME/KEY: VARIANT
<222> LOCATION: (464)..(464)
<223> OTHER INFORMATION: Ile, Leu or Val
<220> FEATURE:
<221> NAME/KEY: VARIANT
<222> LOCATION: (469)..(471)
<223> OTHER INFORMATION: Arg, Lys or His
<220> FEATURE:
<221> NAME/KEY: VARIANT
<222> LOCATION: (472)..(472)
<223> OTHER INFORMATION: Xaa can be any naturally occurring amino acid
<220> FEATURE:
<221> NAME/KEY: VARIANT
<222> LOCATION: (473)..(474)
<223> OTHER INFORMATION: Asp or Glu
<220> FEATURE:
<221> NAME/KEY: VARIANT
<222> LOCATION: (475)..(475)
<223> OTHER INFORMATION: Ile, Leu or Val
<220> FEATURE:
<221> NAME/KEY: VARIANT
<222> LOCATION: (476)..(476)
<223> OTHER INFORMATION: Ser or Thr
<220> FEATURE:
<221> NAME/KEY: VARIANT
<222> LOCATION: (477)..(477)
<223> OTHER INFORMATION: Ile, Leu or Val
<220> FEATURE:
<221> NAME/KEY: VARIANT
<222> LOCATION: (478)..(478)
<223> OTHER INFORMATION: Ser or Thr
<220> FEATURE:
<221> NAME/KEY: VARIANT
<222> LOCATION: (480)..(480)
<223> OTHER INFORMATION: Ile, Leu or Val
<220> FEATURE:
<221> NAME/KEY: VARIANT
<222> LOCATION: (481)..(482)
<223> OTHER INFORMATION: Ser or Thr
<220> FEATURE:
<221> NAME/KEY: VARIANT
<222> LOCATION: (483)..(484)
<223> OTHER INFORMATION: Ile, Leu or Val
<220> FEATURE:
<221> NAME/KEY: VARIANT
<222> LOCATION: (485)..(485)
<223> OTHER INFORMATION: Ser or Thr
<220> FEATURE:
```

```
<221> NAME/KEY: VARIANT
<222> LOCATION: (487)..(487)
<223> OTHER INFORMATION: Arg, Lys or His
<220> FEATURE:
<221> NAME/KEY: VARIANT
<222> LOCATION: (489)..(489)
<223> OTHER INFORMATION: Ser or Thr
<220> FEATURE:
<221> NAME/KEY: VARIANT
<222> LOCATION: (490)..(490)
<223> OTHER INFORMATION: Ile, Leu or Val
<220> FEATURE:
<221> NAME/KEY: VARIANT
<222> LOCATION: (492)..(492)
<223> OTHER INFORMATION: Ile, Leu or Val
<220> FEATURE:
<221> NAME/KEY: VARIANT
<222> LOCATION: (493)..(493)
<223> OTHER INFORMATION: Ser or Thr
<220> FEATURE:
<221> NAME/KEY: VARIANT
<222> LOCATION: (495)..(495)
<223> OTHER INFORMATION: Ile, Leu or Val
<220> FEATURE:
<221> NAME/KEY: VARIANT
<222> LOCATION: (496)..(496)
<223> OTHER INFORMATION: Arg, Lys or His
<220> FEATURE:
<221> NAME/KEY: VARIANT
<222> LOCATION: (498)..(499)
<223> OTHER INFORMATION: Ser or Thr
<220> FEATURE:
<221> NAME/KEY: VARIANT
<222> LOCATION: (501)..(501)
<223> OTHER INFORMATION: Ile, Leu or Val
<220> FEATURE:
<221> NAME/KEY: VARIANT
<222> LOCATION: (504)..(504)
<223> OTHER INFORMATION: Arg, Lys or His
<220> FEATURE:
<221> NAME/KEY: VARIANT
<222> LOCATION: (505)..(505)
<223> OTHER INFORMATION: Asp or Glu
<220> FEATURE:
<221> NAME/KEY: VARIANT
<222> LOCATION: (508)..(509)
<223> OTHER INFORMATION: Arg, Lys or His
<220> FEATURE:
<221> NAME/KEY: VARIANT
<222> LOCATION: (510)..(510)
<223> OTHER INFORMATION: Ile, Leu or Val
<220> FEATURE:
<221> NAME/KEY: VARIANT
<222> LOCATION: (511)..(511)
<223> OTHER INFORMATION: Arg, Lys or His
<220> FEATURE:
<221> NAME/KEY: VARIANT
<222> LOCATION: (516)..(516)
<223> OTHER INFORMATION: Ser or Thr
<220> FEATURE:
<221> NAME/KEY: VARIANT
<222> LOCATION: (517)..(517)
<223> OTHER INFORMATION: Asp or Glu
<220> FEATURE:
<221> NAME/KEY: VARIANT
<222> LOCATION: (518)..(518)
<223> OTHER INFORMATION: Ser or Thr
<220> FEATURE:
<221> NAME/KEY: VARIANT
<222> LOCATION: (519)..(519)
<223> OTHER INFORMATION: Asp or Glu
<220> FEATURE:
<221> NAME/KEY: VARIANT
<222> LOCATION: (520)..(520)
<223> OTHER INFORMATION: Ile, Leu or Val
<220> FEATURE:
<221> NAME/KEY: VARIANT
<222> LOCATION: (521)..(521)
<223> OTHER INFORMATION: Arg, Lys or His
```

```
<220> FEATURE:
<221> NAME/KEY: VARIANT
<222> LOCATION: (524)..(524)
<223> OTHER INFORMATION: Ile, Leu or Val
<220> FEATURE:
<221> NAME/KEY: VARIANT
<222> LOCATION: (525)..(527)
<223> OTHER INFORMATION: Arg, Lys or His
<220> FEATURE:
<221> NAME/KEY: VARIANT
<222> LOCATION: (528)..(528)
<223> OTHER INFORMATION: Asp or Glu
<220> FEATURE:
<221> NAME/KEY: VARIANT
<222> LOCATION: (530)..(530)
<223> OTHER INFORMATION: Arg, Lys or His
<220> FEATURE:
<221> NAME/KEY: VARIANT
<222> LOCATION: (532)..(534)
<223> OTHER INFORMATION: Xaa can be any naturally occurring amino acid
     or absent
<220> FEATURE:
<221> NAME/KEY: VARIANT
<222> LOCATION: (535)..(535)
<223> OTHER INFORMATION: Xaa can be any naturally occurring amino acid
<220> FEATURE:
<221> NAME/KEY: VARIANT
<222> LOCATION: (537)..(537)
<223> OTHER INFORMATION: Xaa can be any naturally occurring amino acid
     or absent
<220> FEATURE:
<221> NAME/KEY: VARIANT
<222> LOCATION: (538)..(539)
<223> OTHER INFORMATION: Xaa can be any naturally occurring amino acid
<220> FEATURE:
<221> NAME/KEY: VARIANT
<222> LOCATION: (540)..(540)
<223> OTHER INFORMATION: Ile, Leu or Val
<220> FEATURE:
<221> NAME/KEY: VARIANT
<222> LOCATION: (541)..(541)
<223> OTHER INFORMATION: Arg, Lys or His
<220> FEATURE:
<221> NAME/KEY: VARIANT
<222> LOCATION: (542)..(542)
<223> OTHER INFORMATION: Ile, Leu or Val
<220> FEATURE:
<221> NAME/KEY: VARIANT
<222> LOCATION: (543)..(543)
<223> OTHER INFORMATION: Ser or Thr
<220> FEATURE:
<221> NAME/KEY: VARIANT
<222> LOCATION: (543)..(543)
<223> OTHER INFORMATION: Ser or Thr
<220> FEATURE:
<221> NAME/KEY: VARIANT
<222> LOCATION: (544)..(545)
<223> OTHER INFORMATION: Arg, Lys, or His
<220> FEATURE:
<221> NAME/KEY: VARIANT
<222> LOCATION: (546)..(546)
<223> OTHER INFORMATION: Asp or Glu
<220> FEATURE:
<221> NAME/KEY: VARIANT
<222> LOCATION: (547)..(548)
<223> OTHER INFORMATION: Ile, Leu or Val
<220> FEATURE:
<221> NAME/KEY: VARIANT
<222> LOCATION: (549)..(550)
<223> OTHER INFORMATION: Arg, Lys or His
<220> FEATURE:
<221> NAME/KEY: VARIANT
<222> LOCATION: (552)..(552)
<223> OTHER INFORMATION: Ser or Thr
<220> FEATURE:
<221> NAME/KEY: VARIANT
<222> LOCATION: (554)..(554)
<223> OTHER INFORMATION: Ile, Leu or Val
<220> FEATURE:
```

```
<221> NAME/KEY: VARIANT
<222> LOCATION: (556)..(556)
<223> OTHER INFORMATION: Asp or Glu
<220> FEATURE:
<221> NAME/KEY: VARIANT
<222> LOCATION: (557)..(557)
<223> OTHER INFORMATION: Ser or Thr
<220> FEATURE:
<221> NAME/KEY: VARIANT
<222> LOCATION: (558)..(559)
<223> OTHER INFORMATION: Arg, Lys or His
<220> FEATURE:
<221> NAME/KEY: VARIANT
<222> LOCATION: (560)..(560)
<223> OTHER INFORMATION: Asp or Glu
<220> FEATURE:
<221> NAME/KEY: VARIANT
<222> LOCATION: (562)..(562)
<223> OTHER INFORMATION: Ile, Leu or Val
<220> FEATURE:
<221> NAME/KEY: VARIANT
<222> LOCATION: (564)..(564)
<223> OTHER INFORMATION: Ile, Leu or Val
<220> FEATURE:
<221> NAME/KEY: VARIANT
<222> LOCATION: (565)..(565)
<223> OTHER INFORMATION: Asp or Glu
<220> FEATURE:
<221> NAME/KEY: VARIANT
<222> LOCATION: (566)..(566)
<223> OTHER INFORMATION: Ser or Thr
<220> FEATURE:
<221> NAME/KEY: VARIANT
<222> LOCATION: (567)..(568)
<223> OTHER INFORMATION: Ile, Leu or Val
<220> FEATURE:
<221> NAME/KEY: VARIANT
<222> LOCATION: (569)..(569)
<223> OTHER INFORMATION: Arg, Lys or His
<220> FEATURE:
<221> NAME/KEY: VARIANT
<222> LOCATION: (570)..(572)
<223> OTHER INFORMATION: Ile, Leu or Val
<220> FEATURE:
<221> NAME/KEY: VARIANT
<222> LOCATION: (573)..(573)
<223> OTHER INFORMATION: Asp or Glu
<220> FEATURE:
<221> NAME/KEY: VARIANT
<222> LOCATION: (574)..(575)
<223> OTHER INFORMATION: Arg, Lys or His
<220> FEATURE:
<221> NAME/KEY: VARIANT
<222> LOCATION: (577)..(577)
<223> OTHER INFORMATION: Ser or Thr
<220> FEATURE:
<221> NAME/KEY: VARIANT
<222> LOCATION: (578)..(580)
<223> OTHER INFORMATION: Asp or Glu
<220> FEATURE:
<221> NAME/KEY: VARIANT
<222> LOCATION: (582)..(582)
<223> OTHER INFORMATION: Xaa can be any naturally occurring amino acid
<220> FEATURE:
<221> NAME/KEY: VARIANT
<222> LOCATION: (585)..(585)
<223> OTHER INFORMATION: Ile, Leu or Val
<220> FEATURE:
<221> NAME/KEY: VARIANT
<222> LOCATION: (586)..(586)
<223> OTHER INFORMATION: Arg, Lys or His
<220> FEATURE:
<221> NAME/KEY: VARIANT
<222> LOCATION: (588)..(588)
<223> OTHER INFORMATION: Arg, Lys or His
<220> FEATURE:
<221> NAME/KEY: VARIANT
<222> LOCATION: (589)..(590)
<223> OTHER INFORMATION: Xaa can be any naturally occurring amino acid
```

```
<220> FEATURE:
<221> NAME/KEY: VARIANT
<222> LOCATION: (591)..(591)
<223> OTHER INFORMATION: Xaa can be any naturally occurring amino acid
      or absent
<220> FEATURE:
<221> NAME/KEY: VARIANT
<222> LOCATION: (592)..(592)
<223> OTHER INFORMATION: Xaa can be any naturally occurring amino acid
<220> FEATURE:
<221> NAME/KEY: VARIANT
<222> LOCATION: (593)..(598)
<223> OTHER INFORMATION: Xaa can be any naturally occurring amino acid
      or absent

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Met Xaa Xaa Xaa Xaa Xaa Xaa Xaa Ala Gln Xaa Xaa Xaa Xaa Xaa
            20                  25                  30

Xaa Xaa Xaa Xaa Xaa Xaa Xaa Xaa Gly Phe Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Ala Gln Xaa Asn Xaa Xaa
            85                  90                  95

Xaa Xaa Xaa Xaa Val Xaa Phe Xaa Xaa Gln Xaa Xaa Ala Arg Xaa Xaa
                100                 105                 110

Xaa Leu Asn Arg Pro Xaa Lys Leu Asn Ala Leu Asn Xaa Xaa Met Xaa
                115                 120                 125

Xaa Xaa Xaa Phe Xaa Xaa Leu Asn Glu Tyr Xaa Lys Ser Xaa Xaa Xaa
            130                 135                 140

Asn Xaa Xaa Xaa Xaa Xaa Ser Xaa Asn Gln Pro Arg Xaa Xaa Cys Ala
145                 150                 155                 160

Gly Gly Asp Val Ala Xaa Xaa Ala Xaa Xaa Asn Xaa Xaa Xaa Xaa Phe
                165                 170                 175

Xaa Xaa Xaa Xaa Xaa Xaa Xaa Phe Phe Xaa Xaa Xaa Tyr Ser Xaa Asn
            180                 185                 190

Phe Gln Xaa Ala Thr Tyr Xaa Lys Pro Xaa Xaa Xaa Xaa Met Xaa Gly
            195                 200                 205

Ile Thr Met Gly Gly Gly Val Gly Xaa Xaa Xaa His Xaa Pro Phe Arg
    210                 215                 220

Xaa Ala Thr Glu Asn Thr Xaa Trp Ala Met Pro Glu Met Asp Ile Gly
225                 230                 235                 240

Phe Phe Pro Asp Val Gly Xaa Xaa Phe Ala Xaa Pro Xaa Xaa Xaa
                245                 250                 255

Xaa Ala Asn Xaa Xaa Xaa Gln Xaa Ala Xaa Tyr Leu Cys Xaa Thr Gly
            260                 265                 270

Xaa Xaa Xaa Xaa Gly Xaa Xaa Ala Tyr Xaa Gly Xaa Ala Ser His
        275                 280                 285

Tyr Xaa Xaa Xaa Xaa Asn Xaa Xaa Xaa Leu Xaa Xaa Arg Leu Gly Glu
    290                 295                 300

Xaa Xaa Pro Xaa Xaa Xaa Xaa Xaa Xaa Xaa Xaa Xaa Xaa Gln Xaa
305                 310                 315                 320

Xaa Xaa Phe Phe Xaa Xaa Xaa Asn Xaa Xaa Xaa Xaa Glu Phe Xaa Xaa
            325                 330                 335
```

```
Pro Xaa Pro Xaa Xaa Tyr Xaa Phe Xaa Tyr Xaa Asn Xaa Xaa Leu
        340                 345                 350

Xaa Val Ile Xaa Xaa Cys Phe Xaa Xaa Xaa Xaa Xaa Xaa Xaa Xaa
            355                 360                 365

Xaa Xaa Xaa Xaa Xaa Leu Xaa Xaa Xaa Xaa Xaa Xaa Tyr Xaa Gly
            370                 375                 380

Xaa Xaa Xaa Ala Xaa Xaa Phe Ala Xaa Xaa Xaa Xaa Xaa Leu Xaa
385                 390                 395                 400

Xaa Lys Ser Pro Xaa Ser Xaa Gln Xaa Ala Xaa Xaa Xaa Xaa Xaa
            405                 410                 415

Asn Xaa Xaa Xaa Xaa Xaa Xaa Ala Xaa Xaa Xaa Asp Leu Xaa Thr
            420                 425                 430

Ala Xaa Asn Met Cys Xaa Asn Xaa Xaa Xaa Gln Xaa Xaa Xaa Xaa
        435                 440                 445

Glu Phe Xaa Xaa Ala Xaa Xaa Xaa Lys Leu Xaa Xaa Lys Gln Xaa Xaa
450                 455                 460

Pro Tyr Pro Trp Xaa Xaa Xaa Xaa Xaa Xaa Xaa Xaa Gln Xaa
465                 470                 475                 480

Xaa Xaa Xaa Xaa Xaa Pro Xaa Pro Xaa Xaa Pro Xaa Xaa Leu Xaa Xaa
            485                 490                 495

Asn Xaa Xaa Asn Xaa Thr Trp Xaa Xaa Tyr Pro Xaa Xaa Xaa Xaa Tyr
            500                 505                 510

Gln Leu Pro Xaa Xaa Xaa Xaa Xaa Gln Tyr Xaa Xaa Xaa Xaa
            515                 520                 525

Asn Xaa Asn Xaa Xaa Xaa Gly Xaa Xaa Xaa Xaa Xaa Xaa Xaa
            530                 535                 540

Xaa Xaa Xaa Xaa Xaa Phe Xaa Asn Xaa Asn Xaa Xaa Xaa Xaa
545                 550                 555                 560

Lys Xaa Gly Xaa Xaa Xaa Xaa Xaa Xaa Xaa Xaa Xaa Xaa Xaa Cys
            565                 570                 575

Xaa Xaa Xaa Xaa Ala Xaa Gly Gly Xaa Xaa Trp Xaa Xaa Xaa Xaa
            580                 585                 590

Xaa Xaa Xaa Xaa Xaa Xaa
            595
```

<210> SEQ ID NO 8
<211> LENGTH: 351
<212> TYPE: PRT
<213> ORGANISM: Artificial Sequence
<220> FEATURE:
<223> OTHER INFORMATION: Bacillus EC 3.1.2.4 malonyl-CoA hydrolase
      consensus sequence
<220> FEATURE:
<221> NAME/KEY: VARIANT
<222> LOCATION: (4)..(4)
<223> OTHER INFORMATION: Arg, Lys or His
<220> FEATURE:
<221> NAME/KEY: VARIANT
<222> LOCATION: (9)..(9)
<223> OTHER INFORMATION: Ile, Leu or Val
<220> FEATURE:
<221> NAME/KEY: VARIANT
<222> LOCATION: (10)..(10)
<223> OTHER INFORMATION: Ser or Thr
<220> FEATURE:
<221> NAME/KEY: VARIANT
<222> LOCATION: (11)..(11)
<223> OTHER INFORMATION: Asp or Glu
<220> FEATURE:
<221> NAME/KEY: VARIANT
<222> LOCATION: (16)..(16)

```
<223> OTHER INFORMATION: Ser or Thr
<220> FEATURE:
<221> NAME/KEY: VARIANT
<222> LOCATION: (31)..(31)
<223> OTHER INFORMATION: Asp or Glu
<220> FEATURE:
<221> NAME/KEY: VARIANT
<222> LOCATION: (45)..(45)
<223> OTHER INFORMATION: Arg, Lys or His
<220> FEATURE:
<221> NAME/KEY: VARIANT
<222> LOCATION: (46)..(47)
<223> OTHER INFORMATION: Asp or Glu
<220> FEATURE:
<221> NAME/KEY: VARIANT
<222> LOCATION: (48)..(48)
<223> OTHER INFORMATION: Arg, Lys or His
<220> FEATURE:
<221> NAME/KEY: VARIANT
<222> LOCATION: (51)..(51)
<223> OTHER INFORMATION: Ile, Leu or Val
<220> FEATURE:
<221> NAME/KEY: VARIANT
<222> LOCATION: (59)..(59)
<223> OTHER INFORMATION: Ser or Thr
<220> FEATURE:
<221> NAME/KEY: VARIANT
<222> LOCATION: (79)..(79)
<223> OTHER INFORMATION: Ile, Leu or Val
<220> FEATURE:
<221> NAME/KEY: VARIANT
<222> LOCATION: (83)..(83)
<223> OTHER INFORMATION: Arg, Lys or His
<220> FEATURE:
<221> NAME/KEY: VARIANT
<222> LOCATION: (86)..(86)
<223> OTHER INFORMATION: Arg, Lys or His
<220> FEATURE:
<221> NAME/KEY: VARIANT
<222> LOCATION: (89)..(89)
<223> OTHER INFORMATION: Asp or Glu
<220> FEATURE:
<221> NAME/KEY: VARIANT
<222> LOCATION: (91)..(91)
<223> OTHER INFORMATION: Ala, Asp, Arg, His, Lys, Ser, Thr, Asn, Gln,
      Tyr
<220> FEATURE:
<221> NAME/KEY: VARIANT
<222> LOCATION: (93)..(93)
<223> OTHER INFORMATION: Asp or Glu
<220> FEATURE:
<221> NAME/KEY: VARIANT
<222> LOCATION: (98)..(98)
<223> OTHER INFORMATION: Ile, Leu or Val
<220> FEATURE:
<221> NAME/KEY: VARIANT
<222> LOCATION: (102)..(102)
<223> OTHER INFORMATION: Arg, Lys or His
<220> FEATURE:
<221> NAME/KEY: VARIANT
<222> LOCATION: (125)..(125)
<223> OTHER INFORMATION: Arg, Lys or His
<220> FEATURE:
<221> NAME/KEY: VARIANT
<222> LOCATION: (131)..(131)
<223> OTHER INFORMATION: Asp or Glu
<220> FEATURE:
<221> NAME/KEY: VARIANT
<222> LOCATION: (132)..(132)
<223> OTHER INFORMATION: Arg, Lys or His
<220> FEATURE:
<221> NAME/KEY: VARIANT
<222> LOCATION: (156)..(156)
<223> OTHER INFORMATION: Arg, Lys or His
<220> FEATURE:
<221> NAME/KEY: VARIANT
<222> LOCATION: (161)..(161)
<223> OTHER INFORMATION: Ser or Thr
<220> FEATURE:
```

```
<221> NAME/KEY: VARIANT
<222> LOCATION: (163)..(163)
<223> OTHER INFORMATION: Arg, Lys or His
<220> FEATURE:
<221> NAME/KEY: VARIANT
<222> LOCATION: (168)..(168)
<223> OTHER INFORMATION: Ser or Thr
<220> FEATURE:
<221> NAME/KEY: VARIANT
<222> LOCATION: (170)..(170)
<223> OTHER INFORMATION: Ser or Thr
<220> FEATURE:
<221> NAME/KEY: VARIANT
<222> LOCATION: (171)..(171)
<223> OTHER INFORMATION: Ile, Leu or Val
<220> FEATURE:
<221> NAME/KEY: VARIANT
<222> LOCATION: (175)..(175)
<223> OTHER INFORMATION: Ser or Thr
<220> FEATURE:
<221> NAME/KEY: VARIANT
<222> LOCATION: (188)..(189)
<223> OTHER INFORMATION: Ser or Thr
<220> FEATURE:
<221> NAME/KEY: VARIANT
<222> LOCATION: (190)..(190)
<223> OTHER INFORMATION: Asp or Glu
<220> FEATURE:
<221> NAME/KEY: VARIANT
<222> LOCATION: (191)..(191)
<223> OTHER INFORMATION: Ser or Thr
<220> FEATURE:
<221> NAME/KEY: VARIANT
<222> LOCATION: (194)..(194)
<223> OTHER INFORMATION: Arg, Lys or His
<220> FEATURE:
<221> NAME/KEY: VARIANT
<222> LOCATION: (197)..(197)
<223> OTHER INFORMATION: Ser or Thr
<220> FEATURE:
<221> NAME/KEY: VARIANT
<222> LOCATION: (198)..(198)
<223> OTHER INFORMATION: Asp or Glu
<220> FEATURE:
<221> NAME/KEY: VARIANT
<222> LOCATION: (199)..(199)
<223> OTHER INFORMATION: Ile, Leu or Val
<220> FEATURE:
<221> NAME/KEY: VARIANT
<222> LOCATION: (200)..(200)
<223> OTHER INFORMATION: Asp or Glu
<220> FEATURE:
<221> NAME/KEY: VARIANT
<222> LOCATION: (200)..(200)
<223> OTHER INFORMATION: Ser or Thr
<220> FEATURE:
<221> NAME/KEY: VARIANT
<222> LOCATION: (201)..(201)
<223> OTHER INFORMATION: Ser or Thr
<220> FEATURE:
<221> NAME/KEY: VARIANT
<222> LOCATION: (202)..(202)
<223> OTHER INFORMATION: Ile, Leu or Val
<220> FEATURE:
<221> NAME/KEY: VARIANT
<222> LOCATION: (205)..(206)
<223> OTHER INFORMATION: Arg, Lys or His
<220> FEATURE:
<221> NAME/KEY: VARIANT
<222> LOCATION: (207)..(209)
<223> OTHER INFORMATION: Asp or Glu
<220> FEATURE:
<221> NAME/KEY: VARIANT
<222> LOCATION: (211)..(211)
<223> OTHER INFORMATION: Arg, Lys or His
<220> FEATURE:
<221> NAME/KEY: VARIANT
<222> LOCATION: (212)..(212)
<223> OTHER INFORMATION: Ser or Thr
```

```
<220> FEATURE:
<221> NAME/KEY: VARIANT
<222> LOCATION: (213)..(213)
<223> OTHER INFORMATION: Arg, Lys or His
<220> FEATURE:
<221> NAME/KEY: VARIANT
<222> LOCATION: (216)..(216)
<223> OTHER INFORMATION: Asp or Glu
<220> FEATURE:
<221> NAME/KEY: VARIANT
<222> LOCATION: (217)..(218)
<223> OTHER INFORMATION: Ile, Leu or Val
<220> FEATURE:
<221> NAME/KEY: VARIANT
<222> LOCATION: (219)..(219)
<223> OTHER INFORMATION: Arg, Lys or His
<220> FEATURE:
<221> NAME/KEY: VARIANT
<222> LOCATION: (220)..(220)
<223> OTHER INFORMATION: Ser or Thr
<220> FEATURE:
<221> NAME/KEY: VARIANT
<222> LOCATION: (223)..(226)
<223> OTHER INFORMATION: Ser or Thr
<220> FEATURE:
<221> NAME/KEY: VARIANT
<222> LOCATION: (227)..(227)
<223> OTHER INFORMATION: Ile, Leu or Val
<220> FEATURE:
<221> NAME/KEY: VARIANT
<222> LOCATION: (228)..(228)
<223> OTHER INFORMATION: Asp or Glu
<220> FEATURE:
<221> NAME/KEY: VARIANT
<222> LOCATION: (229)..(229)
<223> OTHER INFORMATION: Ser or Thr
<220> FEATURE:
<221> NAME/KEY: VARIANT
<222> LOCATION: (230)..(230)
<223> OTHER INFORMATION: Asp or Glu
<220> FEATURE:
<221> NAME/KEY: VARIANT
<222> LOCATION: (232)..(233)
<223> OTHER INFORMATION: Ser or Thr
<220> FEATURE:
<221> NAME/KEY: VARIANT
<222> LOCATION: (234)..(235)
<223> OTHER INFORMATION: Ile, Leu or Val
<220> FEATURE:
<221> NAME/KEY: VARIANT
<222> LOCATION: (237)..(237)
<223> OTHER INFORMATION: Asp or Glu
<220> FEATURE:
<221> NAME/KEY: VARIANT
<222> LOCATION: (238)..(238)
<223> OTHER INFORMATION: Ile, Leu or Val
<220> FEATURE:
<221> NAME/KEY: VARIANT
<222> LOCATION: (240)..(240)
<223> OTHER INFORMATION: Ser or Thr
<220> FEATURE:
<221> NAME/KEY: VARIANT
<222> LOCATION: (245)..(245)
<223> OTHER INFORMATION: Asp or Glu
<220> FEATURE:
<221> NAME/KEY: VARIANT
<222> LOCATION: (246)..(246)
<223> OTHER INFORMATION: Ser or Thr
<220> FEATURE:
<221> NAME/KEY: VARIANT
<222> LOCATION: (247)..(247)
<223> OTHER INFORMATION: Ile, Leu or Val
<220> FEATURE:
<221> NAME/KEY: VARIANT
<222> LOCATION: (249)..(249)
<223> OTHER INFORMATION: Asp or Glu
<220> FEATURE:
<221> NAME/KEY: VARIANT
<222> LOCATION: (252)..(252)
```

```
<223> OTHER INFORMATION: Arg, Lys or His
<220> FEATURE:
<221> NAME/KEY: VARIANT
<222> LOCATION: (256)..(256)
<223> OTHER INFORMATION: Arg, Lys or His
<220> FEATURE:
<221> NAME/KEY: VARIANT
<222> LOCATION: (257)..(257)
<223> OTHER INFORMATION: Asp or Glu
<220> FEATURE:
<221> NAME/KEY: VARIANT
<222> LOCATION: (259)..(260)
<223> OTHER INFORMATION: Ser or Thr
<220> FEATURE:
<221> NAME/KEY: VARIANT
<222> LOCATION: (263)..(263)
<223> OTHER INFORMATION: Ile, Leu or Val
<220> FEATURE:
<221> NAME/KEY: VARIANT
<222> LOCATION: (264)..(264)
<223> OTHER INFORMATION: Arg, Lys or His
<220> FEATURE:
<221> NAME/KEY: VARIANT
<222> LOCATION: (265)..(265)
<223> OTHER INFORMATION: Ser or Thr
<220> FEATURE:
<221> NAME/KEY: VARIANT
<222> LOCATION: (266)..(266)
<223> OTHER INFORMATION: Arg, Lys or His
<220> FEATURE:
<221> NAME/KEY: VARIANT
<222> LOCATION: (267)..(267)
<223> OTHER INFORMATION: Asp or Glu
<220> FEATURE:
<221> NAME/KEY: VARIANT
<222> LOCATION: (268)..(268)
<223> OTHER INFORMATION: Ser or Thr
<220> FEATURE:
<221> NAME/KEY: VARIANT
<222> LOCATION: (275)..(275)
<223> OTHER INFORMATION: Ile, Leu or Val
<220> FEATURE:
<221> NAME/KEY: VARIANT
<222> LOCATION: (285)..(285)
<223> OTHER INFORMATION: Ile, Leu or Val
<220> FEATURE:
<221> NAME/KEY: VARIANT
<222> LOCATION: (286)..(286)
<223> OTHER INFORMATION: Asp or Glu
<220> FEATURE:
<221> NAME/KEY: VARIANT
<222> LOCATION: (288)..(288)
<223> OTHER INFORMATION: Arg, Lys or His
<220> FEATURE:
<221> NAME/KEY: VARIANT
<222> LOCATION: (289)..(289)
<223> OTHER INFORMATION: Asp or Glu
<220> FEATURE:
<221> NAME/KEY: VARIANT
<222> LOCATION: (292)..(292)
<223> OTHER INFORMATION: Ile, Leu or Val
<220> FEATURE:
<221> NAME/KEY: VARIANT
<222> LOCATION: (294)..(294)
<223> OTHER INFORMATION: Asp or Glu
<220> FEATURE:
<221> NAME/KEY: VARIANT
<222> LOCATION: (301)..(301)
<223> OTHER INFORMATION: Ile, Leu or Val
<220> FEATURE:
<221> NAME/KEY: VARIANT
<222> LOCATION: (310)..(310)
<223> OTHER INFORMATION: Asp or Glu
<220> FEATURE:
<221> NAME/KEY: VARIANT
<222> LOCATION: (319)..(319)
<223> OTHER INFORMATION: Ile, Leu or Val
<220> FEATURE:
<221> NAME/KEY: VARIANT
```

```
<222> LOCATION: (321)..(321)
<223> OTHER INFORMATION: Ile, Leu or Val
<220> FEATURE:
<221> NAME/KEY: VARIANT
<222> LOCATION: (332)..(332)
<223> OTHER INFORMATION: Arg, Lys or His
<220> FEATURE:
<221> NAME/KEY: VARIANT
<222> LOCATION: (334)..(334)
<223> OTHER INFORMATION: Ile, Leu or Val
<220> FEATURE:
<221> NAME/KEY: VARIANT
<222> LOCATION: (335)..(335)
<223> OTHER INFORMATION: Ser or Thr
<220> FEATURE:
<221> NAME/KEY: VARIANT
<222> LOCATION: (338)..(338)
<223> OTHER INFORMATION: Ser or Thr
<220> FEATURE:
<221> NAME/KEY: VARIANT
<222> LOCATION: (339)..(341)
<223> OTHER INFORMATION: Asp or Glu
<220> FEATURE:
<221> NAME/KEY: VARIANT
<222> LOCATION: (344)..(344)
<223> OTHER INFORMATION: Arg, Lys or His

<400> SEQUENCE: 8

Met Thr Glu Xaa Val Leu Phe Ser Xaa Xaa Xaa Asn Gly Val Ala Xaa
1               5                   10                  15

Ile Thr Leu Asn Arg Pro Lys Ala Leu Asn Ser Leu Ser Tyr Xaa Met
            20                  25                  30

Leu Gln Pro Ile Gly Gln Lys Leu Lys Glu Trp Glu Xaa Xaa Xaa Xaa
        35                  40                  45

Ile Ala Xaa Ile Val Leu Lys Gly Ala Gly Xaa Lys Gly Phe Cys Ala
    50                  55                  60

Gly Gly Asp Ile Lys Thr Leu Tyr Glu Ala Arg Ser Asn Glu Xaa Ala
65                  70                  75                  80

Leu Gln Xaa Ala Glu Xaa Phe Phe Xaa Glu Xaa Tyr Xaa Ile Asp Thr
            85                  90                  95

Tyr Xaa Tyr Gln Tyr Xaa Lys Pro Ile Ile Ala Cys Leu Asp Gly Ile
        100                 105                 110

Val Met Gly Gly Gly Val Gly Leu Thr Asn Gly Ala Xaa Tyr Arg Ile
            115                 120                 125

Val Thr Xaa Xaa Thr Lys Trp Ala Met Pro Glu Met Asn Ile Gly Phe
        130                 135                 140

Phe Pro Asp Val Gly Ala Ala Tyr Phe Leu Asn Xaa Ala Pro Gly Tyr
145                 150                 155                 160

Xaa Gly Xaa Tyr Val Ala Leu Xaa Ala Xaa Xaa Leu Lys Ala Xaa Asp
            165                 170                 175

Val Leu Phe Ile Asn Ala Ala Asp Tyr Phe Met Xaa Xaa Xaa Xaa Leu
            180                 185                 190

Pro Xaa Phe Leu Xaa Xaa Xaa Xaa Xaa Asn Trp Xaa Xaa Xaa Xaa
        195                 200                 205

Xaa Val Xaa Xaa Xaa Leu Lys Xaa Xaa Xaa Xaa Xaa Phe Ala Xaa Xaa
        210                 215                 220

Xaa Xaa Xaa Xaa Xaa Xaa Leu Xaa Xaa Xaa Glu Xaa Xaa Asn Xaa
225                 230                 235                 240

His Phe Ala Phe Xaa Xaa Xaa Glu Xaa Ile Ile Xaa Ser Leu Glu Xaa
            245                 250                 255

Xaa Gln Xaa Xaa Phe Ala Xaa Xaa Xaa Xaa Xaa Leu Leu Ser Lys
        260                 265                 270
```

-continued

```
Ser Pro Xaa Ser Leu Lys Val Thr Leu Lys Gln Phe Xaa Xaa Gly Xaa
        275                 280                 285

Xaa Lys Ser Xaa Glu Xaa Cys Phe Ala Thr Asp Leu Xaa Leu Ala Lys
    290                 295                 300

Asn Phe Met Arg His Xaa Asp Phe Phe Glu Gly Val Arg Ser Xaa Val
305                 310                 315                 320

Xaa Asp Lys Asp Gln Asn Pro Asn Tyr Lys Tyr Xaa Gln Xaa Xaa Asp
                325                 330                 335

Val Xaa Xaa Xaa Xaa Val Asn Xaa Phe Phe Asn Leu Leu Asn Ala
            340                 345                 350

<210> SEQ ID NO 9
<211> LENGTH: 370
<212> TYPE: PRT
<213> ORGANISM: Artificial Sequence
<220> FEATURE:
<223> OTHER INFORMATION: Pseudomonas EC 3.1.2.4 malonyl-CoA hydrolase
      consensus sequence
<220> FEATURE:
<221> NAME/KEY: VARIANT
<222> LOCATION: (3)..(3)
<223> OTHER INFORMATION: Ile, Leu or Val
<220> FEATURE:
<221> NAME/KEY: VARIANT
<222> LOCATION: (4)..(4)
<223> OTHER INFORMATION: Arg, Lys or His
<220> FEATURE:
<221> NAME/KEY: VARIANT
<222> LOCATION: (7)..(7)
<223> OTHER INFORMATION: Asp or Glu
<220> FEATURE:
<221> NAME/KEY: VARIANT
<222> LOCATION: (8)..(8)
<223> OTHER INFORMATION: Arg, Lys or His
<220> FEATURE:
<221> NAME/KEY: VARIANT
<222> LOCATION: (9)..(10)
<223> OTHER INFORMATION: Ser or Thr
<220> FEATURE:
<221> NAME/KEY: VARIANT
<222> LOCATION: (11)..(11)
<223> OTHER INFORMATION: Ile, Leu or Val
<220> FEATURE:
<221> NAME/KEY: VARIANT
<222> LOCATION: (12)..(12)
<223> OTHER INFORMATION: Arg, Lys or His
<220> FEATURE:
<221> NAME/KEY: VARIANT
<222> LOCATION: (18)..(18)
<223> OTHER INFORMATION: Ile, Leu or Val
<220> FEATURE:
<221> NAME/KEY: VARIANT
<222> LOCATION: (20)..(20)
<223> OTHER INFORMATION: Ser or Thr
<220> FEATURE:
<221> NAME/KEY: VARIANT
<222> LOCATION: (24)..(24)
<223> OTHER INFORMATION: Asp or Glu
<220> FEATURE:
<221> NAME/KEY: VARIANT
<222> LOCATION: (25)..(25)
<223> OTHER INFORMATION: Arg, Lys or His
<220> FEATURE:
<221> NAME/KEY: VARIANT
<222> LOCATION: (26)..(26)
<223> OTHER INFORMATION: Ser or Thr
<220> FEATURE:
<221> NAME/KEY: VARIANT
<222> LOCATION: (31)..(31)
<223> OTHER INFORMATION: Ser or Thr
<220> FEATURE:
<221> NAME/KEY: VARIANT
<222> LOCATION: (36)..(36)
```

```
<223> OTHER INFORMATION: Asp or Glu
<220> FEATURE:
<221> NAME/KEY: VARIANT
<222> LOCATION: (37)..(37)
<223> OTHER INFORMATION: Ile, Leu or Val
<220> FEATURE:
<221> NAME/KEY: VARIANT
<222> LOCATION: (40)..(40)
<223> OTHER INFORMATION: Asp or Glu
<220> FEATURE:
<221> NAME/KEY: VARIANT
<222> LOCATION: (41)..(41)
<223> OTHER INFORMATION: Arg, Lys or His
<220> FEATURE:
<221> NAME/KEY: VARIANT
<222> LOCATION: (42)..(42)
<223> OTHER INFORMATION: Ile, Leu or Val
<220> FEATURE:
<221> NAME/KEY: VARIANT
<222> LOCATION: (43)..(43)
<223> OTHER INFORMATION: Arg, Lys or His
<220> FEATURE:
<221> NAME/KEY: VARIANT
<222> LOCATION: (47)..(47)
<223> OTHER INFORMATION: Arg, Lys or His
<220> FEATURE:
<221> NAME/KEY: VARIANT
<222> LOCATION: (48)..(48)
<223> OTHER INFORMATION: Asp or Glu
<220> FEATURE:
<221> NAME/KEY: VARIANT
<222> LOCATION: (51)..(52)
<223> OTHER INFORMATION: Ile, Leu or Val
<220> FEATURE:
<221> NAME/KEY: VARIANT
<222> LOCATION: (55)..(55)
<223> OTHER INFORMATION: Ile, Leu or Val
<220> FEATURE:
<221> NAME/KEY: VARIANT
<222> LOCATION: (69)..(69)
<223> OTHER INFORMATION: Asp or Glu
<220> FEATURE:
<221> NAME/KEY: VARIANT
<222> LOCATION: (71)..(72)
<223> OTHER INFORMATION: Arg, Lys or His
<220> FEATURE:
<221> NAME/KEY: VARIANT
<222> LOCATION: (74)..(74)
<223> OTHER INFORMATION: Ile, Leu or Val
<220> FEATURE:
<221> NAME/KEY: VARIANT
<222> LOCATION: (75)..(75)
<223> OTHER INFORMATION: Asp or Glu
<220> FEATURE:
<221> NAME/KEY: VARIANT
<222> LOCATION: (78)..(78)
<223> OTHER INFORMATION: Arg, Lys or His
<220> FEATURE:
<221> NAME/KEY: VARIANT
<222> LOCATION: (79)..(79)
<223> OTHER INFORMATION: Asp or Glu
<220> FEATURE:
<221> NAME/KEY: VARIANT
<222> LOCATION: (80)..(80)
<223> OTHER INFORMATION: Arg, Lys or His
<220> FEATURE:
<221> NAME/KEY: VARIANT
<222> LOCATION: (83)..(83)
<223> OTHER INFORMATION: Asp or Glu
<220> FEATURE:
<221> NAME/KEY: VARIANT
<222> LOCATION: (84)..(84)
<223> OTHER INFORMATION: Ile, Leu or Val
<220> FEATURE:
<221> NAME/KEY: VARIANT
<222> LOCATION: (90)..(90)
<223> OTHER INFORMATION: Arg, Lys or His
<220> FEATURE:
<221> NAME/KEY: VARIANT
```

```
<222> LOCATION: (94)..(94)
<223> OTHER INFORMATION: Asp or Glu
<220> FEATURE:
<221> NAME/KEY: VARIANT
<222> LOCATION: (95)..(95)
<223> OTHER INFORMATION: Ala, Asp, Arg, His, Lys, Ser, Thr, Asn, Gln,
      or Tyr
<220> FEATURE:
<221> NAME/KEY: VARIANT
<222> LOCATION: (99)..(99)
<223> OTHER INFORMATION: Asp or Glu
<220> FEATURE:
<221> NAME/KEY: VARIANT
<222> LOCATION: (100)..(100)
<223> OTHER INFORMATION: Arg, Lys or His
<220> FEATURE:
<221> NAME/KEY: VARIANT
<222> LOCATION: (101)..(101)
<223> OTHER INFORMATION: Arg, Lys or His
<220> FEATURE:
<221> NAME/KEY: VARIANT
<222> LOCATION: (102)..(102)
<223> OTHER INFORMATION: Ile, Leu or Val
<220> FEATURE:
<221> NAME/KEY: VARIANT
<222> LOCATION: (104)..(104)
<223> OTHER INFORMATION: Ser or Thr
<220> FEATURE:
<221> NAME/KEY: VARIANT
<222> LOCATION: (109)..(110)
<223> OTHER INFORMATION: Ile, Leu or Val
<220> FEATURE:
<221> NAME/KEY: VARIANT
<222> LOCATION: (116)..(116)
<223> OTHER INFORMATION: Arg, Lys or His
<220> FEATURE:
<221> NAME/KEY: VARIANT
<222> LOCATION: (118)..(118)
<223> OTHER INFORMATION: Ile, Leu or Val
<220> FEATURE:
<221> NAME/KEY: VARIANT
<222> LOCATION: (125)..(125)
<223> OTHER INFORMATION: Ile, Leu or Val
<220> FEATURE:
<221> NAME/KEY: VARIANT
<222> LOCATION: (129)..(129)
<223> OTHER INFORMATION: Ser or Thr
<220> FEATURE:
<221> NAME/KEY: VARIANT
<222> LOCATION: (130)..(130)
<223> OTHER INFORMATION: Ile, Leu or Val
<220> FEATURE:
<221> NAME/KEY: VARIANT
<222> LOCATION: (136)..(137)
<223> OTHER INFORMATION: Ser or Thr
<220> FEATURE:
<221> NAME/KEY: VARIANT
<222> LOCATION: (144)..(144)
<223> OTHER INFORMATION: Ile, Leu or Val
<220> FEATURE:
<221> NAME/KEY: VARIANT
<222> LOCATION: (145)..(145)
<223> OTHER INFORMATION: Ser or Thr
<220> FEATURE:
<221> NAME/KEY: VARIANT
<222> LOCATION: (159)..(159)
<223> OTHER INFORMATION: Ser or Thr
<220> FEATURE:
<221> NAME/KEY: VARIANT
<222> LOCATION: (161)..(161)
<223> OTHER INFORMATION: Ile, Leu or Val
<220> FEATURE:
<221> NAME/KEY: VARIANT
<222> LOCATION: (164)..(164)
<223> OTHER INFORMATION: Arg, Lys or His
<220> FEATURE:
<221> NAME/KEY: VARIANT
<222> LOCATION: (169)..(169)
<223> OTHER INFORMATION: Ile, Leu or Val
```

```
<220> FEATURE:
<221> NAME/KEY: VARIANT
<222> LOCATION: (172)..(172)
<223> OTHER INFORMATION: Ser or Thr
<220> FEATURE:
<221> NAME/KEY: VARIANT
<222> LOCATION: (175)..(175)
<223> OTHER INFORMATION: Arg, Lys or His
<220> FEATURE:
<221> NAME/KEY: VARIANT
<222> LOCATION: (176)..(176)
<223> OTHER INFORMATION: Ile, Leu or Val
<220> FEATURE:
<221> NAME/KEY: VARIANT
<222> LOCATION: (179)..(179)
<223> OTHER INFORMATION: Arg, Lys or His
<220> FEATURE:
<221> NAME/KEY: VARIANT
<222> LOCATION: (182)..(182)
<223> OTHER INFORMATION: Ile, Leu or Val
<220> FEATURE:
<221> NAME/KEY: VARIANT
<222> LOCATION: (185)..(185)
<223> OTHER INFORMATION: Asp or Glu
<220> FEATURE:
<221> NAME/KEY: VARIANT
<222> LOCATION: (191)..(191)
<223> OTHER INFORMATION: Ile, Leu or Val
<220> FEATURE:
<221> NAME/KEY: VARIANT
<222> LOCATION: (192)..(192)
<223> OTHER INFORMATION: Arg, Lys or His
<220> FEATURE:
<221> NAME/KEY: VARIANT
<222> LOCATION: (193)..(193)
<223> OTHER INFORMATION: Asp or Glu
<220> FEATURE:
<221> NAME/KEY: VARIANT
<222> LOCATION: (194)..(194)
<223> OTHER INFORMATION: Arg, Lys or His
<220> FEATURE:
<221> NAME/KEY: VARIANT
<222> LOCATION: (197)..(198)
<223> OTHER INFORMATION: Asp or Glu
<220> FEATURE:
<221> NAME/KEY: VARIANT
<222> LOCATION: (200)..(200)
<223> OTHER INFORMATION: Ile, Leu or Val
<220> FEATURE:
<221> NAME/KEY: VARIANT
<222> LOCATION: (201)..(202)
<223> OTHER INFORMATION: Asp or Glu
<220> FEATURE:
<221> NAME/KEY: VARIANT
<222> LOCATION: (204)..(204)
<223> OTHER INFORMATION: Ile, Leu or Val
<220> FEATURE:
<221> NAME/KEY: VARIANT
<222> LOCATION: (206)..(206)
<223> OTHER INFORMATION: Ile, Leu or Val
<220> FEATURE:
<221> NAME/KEY: VARIANT
<222> LOCATION: (212)..(212)
<223> OTHER INFORMATION: Ser or Thr
<220> FEATURE:
<221> NAME/KEY: VARIANT
<222> LOCATION: (213)..(213)
<223> OTHER INFORMATION: Asp or Glu
<220> FEATURE:
<221> NAME/KEY: VARIANT
<222> LOCATION: (214)..(214)
<223> OTHER INFORMATION: Ile, Leu or Val
<220> FEATURE:
<221> NAME/KEY: VARIANT
<222> LOCATION: (217)..(217)
<223> OTHER INFORMATION: Arg, Lys or His
<220> FEATURE:
<221> NAME/KEY: VARIANT
<222> LOCATION: (220)..(220)
```

```
<223> OTHER INFORMATION: Ile, Leu or Val
<220> FEATURE:
<221> NAME/KEY: VARIANT
<222> LOCATION: (221)..(221)
<223> OTHER INFORMATION: Arg, Lys or His
<220> FEATURE:
<221> NAME/KEY: VARIANT
<222> LOCATION: (223)..(224)
<223> OTHER INFORMATION: Asp or Glu
<220> FEATURE:
<221> NAME/KEY: VARIANT
<222> LOCATION: (225)..(225)
<223> OTHER INFORMATION: Arg, Lys or His
<220> FEATURE:
<221> NAME/KEY: VARIANT
<222> LOCATION: (226)..(226)
<223> OTHER INFORMATION: Arg, Lys or His
<220> FEATURE:
<221> NAME/KEY: VARIANT
<222> LOCATION: (228)..(228)
<223> OTHER INFORMATION: Arg, Lys or His
<220> FEATURE:
<221> NAME/KEY: VARIANT
<222> LOCATION: (229)..(230)
<223> OTHER INFORMATION: Asp or Glu
<220> FEATURE:
<221> NAME/KEY: VARIANT
<222> LOCATION: (231)..(231)
<223> OTHER INFORMATION: Ile, Leu or Val
<220> FEATURE:
<221> NAME/KEY: VARIANT
<222> LOCATION: (233)..(233)
<223> OTHER INFORMATION: Asp or Glu
<220> FEATURE:
<221> NAME/KEY: VARIANT
<222> LOCATION: (236)..(236)
<223> OTHER INFORMATION: Ile, Leu or Val
<220> FEATURE:
<221> NAME/KEY: VARIANT
<222> LOCATION: (242)..(242)
<223> OTHER INFORMATION: Arg, Lys or His
<220> FEATURE:
<221> NAME/KEY: VARIANT
<222> LOCATION: (243)..(243)
<223> OTHER INFORMATION: Ile, Leu or Val
<220> FEATURE:
<221> NAME/KEY: VARIANT
<222> LOCATION: (245)..(245)
<223> OTHER INFORMATION: Asp or Glu
<220> FEATURE:
<221> NAME/KEY: VARIANT
<222> LOCATION: (246)..(246)
<223> OTHER INFORMATION: Ile, Leu or Val
<220> FEATURE:
<221> NAME/KEY: VARIANT
<222> LOCATION: (249)..(249)
<223> OTHER INFORMATION: Ile, Leu or Val
<220> FEATURE:
<221> NAME/KEY: VARIANT
<222> LOCATION: (251)..(251)
<223> OTHER INFORMATION: Asp or Glu
<220> FEATURE:
<221> NAME/KEY: VARIANT
<222> LOCATION: (252)..(252)
<223> OTHER INFORMATION: Ile, Leu or Val
<220> FEATURE:
<221> NAME/KEY: VARIANT
<222> LOCATION: (254)..(254)
<223> OTHER INFORMATION: Ser or Thr
<220> FEATURE:
<221> NAME/KEY: VARIANT
<222> LOCATION: (257)..(257)
<223> OTHER INFORMATION: Arg, Lys or His
<220> FEATURE:
<221> NAME/KEY: VARIANT
<222> LOCATION: (259)..(259)
<223> OTHER INFORMATION: Ile, Leu or Val
<220> FEATURE:
<221> NAME/KEY: VARIANT
```

```
<222> LOCATION: (260)..(260)
<223> OTHER INFORMATION: Asp or Glu
<220> FEATURE:
<221> NAME/KEY: VARIANT
<222> LOCATION: (262)..(262)
<223> OTHER INFORMATION: Ile, Leu or Val
<220> FEATURE:
<221> NAME/KEY: VARIANT
<222> LOCATION: (263)..(263)
<223> OTHER INFORMATION: Arg, Lys or His
<220> FEATURE:
<221> NAME/KEY: VARIANT
<222> LOCATION: (264)..(264)
<223> OTHER INFORMATION: Asp or Glu
<220> FEATURE:
<221> NAME/KEY: VARIANT
<222> LOCATION: (265)..(265)
<223> OTHER INFORMATION: Arg, Lys or His
<220> FEATURE:
<221> NAME/KEY: VARIANT
<222> LOCATION: (266)..(266)
<223> OTHER INFORMATION: Asp or Glu
<220> FEATURE:
<221> NAME/KEY: VARIANT
<222> LOCATION: (270)..(270)
<223> OTHER INFORMATION: Ile, Leu or Val
<220> FEATURE:
<221> NAME/KEY: VARIANT
<222> LOCATION: (272)..(272)
<223> OTHER INFORMATION: Arg, Lys or His
<220> FEATURE:
<221> NAME/KEY: VARIANT
<222> LOCATION: (275)..(276)
<223> OTHER INFORMATION: Arg, Lys or His
<220> FEATURE:
<221> NAME/KEY: VARIANT
<222> LOCATION: (277)..(277)
<223> OTHER INFORMATION: Ile, Leu or Val
<220> FEATURE:
<221> NAME/KEY: VARIANT
<222> LOCATION: (278)..(278)
<223> OTHER INFORMATION: Arg, Lys or His
<220> FEATURE:
<221> NAME/KEY: VARIANT
<222> LOCATION: (279)..(279)
<223> OTHER INFORMATION: Asp or Glu
<220> FEATURE:
<221> NAME/KEY: VARIANT
<222> LOCATION: (283)..(283)
<223> OTHER INFORMATION: Ile, Leu or Val
<220> FEATURE:
<221> NAME/KEY: VARIANT
<222> LOCATION: (284)..(284)
<223> OTHER INFORMATION: Ser or Thr
<220> FEATURE:
<221> NAME/KEY: VARIANT
<222> LOCATION: (286)..(286)
<223> OTHER INFORMATION: Arg, Lys or His
<220> FEATURE:
<221> NAME/KEY: VARIANT
<222> LOCATION: (287)..(287)
<223> OTHER INFORMATION: Ile, Leu or Val
<220> FEATURE:
<221> NAME/KEY: VARIANT
<222> LOCATION: (290)..(290)
<223> OTHER INFORMATION: Asp or Glu
<220> FEATURE:
<221> NAME/KEY: VARIANT
<222> LOCATION: (292)..(292)
<223> OTHER INFORMATION: Ile, Leu or Val
<220> FEATURE:
<221> NAME/KEY: VARIANT
<222> LOCATION: (293)..(293)
<223> OTHER INFORMATION: Arg, Lys or His
<220> FEATURE:
<221> NAME/KEY: VARIANT
<222> LOCATION: (297)..(297)
<223> OTHER INFORMATION: Arg, Lys or His
<220> FEATURE:
```

```
<221> NAME/KEY: VARIANT
<222> LOCATION: (302)..(302)
<223> OTHER INFORMATION: Asp or Glu
<220> FEATURE:
<221> NAME/KEY: VARIANT
<222> LOCATION: (303)..(303)
<223> OTHER INFORMATION: Ile, Leu or Val
<220> FEATURE:
<221> NAME/KEY: VARIANT
<222> LOCATION: (305)..(305)
<223> OTHER INFORMATION: Arg, Lys or His
<220> FEATURE:
<221> NAME/KEY: VARIANT
<222> LOCATION: (309)..(309)
<223> OTHER INFORMATION: Ser or Thr
<220> FEATURE:
<221> NAME/KEY: VARIANT
<222> LOCATION: (310)..(310)
<223> OTHER INFORMATION: Ile, Leu or Val
<220> FEATURE:
<221> NAME/KEY: VARIANT
<222> LOCATION: (319)..(319)
<223> OTHER INFORMATION: Asp or Glu
<220> FEATURE:
<221> NAME/KEY: VARIANT
<222> LOCATION: (321)..(321)
<223> OTHER INFORMATION: Ser or Thr
<220> FEATURE:
<221> NAME/KEY: VARIANT
<222> LOCATION: (329)..(329)
<223> OTHER INFORMATION: Ile, Leu or Val
<220> FEATURE:
<221> NAME/KEY: VARIANT
<222> LOCATION: (331)..(331)
<223> OTHER INFORMATION: Arg, Lys or His
<220> FEATURE:
<221> NAME/KEY: VARIANT
<222> LOCATION: (333)..(333)
<223> OTHER INFORMATION: Arg, Lys or His
<220> FEATURE:
<221> NAME/KEY: VARIANT
<222> LOCATION: (336)..(336)
<223> OTHER INFORMATION: Arg, Lys or His
<220> FEATURE:
<221> NAME/KEY: VARIANT
<222> LOCATION: (338)..(338)
<223> OTHER INFORMATION: Arg, Lys or His
<220> FEATURE:
<221> NAME/KEY: VARIANT
<222> LOCATION: (341)..(341)
<223> OTHER INFORMATION: Asp or Glu
<220> FEATURE:
<221> NAME/KEY: VARIANT
<222> LOCATION: (342)..(342)
<223> OTHER INFORMATION: Ile, Leu or Val
<220> FEATURE:
<221> NAME/KEY: VARIANT
<222> LOCATION: (345)..(345)
<223> OTHER INFORMATION: Ile, Leu or Val
<220> FEATURE:
<221> NAME/KEY: VARIANT
<222> LOCATION: (347)..(347)
<223> OTHER INFORMATION: Asp or Glu
<220> FEATURE:
<221> NAME/KEY: VARIANT
<222> LOCATION: (349)..(350)
<223> OTHER INFORMATION: Ile, Leu or Val
<220> FEATURE:
<221> NAME/KEY: VARIANT
<222> LOCATION: (350)..(350)
<223> OTHER INFORMATION: Ile, Leu or Val
<220> FEATURE:
<221> NAME/KEY: VARIANT
<222> LOCATION: (351)..(351)
<223> OTHER INFORMATION: Asp or Glu
<220> FEATURE:
<221> NAME/KEY: VARIANT
<222> LOCATION: (355)..(355)
<223> OTHER INFORMATION: Asp or Glu
```

```
<220> FEATURE:
<221> NAME/KEY: VARIANT
<222> LOCATION: (356)..(356)
<223> OTHER INFORMATION: Arg, Lys or His
<220> FEATURE:
<221> NAME/KEY: VARIANT
<222> LOCATION: (357)..(357)
<223> OTHER INFORMATION: Ile, Leu or Val
<220> FEATURE:
<221> NAME/KEY: VARIANT
<222> LOCATION: (357)..(357)
<223> OTHER INFORMATION: Ile, Leu or Val
<220> FEATURE:
<221> NAME/KEY: VARIANT
<222> LOCATION: (359)..(359)
<223> OTHER INFORMATION: Asp or Glu
<220> FEATURE:
<221> NAME/KEY: VARIANT
<222> LOCATION: (361)..(362)
<223> OTHER INFORMATION: Arg, Lys or His
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (364)..(364)
<223> OTHER INFORMATION: Ile, Leu or Val
<220> FEATURE:
<221> NAME/KEY: VARIANT
<222> LOCATION: (366)..(366)
<223> OTHER INFORMATION: Asp or Glu
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (367)..(367)
<223> OTHER INFORMATION: Ile, Leu or Val
<220> FEATURE:
<221> NAME/KEY: VARIANT
<222> LOCATION: (368)..(368)
<223> OTHER INFORMATION: Ser or Thr
<220> FEATURE:
<221> NAME/KEY: VARIANT
<222> LOCATION: (369)..(370)
<223> OTHER INFORMATION: Xaa can be any naturally occurring amino acid

<400> SEQUENCE: 9

Met Asn Xaa Xaa Phe Glu Xaa Xaa Xaa Xaa Xaa Gly Ala Arg Ile
1               5                   10                  15

Gly Xaa Ala Xaa Leu Asp Ala Xaa Xaa Xaa Leu Asn Ala Leu Xaa Leu
            20                  25                  30

Pro Met Ile Xaa Xaa Leu Gly Xaa Xaa Xaa Ala Trp Ala Xaa Xaa
        35                  40                  45

Pro Gly Xaa Xaa Cys Val Xaa Leu Arg Gly Asn Gly Ala Lys Ala Phe
    50                  55                  60

Cys Ala Gly Gly Xaa Val Xaa Xaa Leu Xaa Xaa Ala Cys Xaa Xaa Xaa
65                  70                  75                  80

Pro Gly Xaa Xaa Pro Leu Ala Ala Xaa Phe Phe Ala Xaa Xaa Tyr
            85                  90                  95

Arg Leu Xaa Xaa Xaa Xaa His Xaa Tyr Pro Lys Pro Xaa Xaa Cys Trp
            100                 105                 110

Gly His Gly Xaa Val Xaa Gly Gly Gly Met Gly Leu Xaa Gln Gly Ala
            115                 120                 125

Xaa Xaa Arg Ile Val Thr Pro Xaa Xaa Arg Leu Ala Met Pro Glu Xaa
130                 135                 140

Xaa Ile Gly Leu Tyr Pro Asp Val Gly Ala Ser Trp Phe Leu Xaa Arg
```

-continued

```
145                 150                 155                 160

Xaa Pro Gly Xaa Leu Gly Leu Phe Xaa Gly Leu Xaa Gly Ala Xaa Xaa
                165                 170                 175

Asn Ala Xaa Asp Ala Xaa Asp Leu Xaa Leu Ala Asp Arg Phe Xaa Xaa
                180                 185                 190

Xaa Xaa Gln Gln Xaa Xaa Leu Xaa Xaa Xaa Leu Xaa Gln Xaa Asn Trp
                195                 200                 205

Gln Glu Gln Xaa Xaa Xaa Gln Leu Xaa Ser Leu Xaa Xaa Ala Xaa Xaa
210                 215                 220

Xaa Xaa Ala Xaa Xaa Xaa Xaa Pro Xaa Ala Gln Xaa Leu Pro Arg Arg
225                 230                 235                 240

Gln Xaa Xaa Asp Xaa Xaa Leu Asp Xaa Ala Xaa Xaa Ala Xaa Ala Trp
                245                 250                 255

Xaa Ala Xaa Xaa Ala Xaa Xaa Xaa Xaa Asp Pro Leu Xaa Ala Xaa
                260                 265                 270

Ala Ala Xaa Xaa Xaa Xaa Xaa Gly Cys Pro Xaa Xaa Ala Xaa Xaa Val
            275                 280                 285

Trp Xaa Gln Xaa Xaa Arg Ala Arg Xaa Leu Ser Leu Ala Xaa Xaa Phe
            290                 295                 300

Xaa Met Glu Tyr Xaa Xaa Ser Leu Asn Cys Cys Arg His Pro Xaa Phe
305                 310                 315                 320

Xaa Glu Gly Val Arg Ala Arg Leu Xaa Asp Xaa Asp Xaa Gln Pro Xaa
                325                 330                 335

Trp Xaa Trp Pro Xaa Xaa Ala Gln Xaa Pro Xaa Ala Xaa Xaa Xaa Ala
            340                 345                 350

His Phe Xaa Xaa Xaa Trp Xaa Gly Xaa Xaa Pro Xaa Ala Xaa Xaa Xaa
            355                 360                 365

Xaa Xaa
    370

<210> SEQ ID NO 10
<211> LENGTH: 505
<212> TYPE: PRT
<213> ORGANISM: Artificial Sequence
<220> FEATURE:
<223> OTHER INFORMATION: General bacterial EC 3.1.2.4 malonyl-CoA
      hydrolase consensus sequence
<220> FEATURE:
<221> NAME/KEY: VARIANT
<222> LOCATION: (1)..(10)
<223> OTHER INFORMATION: Xaa can be any naturally occurring amino acid
      or absent
<220> FEATURE:
<221> NAME/KEY: VARIANT
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(23)
<223> OTHER INFORMATION: Xaa can be any naturally occurring amino acid
      or absent
<220> FEATURE:
<221> NAME/KEY: VARIANT
<222> LOCATION: (24)..(24)
<223> OTHER INFORMATION: Xaa can be any naturally occurring amino acid
<220> FEATURE:
<221> NAME/KEY: VARIANT
<222> LOCATION: (25)..(30)
<223> OTHER INFORMATION: Xaa can be any naturally occurring amino acid
      or absent
<220> FEATURE:
<221> NAME/KEY: VARIANT
<222> LOCATION: (32)..(32)
<223> OTHER INFORMATION: Xaa can be any naturally occurring amino acid
```

```
-continued

<220> FEATURE:
<221> NAME/KEY: VARIANT
<222> LOCATION: (34)..(35)
<223> OTHER INFORMATION: Xaa can be any naturally occurring amino acid
      or absent
<220> FEATURE:
<221> NAME/KEY: VARIANT
<222> LOCATION: (39)..(40)
<223> OTHER INFORMATION: Ile, Leu or Val
<220> FEATURE:
<221> NAME/KEY: VARIANT
<222> LOCATION: (42)..(42)
<223> OTHER INFORMATION: Ser or Thr
<220> FEATURE:
<221> NAME/KEY: VARIANT
<222> LOCATION: (43)..(43)
<223> OTHER INFORMATION: Ile, Leu or Val
<220> FEATURE:
<221> NAME/KEY: VARIANT
<222> LOCATION: (48)..(48)
<223> OTHER INFORMATION: Ile, Leu or Val
<220> FEATURE:
<221> NAME/KEY: VARIANT
<222> LOCATION: (52)..(52)
<223> OTHER INFORMATION: Ser or Thr
<220> FEATURE:
<221> NAME/KEY: VARIANT
<222> LOCATION: (57)..(57)
<223> OTHER INFORMATION: Arg, Lys or His
<220> FEATURE:
<221> NAME/KEY: VARIANT
<222> LOCATION: (63)..(63)
<223> OTHER INFORMATION: Ser or Thr
<220> FEATURE:
<221> NAME/KEY: VARIANT
<222> LOCATION: (67)..(67)
<223> OTHER INFORMATION: Ile, Leu or Val
<220> FEATURE:
<221> NAME/KEY: VARIANT
<222> LOCATION: (70)..(70)
<223> OTHER INFORMATION: Ile, Leu or Val
<220> FEATURE:
<221> NAME/KEY: VARIANT
<222> LOCATION: (73)..(73)
<223> OTHER INFORMATION: Arg, Lys or His
<220> FEATURE:
<221> NAME/KEY: VARIANT
<222> LOCATION: (74)..(74)
<223> OTHER INFORMATION: Ile, Leu or Val
<220> FEATURE:
<221> NAME/KEY: VARIANT
<222> LOCATION: (75)..(75)
<223> OTHER INFORMATION: Arg, Lys or His
<220> FEATURE:
<221> NAME/KEY: VARIANT
<222> LOCATION: (80)..(80)
<223> OTHER INFORMATION: Asp or Glu
<220> FEATURE:
<221> NAME/KEY: VARIANT
<222> LOCATION: (83)..(83)
<223> OTHER INFORMATION: Ile, Leu or Val
<220> FEATURE:
<221> NAME/KEY: VARIANT
<222> LOCATION: (86)..(87)
<223> OTHER INFORMATION: Ile, Leu or Val
<220> FEATURE:
<221> NAME/KEY: VARIANT
<222> LOCATION: (89)..(89)
<223> OTHER INFORMATION: Arg, Lys or His
<220> FEATURE:
<221> NAME/KEY: VARIANT
<222> LOCATION: (90)..(90)
<223> OTHER INFORMATION: Xaa can be any naturally occurring amino acid
      or absent
<220> FEATURE:
<221> NAME/KEY: VARIANT
<222> LOCATION: (95)..(95)
<223> OTHER INFORMATION: Arg, Lys or His
<220> FEATURE:
```

-continued

```
<221> NAME/KEY: VARIANT
<222> LOCATION: (102)..(102)
<223> OTHER INFORMATION: Asp or Glu
<220> FEATURE:
<221> NAME/KEY: VARIANT
<222> LOCATION: (103)..(103)
<223> OTHER INFORMATION: Ile, Leu or Val
<220> FEATURE:
<221> NAME/KEY: VARIANT
<222> LOCATION: (104)..(104)
<223> OTHER INFORMATION: Arg, Lys or His
<220> FEATURE:
<221> NAME/KEY: VARIANT
<222> LOCATION: (105)..(105)
<223> OTHER INFORMATION: Ser or Thr
<220> FEATURE:
<221> NAME/KEY: VARIANT
<222> LOCATION: (106)..(106)
<223> OTHER INFORMATION: Ile, Leu or Val
<220> FEATURE:
<221> NAME/KEY: VARIANT
<222> LOCATION: (108)..(108)
<223> OTHER INFORMATION: Asp or Glu
<220> FEATURE:
<221> NAME/KEY: VARIANT
<222> LOCATION: (116)..(116)
<223> OTHER INFORMATION: Xaa can be any naturally occurring amino acid
<220> FEATURE:
<221> NAME/KEY: VARIANT
<222> LOCATION: (127)..(127)
<223> OTHER INFORMATION: Asp or Glu
<220> FEATURE:
<221> NAME/KEY: VARIANT
<222> LOCATION: (128)..(128)
<223> OTHER INFORMATION: Xaa can be any naturally occurring amino acid
<220> FEATURE:
<221> NAME/KEY: VARIANT
<222> LOCATION: (128)..(128)
<223> OTHER INFORMATION: Ala, Asp, Arg, His, Lys, Ser, Thr, Asn, Glu,
      Tyr
<220> FEATURE:
<221> NAME/KEY: VARIANT
<222> LOCATION: (131)..(131)
<223> OTHER INFORMATION: Ile, Leu or Val
<220> FEATURE:
<221> NAME/KEY: VARIANT
<222> LOCATION: (132)..(132)
<223> OTHER INFORMATION: Asp or Glu
<220> FEATURE:
<221> NAME/KEY: VARIANT
<222> LOCATION: (135)..(135)
<223> OTHER INFORMATION: Ile, Leu or Val
<220> FEATURE:
<221> NAME/KEY: VARIANT
<222> LOCATION: (142)..(143)
<223> OTHER INFORMATION: Ile, Leu or Val
<220> FEATURE:
<221> NAME/KEY: VARIANT
<222> LOCATION: (150)..(150)
<223> OTHER INFORMATION: Ile, Leu or Val
<220> FEATURE:
<221> NAME/KEY: VARIANT
<222> LOCATION: (164)..(164)
<223> OTHER INFORMATION: Arg, Lys or His
<220> FEATURE:
<221> NAME/KEY: VARIANT
<222> LOCATION: (165)..(166)
<223> OTHER INFORMATION: Ile, Leu or Val
<220> FEATURE:
<221> NAME/KEY: VARIANT
<222> LOCATION: (170)..(170)
<223> OTHER INFORMATION: Ser or Thr
<220> FEATURE:
<221> NAME/KEY: VARIANT
<222> LOCATION: (171)..(171)
<223> OTHER INFORMATION: Arg, Lys or His
<220> FEATURE:
<221> NAME/KEY: VARIANT
<222> LOCATION: (193)..(193)
```

```
<223> OTHER INFORMATION: Arg, Lys or His
<220> FEATURE:
<221> NAME/KEY: VARIANT
<222> LOCATION: (195)..(200)
<223> OTHER INFORMATION: Xaa can be any naturally occurring amino acid
      or absent
<220> FEATURE:
<221> NAME/KEY: VARIANT
<222> LOCATION: (208)..(208)
<223> OTHER INFORMATION: Ile, Leu or Val
<220> FEATURE:
<221> NAME/KEY: VARIANT
<222> LOCATION: (211)..(211)
<223> OTHER INFORMATION: Ser or Thr
<220> FEATURE:
<221> NAME/KEY: VARIANT
<222> LOCATION: (215)..(215)
<223> OTHER INFORMATION: Ile, Leu or Val
<220> FEATURE:
<221> NAME/KEY: VARIANT
<222> LOCATION: (221)..(221)
<223> OTHER INFORMATION: Ile, Leu or Val
<220> FEATURE:
<221> NAME/KEY: VARIANT
<222> LOCATION: (223)..(223)
<223> OTHER INFORMATION: Ile, Leu or Val
<220> FEATURE:
<221> NAME/KEY: VARIANT
<222> LOCATION: (227)..(227)
<223> OTHER INFORMATION: Asp or Glu
<220> FEATURE:
<221> NAME/KEY: VARIANT
<222> LOCATION: (233)..(233)
<223> OTHER INFORMATION: Asp or Glu
<220> FEATURE:
<221> NAME/KEY: VARIANT
<222> LOCATION: (239)..(239)
<223> OTHER INFORMATION: Ile, Leu or Val
<220> FEATURE:
<221> NAME/KEY: VARIANT
<222> LOCATION: (242)..(242)
<223> OTHER INFORMATION: Ile, Leu or Val
<220> FEATURE:
<221> NAME/KEY: VARIANT
<222> LOCATION: (245)..(245)
<223> OTHER INFORMATION: Ile, Leu or Val
<220> FEATURE:
<221> NAME/KEY: VARIANT
<222> LOCATION: (252)..(252)
<223> OTHER INFORMATION: Asp or Glu
<220> FEATURE:
<221> NAME/KEY: VARIANT
<222> LOCATION: (253)..(253)
<223> OTHER INFORMATION: Ile, Leu or Val
<220> FEATURE:
<221> NAME/KEY: VARIANT
<222> LOCATION: (261)..(261)
<223> OTHER INFORMATION: Xaa can be any naturally occurring amino acid
<220> FEATURE:
<221> NAME/KEY: VARIANT
<222> LOCATION: (262)..(262)
<223> OTHER INFORMATION: Xaa can be any naturally occurring amino acid
      or absent
<220> FEATURE:
<221> NAME/KEY: VARIANT
<222> LOCATION: (263)..(263)
<223> OTHER INFORMATION: Xaa can be any naturally occurring amino acid
<220> FEATURE:
<221> NAME/KEY: VARIANT
<222> LOCATION: (265)..(265)
<223> OTHER INFORMATION: Ile, Leu or Val
<220> FEATURE:
<221> NAME/KEY: VARIANT
<222> LOCATION: (275)..(275)
<223> OTHER INFORMATION: Asp or Glu
<220> FEATURE:
<221> NAME/KEY: VARIANT
<222> LOCATION: (278)..(278)
<223> OTHER INFORMATION: Ile, Leu or Val
```

-continued

```
<220> FEATURE:
<221> NAME/KEY: VARIANT
<222> LOCATION: (281)..(284)
<223> OTHER INFORMATION: Xaa can be any naturally occurring amino acid
      or absent
<220> FEATURE:
<221> NAME/KEY: VARIANT
<222> LOCATION: (289)..(289)
<223> OTHER INFORMATION: Ile, Leu or Val
<220> FEATURE:
<221> NAME/KEY: VARIANT
<222> LOCATION: (296)..(298)
<223> OTHER INFORMATION: Xaa can be any naturally occurring amino acid
      or absent
<220> FEATURE:
<221> NAME/KEY: VARIANT
<222> LOCATION: (301)..(301)
<223> OTHER INFORMATION: Ile, Leu or Val
<220> FEATURE:
<221> NAME/KEY: VARIANT
<222> LOCATION: (306)..(306)
<223> OTHER INFORMATION: Xaa can be any naturally occurring amino acid
<220> FEATURE:
<221> NAME/KEY: VARIANT
<222> LOCATION: (308)..(308)
<223> OTHER INFORMATION: Ile, Leu or Val
<220> FEATURE:
<221> NAME/KEY: VARIANT
<222> LOCATION: (311)..(311)
<223> OTHER INFORMATION: Ile, Leu or Val
<220> FEATURE:
<221> NAME/KEY: VARIANT
<222> LOCATION: (313)..(314)
<223> OTHER INFORMATION: Xaa can be any naturally occurring amino acid
      or absent
<220> FEATURE:
<221> NAME/KEY: VARIANT
<222> LOCATION: (316)..(316)
<223> OTHER INFORMATION: Asp or Glu
<220> FEATURE:
<221> NAME/KEY: VARIANT
<222> LOCATION: (328)..(328)
<223> OTHER INFORMATION: Ile, Leu or Val
<220> FEATURE:
<221> NAME/KEY: VARIANT
<222> LOCATION: (332)..(332)
<223> OTHER INFORMATION: Ser or Thr
<220> FEATURE:
<221> NAME/KEY: VARIANT
<222> LOCATION: (334)..(334)
<223> OTHER INFORMATION: Ile, Leu or Val
<220> FEATURE:
<221> NAME/KEY: VARIANT
<222> LOCATION: (335)..(335)
<223> OTHER INFORMATION: Ser or Thr
<220> FEATURE:
<221> NAME/KEY: VARIANT
<222> LOCATION: (337)..(337)
<223> OTHER INFORMATION: Arg, Lys or His
<220> FEATURE:
<221> NAME/KEY: VARIANT
<222> LOCATION: (338)..(338)
<223> OTHER INFORMATION: Ile, Leu or Val
<220> FEATURE:
<221> NAME/KEY: VARIANT
<222> LOCATION: (350)..(350)
<223> OTHER INFORMATION: Ser or Thr
<220> FEATURE:
<221> NAME/KEY: VARIANT
<222> LOCATION: (351)..(351)
<223> OTHER INFORMATION: Ile, Leu or Val
<220> FEATURE:
<221> NAME/KEY: VARIANT
<222> LOCATION: (353)..(353)
<223> OTHER INFORMATION: Asp or Glu
<220> FEATURE:
<221> NAME/KEY: VARIANT
<222> LOCATION: (358)..(358)
<223> OTHER INFORMATION: Asp or Glu
```

```
<220> FEATURE:
<221> NAME/KEY: VARIANT
<222> LOCATION: (361)..(361)
<223> OTHER INFORMATION: Ile, Leu or Val
<220> FEATURE:
<221> NAME/KEY: VARIANT
<222> LOCATION: (367)..(368)
<223> OTHER INFORMATION: Arg, Lys or His
<220> FEATURE:
<221> NAME/KEY: VARIANT
<222> LOCATION: (369)..(372)
<223> OTHER INFORMATION: Xaa can be any naturally occurring amino acid
      or absent
<220> FEATURE:
<221> NAME/KEY: VARIANT
<222> LOCATION: (374)..(374)
<223> OTHER INFORMATION: Asp or Glu
<220> FEATURE:
<221> NAME/KEY: VARIANT
<222> LOCATION: (379)..(379)
<223> OTHER INFORMATION: Ile, Leu or Val
<220> FEATURE:
<221> NAME/KEY: VARIANT
<222> LOCATION: (380)..(380)
<223> OTHER INFORMATION: Arg, Lys or His
<220> FEATURE:
<221> NAME/KEY: VARIANT
<222> LOCATION: (383)..(384)
<223> OTHER INFORMATION: Ile, Leu or Val
<220> FEATURE:
<221> NAME/KEY: VARIANT
<222> LOCATION: (386)..(386)
<223> OTHER INFORMATION: Arg, Lys or His
<220> FEATURE:
<221> NAME/KEY: VARIANT
<222> LOCATION: (387)..(387)
<223> OTHER INFORMATION: Asp or Glu
<220> FEATURE:
<221> NAME/KEY: VARIANT
<222> LOCATION: (393)..(393)
<223> OTHER INFORMATION: Arg, Lys or His
<220> FEATURE:
<221> NAME/KEY: VARIANT
<222> LOCATION: (397)..(397)
<223> OTHER INFORMATION: Ile, Leu or Val
<220> FEATURE:
<221> NAME/KEY: VARIANT
<222> LOCATION: (400)..(400)
<223> OTHER INFORMATION: Ile, Leu or Val
<220> FEATURE:
<221> NAME/KEY: VARIANT
<222> LOCATION: (402)..(402)
<223> OTHER INFORMATION: Asp or Glu
<220> FEATURE:
<221> NAME/KEY: VARIANT
<222> LOCATION: (405)..(419)
<223> OTHER INFORMATION: Xaa can be any naturally occurring amino acid
      or absent
<220> FEATURE:
<221> NAME/KEY: VARIANT
<222> LOCATION: (420)..(420)
<223> OTHER INFORMATION: Ile, Leu or Val
<220> FEATURE:
<221> NAME/KEY: VARIANT
<222> LOCATION: (427)..(427)
<223> OTHER INFORMATION: Ile, Leu or Val
<220> FEATURE:
<221> NAME/KEY: VARIANT
<222> LOCATION: (431)..(431)
<223> OTHER INFORMATION: Xaa can be any naturally occurring amino acid
<220> FEATURE:
<221> NAME/KEY: VARIANT
<222> LOCATION: (433)..(434)
<223> OTHER INFORMATION: Xaa can be any naturally occurring amino acid
      or absent
<220> FEATURE:
<221> NAME/KEY: VARIANT
<222> LOCATION: (440)..(440)
<223> OTHER INFORMATION: Xaa can be any naturally occurring amino acid
```

-continued

```
<220> FEATURE:
<221> NAME/KEY: VARIANT
<222> LOCATION: (441)..(446)
<223> OTHER INFORMATION: Xaa can be any naturally occurring amino acid
      or absent
<220> FEATURE:
<221> NAME/KEY: VARIANT
<222> LOCATION: (447)..(448)
<223> OTHER INFORMATION: Xaa can be any naturally occurring amino acid
<220> FEATURE:
<221> NAME/KEY: VARIANT
<222> LOCATION: (449)..(505)
<223> OTHER INFORMATION: Xaa can be any naturally occurring amino acid
      or absent

<400> SEQUENCE: 10

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Met Xaa
             20                  25                  30

Met Xaa Xaa Thr Glu His Xaa Xaa Phe Xaa Xaa Ser Glu Asn Gly Xaa
             35                  40                  45

Ala Ser Ile Xaa Leu Asn Arg Pro Xaa Ala Leu Asn Ser Leu Xaa Tyr
 50                  55                  60

Asp Met Xaa Gln Pro Xaa Gly Gln Xaa Xaa Xaa Glu Trp Glu Asn Xaa
 65                  70                  75                  80

Glu Arg Xaa Ala Leu Xaa Xaa Leu Xaa Xaa Gly Ala Gly Thr Xaa Gly
                 85                  90                  95

Phe Cys Ala Gly Gly Xaa Xaa Xaa Xaa Xaa Tyr Xaa Ala Arg Ser Asn
            100                 105                 110

Glu Pro Gly Xaa Ala Leu Gln His Ala Glu Arg Phe Phe Glu Xaa Xaa
            115                 120                 125

Tyr Glu Xaa Xaa Thr Tyr Xaa Tyr Gln Tyr Lys Lys Pro Xaa Xaa Ala
130                 135                 140

Cys Leu Asp Gly Ile Xaa Met Gly Gly Val Gly Leu Thr Asn Gly
145                 150                 155                 160

Ala Lys Tyr Xaa Xaa Xaa Thr Glu Arg Xaa Xaa Trp Ala Met Pro Glu
                165                 170                 175

Met Asn Ile Gly Phe Phe Pro Asp Val Gly Ala Ala Tyr Phe Leu Asn
            180                 185                 190

Xaa Ala Xaa Xaa Xaa Xaa Xaa Pro Gly Tyr Leu Gly Arg Tyr Xaa
            195                 200                 205

Ala Leu Xaa Ala Ser Ile Xaa Lys Ala Ser Asp Val Xaa Phe Xaa Asn
210                 215                 220

Ala Ala Xaa Tyr Phe Met Thr Ser Xaa Ser Leu Pro Ala Phe Xaa Thr
225                 230                 235                 240

Glu Xaa Glu Ser Xaa Asn Trp His Lys Glu Asp Xaa Xaa His Thr His
                245                 250                 255

Leu Leu Lys Glu Xaa Xaa Xaa Val Xaa Arg Thr Phe Ala Thr Ala Pro
                260                 265                 270

Asn Leu Xaa Ser Glu Xaa Ala Pro Xaa Xaa Xaa Xaa Ser Leu Glu Glu
            275                 280                 285

Xaa Asn Ser His Phe Ala Phe Xaa Xaa Asp Thr Xaa Glu Glu Ile
290                 295                 300

Trp Xaa Ala Xaa His Ser Xaa Glu Xaa Xaa Lys Xaa Gln Ser Ser Phe
305                 310                 315                 320

Ala Leu Lys Thr Lys Glu Thr Xaa Leu Ser Lys Xaa Pro Xaa Xaa Leu
                325                 330                 335
```

Xaa Xaa Thr Leu Lys Gln Phe Ile Asp Gly Arg Asp Lys Xaa Xaa Glu
            340                 345                 350

Xaa Cys Phe Ala Thr Xaa Leu Val Xaa Ala Lys Asn Phe Met Xaa Xaa
            355                 360                 365

Xaa Xaa Xaa Xaa Glu Xaa Phe Phe Glu Gly Xaa Xaa Ser Val Xaa Xaa
            370                 375                 380

Asp Xaa Xaa Gln Asn Pro Asn Tyr Xaa Tyr Lys Gln Xaa Ser Asp Xaa
385                 390                 395                 400

Ser Xaa Glu Asp Xaa Xaa Xaa Xaa Xaa Xaa Xaa Xaa Xaa Xaa Xaa Xaa
            405                 410                 415

Xaa Xaa Xaa Xaa Asn Arg Phe Phe Asn Leu Xaa Asn Ala Gly Xaa His
            420                 425                 430

Xaa Xaa Pro Leu Ala Asp Leu Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa
            500                 505

<210> SEQ ID NO 11
<211> LENGTH: 60
<212> TYPE: DNA
<213> ORGANISM: Artificial Sequence
<220> FEATURE:
<223> OTHER INFORMATION: Primer A93

<400> SEQUENCE: 11
ccaatatata ataaaatatg gaggaatgcg atgctcagaa atacgctaaa atgtgcccaa    60

<210> SEQ ID NO 12
<211> LENGTH: 60
<212> TYPE: DNA
<213> ORGANISM: Artificial Sequence
<220> FEATURE:
<223> OTHER INFORMATION: Primer A94

<400> SEQUENCE: 12
tgcctggaga tccttactcg agttggatcc ttatttccat cttaagccat cgttaacttc    60

<210> SEQ ID NO 13
<211> LENGTH: 37
<212> TYPE: DNA
<213> ORGANISM: Artificial Sequence
<220> FEATURE:
<223> OTHER INFORMATION: Primer A95

<400> SEQUENCE: 13
ttttactgat gcgtattctt tgaattttca aatagca    37

<210> SEQ ID NO 14
<211> LENGTH: 34
<212> TYPE: DNA
<213> ORGANISM: Artificial Sequence
<220> FEATURE:
<223> OTHER INFORMATION: Primer A96

<400> SEQUENCE: 14
tcaaagaata cgcatcagta aaaaatttga tgga                          34

<210> SEQ ID NO 15
<211> LENGTH: 41
<212> TYPE: DNA
<213> ORGANISM: Artificial Sequence
<220> FEATURE:
<223> OTHER INFORMATION: Primer A97

<400> SEQUENCE: 15
ttttactgat gtttattctt tgaattttca aatagcaact t                  41

<210> SEQ ID NO 16
<211> LENGTH: 39
<212> TYPE: DNA
<213> ORGANISM: Artificial Sequence
<220> FEATURE:
<223> OTHER INFORMATION: Primer A98

<400> SEQUENCE: 16
tcaaagaata aacatcagta aaaaatttga tggacttgg                     39

<210> SEQ ID NO 17
<211> LENGTH: 39
<212> TYPE: DNA
<213> ORGANISM: Artificial Sequence
<220> FEATURE:
<223> OTHER INFORMATION: Primer A99

<400> SEQUENCE: 17
ttttactgat tcgtattctt tgaattttca aatagcaac                     39

<210> SEQ ID NO 18
<211> LENGTH: 36
<212> TYPE: DNA
<213> ORGANISM: Artificial Sequence
<220> FEATURE:
<223> OTHER INFORMATION: Primer A100

<400> SEQUENCE: 18
tcaaagaata cgaatcagta aaaaatttga tggact                        36

<210> SEQ ID NO 19
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(17)
<223> OTHER INFORMATION: n is a, c, g, or t

<400> SEQUENCE: 19
aattttttac tgatnnntat tctttgaatt ttcaaatagc                    40

<210> SEQ ID NO 20
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(15)
<223> OTHER INFORMATION: n is a, c, g, or t

```
<400> SEQUENCE: 20
ttcaaagaat aannnatcag taaaaaattt gatggacttg                           40

<210> SEQ ID NO 21
<211> LENGTH: 55
<212> TYPE: DNA
<213> ORGANISM: Artificial Sequence
<220> FEATURE:
<223> OTHER INFORMATION: Primer A120

<400> SEQUENCE: 21
ccaatatata ataaaatatg gaggaatgcg atgtctacaa cacataacgt ccctc          55

<210> SEQ ID NO 22
<211> LENGTH: 53
<212> TYPE: DNA
<213> ORGANISM: Artificial Sequence
<220> FEATURE:
<223> OTHER INFORMATION: Primer A121

<400> SEQUENCE: 22
tgcctggaga tccttactcg agttggatcc ttactcaaca ggtaaggcgc gag            53

<210> SEQ ID NO 23
<211> LENGTH: 61
<212> TYPE: DNA
<213> ORGANISM: Artificial Sequence
<220> FEATURE:
<223> OTHER INFORMATION: Primer Y1-11_A13-R

<400> SEQUENCE: 23
ctaattacat gactcgaggt cgacggtatc gttatttcca tcttaagcca tcgttaactt    60
c                                                                     61

<210> SEQ ID NO 24
<211> LENGTH: 67
<212> TYPE: DNA
<213> ORGANISM: Artificial Sequence
<220> FEATURE:
<223> OTHER INFORMATION: Primer Y1-11_A13-F

<400> SEQUENCE: 24
cattagaaag aaagcatagc aatctaatct aagtttaaaa caatgactac tcaaccccag    60
ctaaatg                                                               67

<210> SEQ ID NO 25
<211> LENGTH: 60
<212> TYPE: DNA
<213> ORGANISM: Artificial Sequence
<220> FEATURE:
<223> OTHER INFORMATION: Primer YO012

<400> SEQUENCE: 25
gaaagcatag caatctaatc taagtttaaa acaatgaccg aacaagtctt attctcagta    60

<210> SEQ ID NO 26
<211> LENGTH: 59
<212> TYPE: DNA
<213> ORGANISM: Artificial Sequence
<220> FEATURE:
<223> OTHER INFORMATION: Primer YO013

<400> SEQUENCE: 26
ctaattacat gactcgaggt cgacggtatc gttaagcgtt caacaaattg aaaaatctg     59
```

<210> SEQ ID NO 27
<211> LENGTH: 58
<212> TYPE: DNA
<213> ORGANISM: Artificial Sequence
<220> FEATURE:
<223> OTHER INFORMATION: Primer YO014

<400> SEQUENCE: 27
gaaagcatag caatctaatc taagtttaaa acaatgaccg aacatgtatt attctcag       58

<210> SEQ ID NO 28
<211> LENGTH: 57
<212> TYPE: DNA
<213> ORGANISM: Artificial Sequence
<220> FEATURE:
<223> OTHER INFORMATION: Primer YO015

<400> SEQUENCE: 28
ctaattacat gactcgaggt cgacggtatc gttaagcgtt taacaaattg aaaaatc        57

<210> SEQ ID NO 29
<211> LENGTH: 58
<212> TYPE: DNA
<213> ORGANISM: Artificial Sequence
<220> FEATURE:
<223> OTHER INFORMATION: Primer YO016

<400> SEQUENCE: 29
gaaagcatag caatctaatc taagtttaaa acaatgactg aacacgtctt gttctctg       58

<210> SEQ ID NO 30
<211> LENGTH: 59
<212> TYPE: DNA
<213> ORGANISM: Artificial Sequence
<220> FEATURE:
<223> OTHER INFORMATION: Primer YO017

<400> SEQUENCE: 30
ctaattacat gactcgaggt cgacggtatc gttaagcgtt taacaaattg aaaaatctg      59

<210> SEQ ID NO 31
<211> LENGTH: 57
<212> TYPE: DNA
<213> ORGANISM: Artificial Sequence
<220> FEATURE:
<223> OTHER INFORMATION: Primer YO018

<400> SEQUENCE: 31
gaaagcatag caatctaatc taagtttaaa acaatgagaa gatacatcag aggtggt        57

<210> SEQ ID NO 32
<211> LENGTH: 57
<212> TYPE: DNA
<213> ORGANISM: Artificial Sequence
<220> FEATURE:
<223> OTHER INFORMATION: Primer YO019

<400> SEQUENCE: 32
ctaattacat gactcgaggt cgacggtatc gttatgcagc gttcaacaaa ttgaaaa        57

<210> SEQ ID NO 33
<211> LENGTH: 58
<212> TYPE: DNA
<213> ORGANISM: Artificial Sequence
<220> FEATURE:

<223> OTHER INFORMATION: Primer YO020

<400> SEQUENCE: 33
gaaagcatag caatctaatc taagtttaaa acaatgaccg aacaagtctt attctcag    58

<210> SEQ ID NO 34
<211> LENGTH: 58
<212> TYPE: DNA
<213> ORGANISM: Artificial Sequence
<220> FEATURE:
<223> OTHER INFORMATION: Primer YO021

<400> SEQUENCE: 34
ctaattacat gactcgaggt cgacggtatc gttaagcgtt caacaaattg aaaaatct    58

<210> SEQ ID NO 35
<211> LENGTH: 60
<212> TYPE: DNA
<213> ORGANISM: Artificial Sequence
<220> FEATURE:
<223> OTHER INFORMATION: Primer YO024

<400> SEQUENCE: 35
gaaagcatag caatctaatc taagtttaaa acaatgaact tacaatttga agaaagacca    60

<210> SEQ ID NO 36
<211> LENGTH: 57
<212> TYPE: DNA
<213> ORGANISM: Artificial Sequence
<220> FEATURE:
<223> OTHER INFORMATION: Primer YO025

<400> SEQUENCE: 36
ctaattacat gactcgaggt cgacggtatc gttacaaatc agctaaaggg tgttcac    57

<210> SEQ ID NO 37
<211> LENGTH: 59
<212> TYPE: DNA
<213> ORGANISM: Artificial Sequence
<220> FEATURE:
<223> OTHER INFORMATION: Primer YO026

<400> SEQUENCE: 37
gaaagcatag caatctaatc taagtttaaa acaatgaact tacactttga agaattgac    59

<210> SEQ ID NO 38
<211> LENGTH: 57
<212> TYPE: DNA
<213> ORGANISM: Artificial Sequence
<220> FEATURE:
<223> OTHER INFORMATION: Primer YO027

<400> SEQUENCE: 38
ctaattacat gactcgaggt cgacggtatc gttagtagtc agacaaatct gctaaag    57

<210> SEQ ID NO 39
<211> LENGTH: 59
<212> TYPE: DNA
<213> ORGANISM: Artificial Sequence
<220> FEATURE:
<223> OTHER INFORMATION: Primer YO028

<400> SEQUENCE: 39
gaaagcatag caatctaatc taagtttaaa acaatgacaa tccactgtga agtattaac    59

```
<210> SEQ ID NO 40
<211> LENGTH: 55
<212> TYPE: DNA
<213> ORGANISM: Artificial Sequence
<220> FEATURE:
<223> OTHER INFORMATION: Primer YO029

<400> SEQUENCE: 40
ctaattacat gactcgaggt cgacggtatc gttaaccaac gtcagccaaa gggtg        55

<210> SEQ ID NO 41
<211> LENGTH: 58
<212> TYPE: DNA
<213> ORGANISM: Artificial Sequence
<220> FEATURE:
<223> OTHER INFORMATION: Primer YO030

<400> SEQUENCE: 41
gaaagcatag caatctaatc taagtttaaa acaatgaatg tcacctttga agaaagag    58

<210> SEQ ID NO 42
<211> LENGTH: 55
<212> TYPE: DNA
<213> ORGANISM: Artificial Sequence
<220> FEATURE:
<223> OTHER INFORMATION: Primer YO031

<400> SEQUENCE: 42
ctaattacat gactcgaggt cgacggtatc gttatgccaa atcagctaaa gggtg        55

<210> SEQ ID NO 43
<211> LENGTH: 26
<212> TYPE: DNA
<213> ORGANISM: Artificial Sequence
<220> FEATURE:
<223> OTHER INFORMATION: Primer F1

<400> SEQUENCE: 43
atgacgcaat ttgcatttgt gttccc                                       26

<210> SEQ ID NO 44
<211> LENGTH: 19
<212> TYPE: DNA
<213> ORGANISM: Artificial Sequence
<220> FEATURE:
<223> OTHER INFORMATION: Primer F2

<400> SEQUENCE: 44
ttaaagctcg agcgccgct                                               19
```

METHOD FOR PREPARATION OF DIESTER DERIVATIVES OF MALONIC ACID

CROSS-REFERENCE TO RELATED APPLICATIONS

This application claims the benefit of priority under 35 U.S.C. 119(e) and Article 2 of the Paris Convention for the Protection of Industrial Property (1883) to U.S. provisional application Ser. No. 62/630,102, filed 13 Feb. 2018, the entire contents of which are incorporated herein by this reference.

REFERENCE TO SEQUENCE LISTING

This application contains a Sequence Listing submitted via EFS-web in computer readable form and is hereby incorporated by reference in its entirety. The ASCII copy, created on Feb. 8, 2019, is named LYGOS_0012_WO_ST25 and is 78 KB in size.

FIELD

Embodiments disclosed herein relate to methods for extracting and purifying bio-based diester derivatives of malonic acid and the compounds and compositions derived from such methods.

BACKGROUND

The long-term economic and environmental concerns associated with the petrochemical industry have provided impetus for increased research, development, and commercialization of processes that derive industrial and consumer chemicals not from petroleum feedstocks but rather from renewable feedstocks. One approach is the development of biorefining processes to convert renewable feedstocks into products that can replace petroleum-derived chemicals. Two common goals in improving a biorefining process include achieving a lower cost of production and reducing carbon dioxide emissions.

One such presently petroleum-derived chemical is malonic acid (propanedioic acid, CAS No. 141-82-2). Propanedioic acid ("malonate", CAS No. 141-82-2) is currently produced from non-renewable, petroleum feedstocks. Mono- or di-esterification of one or both carboxylic acid moieties of malonate with an alcohol (e.g. methanol or ethanol) yields the monoalkyl and dialkyl malonates, respectively. 2,2-dimethyl-1,3-dioxane-4,6-dione ("Meldrum's acid" CAS No. 2033-24-1) is produced from malonate using either acetone in acetic anhydride or isopropenyl acetate in acid. Malonic acid and chemical derivatives of malonic acid (such as, for example, monoalkyl malonate, dialkyl malonate, and 2,2-dimethyl-1,3-dioxane-4,6-dione are used for the production of many industrial and consumer products, including polyesters, protective coatings, solvents, electronic products, flavors, fragrances, pharmaceuticals, surgical adhesives, and food additives.

Another group of petroleum-derived chemicals are diester derivatives of malonic acid, including diethyl malonate and dimethyl malonate. Diethyl malonate ("DEM", Malonic acid diethyl ester, CAS No. 105-53-3) and dimethyl malonate ("DMM", Malonic acid dimethyl ester, CAS No. 108-59-8) are currently produced from non-renewable, petroleum feedstocks. Malonic acid has two carboxyl groups close together. To form diethyl malonate or dimethyl malonate from malonic acid, the hydroxyl group on each of two malonic acid carboxyl groups is replaced by an ethoxy group. Diester derivatives of malonic acid are used for the production of many industrial and consumer products, including barbituates, artificial flavorings, vitamins (including $B_1$ and $B_6$), polyesters, protective coatings, solvents, resins, polymers, electronic products, fragrances, pharmaceuticals, surgical adhesives, and food additives. Chemical synthesis has traditionally been the preferred route for synthesis of malonic acid, diester derivatives of malonic acid, malonate and malonate-derived compounds. For example, dialkyl malonates are produced through either a hydrogen cyanide or carbon monoxide process. In the hydrogen cyanide process, sodium cyanide is reacted with sodium chloroacetate at elevated temperatures to produce sodium cyanoacetate, which is subsequently reacted with an alcohol/mineral acid mixture to produce the dialkyl malonate. Strittmatter et al. report yields of 75-85% (see "Malonic acid and Derivatives" in: Ullmann's Encyclopedia of Industrial Chemistry, Wiley-VCH, Weinheim, New York (2002)). In the carbon monoxide process, dialkyl malonates (also referred to herein as diester malonates) are produced through cobalt-catalyzed alkoxycarbonylation of chloroacetates with carbon monoxide in the presence of an alcohol at elevated temperatures and pressures. By way of further example, diester derivatives of malonic acid can be produced through a chloroacetic acid/sodium cyanide process followed by Fischer esterification.

Malonic acid, its esters, and methylene malonates provide an opportunity to create an entirely new reactive materials platform capable of addressing limitations in current epoxy, urethane, unsaturated polyester, and acrylic systems. Petrochemical-based materials often require trade-offs to deliver desired end properties. Such limitations can include energy intensive curing, high VOC emissions due to solvent usage, and chemical leaching from consumer products (for example, bisphenol-A). However, the existing, petrochemical-based production routes to the malonate and malonate-derived compounds are low yielding, environmentally damaging, dependent upon non-renewable feedstocks, and require expensive treatment of wastewater and exhaust gas. Furthermore, the cost and other intrinsic problems with incumbent petrochemical manufacturing have limited the adoption of malonates. Global capacity is exclusive to China using a low-yielding process based on toxic sodium cyanide and monochloroacetic acid (MCAA). Due to their high cost and environmental footprint, malonates are currently only used in niche pharmaceutical production, flavor and fragrance formulations, agricultural chemicals, and electronics with unmet potential as a major new materials platform. In addition to cost and raw materials problems, limited global MCAA capacity (about 200 kilotons per annum) also stymies further industry adoption. property In addition to cost and a more robust supply chain, purity is a factor to consider, particularly for reactive resin and polymer systems. Petrochemical malonates are plagued by difficult to remove chlorinated intermediates and cyanoacetate impurities, interfering with polymerization.

Additionally, the existing, petrochemical-based production routes to yield diester derivatives of malonic acid can result in preparations containing impurities that affect many downstream properties, including cure speed and hardness of resins and polymers. Further, these methods depend upon sourcing malonic acid from non-renewable feedstocks and require expensive treatment of wastewater and exhaust gas. Clearly, alternate means of producing malonic acid and its esters are needed.

Biological systems for producing bio-based malonate via biological fermentation have been recently described (see U.S. Pat. No. 9,816,114). However, fermentative production of malonate creates new challenges for extracting and purifying the bio-based malonate produced, and for efficiently integrating extraction and purification processes into the overall production flow. There also remains a need for extracting and purifying diester derivatives of malonic acid, particularly those with substantially fewer impurities.

There remains a need, therefore, for improved methods, processes, and materials for extracting and purifying biosynthetic or bio-based malonate and diester derivatives of malonic acid in high yields with substantially fewer impurities from biological fermentation and improved methods, processes, and materials for the subsequent preparation of downstream chemicals and products.

SUMMARY

The present disclosure provides a variety of techniques for generating recombinant host cells, materials, and methods for the biological production of malonate, methods for detecting the presence of malonate and determining the levels of malonate in malonate producing host cells (referred to herein as "sensing malonate"), and methods for screening host cells for increased malonate production. In addition, the present disclosure provides methods for the purification of biologically produced malonate, purification of bio-based malonic acid (malonate) and diester derivatives of malonic acid (e.g., diethyl malonate, dimethyl malonate) in high yields. In a first aspect, the purification techniques comprise methods for making large and substantially pure calcium malonate crystals that can be separated from impurities to a very great degree, and the resulting preparation of diester derivatives of malonic acid. In a second aspect, the purification techniques comprise methods for making substantially pure soluble ammonium malonate that has been separated from impurities to a very great degree, and the resulting preparation of diester derivatives of malonic acid.

The methods disclosed herein are sustainable and based on US agricultural feedstocks, with a high-yielding (in some embodiments around 1.13 kg malonate/kg glucose) biological route capable of reducing production costs to less than 50% of current market prices, enabling true market transformation. The methods can eliminate most, if not all, current supply chain problems with malonates, allowing customers to develop new materials and applications including a fast, ambient temperature curing formulation that eliminates over curing, the single largest energy expenditure during vehicle manufacturing. This will further enable lightweight materials in said manufacturing processes via low heat and low-cost plastic fibers. For example, the methods disclosed herein can be used to generate base chemicals for use in composites for wind turbine blade manufacturing that allow for decreased processing costs and improved final mechanical properties. Bio-based malonates also allow for novel electrolytes in Li-ion batteries with improved temperature stability, increased battery lifespan and, thus, increased battery value.

The present disclosure provides novel malonate monomers with characteristics that include base-catalyzed anionic polymerization at ambient temperatures without solvent usage, low temperature curing enabling coating of heat sensitive composites for lightweight vehicles, and the production of new polymer systems with improved strength and chemical resistance properties.

The methods comprise, among other things, a direct extractive esterification of either the fermentation intermediate or of a concentrated ammonium malonate mixture, which can significantly lower cost while achieving high purity versus the classical approach of recovering the pure diacid and then esterifying. Benefits of producing the diesters by the methods disclosed herein include a) ease of separation through distillation, b) higher thermal stability during processing with higher yield, c) lower capital and operating costs, and/or d) higher purity. Petrochemically derived malonates are plagued by difficult-to-remove chlorinated intermediates and cyanoacetate impurities, interfering with polymerization. The disclosed processes eliminate these impurities entirely and 2-3× faster cure times have been achieved using biobased vs. petrochemical malonates.

Thus, in various embodiments recombinant host cells provided by the present disclosure can be produced by introduction of one or more of the heterologous (foreign, non-native) nucleic acids provided by this disclosure, which encode a wild-type or mutated form of an acyl-CoA hydrolase, thereby allowing the recombinant host cell to produce malonate. Non-limiting examples of acyl-CoA hydrolases encoded by the nucleic acids provided by this disclosure and suitable for malonyl-CoA hydrolysis include wild-type and modified enzymes selected from the group consisting of 3-hydroxyisobutyryl-CoA hydrolases (EC 3.1.2.4), 3-hydroxypropionyl-CoA hydrolases (EC 3.1.2.4), acetoacetyl-CoA hydrolases (EC 3.1.2.11), methylmalonyl-CoA hydrolases (EC 3.1.2.17), propionyl-CoA hydrolases (EC 3.1.2.18), succinyl-CoA hydrolases (EC 3.1.2.3), and malonyl CoA:ACP transacylases (EC 2.3.1.39) mutated as provided herein to have malonyl CoA hydrolase activity.

In another aspect, this disclosure provides methods for producing malonate in a recombinant host cell, which methods generally comprise culturing the recombinant host cell in fermentation broth under conditions that enable it to produce malonate. In some embodiments, the host cell has been engineered to express more of, or less of, an endogenous enzyme that results in the production of more malonate than a corresponding cell that has not been so engineered. In some embodiments, the methods comprise culturing a recombinant host cell expressing a heterologous enzyme that results in the increased production of malonate. In some embodiments, the host cell used in the methods comprises one or expression vectors comprising encoding heterologous malonyl-CoA hydrolase enzymes. In some embodiments, the fermentation broth is supplemented with carbon sources promoting malonate production and selected from the group consisting of carbon dioxide, ethanol, methanol, glycerol, acetate, and/or fatty acids.

In some aspects, the disclosure provides recombinant host cells suitable for the biosynthetic production of malonate at levels enabling its isolation and use as a starting material for chemical synthesis of other useful products. In some embodiments, the host cell is a yeast cell. In some embodiments, the yeast is a *Candida, Cryptococcus, Issatchenkia, Kluyveromyces, Lipomyces, Pichia, Rhodosporidium, Rhodotorula, Saccharomyces* or *Yarrowia* species. In various embodiments, the yeast is of a species selected from the group consisting of *Candida albicans, Candida tropicalis, Cryptococcus curvatus, Issatchenki orientalis, Kluyveromyces lactis, Lipomyces starkeyi, Pichia angusta, Pichia kodamae, Pichia kudriavzevii, Pichia membranaefaciens, Pichia methanolica, Pichia pastoris, Pichia salictaria, Pichia stipitis, Pichia thermotolerans, Pichia trehalophila, Rhodosporidium toruloides, Rhodotorula glutinis, Rhodoto-* rula graminis, Saccharomyces bayanus, Saccharomyces boulardi, Saccharomyces kluyveri, and Yarrowia lipolytica.

In other embodiments, the host cell is a bacterial cell. In various embodiments, the host cell is a bacterial cell. In some embodiments, the bacterial cell is selected from the group consisting of Bacillus, Clostridium, Corynebacterium, Escherichia, Pseudomonas, and Streptomyces. In some embodiments, the host cell is an E. coli cell.

Generally, the recombinant host cells of this disclosure have been genetically modified for improved malonate yield, titer, and/or productivity. In various embodiments, the host cells have been modified for increased malonate biosynthesis through one or more host cell modifications selected from the group consisting of modifications that result in increased acetyl-CoA biosynthesis, increased malonyl-CoA biosynthesis, decreased malonate catabolism, increased secretion of malonate into the fermentation broth, increased host cell tolerance to malonate in the fermentation broth, and/or increased host cell catabolism of carbon sources (e.g., acetate, alginate, ethanol, fatty acids, lignocellulosic biomass, methanol, pentose sugars, and syn gas).

In a further aspect, this disclosure provides purified malonate isolated from the fermentation broth of a host cell producing malonate, which, in some embodiments, is a host cell provided by this disclosure. This disclosure also provides methods for purifying malonate from the fermentation broth of a host cell producing malonate, the methods generally comprising culturing a host cell in fermentation broth under conditions that enable the host cell to produce malonate and purifying the malonate from the fermentation broth. In some embodiments, the concentration of malonate in the broth is increased by dewatering the fermentation broth during the purification process. In various embodiments, the dewatering is achieved by reverse osmosis processing, evaporation, or a combination of the two. In various embodiments, the purification is achieved by adding one or more of the following: a divalent cation, a monovalent cation, ammonium, a monosubstituted amine, a disubstituted amine, a trisubstituted amine, a cationic purification resin, or an acid. In various embodiments, these agents are added in conjunction with one or more organic solvents. In some embodiments, a hydrophobic solvent is used in a liquid-liquid extraction of the fermentation broth. In other embodiments, malonate is purified from the fermentation broth by reactive extraction or distillation with an acid catalyst and an alcohol.

In some embodiments, malonate is produced in a fermentation broth that has been seeded with ammonium hydroxide in order to produce a soluble ammonium malonate salt. Malonate is thereafter purified from the fermentation broth by: centrifuging the fermentation broth a first time to generate a first centrate and a heavy phase; collecting the first centrate; washing the heavy phase with a cell wash to liberate any residual malonate therefrom; centrifuging the washed heavy phase; combining the first centrate with the centrate from the heavy phase centrifugation; ultrafiltering the combined centrates; and passing the ultrafiltration permeate to an evaporator to produce a concentrated ammonium malonate solution.

In another aspect, this disclosure provides methods of making compounds derived from malonate and compounds produced by such methods. The methods generally comprise reacting malonate with one or more substrates to produce a compound. In some embodiments, chemicals with established synthetic routes from malonate are produced using biologically derived malonate. In other embodiments, new synthetic routes for the production of useful chemicals are provided that are suitable for use with either a synthetically or biologically derived malonate. In some embodiments, monoalkyl malonate esters are synthesized from biologically derived malonate. In other embodiments, dialkyl malonate esters are synthesized from biologically derived malonate. In some embodiments, an acrylate is synthesized from malonate or malonic acid. In other embodiments, an acrylate is synthesized from malonate monoesters or diesters. In other embodiments, dicarboxylic acids are produced from malonate. Illustrative dicarboxylic acids that can be produced in accordance with the methods of this disclosure include pentanedioic acid, hexanedioic acid, heptanedioic acid, octanedioic acid, nonanedioic acid, decanedioic acid, undecanedioic acid, dodecanedioic acid, the corresponding monoalkyl and dialkyl esters of each and combinations of any of the foregoing. In other embodiments of this disclosure, dicarboxylic acids are produced from a malonate-derived compound. In other embodiments of this disclosure, ε-caprolactam is produced from malonate. In other embodiments of this disclosure, δ-valerolactam is produced from malonate.

These and other aspects and embodiments of this disclosure are illustrated in the accompanying drawings and described in more detail below.

DETAILED DESCRIPTION

Figure 1A:
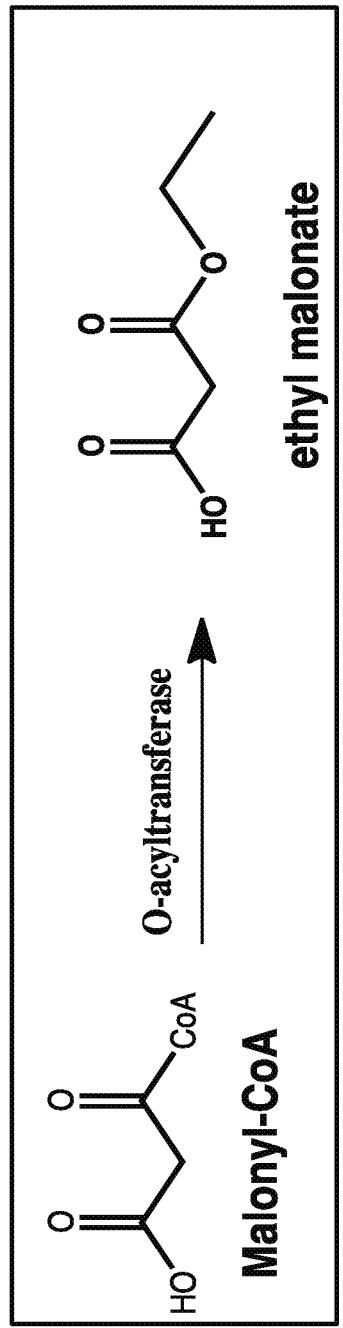
FIG. 1A provides a schematic of a malonyl-CoA hydrolase pathway provided by embodiments of the present disclosure.

In the following sections, various bio-based compositions and methods for extracting and purifying these bio-based compositions are described in order to detail various embodiments. It is recognized by one skilled in the art that practicing the various embodiments does not require the employment of all or even some of the specific details outlined herein, but rather that concentrations, times and other specific details may be modified through routine experimentation. In some cases, well known methods or components have not been included in the description.

The present disclosure provides recombinant host cells, materials, and methods for the biological production of malonate, screening malonate producing host cells for improved malonate production, purification of biologically produced malonate, and the synthetic conversion of malonate to industrially important chemicals.

Provided herein are compositions, methods and processes for extracting and purifying bio-based malonic acid compositions and diester derivatives of malonic acid. The current disclosure is based on discoveries made by the inventors of individual methods and specific and powerful combinations of methods for extracting and purifying malonic acid compositions from biological systems, including without limitation fermentation broths, and for extracting and purifying diester derivatives of malonic acid. In some embodiments, these methods comprise the inclusion of seed crystals in fermentation broth. In some embodiments, these methods also comprise the removal of impurities which have been discovered to adversely affect the quality of bio-based malonic acid containing compositions, including diester derivatives of malonic acid. In some embodiments, these methods comprise the addition of ammonium and the generation of a soluble ammonium malonate salt.

In addition to the overall benefit of biological methods for production of chemicals from renewable feedstock, the specific advantages of the methods provided herein include but are not limited to the elimination of hazardous raw materials that are used for production of petroleum-derived malonic acid and diester derivatives of malonic acid (e.g., cyanide, and chloroacetic acid), and the elimination of contaminants present in other bio-based or petroleum-derived malonic acid and diester derivatives of malonic acid (e.g., cyanoacetate and sodium cyanide), that can affect industrially useful characteristics of the final product such as curing speed, hardness, odor and color.

In certain embodiments, provided herein are methods for extracting and purifying bio-based malonic acid and diester derivatives of malonic acid compositions from fermentation broth. In certain embodiments, provided herein are methods for preparation of compositions comprising malonic acid or diester derivatives of malonic acid from malonic acid produced by a microorganism, such as an engineered microorganism, for example, derived from a renewable carbon source.

While the present disclosure is described herein with reference to aspects and specific embodiments thereof, those skilled in the art will recognize that various changes may be made, and equivalents may be substituted, without departing from this disclosure. The present disclosure is not limited to particular nucleic acids, expression vectors, enzymes, host microorganisms, or processes, as such may vary. The terminology used herein is for purposes of describing particular aspects and embodiments only and is not to be construed as limiting. In addition, many modifications may be made to adapt a particular situation, material, composition of matter, process, process step or steps, in accordance with this disclosure. All such modifications are within the scope of the claims appended hereto.

Amino acids in a protein coding sequence are identified herein by providing the single-letter abbreviation as follows A (alanine), R (arginine), N (asparagine), D (aspartic acid), C (cysteine), Q (glutamine), E (glutamic acid), G (glycine), H (histidine), L (leucine), I (isoleucine), K (lysine), M (methionine), F (phenylalanine), P (proline), S (serine), T (threonine), W (tryptophan), Y (tyrosine), V (valine). Specific amino acids in a protein coding sequence are identified by their single-letter abbreviation followed by the amino acid position in the protein coding sequence where 1 corresponds to the amino acid (typically methionine) at the N-terminus of the protein. For example, E124 in *S. cerevisiae* wild type EHD3 refers to the glutamic acid at position 124 from the EHD3 N-terminal methionine (i.e., M1). Amino acid substitutions (i.e., point mutations) are indicated by identifying the mutated (i.e., progeny) amino acid after the single-letter code and number in the parental protein coding sequence; for example, E124A in *S. cerevisiae* EHD3 refers to substitution of alanine for glutamic acid at position 124 in the EHD3 protein coding sequence. The mutation may also be identified in parentheticals, for example EHD3 (E124A). Multiple point mutations in the protein coding sequence are separated by a backslash (/); for example, EHD3 E124A/E125A indicates that mutations E124A and E125A are both present in the EHD3 protein coding sequence.

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "bio-based" or "renewable" as used herein refers to an organic compound that is synthesized from biologically produced organic components by fermenting a microorganism. For example, diester derivatives of malonic acid which was itself synthesized from glucose (e.g., derived from cornstarch) by a genetically engineered microorganism is bio-based. Bio-based compounds are distinguished from wholly petroleum-derived compounds or those entirely of fossil origin. A compound of renewable or non-petrochemical origin include carbon atoms that have a non-petrochemical origin. Such non-petrochemical (or bio based or renewable) compounds have a $^{14}C$ amount substantially higher than zero, such as about 1 parts per trillion or more, because they are derived from photosynthesis based starting material, such as, for example, glucose or another feedstock used in producing such a compound As used herein, the term "express", when used in connection with a nucleic acid encoding an enzyme or an enzyme itself in a cell, means that the enzyme, which may be an endogenous or exogenous (heterologous) enzyme, is produced in the cell. The term "overexpress", in these contexts, means that the enzyme is produced at a higher level, i.e., enzyme levels are increased, as compared to the wild-type, in the case of an endogenous enzyme. Overexpression of an enzyme can be achieved by increasing the strength or changing the type of the promoter used to drive expression of a coding sequence, increasing the strength of the ribosome binding site or Kozak sequence, increasing the stability of the mRNA transcript, altering the codon usage, increasing the stability of the enzyme, and the like.

The terms "expression vector" or "vector" refer to a nucleic acid and/or a composition comprising a nucleic acid that can be introduced into a host cell, e.g., by transduction, transformation, or infection, such that the cell then produces ("expresses") nucleic acids and/or proteins other than those native to the cell, or in a manner not native to the cell, that are contained in or encoded by the nucleic acid so introduced. Thus, an "expression vector" contains nucleic acids (ordinarily DNA) to be expressed by the host cell. Optionally, the expression vector can be contained in materials to aid in achieving entry of the nucleic acid into the host cell, such as the materials associated with a virus, liposome, protein coating, or the like. Expression vectors suitable for use in various aspects and embodiments of the present disclosure include those into which a nucleic acid sequence can be, or has been, inserted, along with any operational elements. Thus, an expression vector can be transferred into a host cell and, typically, replicated therein (although, one can also employ, in some embodiments, non-replicable vectors that provide for "transient" expression). In some embodiments, an expression vector that integrates into chromosomal, mitochondrial, or plastid DNA is employed. In other embodiments, an expression vector that replicates extrachromasomally is employed. Typical expression vectors include plasmids, and expression vectors typically contain the operational elements for transcription of a nucleic acid in the vector. Such plasmids, as well as other expression vectors, are described herein or are well known to those of ordinary skill in the art.

The term "heterologous" as used herein refers to a material that is non-native to a cell. For example, a nucleic acid is heterologous to a cell, and so is a "heterologous nucleic acid" with respect to that cell, if at least one of the following is true: (a) the nucleic acid is not naturally found in that cell (that is, it is an "exogenous" nucleic acid); (b) the nucleic acid is naturally found in a given host cell (that is, "endogenous to"), but the nucleic acid or the RNA or protein is produced or present in the host cell in an unnatural (e.g., greater or lesser than naturally present) amount; (c) the nucleic acid comprises a nucleotide sequence that encodes a protein endogenous to a host cell but differs in sequence from the endogenous nucleotide sequence that encodes that same protein (having the same or substantially the same amino acid sequence), typically resulting in the protein being produced in a greater amount in the cell, or in the case of an enzyme, producing a mutant version possessing altered (e.g. higher or lower or different) activity; and/or (d) the nucleic acid comprises two or more nucleotide sequences that are not found in the same relationship to each other in the cell. As another example, a protein is heterologous to a host cell if it is produced by translation of an RNA or the corresponding RNA is produced by transcription of a heterologous nucleic acid; a protein is also heterologous to a host cell if it is a mutated version of an endogenous protein, and the mutation was introduced by genetic engineering.

The terms "host cell" and "host microorganism" are used interchangeably herein to refer to a living cell that can be (or has been) transformed via insertion of an expression vector. A host microorganism or cell as described herein may be a prokaryotic cell (e.g., a microorganism of the kingdom Eubacteria) or a eukaryotic cell. As will be appreciated by one of skill in the art, a prokaryotic cell lacks a membrane-bound nucleus, while a eukaryotic cell has a membrane-bound nucleus.

The terms "isolated" or "pure" refer to material that is substantially, e.g. greater than 50%, 75%, 90%, 95%, or 99%, free of components that normally accompany it in its native state, e.g. the state in which it is naturally found or the state in which it exists when it is first produced.

The term "fermentation" or "fermenting" as used herein refers to the feeding of a renewable carbon source (e.g., glucose) to a microorganism under conditions that enable the microorganism to consume the carbon source and to produce malonate.

The term "fermentation broth" as used herein refers to a mixture comprising a fermentation medium (liquid; comprising, for example, organic acids, salts, metals, sugars) and biomass (solid; comprising, for example, cells and cell debris).

A carboxylic acid as described herein can be a salt, acid, base, or derivative depending on the structure, pH, and ions present. The terms "malonate" and "malonic acid" are used interchangeably herein. Malonic acid is also called propane-dioic acid ($C_3H_4O_4$; CAS #141-82-2).

The term "malonate-derived compounds" as used herein refers to mono-alkyl malonate esters, including, for example and without limitation, mono-methyl malonate (also referred to as monomethyl malonate, CAS #16695-14-0), mono-ethyl malonate (also referred to as monoethyl malonate, CAS #1071-46-1), mono-propyl malonate, mono-butyl malonate, mono-tert-butyl malonate (CAS #40052-13-9), and the like; di-alkyl malonate esters, for example and without limitation, dimethyl malonate (CAS #108-59-8), diethyl malonate (CAS #105-53-3), dipropyl malonate (CAS #1117-19-7), dibutyl malonate (CAS #1190-39-2), and the like, and Meldrum's acid (CAS #2033-24-1). The malonate-derived compounds can be produced synthetically from malonate and are themselves valuable compounds but are also useful substrates in the chemical synthesis of a number of other valuable compounds.

As used herein, the term "nucleic acid" and variations thereof shall be generic to polydeoxyribonucleotides (containing 2-deoxy-D-ribose) and to polyribonucleotides (containing D-ribose). "Nucleic acid" can also refer to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. As used herein, the symbols for nucleotides and polynucleotides are those recommended by the IUPAC-IUB Commission of Biochemical Nomenclature (Biochem. 9:4022, 1970). A "nucleic acid" may also be referred to herein with respect to its sequence, the order in which different nucleotides occur in the nucleic acid, as the sequence of nucleotides in a nucleic acid typically defines its biological activity, e.g., as in the sequence of a coding region, the nucleic acid in a gene composed of a promoter and coding region, which encodes the product of a gene, which may be an RNA, e.g. a rRNA, tRNA, or mRNA, or a protein (where a gene encodes a protein, both the mRNA and the protein are "gene products" of that gene).

The term "operably linked" refers to a functional linkage between a nucleic acid expression control sequence (such as a promoter, ribosome-binding site, and transcription terminator) and a second nucleic acid sequence, the coding sequence or coding region, wherein the expression control sequence directs or otherwise regulates transcription and/or translation of the coding sequence.

As used herein, "recombinant" refers to the alteration of genetic material by human intervention. Typically, recombinant refers to the manipulation of DNA or RNA in a cell or virus or expression vector by molecular biology (recombinant DNA technology) methods, including cloning and recombination. Recombinant can also refer to manipulation of DNA or RNA in a cell or virus by random or directed mutagenesis. A "recombinant" cell or nucleic acid can typically be described with reference to how it differs from a naturally occurring counterpart (the "wild-type"). In addition, any reference to a cell or nucleic acid that has been "engineered" or "modified" and variations of those terms, is intended to refer to a recombinant cell or nucleic acid.

As used herein, the term "transcription factor biosensor" refers to a system to detect a substance, e.g., malonate, by activating expression of a "marker" or "reporter" gene where reporter gene expression is mediated by a transcription factor that is capable of binding to a promoter and activating transcription upon binding of that substance, e.g., malonate. For example, malonate may bind to a transcription factor (e.g., MdcY) and activate transcription from a promoter (e.g., $P_{MdcL}$). A "malonate transcription factor" is a transcription factor that, when bound to malonate, can activate a promoter. Thus, MdcY is a malonate transcription factor.

The terms "transduce", "transform", "transfect", and variations thereof as used herein refers to the introduction of one or more nucleic acids into a cell. For practical purposes, the nucleic acid is stably maintained or replicated by the cell for a sufficient period of time to enable the function(s) or product(s) it encodes to be expressed for the cell to be referred to as "transduced", "transformed", or "transfected". Stable maintenance or replication of a nucleic acid may take place either by incorporation of the sequence of nucleic acids into the cellular chromosomal DNA, e.g., the genome, as occurs by chromosomal integration, or by replication extrachromosomally, as occurs with a freely-replicating plasmid. A virus can be stably maintained or replicated when it is "infective": when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

Examples of methods and materials are described below, although methods and materials similar or equivalent to those described herein can also be used in the practice of the present disclosure and will be apparent to those of skill in the art. The materials, methods, and examples are illustrative only and not intended to be limiting.

Wherever a range of values is recited, that range includes every value falling within the range, as if written out explicitly, and further includes the values bounding the range. Thus, a range of "from X to Y" includes every value falling between X and Y, and includes X and Y.

Malonyl-CoA Hydrolase Enzymes

In accordance with one aspect of this disclosure, malonate is produced through the action of a malonyl-CoA hydrolase catalyzing the conversion of malonyl-CoA to malonate. The host cell making the malonyl-CoA hydrolase is a recombinant host cell; in many embodiments, the host cell has been genetically modified to comprise heterologous nucleic acid(s) encoding malonyl-CoA hydrolase enzyme(s) catalyzing hydrolysis of malonyl-CoA to malonate. In some embodiments, the recombinant host cell is a eukaryote. In various embodiments, the eukaryote is a yeast strain selected from the non-limiting example genera; *Candida, Cryptococcus, Issatchenkia, Kluyveromyces, Lipomyces, Pichia, Rhodosporidium, Rhodotorula, Saccharomyces* or *Yarrowia*, which broadly encompass yeast, including those distinguished as oleaginous yeast. In some embodiments, the host cell is *Saccharomyces cerevisiae*. In some embodiments, the host cell is *Pichia kudriavzevii*. In other embodiments, the recombinant host cell is a prokaryote selected from the non-limited example genera: *Bacillus, Clostridium, Corynebacterium, Escherichia, Pseudomonas,* and *Streptomyces*. In some embodiments, the host cell is *E. coli*.

Figure 1B:
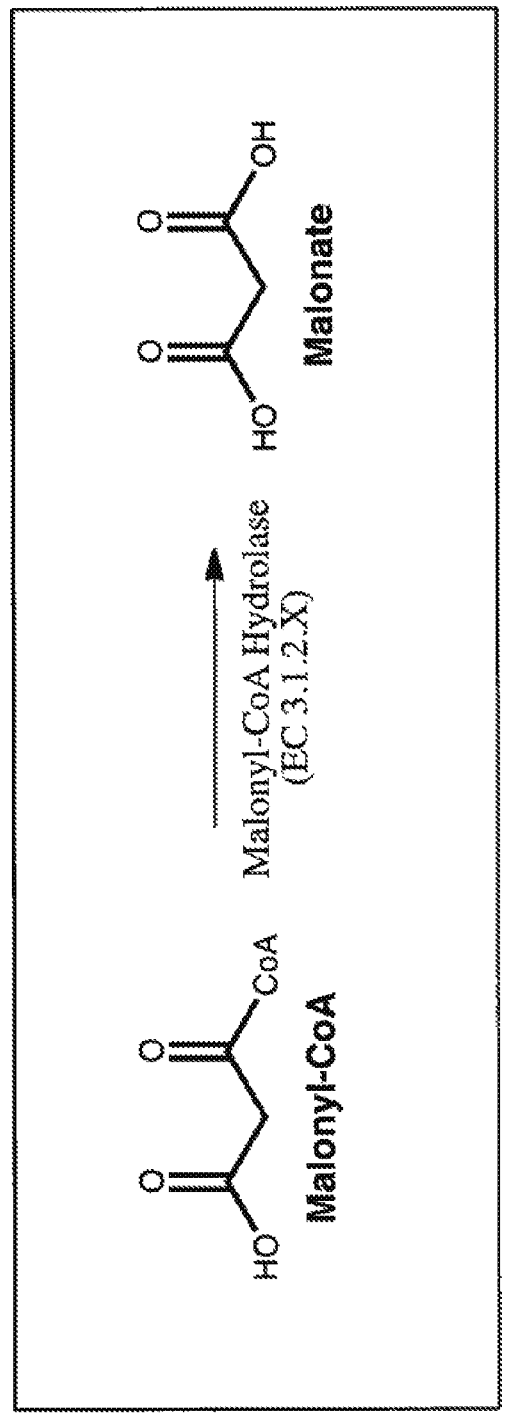
FIG. 1B provides a schematic of the conversion of malonyl-CoA to malonate, as catalyzed by a malonyl-CoA hydrolase (EC 3.1.2.X), according to embodiments of the present disclosure.
Figure 2:
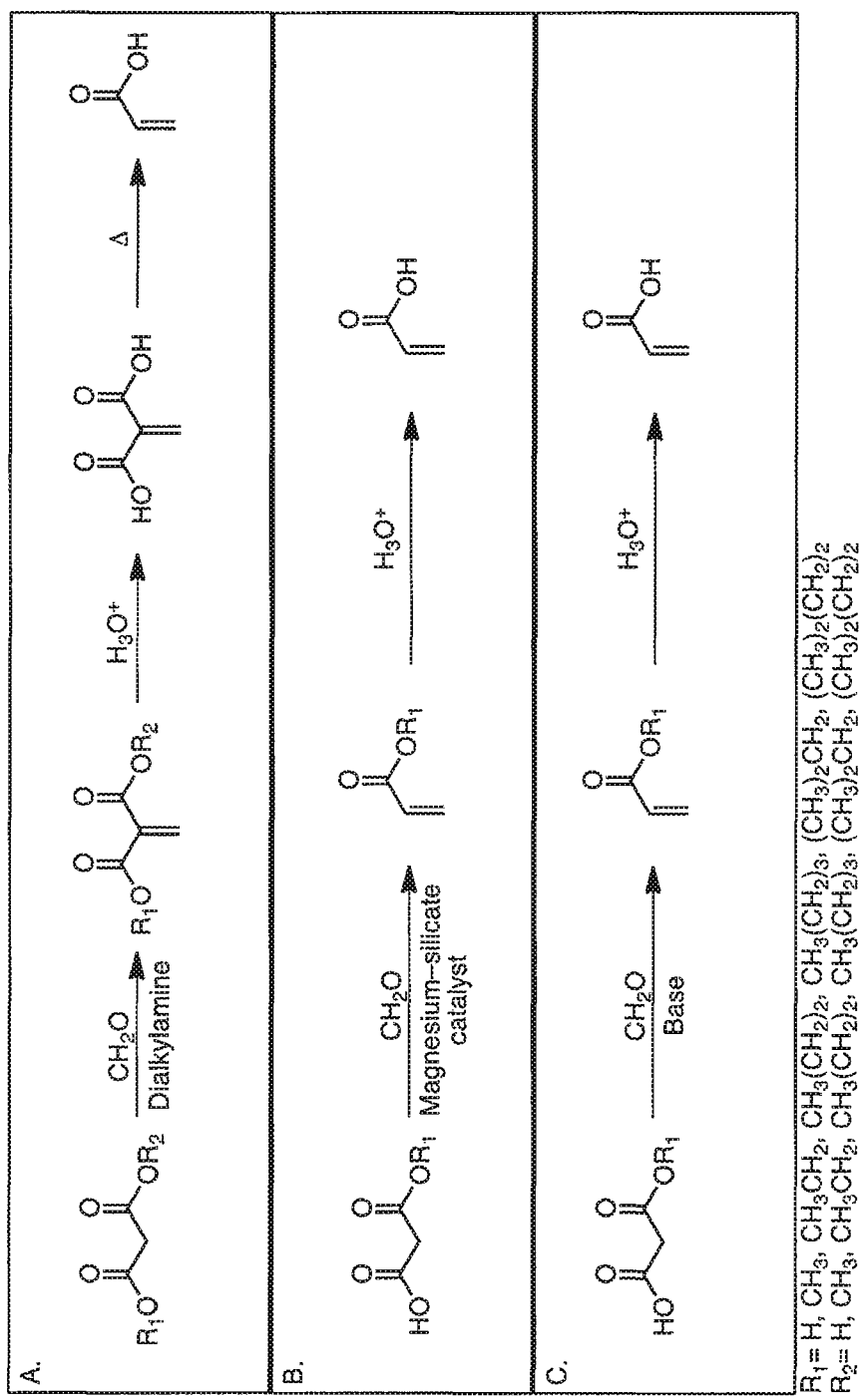
FIG. 2 provides a schematic of the synthetic conversion of malonate and malonate-derived compounds to an acrylate in accordance with embodiments of this disclosure. When a malonate-derived compound is used, malonate is first converted into the mono- or di-alkyl ester suitable for the described reaction. A) malonate and malonate-derived compounds are converted to acrylate by a Mannich reaction with formaldehyde in a dialkylamine. B) malonate and monoalkyl malonates are converted to an acrylate in the presence of a magnesium-silicate catalyst using the Doebner modification of the Knoevenagel condensation reaction with formaldehyde. C) malonate and malonate-derived compounds are converted to acrylate by the Doebner modification of the Knoevenagel condensation reaction with formaldehyde in a suitable base.
Figure 3:
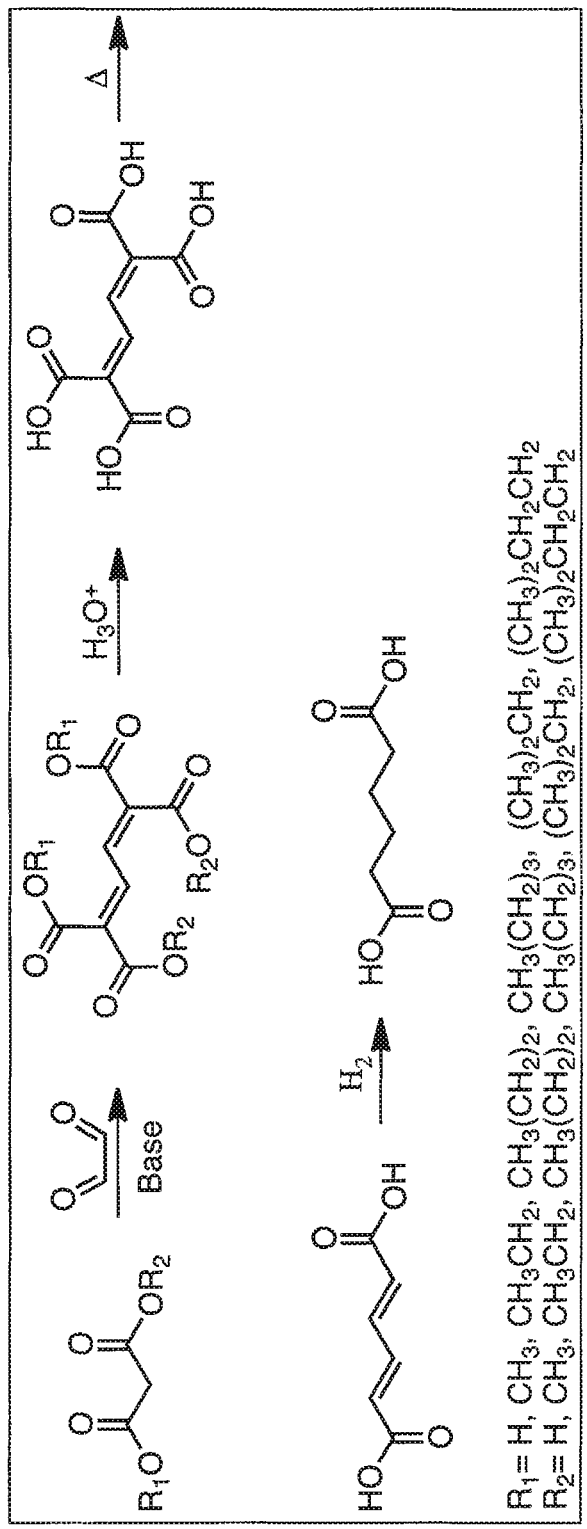
FIG. 3 provides a schematic of the synthetic conversion of malonate and malonate-derived compounds to hexanedioic acid in accordance with embodiments of this disclosure. The reaction proceeds through two intermolecular Knoevenagel condensations with ethanedial to yield the dialkylated bismalonate ester; subsequent treatment with acid to hydrolyze the ester groups followed by thermally-induced decarboxylation yields the unsaturated dicarboxylic acid. Hydrogenation of the unsaturated dicarboxylic acid yields hexanedioic acid.
Figure 4:
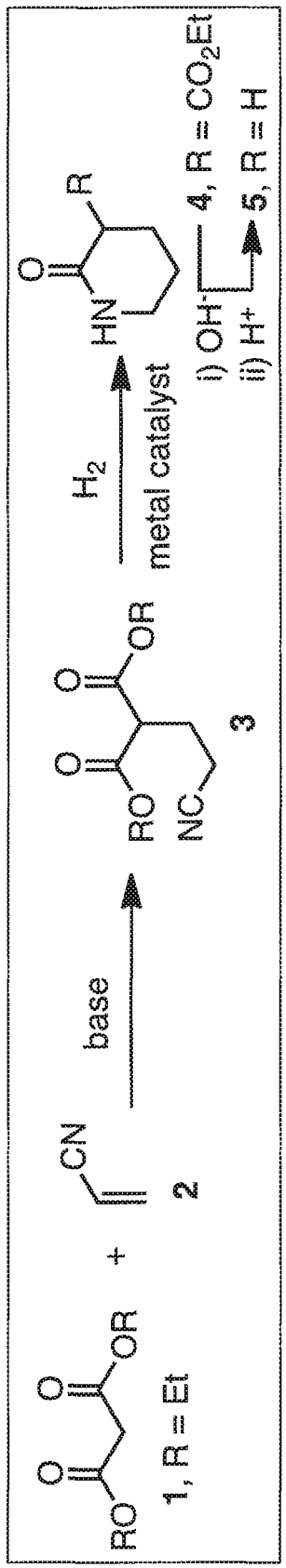
FIG. 4 provides a schematic of the synthetic conversion of diethyl malonate to δ-valerolactam in accordance with embodiments of this disclosure. Diethyl malonate 1 can be produced by Fischer esterification of malonate with ethanol. Michael addition of 1 to acrylonitrile 2 affords 3. Hydrogenation of the nitrile moiety in 3 yields an amine that undergoes spontaneous lactamization to 4. Saponification of the ester moiety in 4 followed by treatment with acid results in decarboxylation to afford δ-valerolactam 5.

A schematic representation of one of the malonyl-CoA hydrolase pathways provided by this disclosure is shown in FIG. 1. The present disclosure results in part from the discovery that various acyl-CoA hydrolases and transacylases can be engineered to have malonyl-CoA hydrolase activity and so be useful for biological production of malonate. Non-limiting examples of acyl-CoA hydrolases suitable for modification for malonyl-CoA hydrolysis include any of those from the group consisting of 3-hydroxyisobutyryl-CoA hydrolases (EC 3.1.2.4), 3-hydroxypropionyl-CoA hydrolases (EC 3.1.2.4), acetoacetyl-CoA hydrolases (EC 3.1.2.11), methylmalonyl-CoA hydrolases (EC 3.1.2.17), propionyl-CoA hydrolases (EC 3.1.2.18), succinyl-CoA hydrolases (EC 3.1.2.3), and malonyl CoA: ACP transacylases (EC 2.3.1.39) mutated as provided herein to have malonyl CoA hydrolase activity.

In some embodiments, the malonyl-CoA hydrolase used to produce malonate in accordance with this disclosure is a mutated *S. cerevisiae* EHD3 acyl-CoA hydrolase (see SEQ ID NO:1 for the wild-type EHD3 amino acid sequence). One such mutant with altered substrate specificity is the E124V mutant (see Rouhier, "Characterization of YDR036C from *Saccharomyces cerevisiae*." Dissertation, Miami University, Miami University and OhioLINK (2011)), which, while previously reported, was not reported to have malonyl-CoA hydrolase activity. In some embodiments of this disclosure, an *E. coli* host cell expressing the E124V mutant is used to produce malonate, which is then purified from the cell or fermentation broth. In other embodiments of this disclosure, a yeast cell expressing the E124V mutant is used to produce malonate in accordance with this disclosure. In yet another embodiment, an oleaginous yeast cell expressing the E124V mutant is used to produce malonate in accordance with this disclosure.

Prior attempts to produce the E124A mutant of EHD3 resulted in cell death upon induction of protein expression from a pET28a expression vector; the protein was unable to be purified (see Rouhier, supra). The present disclosure provides expression vectors for the E124A mutant that can be used in *E. coli* host cells, rendering them capable of producing malonate. These *E. coli* expression vectors are characterized in that, relative to the pET28a vector of Rouhier, the E124A mutant is produced at a lower, non-toxic level. This is achieved, for example, by employing expression vectors with a lower copy number or weaker promoter than used by Rouhier. Examples of lower copy number expression vectors include, but are not limited to pSC101 origin expression vectors, p15a origin expression vectors, and expression vectors that integrate into the chromosomal DNA. Examples of weaker promoters than the T7 promoter used by Rouhier include, but are not limited to the $P_{LacO1}$, PTRC, and PBAD promoters. In some embodiments, the vector has a pSC101 origin of replication. In other embodiments, the promoter used for expression of the EHD3 E124A mutant coding sequence is the $P_{lacO1}$ promoter. Additionally, the present disclosure provides vectors for yeast host cells that code for the expression of the E124A mutant. The genetically modified *S. cerevisiae* EHD3 E124A expression vectors of this disclosure can be used in vivo for the production of malonate in *E. coli*, *S. cerevisiae* and *P. kudriavzevii*, and the methods of this disclosure provide means for the subsequent purification of malonate from fermentation broth of these strains, and the synthetic conversion of malonate into derivative small-molecule compounds.

The present disclosure also provides the E124S mutant of EHD3 for use as a malonyl-CoA hydrolase, vectors for expressing this mutant, and host cells that express this mutant and produce malonate (see Example 31). Wild-type *S. cerevisiae* EHD3 catalyzes the hydrolysis of 3-hydroxypropionyl-CoA (3HPA-CoA) and 3-hydroxyisobutyryl-CoA (3HIBA-CoA) and E124 is predicted to interact with the terminal hydroxyl moiety on 3HPA-CoA, stabilizing the substrate in the EHD3 active site (see Rouhier, supra). Certain aspects of this disclosure arise from the discovery that specific E124 point mutations increase enzyme hydrolysis of malonyl-CoA, producing malonate. Mutation of E124 to a nucleophilic amino acid (e.g., S or T), basic amino acid (e.g., H, K, or R), or amide amino acid (e.g., N or Q) improves the binding of malonyl-CoA in the EHD3 active site over 3-hydroxypropionyl-CoA and increases malonate production (relative to the unmutated counterpart enzyme). The E124S, E124T, E124N, E124Q, E124H, E124K, and E124R mutations also decrease production of byproducts (e.g., acetate, propionate, isobutyrate, and succinate) due to decreased hydrolysis of endogenous host cell acyl-CoA molecules. The E124S point mutation places a hydroxyl moiety in a position that promotes hydrogen bonding between the serine residue and the terminal carboxylate group of malonyl-CoA. The E124Q point mutation places the glutamine amide group in a position near the terminal carboxylate group of malonyl-CoA. The E124K point mutation places the lysine amine group in a position that promotes hydrogen bonding between the lysine residue and the terminal carboxylate group of malonyl-CoA. In contrast to the nucleophilic, amide, and basic E124 point mutations described above, mutations E124A and E124V remove the presence of a charged amino acid at position 124; these mutations both eliminate hydrogen bonding between the terminal carboxylate on malonate and the EHD3 124 amino acid sidechain and open the EHD3 active site to promiscuous activity, increasing undesirable byproduct formation and decreasing malonate production.

In some embodiments of this disclosure, an *E. coli* host cell expressing the E124S mutant is used to produce malonate. In other embodiments of this disclosure, a yeast host cell, for example a *Pichia kudriavzevii* host cell, expressing the E124S mutant is used to produce malonate. In other embodiments, an oleaginous yeast host cell expressing the E124S mutant is used to produce malonate. In some embodiments of this disclosure, an *E. coli* host cell expressing the E124Q mutant is used to produce malonate. In other embodiments of this disclosure, a yeast host cell, for example a *Pichia kudriavzevii* host cell, expressing the E124Q mutant is used to produce malonate. In other embodiments, an oleaginous yeast host cell expressing the E124Q mutant is used to produce malonate. In some embodiments of this disclosure, an *E. coli* host cell expressing the E124K mutant is used to produce malonate. In other embodiments of this disclosure, a yeast host cell, for example a *Pichia kudriavzevii* host cell, expressing the E124K mutant is used to produce malonate. In other embodiments, an oleaginous yeast host cell expressing the E124K mutant is used to produce malonate. In some embodiments of this disclosure, an *E. coli* host cell expressing the E124H mutant is used to produce malonate. In other embodiments of this disclosure, a yeast host cell, for example a *Pichia kudriavzevii* host cell, expressing the E124H mutant is used to produce malonate. In other embodiments of this disclosure, an oleaginous yeast host cell expressing the E124H mutant is used to produce malonate. In some embodiments of this disclosure, an *E. coli* host cell expressing the E124R mutant is used to produce malonate. In other embodiments of this disclosure, a yeast host cell, for example a *Pichia kudriavzevii* host cell, expressing the E124R mutant is used to produce malonate. In other embodiments of this disclosure, an oleaginous yeast host cell expressing the E124R mutant is used to produce malonate. In other embodiments, a recombinant host cell expressing an EHD3 E124 nucleophilic amino acid point mutation (i.e., E124S or E124T) is used to produce malonate. In other embodiments, a recombinant host cell expressing an EHD3 E124 basic amino acid point mutation (i.e., E124H, E124K, or E124R) is used to produce malonate. In other embodiments, a recombinant host cell expressing an EHD3 E124 amide amino acid point mutation (i.e., E124N or E124Q) is used to produce malonate.

The present disclosure also provides a mutated EHD3 comprising a mutated active site, vectors for expressing the mutant, and host cells that express the mutant and produce malonate. Certain aspects of the present disclosure arose, in part, from the discovery that specific amino acids (i.e., F121, and F177) are involved in acyl-CoA substrate binding, and introduction of specific point mutations increase malonyl-CoA hydrolysis and production of malonate. Introduction of mutation F121I or F121L increases malonyl-CoA access to the active site. Similarly, introduction of mutation F177I or F177L increases malonyl-CoA access to the active site. One or more point mutations at amino acid positions F121 or F177 can be introduced alone, or along with an E124 point mutation. In various embodiments, a F121 and/or F177 point mutation is introduced along with an E124 point mutation. In some embodiments, a recombinant host cell expressing an EHD3 F121I or F121L mutant is used to produce malonate. In other embodiments, a recombinant host cell expressing an EHD3 F177I or F178L mutant is used to produce malonate. In these embodiments, the recombinant host cell can be, without limitation, an *E. coli* or yeast, including but not limited to *S. cerevisiae*, *P. kudriavzevii* or other yeast, host cell.

The present disclosure also provides mutated EHD3 comprising a mutated mitochondrial targeting sequence, vectors for expressing the mutant, and host cells that express the mutant and produce malonate. In an *S. cerevisiae* host, wild-type EHD3 is localized in the mitochondria. Malonyl-CoA is found in both the mitochondria and the cytosol; EHD3 catalyzed hydrolysis of cytosolic malonyl-CoA requires localization of an EHD3 to the cytosol. Certain aspects of the present disclosure arose from the discovery that mutations of the EHD3 mitochondrial targeting sequence can increase production of malonate. The EHD3 amino acids involved in mitochondrial targeting include R3, K7, K14, K18, and R22, and mutation of one or more of these basic amino acids to a hydrophobic amino acid (i.e., A or V) abrogates mitochondrial targeting. In some embodiments, a recombinant host comprising an EHD3 consisting of one or more mutations to A or V at amino acids selected from the group consisting of R3, K7, K14, K18, and R22 is used to produce malonate. In some embodiments, the recombinant host is a yeast strain. In some embodiments, the recombinant host is *S. cerevisiae*. In some embodiments, the recombinant host cell is *P. kudriavzevii*. In still further embodiments, the recombinant host cell contains one or more copies of an EHD3 with the mitochondrial targeting sequence unaltered (i.e., wild-type) and one or more copies of an EHD3 with the mitochondrial targeting sequence mutated.

Thus, in one aspect of this disclosure, the recombinant host cell comprises a heterologous nucleic acid encoding a mutant *S. cerevisiae* EHD3 that results in increased production of malonate relative to host cells not comprising the mutant EHD3. In some embodiments, the mutant EHD3 is heterologously expressed in *E. coli*. In other embodiments, the mutant EHD3 is heterologously expressed in *S. cerevisiae*. In other embodiments, the mutant EHD3 is heterologously expressed in *P. kudriavzevii*. In other embodiments, the mutant EHD3 is heterologously expressed in an oleaginous yeast cell. In some embodiments, the mutant EHD3 contains a point mutation at position E124. In some embodiments, the point mutation at residue E124 is either E124A or E124V. In some embodiments, the point mutation at E124 is E124S or E124T. In some embodiments, the point mutation at E124 is E124S. In some embodiments, the point mutation at E124 is a basic amino acid selected from the group consisting of E124H, E124K, and E124R. In some embodiments, the point mutation at E124 is E124H. In some embodiments, the point mutation at E124 is E124K. In some embodiments, the point mutation at E124 is E124R. In some embodiments, the point mutation at residue E124 is E124N or E124Q. In some embodiments, the point mutation at residue E124 is E124Q. In some embodiments, one or more EHD3 amino acids selected from the group consisting of F121 and F177 are mutated to I or L. In some embodiments, one or more EHD3 amino acids selected from the group consisting of R3, K7, K14, K18, and R22 are mutated to either A or V.

In another aspect of this disclosure, an enzyme other than, or in addition to, EHD3 is utilized as a malonyl-CoA hydrolase to produce malonate in accordance with this disclosure. In some embodiments, *Haemophilus influenzae* YciA is heterologously expressed in a host cell to produce malonate in accordance with this disclosure (see Zhuang et al. *Biochemistry* 47: 2789-2796 (2008)). In other embodiments, the malonyl-CoA hydrolase is an acyl-CoA hydrolase endogenous to *Rattus norvegicus* (see Kovachy et al., *J. Biol. Chem.* 258:11415-11421 (1983)). In other embodiments, the malonyl-CoA hydrolase is the acyl-CoA hydrolase from brown adipose tissue mitochondrial protein fraction from Mesocricetus auratus (see Alexson et al., *J. Biol. Chem.* 263:13564-13571 (1988)).

Thus, in accordance with some embodiments of this disclosure, acyl-CoA hydrolases other than, or in addition to, EHD3 (from *S. cerevisiae* or homologous enzymes from other organisms) can be used for biological synthesis of malonate in a recombinant host. In some embodiments, the recombinant host is *S. cerevisiae*. In other embodiments, the recombinant host is *E. coli*. In other embodiments, the recombinant host is a yeast other than *S. cerevisiae*, for example a *Pichia kudriavzevii* host cell. In various embodiments, the host is modified to express a mutated enzyme selected from the group consisting of S. albicans EHD3, *H. sapiens* HIBCH (UniProt:Q6NVY1), *A. thaliana* CHY1 (UniProt:Q9LKJ1), *R. norvegicus* HIBCH (UniProt: Q5XIE6), *M. musculus* HIBCH (UniProt: Q8QZ S1), *G. gallus* HIBCH (UniProt:Q5ZJ60), *B. taurus* HIBCH (UniProt:Q2HJ73), *D. rerio* HIBCH (UniProt: Q58EB4), *B. cereus* Bch, *P. aeruginosa* Hich, *E. coli* YciA, *H. influenzae* YciA, *M. musculus* ACOT4, *M. musculus* ACOT8, *S. enterica* SARI 01218, *A. pernix* K1, *C. hutchinsonii* Chut02003666, *S. solfataricus* P2 SS02287, *S. acidocaldarius* DSM 639 Saci_0145, *P. aerophilum* str. IM2 PAE3404, *D. melanogaster* CG1635, *P. carbinolicus* DSM 2380 Pcar 1366, *A. dehalogenans* 2CP-C 110, *G. gallus* ACOT9, and *X. laevis* MGC114623.

One or multiple suitably mutated acyl-CoA hydrolases can be used in accordance with this disclosure to convert malonyl-CoA to malonate in a host cell. Moreover, acyl-CoA hydrolases other than those specifically disclosed herein can be utilized in mutated or heterologously expressed form, and other appropriate enzymes can be identified, modified, and expressed to achieve the desired malonyl-CoA hydrolase activity as disclosed herein.

Consensus Sequences

Malonyl-CoA hydrolases of this disclosure include those that are homologous to consensus sequences provided by this disclosure. As noted above, any enzyme substantially homologous to an enzyme specifically described herein can be used in a host cell of this disclosure. One enzyme is homologous to another (the "reference enzyme") when it exhibits the same activity of interest and can be used for substantially similar purposes. Generally, homologous enzymes share substantial sequence identity. Sets of homologous enzymes generally possess one or more specific amino acids that are conserved across all members of the consensus sequence protein class.

The present disclosure provides consensus sequences useful in identifying and constructing malonyl-CoA hydrolases of this disclosure. In various embodiments, these malonyl-CoA hydrolase consensus sequences contain active site amino acid residues believed to contribute to the formation of an oxyanion hole responsible for stabilizing the enolate anion intermediate derived from a malonyl-CoA substrate as well as the amino acid residues involved with malonyl-CoA binding. A homologous enzyme, relative to a consensus sequence provided by this disclosure, may have different amino acids at non-conserved positions or amino acid(s) inserted or deleted, so long as those differences do not negatively affect or only insignificantly negatively affect the malonyl-CoA hydrolysis activity of interest. Thus, a homologous enzyme has an enzymatic activity that is identical, or essentially identical, or at least substantially similar with respect to ability to hydrolyze malonyl CoA to that of one of the enzymes exemplified herein. A homologous enzyme may be found in nature or be an engineered mutant thereof. A homologous enzyme may be identified or constructed from another enzyme by comparison to a consensus sequence herein; if an enzyme shares substantial homology to a consensus sequence herein but has suboptimal, including no, malonyl-CoA hydrolase activity, then, in accordance with this disclosure, it is mutated to conform to a consensus sequence provided herein to provide a malonyl-CoA hydrolase of this disclosure.

This disclosure provides four malonyl-CoA hydrolase consensus sequences: (i) malonyl-CoA hydrolase based on EHD3 EC 3.1.2.4 (ii) malonyl-CoA hydrolase based on *Bacillus* EC 3.1.2.4 malonyl-CoA hydrolase, (iii) malonyl-CoA hydrolase based on *Pseudomonas* EC 3.1.2.4 malonyl-CoA hydrolase, and (iv) malonyl-CoA hydrolase based on from both *Bacillus* and *Pseudomonas* EC 3.1.2.4. The consensus sequences provide a sequence of amino acids in which each position identifies the amino acid most likely to be found at a specified position in a malonyl-CoA hydrolase of that class. In the consensus sequences, a dash (−) indicates the presence of a gap that may exist when a homologous enzyme sequence is aligned against the consensus sequence. A plus (+) indicates a position in the consensus sequence where the amino acid is highly non-conserved; a homologous protein may contain one of many different amino acids at these non-conserved positions. One-letter amino acid codes are defined above. At some positions shown in the consensus sequence, the homologus enzyme may contain one of several amino acids, and for these positions, additional one letter codes are as follows: B (amino acid is R, K, or H), J (amino acid is D or E), 0 (amino acid is I, L, or V), U (amino acid is S or T), and $X_1$ (amino acid is R, H, K, S, T, N, Q, Y).

EHD3 EC 3.1.2.4 Malonyl-CoA Hydrolase Consensus Sequence

This disclosure provides an EHD3 malonyl-CoA hydrolase consensus sequence (SEQ ID NO:7), and in various embodiments, suitable malonyl-CoA hydrolases for use in the methods of this disclosure have at least 63% identity to this EHD3 malonyl-CoA hydrolase consensus sequence. In various embodiments, the malonyl-CoA hydrolases suitable for use in the methods of this disclosure have 65%, 70%, 80%, 90%, or 95% or more identity to this EHD3 consensus sequence. Proteins having homology to this consensus sequence include UniProt ID: C5DE94 (63% identity), UniProt ID: Q6CJH2 (64% identity), UniProt ID: G2WAE2 (66% identity), UniProt ID: J8Q6P9 (66% identity), UniProt ID: G8COHO (68% identity), UniProt ID: C5DX08 (68% identity), UniProt ID: P28817 (69% identity), UniProt ID: A7TTD5 (69% identity), UniProt ID: J7S9J9 (70% identity), UniProt ID: Q6FM09 (71% identity), UniProt ID: I2H4L2 (71% identity), UniProt ID: H2AME2 (73% identity), UniProt ID: G8ZTJ4 (77% identity), UniProt ID: G0W4I8 (77% identity), UniProt ID: G0V818 (78% identity), and UniProt ID: J5S5X3 (79% identity). In some embodiments, an EHD3 malonyl-CoA hydrolase with equal to or greater than 63% identity to the consensus sequence SEQ ID NO:7 is expressed in a recombinant host cell and used to produce malonate in accordance with this disclosure.

In mutant and wild-type enzymes homologous to this consensus sequence (SEQ ID NO: 7), amino acids that are highly conserved are V101, R110, L114, R116, K119, L120, N121, A122, L123, L135, E137, Y138, K140, S141, S151, R156, C159, G161, G162, D163, V164, A168, F185, E188, Y189, S190, N192, A196, T197, K200, M206, G208, I209, T210, M211, G212, G213, G214, V215, G216, H220, P222, F223, R224, T227, E228, T230, M234, P235, E236, D238, I239, G240, F242, P243, D244, V245, F249, P252, Q263, Y267, L268, T271, G272, G277, G284, S287, H288, Y289, L298, R301, L302, E304, E333, F334, L352, V354, I355, F359, L374, F391, L399, K402, S403, S406, N417, D429, L430, T432, A433, E449, F450, K457, L458, K461, W468, L494, T502, Y506, P507, L514, P515, and K561. In various embodiments, malonyl-CoA hydrolase enzymes homologous to this consensus sequence (SEQ ID NO:7) contain at least a plurality of these conserved amino acids, often a majority of these conserved amino acids, and sometimes all of these conserved amino acids.

Some amino acids in this consensus sequence (SEQ ID NO:7) contribute to activity and conserved across all members of the class. Malonyl-CoA hydrolase enzymes in the EHD3 class contain six active site residues involved with hydrolase activity: (i) three active site amino acid residues (G161, G162, G213) in the consensus sequence believed to contribute to the formation of an oxyanion hole responsible for stabilizing the enolate anion intermediate derived from the malonyl-CoA substrate; (ii) two amino acid residues (E236, D244) of the consensus sequence useful for acyl-CoA hydrolysis; and (iii) an amino acid residue at position 188 (of SEQ ID NO:7) believed to contribute to malonyl-CoA substrate binding. Of these six residues, then, five are present in the consensus sequence (SEQ ID NO:7), and the sixth, at position 188 (amino acid $X_1$ in the consensus) is selected from the group of polar or positively charged amino acids (R, H, K, S, T, N, Q, Y) to provide a malonyl CoA hydrolase of this disclosure capable of producing malonate in a recombinant host cell. The six residues from the consensus sequence (G161, G162, G213, E236, D244, $X_1$188) correspond to G99, G100, G149, E172, D180, and E124 (typically mutated to $X_1$), respectively, in *S. cerevisiae* EHD3 used to illustrate this disclosure in example 31.

*Bacillus* EC 3.1.2.4 Malonyl-CoA Hydrolase Consensus Sequence

This disclosure provides a *Bacillus* EC 3.1.2.4 malonyl-CoA hydrolase consensus sequence (SEQ ID NO:8), and in various embodiments, suitable malonyl-CoA hydrolases for use in the methods of this disclosure have at least 86% identity to this *Bacillus* EC 3.1.2.4 malonyl-CoA hydrolase consensus sequence. In various embodiments, the malonyl-CoA hydrolases suitable for use in the methods of this disclosure have 90%, or 95% or more identity to this *Bacillus* EC 3.1.2.4 malonyl-CoA hydrolase consensus sequence. Proteins having homology to this consensus sequence include *Bacillus* EC 3.1.2.4 proteins UniProt ID: C2TX63 (92% identity), UniProt ID: C2UV40 (91% identity), UniProt ID: C2QBT2 (93% identity), UniProt ID: C2XTU0 (93% identity), UniProt ID: C2PVQ0 (93% identity), UniProt ID: C3A5N3 (93% identity), UniProt ID: C2SJV4 (93% identity), UniProt ID: C2Z7U1 (92% identity), UniProt ID: C2VTI4 (97% identity), UniProt ID: B3Z9Y3 (97% identity), UniProt ID: B7JNH7 (97% identity), UniProt ID: Q63BK8 (97% identity), UniProt ID: B0Q3Q4 (97% identity), UniProt ID: B0AQXO (97% identity), UniProt ID: B3YSW2 (97% identity), UniProt ID: C2NHG5 (97% identity), UniProt ID: B3ZIZ8 (97% identity), UniProt ID: C2QSV2 (97% identity), UniProt ID: C3C255 (97% identity), UniProt ID: B5UZZ1 (96% identity), UniProt ID: C2MKL7 (95% identity), UniProt ID: B9IZZ9 (95% identity), UniProt ID: FOPNG8 (95% identity), UniProt ID: Q738L0 (97% identity), UniProt ID: C2PEV7 (95% identity), UniProt ID: C2YRH7 (96% identity), UniProt ID: Q4MU30 (95% identity), UniProt ID: Q81DR3 (96% identity), UniProt ID: C2W7W8 (89% identity), and UniProt ID: A7GPH6 (86% identity). In various embodiments, a Bacillus EC 3.1.2.4 malonyl-CoA hydrolase with equal to or greater than 86% identity to the consensus sequence SEQ ID NO:8 is expressed in a recombinant host cell and used to produce malonate in accordance with this disclosure.

In mutant and wild type enzymes homologous to this consensus sequence (SEQ ID NO:8) amino acids that are highly conserved are M1, T2, E3, V5, L6, F7, S8, G13, V14, A15, I17, T18, L19, N20, R21, P22, K23, A24, L25, N26, S27, L28, S29, Y30, M32, L33, I36, G37, K39, L40, K41, E42, W43, E44, I49, I52, V53, L54, K55, G56, A57, G58, K60, G61, F62, C63, A64, G65, G66, D67, I68, K69, T70, L71, Y72, E73, A74, R75, S76, N77, E78, A80, L81, Q82, A84, E85, F87, F88, E90, E91, Y92, I94, D95, T96, Y99, Y101, K103, P104, I105, I106, A107, C108, L109, D110, G111, I112, V113, M114, G115, G116, G117, V118, G119, L120, T121, N122, G123, A124, R127, I128, V129, T130, T133, K134, W135, A136, M137, P138, E139, M140, N141, I142, G143, F144, F145, P146, D147, V148, G149, A150, A151, Y152, F153, L154, N155, A157, P158, G159, G162, V165, A166, L167, A169, L172, K173, A174, D176, V177, L178, I180, A182, A183, D184, L192, F195, L196, W204, V210, L214, K215, L231, E236, H241, F242, E248, I250, I251, S253, L254, E255, F261, L269, L270, S271, K272, S273, P274, S276, L277, K278, V279, T280, L281, K282, Q283, G287, K290, S291, E293, C295, F296, A297, T298, D299, L300, L302, A303, K304, N305, F306, M307, R308, H309, D311, F312, F313, E314, G315, V316, R317, S318, V320, D322, K323, D324, Q325, N326, P327, Y329, K330, Y331, D336, V337, V342, N343, F345, F346, L348, and L349. In various embodiments, malonyl-CoA hydrolase enzymes homologous to this consensus sequence (SEQ ID NO:8) contain at least a plurality of these conserved amino acids, often a majority of these conserved amino acids, and sometimes all of these conserved amino acids.

Some amino acids in this consensus sequence (SEQ ID NO:8) contribute to activity and conserved across all members of the class. Malonyl-CoA hydrolase enzymes in the Bacillus EC 3.1.2.4 class contain six active site residues involved with hydrolase activity: (i) three active site amino acid residues (G65, G66, G116) of the consensus sequence believed to contribute to the formation of an oxyanion hole responsible for stabilizing the enolate anion intermediate derived from the malonyl-CoA substrate; (ii) two amino acid residues (E139, D147) of the consensus sequence contribute to acyl-CoA hydrolysis; and (iii) a mutated amino acid ($X_1$91) (of SEQ ID NO:8) believed to contribute to malonyl-CoA substrate binding. Of these six residues, then, five are present in the consensus sequence (SEQ ID NO:8), and the sixth, $X_1$91 provides a malonyl CoA hydrolase of this disclosure capable of producing malonate in a recombinant host cell. The six residues from the consensus sequence (G65, G66, G116, E139, D147, $X_1$91) correspond to G65, G66, G116, E139, D147, and E91 (typically mutated to $X_1$), respectively, in Bacillus thuringiensis subsp. *finitimus* (strain YBT-020) FOPNG8 used to illustrate this disclosure in example 31.

Non-limiting examples of enzymes suitable for malonyl-CoA hydrolysis homologous to the consensus sequence (SEQ ID NO:8) and encoded by cloned or synthesized nucleic acids provided by this disclosure include mutant enzymes containing at least one mutation illustrated by the group of mutant enzymes consisting of *Bacillus cereus* (strain Q1) B9IZZ9 (E91S), B9IZZ9 (E91A), B9IZZ9 (E91H), B9IZZ9 (E91K), B9IZZ9 (E91R), B9IZZ9 (E91Q); *Bacillus thuringiensis* subsp. *finitimus* (strain YBT-020) FOPNG8 (E91S), FOPNG8 (E91A), FOPNG8 (E91H), FOPNG8 (E91K), FOPNG8 (E91R), FOPNG8 (E91Q); *Bacillus cereus* (strain ATCC 14579/DSM 31) Q81DR3, Q81DR3 (E91S), Q81DR3 (E91A), Q81DR3 (E91H), Q81DR3 (E91K), Q81DR3 (E91R), Q81DR3 (E91Q); *Bacillus cereus* (strain ZK/E33L) Q63BK8, Q63BK8 (E91S), Q63BK8 (E91A), Q63BK8 (E91H), Q63BK8 (E91K), Q63BK8 (E91R), Q63BK8 (E91Q).

*Pseudomonas* EC 3.1.2.4 Malonyl-CoA Hydrolase Consensus Sequence

This disclosure provides a *Pseudomonas* EC 3.1.2.4 malonyl-CoA hydrolase consensus sequence (SEQ ID NO:9), and in various embodiments, suitable malonyl-CoA hydrolases for use in the methods of this disclosure have at least 75% identity to this Pseudomonas EC 3.1.2.4 malonyl-CoA hydrolase consensus sequence. In various embodiments, the malonyl-CoA hydrolases suitable for use in the methods of this disclosure have 80%, 90%, or 95% or more identity to this Pseudomonas EC 3.1.2.4 consensus sequence. Proteins having homology to this consensus sequence Pseudomonas EC 3.1.2.4 proteins UniProt ID: F5KBQ4 (80% identity), UniProt ID: A6VAN3 (81% identity), UniProt ID: A4XS22 (81% identity), UniProt ID: F6AA82 (75% identity), UniProt ID: E2XN63 (84% identity), UniProt ID: F2KE35 (85% identity), UniProt ID: C3KDS5 (83% identity), UniProt ID: F8G3B7 (86% identity), UniProt ID: G8PYD2 (85% identity), UniProt ID: Q4KGS1 (82% identity), UniProt ID: Q3KGL5 (85% identity), UniProt ID: BOKV51 (86% identity), UniProt ID: B1J4J2 (86% identity), UniProt ID: A5W8H3 (86% identity), UniProt ID: Q88N06 (86% identity), UniProt ID: Q1I5T5 (84% identity), UniProt ID: F8H1A4 (77% identity), UniProt ID: A4VIV7 (77% identity), and UniProt ID: Q915I5 (81% identity). In some embodiments, a *Pseudomonas* EC 3.1.2.4 malonyl-CoA hydrolase with equal to or greater than 75% identity to the consensus sequence SEQ ID NO:9 is expressed in a recombinant host cell and used to produce malonate in accordance with this disclosure.

Highly conserved amino acids in this consensus sequence (SEQ ID NO:9) are M1, E6, G13, R15, I16, A19, L21, D22, A23, L27, N28, A29, L30, L32, P33, M34, I35, L38, W45, A46, C53, V54, L56, R57, G58, N59, G60, K62, A63, F64, C65, A66, G67, G68, V70, L73, C77, P81, G82, P85, L87, A88, F91, F92, Y96, R97, L98, H103, P106, K107, P108, C111, W112, H114, G115, V117, G119, G120, G121, M122, G123, L124, Q126, R131, I132, V133, T134, P135, R138, L139, M141, P142, E143, I146, G147, L148, D151, V152, G153, S155, F157, L158, R160, P162, G163, L165, G166, L167, F168, L171, N177, D180, A181, D183, L184, L186, A187, D188, R189, Q195, Q196, L199, L203, Q205, N207, W208, E210, Q215, L216, S218, L219, A222, P232, L237, R239, R240, D244, L247, D248, A258, D267, L269, G280, P282, V288, W289, Q291, R294, R296, L298, S299, L300, E307, Y308, S311, L312, N313, C314, R316, H317, P318, F320, E322, G323, V324, R325, A326, R327, L328, D330, D332, P335, W337, W339, P346, A352, H353, and F354. In various embodiments, malonyl-CoA hydrolase enzymes homologous to this consensus sequence (SEQ ID NO:9) contain at least a plurality of these conserved amino acids, often a majority of these conserved amino acids, and sometimes all of these conserved amino acids.

Some amino acids in this consensus sequence (SEQ ID NO:9) contribute to activity and conserved across all members of the class. Malonyl-CoA hydrolase enzymes in the Pseudomonas EC 3.1.2.4 class contain six conserved active site residues that contribute to hydrolase activity (i) three active site amino acid residues (G67, G68, G120) of the consensus sequence believed to contribute to the formation of an oxyanion hole responsible for stabilizing the enolate anion intermediate derived from an acyl-CoA substrate; (ii) two amino acid residues (E143, D151) of the consensus sequence believed to contribute to acyl-CoA hydrolysis; and (iii) amino acid $X_1 95$ (of SEQ ID NO:9) is believed to contribute to malonyl-CoA substrate binding. In various embodiments of this disclosure, the wild-type glutamic acid residue (E95) is (has been) mutated to a polar or positively charged amino acid (i.e. R, H, K, S, T, N, Q, Y) to produce $X_1 95$ and provide a malonyl CoA hydrolase of this disclosure capable of producing malonate in a recombinant host cell. The six residues from the consensus sequence (G67, G68, G120, E143, D151, $X_1 95$) correspond to G67, G68, G120, E143, D151, and E95 (typically mutated to $X_1$), respectively, in *Pseudomonas aeruginosa* (strain ATCC 15692/PAO1/1C/PRS 101/LMG 12228) F6AA82-2 used to illustrate this disclosure in example 31.

Non-limiting examples of enzymes suitable for malonyl-CoA hydrolysis homologous to the consensus sequence (SEQ ID NO:9) and encoded by cloned or synthesized nucleic acids provided by this disclosure include mutant enzymes containing at least one mutation illustrated by the group of mutant enzymes consisting of *Pseudomonas aeruginosa* (strain ATCC 15692/PAO1/1C/PRS 101/LMG 12228) F6AA82-2 (E95S), F6AA82-2 (E95A), F6AA82-2 (E95H), F6AA82-2 (E95K), F6AA82-2 (E95R), F6AA82-2 (E95Q); *Pseudomonas fluorescens* WH6 E2XN63-1 (E95S), E2XN63-1 (E95A), E2XN63-1 (E95H), E2XN63-1 (E95K), E2XN63-1 (E95R), E2XN63-1 (E95Q); *Pseudomonas mendocina* (strain ymp) A4XS22-1 (E95S), A4XS22-1 (E95A), A4XS22-1 (E95H), A4XS22-1 (E95K), A4XS22-1 (E95R), A4XS22-1 (E95Q); *Pseudomonas putida* (strain F1/ATCC 700007) A5W8H3-1 (E95S), A5W8H3-1 (E95A), A5W8H3-1 (E95H), A5W8H3-1 (E95K), A5W8H3-1 (E95R), A5W8H3-1 (E95Q).

In various embodiments of this disclosure the malonyl-CoA hydrolase is E95S mutation of F6AA82-2 from *Pseudomonas aeruginosa* (strain ATCC 15692/PAO1/1C/PRS 101/LMG 12228), E2XN63-1 from *Pseudomonas fluorescens* WH6, A4XS22-1 from *Pseudomonas mendocina* (strain ymp) or A5W8H3-1 from *Pseudomonas putida* (strain F1/ATCC 700007) as illustrated in Example 31.

Bacterial EC 3.1.2.4 Malonyl-CoA Hydrolase Consensus Sequence

Despite *Bacillus* and *Pseudomonas* being evolutionarily distant (i.e. *Bacillus* is gram-positive and *Pseudomonas* is gram-negative), there is sequence conservation between the *Bacillus* EC 3.1.2.4 and *Pseudomonas* EC 3.1.2.4 proteins, The present disclosure provides a malonyl-CoA hydrolase consensus sequence for bacterial EC 3.1.2.4 acyl-CoA hydrolases (SEQ ID NO:10). Proteins homologous to the bacterial EC 3.1.2.4 malonyl-CoA hydrolase consensus sequence typically possess a plurality (or a majority or all) of the highly conserved amino acids from this sequence, which conserved amino acids are selected from the group consisting of L53, L59, N60, L62, M66, L88, F97, C98, A99, G100, G101, F124, F125, Y129, K140, P141, G148, G152, G153, G154, G156, L157, T167, M174, P175, E176, I179, G180, D184, V185, G186, L191, L210, D219, A226, P333, N364, F375, E377, D385, and P390. A suitable malonyl-CoA hydrolase provided by this disclosure that is homologous to this consensus sequence will comprise the active site amino acids that contribute to malonyl-CoA hydrolysis (G100, G101, G153, E176, and D184) of the consensus sequence, as well as a $X_1 128$, where the wild-type glutamic acid residue (E128) is (has been) mutated to a polar or charged amino acid (i.e. R, H, K, S, T, N, Q, Y) and is capable of producing malonate in a recombinant host cell.

Malonyl-CoA Hydrolases Derived from Malonyl CoA: ACP Transacylases

In yet other embodiments of this disclosure, the malonyl-CoA hydrolase selected from the group malonyl CoA:ACP transacylases (EC 2.3.1.39), containing any or all of the following amino acid modifications: S92, S92C, H201, H2O1N, R117, R117D, R117E, R117N, R117Y, R117G, R117H, Q11, Q11D, Q11E, Q11N, Q11Y, Q11G, Q11H, L93, L93A, L93V, L93I, L93F, L93S, L93G. These positions are based on *Escherichia coli* malonyl CoA:ACP transacylases, FabD.

In some embodiments of this disclosure the malonyl CoA:ACP transacylase is *E. coli* FabD. Example 37 teaches that yeast cells expressing a heterologous FabD containing the following combinations of mutations S92C/L91V/R117H, L91I/R117Y/A246E, Q80L/L91S/R117G, and L91I/R117Y produce malonic acid at levels higher than cells not expressing these mutant proteins.

Section 3: Expression Vectors

In various aspects of the present disclosure, the recombinant host cell has been modified by "genetic engineering" to produce a recombinant malonyl-CoA hydrolase enzyme and malonate. The host cell is typically engineered via recombinant DNA technology to express heterologous nucleic acids that encode a malonyl-CoA hydrolase, which is either a mutated version of a naturally occurring acyl-CoA hydrolase or transacylase or a non-naturally occurring malonyl-CoA hydrolase prepared in accordance with one of the consensus sequences provided herein or is a naturally occurring acyl-CoA hydrolase with malonyl-CoA hydrolase activity that is either overexpressed in the cell in which it naturally occurs or is heterologously expressed in a cell in which it does not naturally occur.

Nucleic acid constructs of the present disclosure comprise expression vectors that comprise nucleic acids encoding one or more malonyl-CoA hydrolase enzymes. The nucleic acids encoding the enzymes are operably linked to promoters and optionally other control sequences such that the subject enzymes are expressed in a host cell containing the expression vector when cultured under suitable conditions. The promoters and control sequences employed depend on the host cell selected for the production of malonate. Thus, this disclosure provides not only expression vectors but also nucleic acid constructs useful in the construction of expression vectors. Methods for designing and making nucleic acid constructs and expression vectors generally are well known to those skilled in the art and so are only briefly reviewed herein.

Nucleic acids encoding the malonyl-CoA hydrolase enzymes can be prepared by any suitable method known to those of ordinary skill in the art, including, for example, direct chemical synthesis and cloning. Further, nucleic acid sequences for use in this disclosure can be obtained from commercial vendors that provide de novo synthesis of the nucleic acids.

A nucleic acid encoding the desired enzyme can be incorporated into an expression vector by known methods that include, for example, the use of restriction enzymes to cleave specific sites in an expression vector, e.g., plasmid, thereby producing an expression vector of this disclosure. Some restriction enzymes produce single stranded ends that may be annealed to a nucleic acid sequence having, or synthesized to have, a terminus with a sequence complementary to the ends of the cleaved expression vector. The ends are then covalently linked using an appropriate enzyme, e.g., DNA ligase. DNA linkers may be used to facilitate linking of nucleic acids sequences into an expression vector.

A set of individual nucleic acid sequences can also be combined by utilizing polymerase chain reaction (PCR)-based methods known to those of skill in the art. For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be joined and subsequently transduced into a host cell simultaneously. Thus, expression of each of the plurality of nucleic acid sequences is affected.

A typical expression vector contains the desired nucleic acid sequence preceded and optionally followed by one or more control sequences or regulatory regions, including a promoter and, when the gene product is a protein, ribosome binding site, e.g., a nucleotide sequence that is generally 3-9 nucleotides in length and generally located 3-11 nucleotides upstream of the initiation codon that precede the coding sequence, which is followed by a transcription terminator in the case of E. coli or other prokaryotic hosts. See Shine et al., Nature 254:34 (1975) and Steitz, in Biological Regulation and Development: Gene Expression (ed. R. F. Goldberger), vol. 1, p. 349 (1979) Plenum Publishing, N.Y. In the case of eukaryotic hosts like yeast a typical expression vector contains the desired nucleic acid coding sequence preceded by one or more regulatory regions, along with a Kozak sequence to initiate translation and followed by a terminator. See Kozak, Nature 308:241-246 (1984).

Regulatory regions or control sequences include, for example, those regions that contain a promoter and an operator. A promoter is operably linked to the desired nucleic acid coding sequence, thereby initiating transcription of the nucleic acid sequence via an RNA polymerase. An operator is a sequence of nucleic acids adjacent to the promoter, which contains a protein-binding domain where a transcription factor can bind. Transcription factors activate or repress transcription initiation from a promoter. In this way, control of transcription is accomplished, based upon the particular regulatory regions used and the presence or absence of the corresponding transcription factor. Non-limiting examples for prokaryotic expression include lactose promoters (Lad repressor protein changes conformation when contacted with lactose, thereby preventing the Lad repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Non-limiting examples of promoters to use for eukaryotic expression include pTDH3, pTEF1, pTEF2, pRNR2, pRPL18B, pREV1, pGAL1, pGAL10, pGAPDH, pCUP1, pMET3, pPGK1, pPYK1, pHXT7, pPDC1, pFBA1, pTDH2, pPGI1, pPDC1, pTPI1, pENO2, pADH1, and pADH2. As will be appreciated by those of ordinary skill in the art, these and other expression vectors or elements may be used in the present disclosure, and this disclosure is not limited in this respect.

Although any suitable expression vector may be used to incorporate the desired sequences, readily available expression vectors include, without limitation: plasmids, such as pESC, pTEF, p414CYC1, p414GALS, pSC101, pBR322, pBBR1MCS-3, pUR, pEX, pMR100, pCR4, pBAD24, pUC19, pRS series; and bacteriophages, such as M13 phage and λ phage. Of course, such expression vectors may only be suitable for particular host cells or for expression of particular malonyl-CoA hydrolases. One of ordinary skill in the art, however, can readily determine through routine experimentation whether any particular expression vector is suited for any given host cell or protein. For example, the expression vector can be introduced into the host cell, which is then monitored for viability and expression of the sequences contained in the vector. In addition, reference may be made to the relevant texts and literature, which describe expression vectors and their suitability to any particular host cell. In addition to the use of expression vectors, strains are built where expression cassettes are directly integrated into the host genome.

The expression vectors are introduced or transferred, e.g. by transduction, transfection, or transformation, into the host cell. Such methods for introducing expression vectors into host cells are well known to those of ordinary skill in the art. For example, one method for transforming E. coli with an expression vector involves a calcium chloride treatment wherein the expression vector is introduced via a calcium precipitate.

For identifying whether a nucleic acid has been successfully introduced or into a host cell, a variety of methods are available. For example, a culture of potentially transformed host cells may be separated, using a suitable dilution, into individual cells and thereafter individually grown and tested for expression of a desired gene product of a gene contained in the introduced nucleic acid. For example, an often-used practice involves the selection of cells based upon antibiotic resistance that has been conferred by antibiotic resistance-conferring genes in the expression vector, such as the amp, gpt, neo, and hyg genes.

Typically, a host cell of this disclosure will have been transformed with at least one expression vector. When only a single expression vector is used, the vector will typically contain a malonyl-CoA hydrolase gene. Once the host cell has been transformed with the expression vector, the host cell is cultured in a suitable medium containing a carbon source, such as a sugar (e.g., glucose). As the host cell is cultured, expression of the enzyme(s) for producing malonate occurs. Once expressed, the enzyme(s) catalyzes the steps shown in FIG. 1.

If a host cell of this disclosure is to comprise more than one heterologous gene, the multiple genes can be expressed from one or more vectors. For example, a single expression vector can comprise one, two, or more genes encoding one, two, or more malonyl-CoA hydrolase enzyme(s) and/or other proteins providing some useful function, e.g. improved malonate yield, titer, and/or productivity. The heterologous genes can be contained in a vector replicated episomally or in a vector integrated into the host cell genome, and where more than one vector is employed, then all vectors may replicate episomally (extrachromasomally), or all vectors may integrate, or some may integrate and some may replicate episomally. Chromosomal integration is typically used for cells that will undergo sustained propagation, e.g., cells used for production of malonate for industrial applications. While a "gene" is generally composed of a single promoter and a single coding sequence, in certain host cells, two or more coding sequences may be controlled by one promoter in an operon. In some embodiments, a two or three operon system is used.

In some embodiments, the coding sequences employed have been modified, relative to some reference sequence, to reflect the codon preference of a selected host cell. Codon usage tables for numerous organisms are readily available and can be used to guide sequence design. The use of prevalent codons of a given host organism generally improves translation of the target sequence in the host cell. As one non-limiting example, in some embodiments the subject nucleic acid sequences will be modified for yeast codon preference (see, for example, Bennetzen et al., *J. Biol. Chem.* 257: 3026-3031 (1982)). In some embodiments, the nucleotide sequences will be modified for *E. coli* codon preference (see, for example, Nakamura et al., *Nucleic Acids Res.* 28:292 (2000)).

Nucleic acids can be prepared by a variety of routine recombinant techniques. Briefly, the subject nucleic acids can be prepared from genomic DNA fragments, cDNAs, and RNAs, all of which can be extracted directly from a cell or recombinantly produced by various amplification processes including but not limited to PCR and rt-PCR. Subject nucleic acids can also be prepared by a direct chemical synthesis.

The nucleic acid transcription levels in a host microorganism can be increased (or decreased) using numerous techniques. For example, the copy number of the nucleic acid can be increased through use of higher copy number expression vectors comprising the nucleic acid sequence, or through integration of multiple copies of the desired nucleic acid into the host microorganism's genome. Non-limiting examples of integrating a desired nucleic acid sequence onto the host chromosome include recA-mediated recombination, lambda phage recombinase-mediated recombination and transposon insertion. Nucleic acid transcript levels can be increased by changing the order of the coding regions on a polycistronic mRNA or breaking up a polycistronic operon into multiple poly- or mono-cistronic operons each with its own promoter. RNA levels can be increased (or decreased) by increasing (or decreasing) the strength of the promoter to which the protein-coding region is operably linked. Illustrative techniques for plasmid design and assembly to afford malonate production are provided in Examples 31 and 37.

The translation level of a desired polypeptide sequence in a host microorganism can also be increased in a number of ways. Non-limiting examples include increasing the mRNA stability, modifying the ribosome binding site (or Kozak) sequence, modifying the distance or sequence between the ribosome binding site (or Kozak sequence) and the start codon of the nucleic acid sequence coding for the desired polypeptide, modifying the intercistronic region located 5' to the start codon of the nucleic acid sequence coding for the desired polypeptide, stabilizing the 3'-end of the mRNA transcript, modifying the codon usage of the polypeptide, altering expression of low-use/rare codon tRNAs used in the biosynthesis of the polypeptide. Determination of preferred codons and low-use/rare codon tRNAs can be based on a sequence analysis of genes derived from the host microorganism.

The polypeptide half-life, or stability, can be increased through mutation of the nucleic acid sequence coding for the desired polypeptide, resulting in modification of the desired polypeptide sequence relative to the control polypeptide sequence. When the modified polypeptide is an enzyme, the activity of the enzyme in a host may be altered due to increased solubility in the host cell, improved function at the desired pH, removal of a domain inhibiting enzyme activity, improved kinetic parameters (lower Km or higher Kcat values) for the desired substrate, removal of allosteric regulation by an intracellular metabolite, and the like. Altered/modified enzymes can also be isolated through random mutagenesis of an enzyme, such that the altered/modified enzyme can be expressed from an episomal vector or from a recombinant gene integrated into the genome of a host microorganism.

Recombinant Host Cells

In one aspect, this disclosure provides recombinant host cells suitable for biological production of malonate. Any suitable host cell may be used in practice of the methods of the present disclosure. In some embodiments, the host cell is a recombinant host microorganism in which nucleic acid molecules have been inserted, deleted or modified (i.e., mutated; e.g., by insertion, deletion, substitution, and/or inversion of nucleotides), either to produce malonate, or to increase yield, titer, and/or productivity of malonate relative to a "control cell" or "reference cell". A "control cell" can be used for comparative purposes and is typically a wild-type or recombinant parental cell that does not contain one or more of the modification(s) made to the host cell of interest.

The present disclosure provides recombinant yeast cells suitable for the production of malonate at levels sufficient for subsequent purification and use as described herein. Yeast host cells are excellent host cells for construction of recombinant metabolic pathways comprising heterologous enzymes catalyzing production of small molecule products. There are established molecular biology techniques and nucleic acids encoding genetic elements necessary for construction of yeast expression vectors, including, but not limited to, promoters, origins of replication, antibiotic resistance markers, auxotrophic markers, terminators, and the like. Second, techniques for integration of nucleic acids into the yeast chromosome are well established. Yeast also offers a number of advantages as an industrial fermentation host. Yeast can tolerate high concentrations of organic acids and maintain cell viability at low pH and can grow under both aerobic and anaerobic culture conditions, and there are established fermentation broths and fermentation protocols.

In some embodiments of the disclosure, the recombinant host cell comprising a heterologous nucleic acid encoding a malonyl-CoA hydrolase is a eukaryote. In various embodiments, the eukaryote is a yeast selected from the non-limiting list of genera; *Candida, Cryptococcus, Hansenula, Issatchenki, Kluyveromyces, Lipomyces, Pichia, Rhodosporidium, Rhodotorula, Saccharomyces* or *Yarrowia* species. In various embodiments, the yeast is of a species selected from the group consisting of *Candida albicans, Candida ethanohca, Candida krusei, Candida inethanosorbosa, Candida sonorensis, Candida tropicalis, Cryptococcus curvatus, Hansenula polymorpha, Issatchenki orientalis, Kluoyveromyces lactis, Kluoyveromyces marxianus, Kluyveromyces thermotolerans, Lipomyces starkeyi, Pichia angusta, Pichia deserticola, Pichia galeiformis, Pichia kodamae, Pichia kudriavzevii, Pichia membranaefaciens, Pichia methanolica, Pichia pastoris, Pichia salictaria, Pichia stipitis, Pichia thermotolerans, Pichia trehalophila, Rhodosporidium toruloides, Rhodotorula glutinis, Rhodotorula graminis, Saccharomyces bayanus, Saccharomyces boulardi, Saccharomyces cerevisiae, Saccharomyces kluyveri*, and *Yarrowia lipolytica*. This list encompasses yeast in the broadest sense, including both oleaginous and non-oleaginous strains.

Alternative recombinant host cells are provided by the disclosure for biological production of malonate. Illustrative examples include eukaryotic, prokaryotic, and archaea cells. Illustrative examples of eukaryotic cells include, but are not limited to: *Aspergillus niger, Aspergillus oryzae, Cryptheco-dinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded As Safe (or GRAS) and so can be conveniently employed in various embodiments of the methods of the disclosure.

Illustrative examples of recombinant prokaryotic host cells provided by the disclosure include, but are not limited to, *Bacillus subtilis, Brevibacterium ammoniagenes, Clostridium beigerinckii, Enterobacter sakazakii, Lactococcus lactis, Mesorhizobium loti, Pseudomonas aeruginosa, Pseudomonas putida, Rhodobacter capsulatus, Rhodobacter sphaeroides, Salmonella enterica, Salmonella typhi, Salmonella typhimurium, Shigella flexneri, Staphylococcus aureus, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis*, and *Streptomyces vinaceus*. Certain of these cells, including *Bacillus subtilis, Lactobacillus acidophilus*, have been designated by the Food and Drug Administration as Generally Regarded As Safe (or GRAS) and so are employed in various embodiments of the methods of the disclosure.

*Escherichia coli* is also an excellent prokaryotic host cell for metabolic pathway construction, and *E. coli* is also well utilized in industrial fermentation of small-molecule products. Unlike most wild type yeast strains, wild type *E. coli* can catabolize both pentose and hexose sugars as carbon sources. *E. coli* also has a shorter doubling time relative to yeast, enabling experiments to be conducted more rapidly. The present disclosure provides a wide variety of *E. coli* host cells suitable for the production of malonate as described herein. In various embodiments of the methods of the disclosure, the recombinant host cell comprising a heterologous nucleic acid encoding a malonyl-CoA hydrolase is an *E. coli* cell.

Additional Modifications and Fermentation Conditions for Improved Malonate Production In other aspects of the disclosure, increased malonate yield, titer, and/or productivity is achieved by employing host cells provided by the disclosure that have been genetically modified in ways other than, or in addition to, introduction of a heterologous malonyl-CoA hydrolase and/or by employing fermentation conditions provided by certain methods of the disclosure. In brief, embodiments of the recombinant host cells of the disclosure can comprise genetic modifications that increase acetyl-CoA biosynthesis, increase malonyl-CoA biosynthesis, decrease malonate catabolism, increase secretion of malonate from the host cell, increase host cell tolerance to malonate, increase catabolism of various carbon sources and/or any combination of the foregoing.

Genetic Modifications and Fermentation Conditions that Increase Acetyl-CoA Biosynthesis In accordance with embodiments of the disclosure, increased malonate titer, yield, and/or productivity can be achieved by genetic modifications that increase acetyl-CoA biosynthesis, and the disclosure provides enzymes that increase acetyl-CoA biosynthesis, vectors for expressing enzymes that increase acetyl-CoA biosynthesis, host cells expressing enzymes that increase acetyl-CoA biosynthesis and increase malonate titer, yield, and/or productivity, and methods relating thereto. As described above, malonate is produced by hydrolysis of malonyl-CoA, which, can be produced from acetyl-CoA; thus, increases in acetyl-CoA biosynthesis can improve malonate production.

One route by which acetyl-CoA is produced is by an acetyl-CoA synthetase (EC 6.2.1.1), which catalyzes the formation of acetyl-CoA from acetate and coenzyme A (CoA). Embodiments of this disclosure provide recombinant host cells suitable for producing malonate in accordance with the methods of the disclosure comprising one or more heterologous acetyl-CoA synthetase (ACS) enzymes that increase malonate titer, yield, and/or productivity relative to a host cell not comprising a heterologous acetyl-CoA synthetase. Non-limiting examples of suitable ACS enzymes are *S. cerevisiae* ACS1 (GenBank: AAC04979.1) and ACS2 (GenBank: CAA97725.1). In some embodiments, a recombinant host cell comprising *S. cerevisiae* acetyl-CoA synthetase ACS1 and/or ACS2 is used to increase malonate titer, yield, and/or productivity. In other embodiments, a recombinant host cell comprising an acetyl-CoA synthetase selected from the group consisting of *Salmonella enterica* Acs, *Escherichia coli* AcsA, and *Bacillus subtilis* AcsA is used to increase malonate yield, titer, and/or productivity. Other acetyl-CoA synthetases can be expressed in a recombinant host cell producing malonate in accordance with the disclosure to increase malonate yield, titer, and/or productivity.

A second route through which acetyl-CoA is produced is by a pyruvate dehydrogenase complex, which catalyzes the formation of acetyl-CoA from pyruvate. Embodiments of this disclosure provide recombinant host cells suitable for producing malonate in accordance with the methods of the disclosure that comprise one or more heterologous pyruvate dehydrogenase complex enzymes that increase malonate titer, yield, and/or productivity relative to a host cell not comprising a heterologous pyruvate dehydrogenase complex enzyme. Non-limiting examples of suitable pyruvate dehydrogenase complex enzymes include *S. cerevisiae* PDA1, PDB1, LAT1, LPD1, and PDX1. In some embodiments of the disclosure, malonate yield, titer, and/or productivity are increased in a recombinant host cell used to produce malonate by expressing one or more pyruvate dehydrogenase enzymes selected from the group consisting of *S. cerevisiae* PDA1, PDB1, LAT1, LPD1, and PDX1. Other pyruvate dehydrogenase enzymes can be expressed in a recombinant host cell producing malonate in accordance with the disclosure to increase malonate yield, titer, and/or productivity.

A third route through which acetyl-CoA is produced is by a heterologous ethanol catabolic pathway comprising enzymes catalyzing the conversion of ethanol to acetyl-CoA. Compared to malonate, ethanol is a less expensive chemical, and host cells producing malonate and expressing an ethanol catabolic pathway can convert ethanol to malonate. An alcohol dehydrogenase (EC 1.1.1.1) catalyzes conversion of ethanol to acetaldehyde. Non-limiting examples of suitable alcohol dehydrogenase enzymes include those selected from the group consisting of *S. cerevisiae* ADH2, *E. coli* AdhP, *H. sapiens* ADH1A, *H. sapiens* ADH1B, and *H. sapiens* ADH1C. In addition to the alcohol dehydrogenase, an ethanol catabolic pathway also comprises either an acetaldehyde dehydrogenase (acylating; EC 1.2.1.10), or an aldehyde dehydrogenase (EC 1.2.1.3)

and an acetyl-CoA synthetase (EC 6.2.1.1). An acetaldehyde dehydrogenase (acylating) catalyzes the conversion of acetaldehyde to acetyl-CoA, an aldehyde dehydrogenase catalyzes the conversion of acetaldehyde to acetate, and an acetyl-CoA synthase, as described above, catalyzes the formation of acetyl-CoA from acetate and CoA. Non-limiting examples of suitable acetaldehyde dehydrogenases (acylating) include those selected from the group consisting of *E. coli* MhpF, *E. coli* AdhE, *Pseudomonas* sp CF600 DmpF, and *Pseudomonas putida* TodL. Non-limiting examples of aldehyde dehydrogenases include *S. cerevisiae* ALD2, ALD3, ALD4, ALD5, and ALD6; and *H. sapiens* ALD1, ALD2, ALD4, and ALD10. Non-limiting examples of acetyl-CoA synthetase enzymes include *S. cerevisiae* ACS1, *S. cerevisiae* ACS2, and *E. coli* Acs.

Embodiments of the present disclosure provide recombinant host cells suitable for producing malonate in accordance with the methods of the disclosure comprising one or more heterologous ethanol catabolic pathway enzymes that increase malonate yield, titer, and/or productivity relative to host cells not comprising the heterologous ethanol catabolic pathway enzyme(s). In some embodiments, the heterologous ethanol catabolic pathway enzymes are an ethanol dehydrogenase and an acetaldehyde dehydrogenase (acylating). In some embodiments, the heterologous ethanol catabolic pathway enzymes are *S. cerevisiae* ADH2 ethanol dehydrogenase and *E. coli* MhpF acetaldehyde dehydrogenase (acylating). In some embodiments, a heterologous *S. cerevisiae* ADH2 and *E. coli* MhpF are expressed in recombinant *E. coli* expressing a heterologous *S. cerevisiae* EHD3 malonyl-CoA hydrolase. In other embodiments, a heterologous *S. cerevisiae* ADH2 and *E. coli* MhpF are expressed in recombinant *S. cerevisiae* expressing a heterologous *S. cerevisiae* EHD3 malonyl-CoA hydrolase. In other embodiments, a heterologous *S. cerevisiae* ADH2 and *E. coli* MhpF are expressed in a recombinant oleaginous yeast expressing a heterologous *S. cerevisiae* EHD3 malonyl-CoA hydrolase. In other embodiments, the heterologous ethanol catabolic pathway enzymes are *S. cerevisiae* ADH2 ethanol dehydrogenase and *Pseudomonas* sp. CF600 DmpF acetaldehyde dehydrogenase (acylating). In some embodiments, a heterologous *S. cerevisiae* ADH2 and *Pseudomonas* sp. CF600 DmpF are expressed in recombinant *E. coli* expressing a heterologous *S. cerevisiae* EHD3 malonyl-CoA hydrolase. In some embodiments, a heterologous *S. cerevisiae* ADH2 and *Pseudomonas* sp. CF600 DmpF are expressed in recombinant *S. cerevisiae* expressing a *S. cerevisiae* EHD3 malonyl-CoA hydrolase. In some embodiments, a heterologous *S. cerevisiae* ADH2 and *Pseudomonas* sp. CF600 DmpF are expressed in a recombinant oleaginous yeast expressing a heterologous *S. cerevisiae* EHD3 malonyl-CoA hydrolase. In other embodiments, the heterologous ethanol catabolic pathway enzymes are *S. cerevisiae* ADH2 ethanol dehydrogenase and *Pseudomonas putida* TodL acetaldehyde dehydrogenase (acylating). In some embodiments, a heterologous *S. cerevisiae* ADH2 and *Pseudomonas putida* TodL are expressed in recombinant *E. coli* expressing a heterologous *S. cerevisiae* EHD3 malonyl-CoA hydrolase. In some embodiments, a heterologous *S. cerevisiae* ADH2 and *Pseudomonas putida* TodL are expressed in recombinant *S. cerevisiae* expressing a heterologous *S. cerevisiae* EHD3 malonyl-CoA hydrolase. In some embodiments, a heterologous *S. cerevisiae* ADH2 and *Pseudomonas putida* TodL are expressed in a recombinant oleaginous yeast expressing a heterologous *S. cerevisiae* EHD3 malonyl-CoA hydrolase. In other embodiments, the heterologous ethanol catabolic pathway enzymes are one or more alcohol dehydrogenase selected from the group containing *S. cerevisiae* ADH2, *E. coli* AdhP, *H. sapiens* ADH1A, *H. sapiens* ADH1B, and/or *H. sapiens* ADH1C and one or more acetaldehyde dehydrogenase (acylating) selected from the group containing *E. coli* MhpF, *E. coli* AdhE, *Pseudomonas* sp CF600 DmpF, and *Pseudomonas putida* TodL. Other alcohol dehydrogenase enzymes and acetaldehyde dehydrogenase (acylating) enzymes can be expressed in a recombinant host cell suitable for producing malonate in accordance with the methods of the disclosure to increase malonate yield, titer, and/or productivity.

In other embodiments, the heterologous ethanol catabolic pathway enzymes are an ethanol dehydrogenase, an aldehyde dehydrogenase, and an acetyl-CoA synthetase. In some embodiments, the heterologous ethanol catabolic pathway enzymes are a *S. cerevisiae* ALD2 alcohol dehydrogenase, a *S. cerevisiae* ALD2 aldehyde dehydrogenase, and a *S. cerevisiae* ACS1 acetyl-CoA synthetase. In other embodiments, the heterologous ethanol catabolic pathway enzymes are a *S. cerevisiae* ALD2 alcohol dehydrogenase, a *S. cerevisiae* ALD2 aldehyde dehydrogenase, and a *S. cerevisiae* ACS2 acetyl-CoA synthetase. In other embodiments, the heterologous ethanol catabolic pathway enzymes are a *S. cerevisiae* ALD2 alcohol dehydrogenase, a *S. cerevisiae* ALD6 aldehyde dehydrogenase, and a *S. cerevisiae* ACS1 acetyl-CoA synthetase. In other embodiments, the heterologous ethanol catabolic pathway enzymes are a *S. cerevisiae* ALD2 alcohol dehydrogenase, a *S. cerevisiae* ALD6 aldehyde dehydrogenase, and a *S. cerevisiae* ACS2 acetyl-CoA synthetase. In other embodiments, the heterologous ethanol catabolic pathway enzymes are one or more alcohol dehydrogenases selected from the group containing *S. cerevisiae* ADH2, *E. coli* AdhP, *H. sapiens* ADH1A, *H. sapiens* ADH1B, and/or *H. sapiens* ADH1C, one or more aldehyde dehydrogenases selected from the group containing *S. cerevisiae* ALD2, *S. cerevisiae* ALD3, *S. cerevisiae* ALD4, *S. cerevisiae* ALD5, *S. cerevisiae* ALD6, *H. sapiens* *H. sapiens* ALD1, *H. sapiens* ALD2, *H. sapiens* ALD4, and/or *H. sapiens* ALD10, and one or more acetyl-CoA synthetases selected from the group containing *S. cerevisiae* ACS1, *S. cerevisiae* ACS2, and/or *E. coli* Acs.

In some embodiments, recombinant host cells suitable for producing malonate according to the methods of the disclosure comprise a heterologous ethanol catabolic pathway enzyme and convert endogenously produced ethanol into acetyl-CoA and increase malonate yield, titer, and/or productivity. In other embodiments, ethanol is exogenously added to the fermentation broth and recombinant host cells suitable for producing malonate according to the methods of the disclosure comprise a heterologous ethanol catabolic pathway enzyme and convert exogenously added ethanol into acetyl-CoA and increase malonate yield, titer, and/or productivity. When exogenously added to the fermentation broth, ethanol is added to obtain a minimal concentration of 1% ethanol volume/volume and is typically added to the fermentation broth to obtain a concentration between 1-15% volume/volume.

Increased cytosolic pools of acetyl-CoA is a fourth route to increase malonate biosynthesis; in numerous plant and animal cells, but not *S. cerevisiae*, ATP citrate lyase (EC 2.3.3.8) is the primary enzyme responsible for cytosolic acetyl-CoA biosynthesis. In more detail, acetyl-CoA in the mitochondrion is condensed with oxaloacetate to form citrate through the activity of citrate synthase. Subsequently, citrate is transported from the mitochondrion into the cytosol where ATP citrate lyase catalyzes the formation of acetyl-CoA, oxaloacetate, and ADP. While *S. cerevisiae* does not contain a native ATP citrate lyase, suitable heterologous ATP citrate lyase enzymes have been described in oleaginous yeast strains (see, for example, Boulton et al., J. Gen. Microbiol. 127:169-176 (1981)). Embodiments of the present disclosure provide recombinant host cells comprising one or more heterologous nucleic oleaginous yeast ATP citrate lyase enzymes. Non-limiting examples of oleaginous yeast ATP citrate lyase enzymes include those selected from the group of oleaginous yeasts consisting of *Candida curvata, Cryptococcus albidus, Lipomyces lipofer, Rhodospiridium toruloides, Rhodotorula glutanis, Trichosporon cutaneum, Yarrowia lipolytica*, and the like. In various embodiments, the recombinant host cell comprises a heterologous nucleic acid encoding an ATP citrate lyase. In various embodiments, the ATP citrate lyase is from an organism selected from the group consisting of *Candida curvata, Cryptococcus albidus, Lipomyces lipofer, Rhodospiridium toruloides, Rhodotorula glutanis, Trichosporon cutaneum, Yarrowia hpolytica*.

Acetyl-CoA biosynthesis can also be increased in accordance with the disclosure by altering expression of one or more nucleic acids encoding proteins affecting fatty acid storage or catabolism. The present disclosure provides host cells comprising genetic modifications of one or more nucleic acids encoding proteins affecting fatty acid storage and catabolism. In *Saccharomyces cerevisiae*, these proteins include SNF2, IRA2, PRE9, PHO90, SPT21, PDX1, ANTI, FOX3, PAS1, PAS3, ARE1, ARE2, DGA1, LRO1, ACL1, MAE1, GLC3, GLG1, GLG2, PAT1, and PEX11.

In some embodiments of the disclosure, the host cell comprises genetic modifications affecting expression and/or activity of proteins involved in fatty acid catabolism. For example, most host cells will naturally degrade fatty acids, hydroxy fatty acids and many diacids through beta-oxidation pathways. Beta-oxidation occurs, in most cases, by activating free fatty acid groups to CoA thioesters with acyl-CoA ligases. The acyl-CoA intermediate is further oxidized and degraded—proceeding through a 2,3 enoyl-CoA, 3-hydroxyacyl-CoA, and 3-ketoacyl-CoA—and subsequent cleavage results in production of acetyl-CoA and an acyl-CoA shortened by two carbons relative to the initial substrate. The enzymatic activities required for beta-oxidation are known. The present disclosure provides host cells that possess increased catabolic pathway activity for medium (C4-C8)- and long (>C8)-chain fatty acids, hydroxyl fatty acids, and diacids compared to control host cells. For example, in yeast (e.g., *Saccharomyces cerevisiae*), beta-oxidation occurs in the peroxisome; non-limiting nucleic acid products affecting peroxisomal beta-oxidation are *Saccharomyces cerevisiae* PAT1 and PEX11. In some embodiments of the disclosure, a host cell modified for increased expression of PAT1 and/or PEX11 is provided for use in the methods herein for the production of malonate.

Genetic Modifications and Fermentation Conditions that Increase Malonyl-CoA Biosynthesis In accordance with the disclosure, increased malonate titer, yield, and/or productivity can be achieved through increased malonyl-CoA biosynthesis, and the disclosure provides host cells, vectors, enzymes, and methods relating thereto. Malonyl-CoA is produced in host cells through the activity of an acetyl-CoA carboxylase (EC 6.4.1.2) catalyzing the formation of malonyl-CoA from acetyl-CoA and carbon dioxide. The disclosure provides recombinant host cells for producing malonate that express a heterologous acetyl-CoA carboxylase (ACC). In some embodiments, the host cell is a *S. cerevisiae* cell comprising a heterologous *S. cerevisiae* acetyl-CoA carboxylase ACC1 or an enzyme homologous thereto. In some embodiments, the host cell modified for heterologous expression of an ACC such as *S. cerevisiae* ACC1 is further modified to eliminate ACC1 post-translational regulation by genetic modification of *S. cerevisiae* SNF1 protein kinase or an enzyme homologous thereto. The disclosure also provides a recombinant host cell suitable for producing malonate in accordance with the disclosure that is an *E. coli* cell that comprises a heterologous nucleic acid coding for expression of *E. coli* acetyl-CoA carboxylase complex proteins AccA, AccB, AccC and AccD or one or more enzymes homologous thereto. In accordance with the disclosure, additional acetyl-CoA carboxylases can be heterologously expressed to increase malonate biosynthesis.

In various embodiments of the disclosure, expression of BirA, biotin-[acetylCoA carboxylase] holoenzyme synthetase, is coexpressed with *E. coli* acetyl-CoA carboxylase complex proteins AccA, AccB, AccC and AccD to enhance the activity of the ACC complex and result in an increase in malonate production. In various embodiments of the disclosure, *S. cerevisiae* ACC1 is further modified to eliminate ACC1 post-translational regulation by introducing serine to alanine mutations at any, all, or any combination of the following residues; S10, S233, S430, S1114, S1145, S1148, S1157, S1159, S1162, S1163, S1169. In some embodiments of the disclosure, the acetyl-CoA carboxylase used is from *Yarrowia lipolytica* CLIB122. In additional embodiments of the disclosure, this enzyme is coexpressed with a biotin-[acetyl-CoA carboxylase] holoenzyme synthetase, also derived from this organism. In additional embodiments of the disclosure, the acetyl-CoA carboxylases and biotin-[acetylCoA carboxylase] holoenzyme synthetase encoding genes are dtsR1 accBc and derived from *Corynebacterium glutamicum*. In additional embodiments of the disclosure, these genes are derived from a yeast strain including, but not limited to those of the genera, *Candida, Pichia*, or any of the other yeast herein. In various embodiments of the disclosure, the host cell producing malonate expresses any combination of these acetyl-CoA carboxylases and biotin-[acetylCoA carboxylase] holoenzyme synthetase enzymes.

In some embodiments of the disclosure, a host cell suitable for producing malonate according to the methods of the disclosure comprises genetic modifications affecting expression and/or activity of proteins involved in fatty acid biosynthesis. Malonyl-CoA is naturally a substrate in the biosynthesis of fatty acids, and diversion of malonyl-CoA to fatty acid production decreases the ability for the host cell to produce malonate. The disclosure provides recombinant host cells for producing malonate that express a heterologous fatty acid synthase (FAS) multienzyme complex. Temperature sensitive mutations of *S. cerevisiae* fatty acid synthase complex are known (see, Knobling et al., Eur. J. Biochem., 59:415-421 (1975)). Expression of a heterologous, temperature sensitive fatty acid synthase complex allows diversion of malonyl-CoA to fatty acid biosynthesis to be controlled by the temperature at which the host cell is cultured. In some embodiments, the host cell is a *S. cerevisiae* cell comprising *S. cerevisiae* fatty acid synthases FAS1 and FAS2 or enzymes homologous thereto. In some embodiments of the disclosure, FAS 1 and FAS2 enzymes are temperature-sensitive FAS1 or FAS2 enzymes.

In addition to genetic modification of the host cell, fatty acid biosynthesis can be decreased through addition of a FAS inhibitor to the cell culture media. For example, the FAS inhibitor cerulenin forms a covalent bond with the active site cysteine C1305 in the *S. cerevisiae* ketoacyl synthase domain of the FAS complex, inhibiting enzyme activity (Johansson et al., PNAS, 105:12803-12808 (2008)). Cerulenin is not only effective in inhibiting *S. cerevisiae* FAS activity, but is generally an inhibitor of FAS complexes containing a Cys-His-His or Cys-His-Asn catalytic triad in the ketoacyl synthase domain. In some embodiments, cerulenin is added to the fermentation broth to a final concentration between 5 mg/l and 100 mg/l to inhibit fatty acid biosynthesis and increase malonate production in recombinant host cells producing malonate in accordance with the methods of the disclosure. In various embodiments of a method of the disclosure, a FAS inhibitor is added to fermentation broth containing recombinant host cells producing malonate. In some embodiments of a method of the disclosure, the FAS inhibitor is cerulenin. In some embodiments of the method of the disclosure, cerulenin is supplemented in the fermentation broth at a concentration between 5 mg/l and 100 mg/l. In other embodiments of a method of the disclosure, the fatty acid synthase complex inhibitor is selected from a group consisting of platensimycin, thiolactomycin, and triclosan.

One of the substrates for acetyl-CoA carboxylase is carbon dioxide and increasing the carbon dioxide partial pressure in the fermentation broth promotes formation of malonyl-CoA. In certain embodiments, the fermentation broth has a minimum dissolved carbon dioxide pressure of 0.01 atmospheres, and an increase in dissolved carbon dioxide partial pressure above this threshold is desirable. The fermentation broth should typically contain between 0.1 and 1 atmospheres dissolved carbon dioxide partial pressure. The dissolved carbon dioxide partial pressure in the fermentation broth may be increased to above saturating conditions, or above 1 atmosphere dissolved carbon dioxide. In some embodiments of a method of the disclosure, the dissolved carbon dioxide partial pressure in the fermentation broth is increased to between 0.1 and 1 atmospheres. In some embodiments of the method of the disclosure, carbon dioxide partial pressure is increased through addition of carbonates or bicarbonates to fermentation broth. For example, and without limitation, calcium carbonate can be added to the fermentation broth to increase dissolved carbon dioxide partial pressure. In other embodiments of the method of the disclosure, the fermentation is run in a pressurized vessel that contains carbon dioxide at above atmospheric pressure. In other embodiments of the method of the disclosure, carbon dioxide gas is sparged into the fermentation broth. The gas mixture being sparged may contain other gases if the added components do not interfere with host cell growth or malonate production. It may be advantageous to co-localize the source of the carbon dioxide gas with the malonate fermentation. For example, and without limitation, gaseous carbon dioxide resulting from various fermentation processes (e.g., ethanol, isobutanol, 3-hydroxypropionate, etc.), chemical processes (e.g., downstream malonate synthetic chemistry), or energy generation (e.g., coal or natural gas powerplants) may be pumped into fermentation broth from malonate producing host cells to increase the carbon dioxide partial pressure.

Genetic Modifications that Decrease Malonate Catabolism

In accordance with the disclosure, increased malonate titer, yield, and/or productivity can be achieved by decreasing malonate catabolism, and the disclosure provides host cells, vectors, enzymes, and methods relating thereto. One metabolic pathway by which malonate is catabolized in a host cell is through the activity of an acyl-CoA synthetase catalyzing the conversion malonate and Coenzyme A to malonyl-CoA. In some embodiments of the disclosure, a recombinant host cell suitable for producing malonate in accordance with the methods of the disclosure comprises a genetic modification resulting in the deletion, attenuation, or modification of one or more nucleic acids encoding for an acyl-CoA synthetase. In some embodiments of the disclosure, the recombinant host cell is yeast and the one or more acyl-CoA synthetases are selected from the group consisting of FAA1, FAA2, FAA3, FAA4, LSC1, and LSC2. In other embodiments of the disclosure, the recombinant host cell is *E. coli* and the one or more acyl-CoA synthetases are selected from the group consisting of FadD, FadK, Fadl, SucC, SucD, and YahF.

Genetic Modifications that Increase Malonate Secretion from the Host Cell

In accordance with the disclosure, increased malonate titer, yield, and/or productivity can be achieved by increasing malonate transport into the fermentation broth, and the disclosure provides host cells, materials, and methods relating thereto. In some embodiments of the disclosure, the recombinant host cell suitable for use in the methods of the disclosure is a *S. cerevisiae* cell that comprises a heterologous nucleic acid coding for expression of an *S. cerevisiae* transport protein selected from the group consisting of PDR5, PDR10, PDR11, PDR12, PDR15 and PDR18. In some embodiments of the disclosure, the recombinant host cell suitable for producing malonate in accordance with the methods of the disclosure is an *E. coli* cell that comprises a heterologous nucleic acid coding for expression of *E. coli* DcuC.

Genetic Modifications that Increase Host Cell Tolerance to Malonate

In accordance with the disclosure, increased malonate titer, yield, and/or productivity can be achieved by increasing host cell tolerance to malonate, and the disclosure provides host cells, materials, and methods relating thereto. High concentrations of malonate can competitively inhibit succinate dehydrogenase (EC 1.3.5.1) activity (see Slater, Methods Enzymol. 10:48-57 (1967)). The present disclosure is based, in part, on the discovery that mutant succinate dehydrogenase enzymes exhibit a lower competitive inhibition by malonate. For example, *S. cerevisiae* succinate dehydrogenase SDH1 residues E300, R331, and R442 are involved in substrate (e.g., succinate) recognition. Increasing the size of the SDH1 active site decreases competitive inhibition by malonate while still allowing the enzyme to maintain activity toward the native substrate, succinate. In specific, introduction of one or more mutations selected from the group consisting of E300D, R331K or R331H, and R442K and R442H decreases competitive inhibition of SDH1 by malonate. In some embodiments, a recombinant host cell expressing an SDH1 with point mutation R300D is used to produce malonate in accordance with the disclosure. In other embodiments, a recombinant host cell expressing an SDH1 with point mutation R331K or R331H is used to produce malonate in accordance with the disclosure. In other embodiments, a recombinant host cell expressing an SDH1 with point mutation R442K or R442H is used to produce malonate in accordance with the disclosure.

Genetic Modifications that Increase Catabolism of Various Carbon Sources

In the methods of the disclosure, carbon feedstocks are utilized for production of malonate. Suitable carbon sources include, without limitation, those selected from the group consisting of purified sugars (e.g., dextrose, sucrose, xylose, arabinose, lactose, etc.); plant-derived, mixed sugars (e.g., sugarcane, sweet sorghum, molasses, cornstarch, potato starch, beet sugar, wheat, etc.), plant oils, fatty acids, glycerol, cellulosic biomass, alginate, ethanol, carbon dioxide, methanol, and synthetic gas ("syn gas"). Example 30 demonstrates the production of malonic acid in accordance with the methods of the disclosure using a variety of carbon sources.

The disclosure provides host cells comprising genetic modifications that increase malonate titer, yield, and/or productivity through the increased ability to catabolize non-native carbon sources. Wild type *S. cerevisiae* cells are unable to catabolize pentose sugars, lignocellulosic biomass, or alginate feedstocks. In some embodiments, the disclosure provides a *S. cerevisiae* cell comprising a heterologous nucleic acid encoding enzymes enabling catabolism of pentose sugars useful in production of malonate as described herein. In other embodiments, the heterologous nucleic acid encodes enzymes enabling catabolism of lignocellulosic feedstocks. In yet other embodiments of the disclosure, the heterologous nucleic acid encodes enzymes increasing catabolism of alginate feedstocks.

Detecting Malonate Producing Host Cells and Screening Host Cells for Improved Malonate Production The present disclosure also provides a transcription factor biosensor system that can be used for the accurate sensing of malonate in liquid media. In many applications, this system is used to detect malonate produced within a host cell by sensing the presence of malonate in the fermentation media containing the malonate producing host cell. "Accurate sensing" refers to detecting the presence of and/or directly or indirectly determining the concentration of malonate; therefore, by accurately sensing malonate, this aspect of the disclosure has application in strain improvement, i.e., for increasing malonate production in host cells. In this system, malonate binds to a protein moiety present on a transcription factor. Binding of malonate to the malonate binding moiety results in either binding of the transcription factor to the promoter that is activated by the transcription factor, or in some embodiments, results in derepression of the promoter by the malonate-bound transcription factor.

Any number of transcription factors that bind to malonate, or are activated to bind to a promoter in response to a signal generated by binding of malonate to a binding moiety, are suitable for use in this system.

In some embodiments, the transcription factor can bind malonate, which results in binding of the transcription factor to a cognate promoter and activation of a gene that is operably linked to the promoter. Non-limiting examples of transcription factors that bind malonate include the transcription factors *Acinetobacter calcoaceticus* MdcY (SEQ ID NO:3), *Rhizobium leguminosarum* MatR (SEQ ID NO:4), *Klebsiella pneumoniae* MauR (SEQ ID NO:5), and homologs.

In some embodiments, a transcription factor used in the disclosure is an MdcY transcription factor. An MdcY transcription factor can directly bind malonate and regulate transcription mediated by promoters such as $P_{MdcL}$. MdcY and MdcY-responsive promoters are known in the art (see, e.g., Koo et al., *J Bacteriol.* 182:6382-6390 (2000)).

An example of an MdcY polypeptide sequence from *Acinetobacter calcoaceticus* is provided in SEQ ID NO:3. MdcY polypeptides that can be employed in accordance with the disclosure include variants and homologs of the MdcY polypeptide sequence set forth in SEQ ID NO:3. Thus, a MdcY transcription factor polypeptide may have an amino acid sequence that has at least 60% identity, typically at least 75%, 90%, 95%, 99% or greater amino acid sequence identity, preferably over a region of at least 100 or more amino acids, or at least 200 or more amino acids, or over the length of the entire polypeptide, to an amino acid sequence of SEQ ID NO:3. Variants can also be employed, e.g., using the known sequences as guidance for selecting amino acid substitutions that will not result in loss of function.

An example of an MdcY polypeptide sequence from *Acinetobacter calcoaceticus* is provided in SEQ ID NO:3. MdcY polypeptides that can be employed in accordance with this disclosure include variants and homologs of the MdcY polypeptide sequence set forth in SEQ ID NO:3. Thus, a MdcY transcription factor polypeptide may have an amino acid sequence that has at least 60% identity, typically at least 75%, 90%, 95%, 99% or greater amino acid sequence identity, preferably over a region of at least 100 or more amino acids, or at least 200 or more amino acids, or over the length of the entire polypeptide, to an amino acid sequence of SEQ ID NO:3. Variants can also be employed, e.g., using the known sequences as guidance for selecting amino acid substitutions that will not result in loss of function.

In some embodiments, the MdcY transcription factor for use in the disclosure is naturally present in a host cell. In other embodiments, a host cell is genetically modified to express a foreign transcription factor by introducing a heterologous nucleic acid encoding the malonate transcription factor into the host cell. In some embodiments, the genetically modified host cell comprising a heterologous nucleic acid encoding the malonate transcription factor is an *E. coli* host cell.

The MdcY transcription factor can bind to a number of promoters and activate expression of a gene operably linked to the promoter. An example of a MdcY-responsive promoter suitable for use in accordance with the disclosure is provided in SEQ ID NO:6. In some embodiments, an MdcY-responsive promoter for use in the disclosure, typically comprise an operator sequence ATTGTATACAAT (SEQ ID NO: 6, nucleotides 7-18). In some embodiments, the promoter is at least 75% identical to the promoter sequence shown in SEQ ID NO:6. In some embodiments, the promoter comprises a subsequence of SEQ ID NO:6 comprising 10, 20, 25, 30, 35, or more, contiguous nucleotides of SEQ ID NO:6.

Thus, in one aspect, the present disclosure provides a method for accurately sensing malonate. In some embodiments, the sensing step comprises detecting, e.g., measuring the amount of a gene product of a reporter or marker gene (e.g. a fluorescent reporter gene). In some embodiments, the gene product of the reporter gene influences the growth rate of a host cell comprising the components of a malonate transcription factor biosensor of the disclosure. In some embodiments, the gene product of the reporter gene causes the modified host cell to become resistant or sensitive to a compound. For example, in some embodiments, the reporter gene is an antibiotic resistance gene (e.g. a tetA gene) where the presence of malonate in the culture medium induces antibiotic resistance such that the host cell exhibits improved growth in the presence of malonate when the antibiotic is present. In some embodiments, a host cell that comprises the components of a transcription factor biosensor of the disclosure is a host cell that is capable of producing malonate. Example 36 illustrates practice of this aspect of the disclosure using both antibiotic resistance (tetA) and a colorimetric signal (lacZ) as outputs that are correlated to malonic acid concentration, produced in accordance with other aspects of the disclosure, in fermentation media.

Generally, then, the present disclosure provides for a method for screening or selecting a host cell that produces malonate comprising: (a) providing a modified host cell of the present disclosure, (b) culturing the host cell, and (c) screening or selecting the host cell based on the expression of the reporter gene by the host cell.

In some embodiments of the present disclosure, the method for screening or selecting a host cell that produces malonate comprises: (a) providing a plurality of modified host cells of the present disclosure wherein the modified host cells of different modification are in separate cultures, (b) culturing each separate culture of host cell, (c) screening or selecting the host cell based the expression of the reporter gene by the host cell, and (d) comparing the expression of the reporter genes of the separate cultures. In some embodiments of the present disclosure, step (d) comprises identifying one or more cultures, and/or the corresponding host cell, that have an increased expression of the gene product of the reporter gene.

In some embodiments, the method of the disclosure is a method for selecting a host cell that produces malonate, wherein the selection is a positive selection. In a positive selection, the selecting step selects for host cells that have a higher expression of a reporter gene that increases the probability of remaining viable and doubling, and thus have a higher probability of remaining viable and doubling. For example, host cells producing malonate will remain viable and propagate at a rate faster than host cells not that do not produce malonate. Similarly, host cells with increased malonate production as compared to a control strain will propagate at a rate faster than the control strain.

In some embodiments of the present disclosure, the method for selecting an *E. coli* host cell that produces malonate comprises: (a) providing a plurality of modified *E. coli* host cells of the present disclosure wherein the modified host cells of different modification are in separate cultures, (b) culturing each separate culture of host cell, (c) positively selecting the host cell based the expression of the reporter gene by the host cell, and (d) comparing the expression of the reporter genes of the separate cultures.

In other embodiments of the present disclosure, the method for selecting an *E. coli* host cell that produces malonate comprises: (a) providing a plurality of modified *E. coli* host cells of the present disclosure wherein the modified host cells of different modification are in the same culture, (b) culturing the heterogenous mixture of modified host cells in growth medium containing a positive selecting agent such that the host cells exhibiting a higher production of malonate than the plurality of host cells will propagate at a rate faster than host cells exhibiting lower production of malonate and (d) isolating the host cells exhibiting the highest production of malonate.

Methods for Purifying Bio-Based Malonic Acid and Diester Derivatives of Bio-Based Malonic Acid The general methods described herein are for purifying malonate or malonic acid derivatives from fermentation broth, the methods comprising: (a) culturing a host cell under conditions suitable for production of malonate, (b) and recovering (i.e., purifying) the malonate from fermentation broth. This disclosure also provides purified malonate produced in accordance with the methods of this disclosure. The methods described herein further relate to the purification of bio-based diester derivatives of malonic acid from malonic acid. This malonic acid may be derived from a fermentation broth of a microorganism that is able to produce malonic acid from a fermentable carbon source. In some embodiments, this method may occur at a commercially viable level. Biosynthesized malonate can be produced intracellularly and/or secreted into the culture medium. Intracellulary produced malonate is typically secreted into the culture medium using a membrane transporter, as described above. If not secreted, malonate can be removed from the host cell by chemical, enzymatic, or mechanical cell lysis. Malonate can be recovered from the cells, from the fermentation broth, or both. If the cell is engineered to secrete malonate, one can opt to recover the malonate only from the fermentation broth or one can opt to recover it both from the media and from the cell (i.e., by lysing the cell). If the cell is not engineered to secrete malonate one can lyse the host cell to isolate the malonate therein. This malonic acid may alternatively be derived from other sources.

The present disclosure provides some methods to isolate malonate produced biologically. As used herein, "isolate", "purify", and "recover" are used to refer to separation of the malonate from other substances present. "Isolation", "purification", or "recovery" as used in this context is intended to convey a preparation of malonate that is enriched in malonate relative to the cell or fermentation broth that produced it but that may or may not be substantially (i.e., more than 50%) pure on a weight/weight (w/w) basis. Isolating malonate in accordance with these methods involves separating the malonate produced from at least part or all of the fermentation medium, host cells, and parts thereof, from which malonate is produced. Malonate may be purified, i.e., to more than 50% purity on a w/w basis, in accordance with this disclosure from the fermentation broth and/or from the producing cell in which any naturally occurring or recombinant host cell (e.g., *E. coli, S. cerevisiae*, oleaginous yeast, and the like) producing malonate is grown, i.e., the host cell is not limited to a recombinant host cell of this disclosure. The isolated malonate may be free or essentially free of impurities from the host cells. The malonate is isolated or purified to a degree such that any impurities present do not interfere in the subsequent use of the malonate. For example, if the subsequent use is as an industrial chemical, such as a chemical to be used in a polymerization reaction, then the malonate is essentially free of impurities when any remaining impurities would not interfere with the use of the malonate in a polymerization reaction. Typically malonate used for polymerization reactions has a purity of at least 95% w/w or higher. If the malonate is to be used as a fuel, such as a fuel to be used in a combustion reaction, then the compound is essentially free of impurities when any impurities remaining would not interfere with the use of the malonate as a fuel. If the malonate is used as an animal feed, then the malonate is essentially free of impurities when any impurities remaining would not interfere with the use of the material as animal feed. When malonate is used as an animal feed, one may opt to recover the biomass containing malonate from the fermentation broth and use the biomass as animal feed.

In some embodiments of the purification methods of this disclosure, the fermentation broth is concentrated to increase the working concentration of malonate and decrease the volume of liquid for processing. In various embodiments of the purification methods of this disclosure, this concentration is achieved by evaporation, including vacuum and heat, reverse osmosis, "high pass" membrane dewatering, and/or thin film evaporation.

In some embodiments, the purification methods of this disclosure comprise the step of recovering the malonate produced, wherein the recovering step is concurrent or subsequent to the culturing step. In some embodiments, the malonate is purified from the fermentation broth and the host cells. In other embodiments, the host cells are separated from the fermentation broth, lysed, and then malonate is recovered from the host cells. In other embodiments, the host cells are lysed in the fermentation broth and malonate is recovered from the lysed cells and fermentation broth. One method for recovering malonate from the fermentation broth provided by this disclosure is precipitation of malonate with a cation. In some embodiments this is a monovalent cation, in other embodiments it is a divalent cation. Typically the cation is added to the fermentation broth (or lysate) as a salt. For example, precipitation of calcium malonate from an aqueous solution, which may be fermentation broth or a cell lysate or a mixture of both, containing malonate in accordance with this disclosure is accomplished by the addition of a calcium salt (Weiner, *Org. Synth.* 18:50 (1938); Weiner, *Org. Synth. Coll.* 2:376 (1943)). Various calcium salts (e.g., calcium hydroxide, calcium carbonate, calcium chloride) can be used in accordance with this disclosure to precipitate malonate from fermentation broth.

In some embodiments of preparing bio-based compositions from fermentation, a growth vessel, typically a fermenter, can be used to grow a microbial culture that is subsequently used for the production of calcium malonate, malonic acid, and/or diester derivatives of malonic acid-containing fermentation broth. Such fermentation vessels are known in the art. The general fermentation process can utilize any number of commercially available carbohydrate substrates, preferably glucose. Fermentation methodology is well-known in the art and can be carried out in a batch-wise, continuous or semi-continuous manner. In some embodiments, the purification of bio-based diester derivatives of malonic acid can take place in a vessel capable of holding the desired volume. In some embodiments, this vessel is a reactor. The vessel can be a capable of holding from 1 gallon to 500 gallons. Such vessels are known in the art.

In some embodiments, the microbial culture (i.e., fermentation broth) may comprise a fermentable carbon source (e.g., glucose monohydrate), and, optionally, a source of nitrogen, phosphorous, and additional media components such as vitamins, salts, and other materials that can improve cellular growth and/or product formation, and water. These components may be fed into a fermenter to regulate or promote growth and sustenance of the microbial culture. In some embodiments, the microbial culture may be grown under aerobic conditions provided by sparging an oxygen containing gas (e.g., air or the like). In some embodiments, calcium hydroxide can be provided for pH control during the growth of the microbial culture.

In some embodiments, the microbial culture may comprise microorganisms capable of producing malonic acid from fermentable carbon sources (e.g., glucose, sucrose, and/or other carbohydrate sugars). Representative examples of microorganisms include, but are not limited to, those selected from the group consisting of *Pichia kudriavzevii* (*P. kudriavzevii*), *Saccharomyces cerevisiae*, *Escherichia coli*, mixtures thereof and the like. A preferred microorganism is a *Pichia kudriavzevii* strain.

In some embodiments, the method comprises the following steps: (1) fermenting a microorganism capable of producing malonic acid in the presence of a fermentable carbon source and an alkaline earth metal base under suitable fermentation conditions to obtain a fermentation broth that includes an insoluble alkaline earth metal malonate salt; (2) separating the insoluble alkaline earth metal malonate salt from the fermentation broth such that the isolated alkaline earth metal malonate salt is substantially free of cells; (3) converting the isolated alkaline earth metal malonate salt to soluble malonic acid; and crystallizing said soluble malonic acid; and (4) synthesizing diester derivatives of malonic acid.

In some embodiments, the method may further comprise the step of (3b) removing impurities from the soluble malonic acid prior to crystallizing the malonic acid.

In some embodiments, the method may comprise growing a microorganism in broth containing fermentable carbon sources (e.g., glucose, sucrose, and/or other carbohydrate sugars, often glucose is the primary carbon source) to produce malonic acid, separation of calcium malonate from the cells and fermentation broth, reactive crystallization of calcium malonate and sulfuric acid in a gypsum crystallizer, and final crystallization in a malonic acid crystallizer.

In some embodiments, the method may further comprise the step of removing impurities from the soluble malonic acid prior to crystallization of the malonic acid.

In some embodiments in which the alkaline earth metal base is a calcium base, the calcium base may be calcium hydroxide, calcium carbonate, or calcium oxide. In specific embodiments, the alkaline earth metal base is calcium hydroxide. In other embodiments, the alkaline earth metal base is calcium carbonate. In still further embodiments, the alkaline earth metal base is calcium oxide. In those embodiments in which the alkaline earth metal base is calcium hydroxide or calcium carbonate, the insoluble alkaline earth metal malonate salt is calcium malonate dihydrate.

Certain embodiments of the present disclosure relate to malonic acid compositions and/or diester derivatives of malonic acid compositions that are 100% bio-based as determined by ASTM International Radioisotope Method D 6866. Additional embodiments relate to malonic acid compositions and/or diester derivatives of malonic acid compositions that are 100% bio-based and have decreased acetic acid content and/or decreased impurities. By providing increased bio-based content, lower acetic acid content, and/or decreased impurities the composition is more advantageous of use in industry, and it may enable increased control over cure speed and the hardness of resulting resins and polymers.

In other embodiments of the present disclosure, the method may comprise a process for purifying calcium malonate from cell-containing fermentation broth, said process comprising the steps of: (1) separating calcium malonate crystals of at least 10 microns in diameter from cell-containing fermentation broth by centrifugation, (2) generation of dissolved malonic acid and calcium sulfate crystals in a gypsum reactive crystallizer, (3) recrystallization of the dissolved malonic acid in a malonic acid crystallizer, and (4) synthesizing diester derivatives of malonic acid. A particularly useful method for separation of the calcium malonate crystals from cell-containing fermentation broth is separation via the use of a hydrocyclone.

In other embodiments of the present disclosure, the method may comprise a process for synthesizing or purifying diester derivatives of malonic acid from alternative malonic acid source(s).

In some embodiments, the microorganism is *Pichia kudriavzevii*. In some embodiments, the fermentation of *Pichia kudriavzevii* is carried out in the presence of calcium hydroxide. In some embodiments, the calcium hydroxide is concentrated to 3M.

In other embodiments, the resulting composition is bio-based calcium malonate. In other embodiments, the resulting composition is bio-based malonic acid. In other embodiments, the resulting composition is a bio-based diester derivative of malonic acid.

Calcium Malonate Crystals

There are many objectives of the methods disclosed herein. One objective of the methods disclosed herein is to crystalize calcium malonate in well-defined crystals, avoiding the formation of poorly defined calcium malonate crystals of relatively small size, thus permitting easy separation of calcium malonate from calcium malonate-containing fermentation broth. A second objective is to obtain calcium malonate crystals of relatively high purity, free from accompanying cells, organic acids, salts, metals, and residual sugars that are normally contained in the fermentation broth. A third objective is to obtain calcium malonate crystals that can be separated from the fermentation broth with a good yield and at low cost.

Poor calcium malonate crystal quality and size means crystals of a needle-like, spindle-like, or plate-like shape of less than 10 micrometers or an amorphous calcium malonate precipitate. When calcium malonate crystals of poor quality are formed, it is difficult to separate the calcium malonate crystals from the cells and fermentation broth.

Accordingly, as detailed herein, the inventors discovered that large calcium malonate crystals, which are more readily separated from the cells and fermentation broth, can be produced through the introduction of seed crystals to the fermentation. The seed crystals may be any crystal that causes the accumulated calcium malonate in the fermentation broth to crystallize into large crystals. Preferably the seed crystals are calcium malonate seed crystals. National Center for Biotechnology Information. PubChem Compound Database; CID=517114, https://pubchem.ncbi.nlm.nih.gov/compound/417113 (accessed Sep. 10, 2016) and Varughese, P. A., Saban, K. V., George, J. et al. Journal of Materials Science (2004) 39: 6235.

The timing of addition of the calcium malonate seed crystals may assist with obtaining large calcium malonate crystals that can be readily separated from the cells and fermentation broth. In some embodiments, seed crystals can be added at the start of the fermentation (i.e., before the cells begin producing malonic acid) or at any point during the fermentation. In some embodiments, seed crystals can be added once during the fermentation or more than one time during the fermentation. In a preferred embodiment of the methods as disclosed herein, calcium malonate seed crystals are added only to the fermentation at the start of the fermentation.

The formation of larger crystalline forms of the alkaline earth metal malonate salt can be aided by fermenting the microorganism in the further presence of seed crystals. The seed crystals may be any crystals added in any amount that aid in formation of larger crystalline forms of the malonate salt. In some embodiments in which the alkaline earth metal malonate salt is calcium malonate dihydrate, the seed crystals are calcium malonate dihydrate seed crystals (National Center for Biotechnology Information. PubChem Compound Database; CID=517114, https://pubchem.ncbi.nlm.nih.gov/compound/417113 [accessed Sep. 10, 2016] and Varughese, P. A., Saban, K. V., George, J. et al. Journal of Materials Science (2004) 39: 6235). The seed crystals can be added to the fermentation broth at any one or multiple times, including at the start, during, or at the end of the fermenting.

In some embodiments, seed crystals can be added before the amount of alkaline earth metal malonate salt in the fermentation broth exceeds the solubility limit of the alkaline earth metal malonate salt. In some embodiments, the seed crystals may be added to a concentration that is in excess of the solubility limit of the alkaline earth metal malonate salt. In some embodiments in which the alkaline earth metal malonate salt is CaM, CaM seed crystals may be added to an amount that is in excess of the solubility limit of calcium malonate dihydrate (which is about 6 g/l at 30° C.). In some such embodiments, CaM seed crystals may be added to a concentration of at least 5 g/l, at least 6 g/l, at least 7 g/l, at least 8 g/l, at least 9 g/l, or at least 10 g/l.

If the amount of the accumulated calcium malonate in the fermentation exceeds the saturation solubility of calcium malonate, or exceeds oversaturation, the calcium malonate spontaneously precipitates. The resulting calcium malonate crystals are small, needle-like and difficult to separate from the biomass and fermentation broth. Calcium malonate is soluble to about 6 g/l at 30° C. in fermentation broth; therefore, it may be desirable to add the seed crystals before the dissolved calcium malonate concentration in the fermentation exceeds 6 g/l.

Method of Fermentation

Embodiments of the methods provided herein may comprise the step of fermenting a microorganism capable of producing malonic acid in the presence of a fermentable carbon source and an alkaline earth metal base under suitable fermentation conditions to obtain an aqueous fermentation broth that comprises an insoluble alkaline earth metal malonate salt (i.e., the salt formed between the alkaline earth metal and malonic acid). In some embodiments, seed crystals can be added at the start of the fermentation (i.e., before the cells begin producing malonic acid) or at any point during the fermentation. The microorganism can be any microorganism capable of producing malonic acid. Non-limiting examples of microorganisms include those selected from the group comprising *Pichia kudriavzevii*, *Saccharomyces cerevisiae*, *Escherichia coli*, and derivatives thereof. In some embodiments, the microorganism is a *Pichia kudriavzevii* strain, http://www.mycobank.org/name/Pichia%20kudriavzevii.

As described herein, fermentation may comprise the inoculation of a microorganism capable of producing malonic acid in the presence of a fermentable carbon source and an alkaline earth metal base under suitable fermentation conditions into fermentation broth containing a fermentable carbon source. The fermentation conditions may be altered as needed for the organism used. In one example, *Pichia kudriavzevii* is grown in an appropriate medium. In some embodiments, malonate salt seed crystals may be further added to the fermentation broth before, during, or both before and during fermentation. A preferred malonate salt is calcium malonate. The amount of seed crystals added to the fermentation can be an amount needed to obtain a concentration above the solubility limit of calcium malonate, which may be about 6 g/l at pH 5. Thus, the concentration of crystals that may be added is about 6 g/l or more.

Suitable media for fermenting typically depend on the choice of microorganism used. A typical nutrient medium contains a fermentable carbon source, a nitrogen source, a phosphorous source, inorganic salts, and optionally other trace organic nutrients, including vitamins that can improve the health and growth of the microorganism. Either a synthetic or a natural medium can be used so long as the microorganism is capable of growth in the medium.

The fermentable carbon source may be any fermentable carbon source. Non-limiting examples of fermentable carbon sources include glucose, sucrose, maltose, glycerol, ethanol, acetic acid, and mixtures thereof. In one embodiment, the fermentable carbon source is glucose. In another embodiment, the fermentable carbon source is sucrose.

The nitrogen source may be any assimilable nitrogen source. Either synthetic or natural nitrogen sources, or a mixture of synthetic and natural nitrogen sources, may be used. Non-limiting examples of synthetic assimilable nitrogen sources include ammonia, ammonium salts (e.g., ammonium sulfate, ammonium carbonate, and ammonium phosphates), and nitrates. Non-limiting examples of natural nitrogen sources include yeast extract and peptone.

Suitable fermentation conditions are typically dependent on the choice of microorganism used (see, e.g., Krahe, M. 2003. Biochemical Engineering. Ullmann's Encyclopedia of Industrial Chemistry). Fermentation conditions comprise a suitable growth media, suitable fermentation method, suitable temperature, suitable oxygenation, and suitable pH. Examples of fermentation conditions and media recipes are disclosed in U.S. patent application Ser. No. 14/386,272.

Suitable temperatures for fermenting typically depend on the choice of microorganism used. In embodiments in which the microorganism is a yeast, a suitable temperature for fermenting can be from 15° C. to 45° C., to 40° C., to 35° C., or to 30° C.; more preferably from 20° C. to 35° C., or to 30° C.; and most preferably about 30° C.

Another consideration to isolating a high yield of high quality CaM crystals is the size of the crystals. During fermentation, particle size may be measured by a Coulter counter, such as the Beckmann Multisizer 4e. Ideally, the particles of CaM are at least 10 microns in diameter.

To produce malonic acid, oxygen is transferred into the fermentation broth; in other words, there is a positive oxygen transfer rate (OTR). Microbial production of malonic acid results in the concomitant formation of the redox cofactors NADH and/or NADPH, which are recycled to $NAD^+$ and $NADP^+$, respectively, in order to maintain the redox balance for cell health and efficient malonic acid production. Molecular oxygen is typically the electron acceptor used to recycle NAD(P)H back to $NAD(P)^+$ and suitable oxygenation of the fermentation broth can efficiently produce malonic acid in a fermentation. Oxygenation of the fermentation broth may be generally achieved by pumping in either atmospheric air (i.e., air that is about 21% molecular oxygen) or oxygen-enriched air. The rate at which oxygen is transferred into the fermentation broth (oxygen transfer rate, or OTR), expressed as mmol-O2/l/hr, describes the oxygenation of the fermentation broth. In many embodiments of the present disclosure, the fermentation OTR is at least 5 mmol/l/h, at least 10 mmol/l/hr, at least 20 mmol/l/hr, at least 30 mmol/l/hr, at least 40 mmol/l/hr, or at least 50 mmol/l/hr.

Fermentations at neutral or near neutral pH values (i.e., from about pH 6 to about pH 8) have an increased risk of contamination by undesired, non-malonic acid producing microbes from the external environment. Therefore, it may be preferable for at least a portion, and often a majority, and sometimes all, of a fermentation to be operated at a pH value less than or equal to pH 7. However, at the same time, a high concentration of malonic acid at a low pH is toxic to most microorganisms and results in decreased growth rate, cell viability, and/or malonic acid production. Thus, a suitable fermentation pH depends on both the choice of the microorganism used (i.e., its ability to grow and produce malonic acid at a lower fermentation pH) and the concentration of fully protonated malonic acid in solution. Generally speaking, to decrease malonic acid-induced toxicity it is often desirable to culture the malonic acid producing microorganism at a pH at least as high as the pKa of the first carboxylic acid of malonic acid, and often times at a pH of at least as high as the pKa of the second carboxylic acid of malonic acid. Doing so minimizes the concentration of fully protonated malonic acid the cells are exposed to and thus minimizes malonic acid-induced toxicity.

In some embodiments, the preferred pH of the fermentation is kept around pH 5.0. Using calcium hydroxide to control the pH is a preferred method. The fermentation process may result in a mixture of cells, solid calcium malonate dihydrate (CaM), and a variety of soluble organic compounds (e.g., calcium acetate and calcium succinate). When carrying out the fermentation at pH 5.0, the concentration of succinate at 11 g/l or below can be monitored. If the concentration of succinate is too high, it will form an insoluble calcium salt, which will be difficult to separate from the calcium malonate. Achieving high quality, washed and highly pure CaM crystals is helpful to be able to ultimately provide bio-based malonic acid in high yield, thus yielding a higher yield of diester derivatives of malonic acid that are substantially free from impurities.

Various methods can be used to decrease the concentration of succinate in the fermentation broth, including adjustment of the fermentation oxygen transfer rate and/or modification of the fermentation process such that the majority of succinate produced during the fermentation is reconsumed at the end of the run. In many cases, succinate is produced as a byproduct of native yeast metabolism in response to a redox imbalance, due to, for example, an insufficiently low oxygen transfer rate. In these cases, succinate byproduct formation can be decreased by increasing the fermentation oxygen transfer rate and the succinate concentration can be maintained to less than 11 g/l.

A second method useful for decreasing the concentration of succinate concentration in the fermentation broth is to adjust the fermentation process such that any succinate produced is reconsumed by the engineered microbe. Since succinate is a small-molecule required in nearly all microbe's native metabolism, most microbes, including *P. kudriavzevii* as well as other yeast cells, will reconsume succinate once more preferred carbon sources (for example, glucose) have been depleted from the fermentation broth. The operator can allow the concentration glucose to decrease to about zero g/l and the engineered microbe will begin reconsuming the succinate in the broth. While this method can be employed at any point during a fermentation it is typically used at the end of the fermentation. Additionally, this method is particularly advantageous when producing malonic acid since most microbes (including *P. kudriavzevii* and other yeast) cannot reconsume malonic acid; thus, the amount of malonic acid produced in the fermentation is not decreased when using this approach.

The fermentation pH can be controlled by the addition of various inorganic bases at the beginning and/or throughout the course of the fermentation, and the choice of the fermentation base affects the pKa values for the two carboxylic acid groups. In the presence of a monovalent cation (for example, a sodium cation when sodium hydroxide is used as a base) the two carboxylic acid pKa values are about 2.83 and 5.69. Thus, when sodium hydroxide is used as a base the fermentation pH will often be greater than or equal to pH 5.69.

Surprisingly, as detailed herein, the inventors have discovered that the apparent pKa of the carboxylic acids shift when using calcium hydroxide as base.

According to this discovery, in the presence of certain alkaline earth metals, the second carboxylic acid pKa value surprisingly decreases. For example, in the presence of calcium, the second carboxylic acid pKa of malonic acid decreases to about 3.15. It is therefore possible to ferment a malonic acid producing microorganism at a lower fermentation pH without observing malonic acid-induced toxicity when neutralizing the broth with a calcium base or other alkaline earth metal bases as compared to bases for which the cation is monovalent. In many embodiments, the fermentation pH is less than or equal to pH 7 for all or part of the fermentation. In some embodiments, the fermentation pH is less than or equal to pH 6 for all or part of the fermentation. In some embodiments, the fermentation pH is less than or equal to pH 5 for all or part of the fermentation.

In addition to neutralizing the malonic acid, alkaline earth metal bases also precipitate out the malonic acid from the culture medium as an insoluble alkaline earth metal malonate salt. Suitable alkaline earth metal bases used to neutralize the malonic acid include calcium bases, magnesium bases, and barium bases. The solubility of the resulting malonate salts that form with calcium, magnesium, and barium have a solubility of less than about 5 g/l at room temperature and pressure, and thus aid in efficient separation of the alkaline earth metal-malonate salt from the fermentation broth.

In some embodiments, specific calcium bases useful in accordance with the methods of the present disclosure include calcium carbonate ($CaCO_3$), calcium oxide (CaO), and calcium hydroxide ($Ca(OH)_2$). Specific magnesium bases useful in accordance with the methods of this disclosure include magnesium carbonate ($MgCO_3$), magnesium oxide (MgO), and magnesium hydroxide ($Mg(OH)_2$). Specific barium bases useful in accordance with the methods of this disclosure include barium carbonate ($BaCO_3$), barium oxide (BaO), and barium hydroxide ($Ba(OH)_2$).

Calcium bases are particularly advantageous for use in controlling the fermentation pH in that they are readily available and inexpensive. Calcium and malonic acid react to form calcium malonate dihydrate (CaM), a low-solubility, dense salt that is readily separated from the fermentation broth and the cells contained in the fermentation broth. In some embodiments in which the alkaline earth metal base is a calcium base, the calcium is added as $Ca(OH)_2$, $CaCO_3$, or CaO. In specific embodiments, the alkaline earth metal base is calcium carbonate. In other embodiments, the alkaline earth metal base is calcium oxide. In still further embodiments, the alkaline earth metal base is calcium hydroxide.

The method of addition of the alkaline earth metal base to the fermentation is also of focus. In some embodiments, the alkaline earth metal base may be added to the fermentation as a slurry, and in these cases, maximizing the concentration of the alkaline earth metal base used in the slurry may improve yield. Use of a dilute base can result in the addition of excess water to the fermentation and can hinder isolation of the alkaline earth metal malonate salt. In some embodiments, in which the alkaline earth metal base is a calcium base, at least a 1M, at least a 2M, at least a 3M, at least a 4M, or at least a 5M solution of $Ca(OH)_2$, $CaCO_3$, or CaO are used to control the fermentation pH. In other embodiments in which the alkaline earth metal base is a calcium base, the calcium base is added dry (i.e., substantially free of water) to the fermentation.

In some embodiments, to maximize yields of the insoluble alkaline earth metal malonate salt, the molar amount of alkaline earth metal may be at least equivalent to the molar amount of malonic acid produced by the microorganism prior to separation of the insoluble alkaline earth metal malonate salt from the fermentation broth. Therefore, in some embodiments, the molar ratio of alkaline earth metal to malonic acid at any time point during the fermenting may be at least 1:1, at least 1.5:1, or at least 2:1. In many embodiments, the molar ratio of alkaline earth metal to malonic acid prior to separation of the insoluble alkaline earth metal malonate salt from the fermentation broth is at least 1:1. In specific embodiments in which the alkaline earth metal base is calcium hydroxide, the molar ratio of calcium hydroxide to malonic acid is at least 1:1.

The alkaline earth metal base can be added to the fermentation broth at any one or multiple times of the fermenting, including at the start (i.e., before the microorganism begins producing malonic acid), during, or at the end of the fermenting (i.e., prior to separation of insoluble alkaline earth metal malonate salt from the fermentation broth).

In some embodiments, the fermentation broth may comprise an insoluble alkaline earth metal malonate salt. In other words, all or part of the alkaline earth metal malonate salt may be found in a solid form in the fermentation broth. The alkaline earth metal malonate salt in the fermentation broth precipitates from solution when the concentration of alkaline earth metal malonate salt in the fermentation broth exceeds its solubility limit. A higher concentration of alkaline earth metal malonate salt means a larger fraction of total malonic acid produced will be found as the insoluble alkaline earth metal malonate salt. Obtaining a high concentration of alkaline earth metal malonate salt results in higher yields of bio-based malonic acid produced by the methods provided herein, and reduced percentage loss due to solubilized alkaline earth metal malonate salt. In some such embodiments, the concentration of alkaline earth metal malonate salt in the fermentation broth may be at least 75 g/l, at least 100 g/l, at least 110 g/l, at least 120 g/l, at least 130 g/l, at least 140 g/l, or at least 150 g/l. In those embodiments in which the alkaline earth metal malonate salt is calcium malonate dihydrate (CaM), the concentration calcium malonate dihydrate in the fermentation broth may be at least 75 g/l, at least 100 g/l, at least 110 g/l, at least 120 g/l, at least 130 g/l, at least 140 g/l, or at least 150 g/l.

Embodiments of the fermentation method as disclosed herein are not particularly limited and suitable fermentation methods include batch, fed-batch, and continuous fermentations. However, in order to obtain a larger yield of malonic acid, a fed batch culture where the fermentable carbon source is sequentially added over time may be typically used. In many embodiments of the present disclosure, the fermentation method is a fed-batch fermentation method.

Collection of Fermentation Broth

In some embodiments, when the fermentation has been carried out for the desired amount of time, the fermentation broth may be cleared of cells and cells debris by centrifugation. If desired, the process may be carried out by proceeding directly to filtration. Centrifugation can be carried out in a decanter centrifuge, preferably the horizontal type, or hydrocyclones. Hydrocyclones may be used to separate the CaM from the biomass. Hydrocyclones are quite efficient at removing cellular debris from the fermentation broth, to yield the isolation of highly purified CaM crystals. Hydrocyclones work best if the range of total suspended solids is kept at 5-25%. Higher % TSS may result in the loss of CaM to the overflow. If desired the fermentation broth may be diluted or concentrated to bring the % TSS within the 5-25% range. Reproducibility will be enhanced if the process is generally carried out using the same % TSS each time.

In one embodiment, a series of three hydrocyclones may be used to separate the CaM crystals from the majority of the cells. Efficient cell removal is a parameter to be monitored for producing a CaM cake in the subsequent filtration unit operations where the fermentation medium (containing soluble organic and salt impurities) can be washed away from the CaM crystals.

The hydrocyclone separates materials of different sizes and/or densities using a centrifugal force. The centrifugal force is generated by introduction of the slurry into the cyclone under pressure; larger and/or denser particles are pushed to the outside of the cone while smaller and/or less dense particles are kept closer to the center. The vortex finder draws the majority of the water and fine particles to the overflow while the larger/denser materials are drawn out of the apex.

Depending on the scale of the operation, different routes may be followed to obtain CaM crystals from the fermentation broth. In smaller scale or benchtop operations, the underflows from the hydrocyclones can be taken after centrifugation and sent them to a reslurry tank. Wash water from the process can be used to bring the total suspended solids (% TSS) to a level of 20-25%. The use of wash water may help dilute out the cells and the impurities in the fermentation broth.

In larger operations such as continuous or semi-continuous manufacturing, the wash water may be obtained after horizontal vacuum belt (HVBF) unit operation. In either case, reusing wash water may be beneficial due to the solubility of CaM in water at pH 5 (about 6 g/l at room temperature); thus, more CaM may be recovered by reusing the wash water.

In some embodiments, the fermentation broth obtained at the end of fermenting may be largely free of other insoluble organic acids other than the alkaline earth metal malonate salt. In some embodiments, the fermentation broth at the end of the fermentation may comprise a lower amount of succinic acid than the amount of succinic acid that would form an insoluble alkaline earth metal succinate salt. In those embodiments where the alkaline earth metal base is a calcium base, the fermentation broth at the end of the fermentation may comprise less than 11 g/l succinic acid.

The ease by which the insoluble alkaline earth metal malonate salt can be separated from the fermentation broth and cells contained in the fermentation broth increases with increasing size of the alkaline earth metal malonate salt crystals formed. Conventional procedures for obtaining alkaline earth metal malonate salt crystals typically yield high fractions of crystalline forms of poor quality and small size (i.e., crystals of a needle-like, spindle-like, or plate-like shape of less than 10 micrometers) or of an amorphous alkaline earth metal malonate salt precipitate.

An objective of the methods provided herein is to obtain malonate salt in crystalline form of high quality (i.e., highly pure and well defined) and large size. Therefore, in some embodiments of the methods provided herein, at the end of the fermenting the fermentation broth may comprise at least 80%, at least 85%, at least 90%, or at least 95%; from 80% to 100%, to 95%, to 90%, or to 85%; from 85% to 100%, to 95%, or to 90%; from 90% to 100%, or to 95%; or from 95% to 100% by weight of insoluble malonate salt in crystalline form.

In some embodiments, the malonate salt may have a diameter of at least 10 µm, at least 15 µm, at least 20 µm, or at least 25 µm; between 10 µm and 30 µm, 25 µm, 20 µm, or 15 µm; between 15 micros and 30 µm, 25 µm, or 20 µm; between 20 µm and 30 µm, or 25 µm; or between 25 µm and 30 µm. The size of a crystalline form can be measured using a Coulter counter (e.g., Beckmann Multisizer 4e).

In other embodiments, a suitable size of the crystalline form of malonate salt can be defined by determining the ease with which the crystalline form can be isolated from the fermentation broth or certain components in the fermentation broth. Such defining can be done, for example, by centrifuging aliquots of fermentation broths at low g-force and measuring the yield of large crystalline forms (diameters >10 µm) in the pellet obtained and of fine crystalline forms (diameters <10 µm) in the supernatant or suspended fines obtained, and defining as the suitable size of the crystalline form any size that maximizes the yield of the large crystalline forms.

Isolating insoluble alkaline earth metal malonate salt from the biomass.

One advantage to forming an insoluble alkaline earth metal malonate salt in a fermentation broth is that the alkaline earth metal malonate salt crystals can be separated from both soluble and insoluble impurities in this fermentation broth. Non-limiting examples of soluble impurities in the biomass include salts, metabolic byproducts produced by the cell, and unconsumed carbohydrates. The primary insoluble impurity present in fermentation broth is cells (i.e., biomass). Cells are particularly problematic in that their occurrence in downstream purification steps can decrease malonic acid yields and product quality through cell lysis and release of various intracellular compounds (e.g., metabolites, proteins, and cell debris). Therefore, it is preferable to separate the insoluble alkaline earth metal malonate salt from both the fermentation broth and cells present in the fermentation broth.

In many embodiments, a process of isolating an alkaline earth metal malonate salt from a fermentation broth involves separating a heavy phase that is enriched in the alkaline earth metal malonate salt and is substantially free of biomass. As used herein, "substantially free" can mean less than 1% w/w, less than 2% w/w, less than 3% w/w, less than 4% w/w, or less than 5% w/w of cells in the heavy phase. If, for example, the heavy phase has a total mass of 1000 kg and contains 750 kg calcium malonate dihydrate and 20 kg cells, the % w/w of cells in the heavy phase is 2% (i.e., 20 kg-cells/1000 kg total mass).

The insoluble alkaline earth metal malonate salt can be isolated from the fermentation broth and cells based on size or mass or density, or a combination of size, mass, and density so long as the isolated insoluble alkaline earth metal malonate salt is substantially free of cells.

In some embodiments, isolation based on size can be accomplished via filtration using, for example, a filter press, candlestick filter, or other industrially used filtration system with a molecular weight cutoff that retains the insoluble alkaline earth metal malonate salt and allows the fermentation broth and cells to pass through.

In other embodiments, isolation based on size and density can be accomplished via settling or centrifugation, using, for example, a settler, centrifuge, or hydrocyclone. Settling, centrifugation, and hydrocyclones all produce a heavy phase, which may be enriched in insoluble alkaline earth metal malonate salt and may be substantially free of cells, and a light phase, which includes primarily the fermentation broth and contains the majority of the cells. When the alkaline earth metal malonate salt is CaM, isolation by settling and/or centrifugation is a particularly attractive option. Yeast cells, for example, typically have a particle size of between 4-6 microns and a density of around 1.1 g/ml. CaM particles, in contrast, are typically greater than 10 microns and have a density of around 1.55 g/ml. The difference in size and density between CaM particles and cells allows for efficient production of a heavy phase enriched in CaM and substantially free of cells.

When separating two solids by centrifugation, two parameters to consider are time and g-force. When separating an alkaline earth metal malonate salt from cells, any combination of time and g-force can be applied so long as the resulting heavy phase is both enriched in the alkaline earth metal malonate salt and is substantially free of cells. Suitable times and g-forces can be determined using methods known in the art. In some embodiments in which the alkaline earth metal malonate salt is CaM, the CaM can be separated from the fermentation broth by settling at a g-force of 1 for a period of 30 minutes to 2 hours. In other embodiments, the CaM can be separated from the fermentation broth by centrifugation for a period of time from 0.5-3 minutes and a g-force from 200×-g to 500×-g.

In many embodiments, centrifugation can be performed using a decanter centrifuge. Fermentation material can be fed into the decanter, which is operated at pre-determined parameters that allow for efficient production of heavy phase enriched in solid CaM and substantially free of cells.

In some embodiments, the CaM can be separated from the fermentation broth using a hydrocyclone. The centrifugal force in a hydrocyclone is generated by introduction of a slurry into the cyclone under pressure; larger and/or denser particles are pushed to the outside of the cone while smaller and/or less dense particles are kept closer to the center. The vortex finder draws the majority of the water and fine particles to the overflow while the larger/denser materials are drawn out of the apex. Hydrocyclones work best if the solution to be centrifuged has a TSS in the range of from 5% to 25%, or is concentrated or diluted to such TSS, because a higher TSS may result in loss of malonate dihydrate in crystalline form to overflow. In some embodiments, a series of hydrocyclones (e.g., 2, 3, or more hydrocyclones) can be used. In smaller scale or benchtop operations, underflow (i.e., wash water) from a hydrocyclone in the series can be sent to a reslurry tank and used to dilute the solution to be centrifuged to the optimal TSS prior to the next hydrocyclone.

In larger operations, such as continuous or semi-continuous manufacturing, the wash water can be derived from a horizontal vacuum belt (HVBF) unit operation or rotary drum vacuum filter (RDVF), which can be continuously fed by the hydrocyclone underflow. In either case, reusing wash water comprising soluble malonate salt can increase the yield of malonate salt in crystalline form obtained.

In many embodiments, two or more centrifugation steps are used in series. In many cases it is advantageous to use a combination of CaM separation unit operations in series in order to optimize both CaM yields and/or CaM purity. For example, a high g-force centrifugation step (see Example 4) can be used to provide a heavy phase enriched in insoluble CaM at a high yield (for example, a greater than 90%, greater than 95%, or greater than 98% yield of insoluble CaM). The wet CaM cake can then be resuspended to a total suspended solids concentration (for example, between 5-25% TSS) that provides optimum performance on a second, more selective and lower g-force centrifugation unit operation (for example, a low-speed decanter centrifuge as described in Example 3 or a hydrocyclone). The resulting CaM in the heavy phase from the second, low g-force centrifugation step is thus used to achieve a high purity CaM (for example, greater than 95% w/w, greater than 98% w/w, or greater than 99% w/w) than either centrifugation operation could provide alone. Additionally, the centrate from the second centrifugation step can also be recycled to the high g-force centrifugation step to recover any insoluble CaM while rejecting the majority of the yeast and other impurities in this recycle stream, thereby increasing CaM yield. Lastly, in many embodiments, the wash water used in the described series of centrifugation steps is used in countercurrent flow. Washing in countercurrent both reduces the soluble CaM losses and reduces the amount of fresh water used during processing.

Isolation of Calcium Malonate Crystals

After separation from biomass, the calcium malonate crystal-containing fermentation broth can be then passed through an appropriate filter. A particularly preferred filtration method is to pass the liquid through a horizontal vacuum belt filter (HVBF) or rotary drum filter. In some embodiments, the crystals can be collected on the filter and washed. The importance of the filtering and washing of the crystals is to achieve a clean and uniform cake discharge to take into the next step of the process. The hydrocyclone underflow may be continuously output into the HVBF process. The HVBF is the ideal equipment as it allows for multi-stage washing and variable dewatering times. A preferred washing liquid is water.

In a preferred embodiment, hydrocycloned CaM slurry can be applied to the filter bed at about 50% TSS. The slurry can be allowed to sit on the filter for 30 seconds before a full vacuum of 20 in Hg below atmospheric pressure is applied. The slurry can be placed on a filter such that there is an effective filtration surface area of 49 in$^2$. The initial filtered cake can then be rewashed twice with distilled or reverse osmosis water and then finally dewatered.

In some embodiments, the slurry comprising filtered or centrifuged alkaline earth metal malonate salt can be further washed and/or dewatered. In some such embodiments, the slurry can be applied to a filter bed at a TSS of about 50% and such that there is an effective filtration surface area of 49 in$^2$. In some embodiments, the slurry can be washed at least once with distilled or reverse osmosis water. In some embodiments, the slurry can be dewatered by applying full vacuum of 20 mmHg below atmospheric pressure. Suitable devices for such washing and/or dewatering can include a HVBF or RDVF.

Acidifying Insoluble Alkaline Earth Metal Malonate Salt

The methods provided herein may further comprise the step of converting insoluble alkaline earth metal malonate salt to soluble malonic acid. Such conversion may be accomplished by acidifying (i.e., protonating) the malonate in the alkaline earth metal malonate salt. Acidification can be accomplished by reacting an aqueous slurry of the alkaline earth metal malonate salt with a mineral acid. Such acidification can produce malonic acid and a corresponding salt comprising the alkaline earth metal of the alkaline earth metal malonate salt and the anion from the mineral acid.

Calcium malonate is acidified to form malonic acid as the final product, which is often desired. Reacting calcium malonate with a strong acid in water generates malonic acid and the corresponding calcium salt. When sulfuric acid is used, its conjugate base sulfate reacts with the displaced calcium ion to form the slightly soluble salt calcium sulfate (also known as gypsum, which has a solubility of about 2.4 g/L at room temperature). Sulfuric acid achieves two goals: 1) the protonation of malonate to form malonic acid and 2) the removal of calcium from solution via the generation of gypsum. In a preferred embodiment, calcium malonate can be reslurried at 40% TSS to achieve gypsum formation at 25-30% TSS when acidified with 25% sulfuric acid. Use of a sulfuric acid feed concentration of 25% v/v may minimize diluting the malonic acid concentration in the overflow as well as allowing for fine pH control by adjusting the feed rate. When running at a large scale, the sulfuric acid concentration can be increased with the use of more sophisticated pH controllers are used, thus increasing the ultimate malonic acid concentration.

Large gypsum crystal formation has been found to ease the separation of solids using an overflow continuous stirred tank reactor (CSTR) fitted with baffles and a radial flow impeller. Calcium malonate can be fed into the reactor at a constant rate. The concentration of the slurry can be measured so that when reacted with a fed sulfuric acid solution, the resulting gypsum solution can be a 25-30% TSS. The reaction can be controlled by adjusting the flow rate of sulfuric acid solution to keep the reactor volume constant at pH 1.5. Since the precipitated solids concentration may be high, the preferred method of separation in some embodiments may be filtration using an HVBF where washing and dewatering can be applied to the filter cake to recover any residual liquor. HVBF may be utilized in the filtration of gypsum due to the ability to manipulate the wash and drying times, as gypsum tends to retain liquor if crystallization produces fine crystals. A rotary drum vacuum filter (RDVF) may be used in lieu of HVBF, although HVBF may be preferred due to its ability to provide purer gypsum crystals. In order to promote even larger crystal growth calcium seed crystals may be introduced.

In a preferred embodiment, a continuous draft tube baffled crystallizer can be employed.

In some embodiments, the composition may then be crystallized, preferably in a draft tube baffle crystallizer in a solution of 25% aqueous $H_2SO_4$. A continuous crystallization process may be preferred over a semi-batch crystallizer because the crystals are easier to filter, wash and dewater. It also allows for more precise control of the pH which improves the yield of high quality, large calcium malonate crystals.

In some embodiments, water may be added to the crystallizer to achieve the desired reaction volume, in the preferred embodiment this is 395 ml total volume. In some embodiments, gypsum seed crystals, which can be 6% by mass, may be introduced with the agitator operating at 800 rpm. In some embodiments, the calcium malonate slurry may be stirred in a separate vessel. In some embodiments, the feed tubes may be placed in the reactor next to the baffles on opposite sides of one another and the feed outlets placed just outside the tip of the impeller. In some embodiments, the initial feed rates may be such that the calcium malonate and sulfuric acid are fed at the same molar rate and the sulfuric acid feed rate is adjusted to control the pH at 1.5. In some embodiments, the reaction may be carried out at ambient temperature. In some embodiments, the reaction may be carried out for approximately 9 minutes. If desired, the material may again be washed and filtered, preferably on a horizontal vacuum belt filter or rotary drum.

Non-limiting examples of mineral acids that can be used for the acidification step include sulfuric acid ($H_2SO_4$), hydrochloric acid, phosphoric acid, and nitric acid. In some embodiments, a concentrated acid may be used to limit dilution of the soluble malonic acid with water. In many embodiments, a mineral acid may be used that forms an insoluble salt with the alkaline earth metal that is easy to separate from the soluble malonic acid. In some embodiments, the mineral acid is $H_2SO_4$. In some such embodiments, the $H_2SO_4$ has a concentration of at least 10% v/v in water to minimize dilution of the malonic acid.

In embodiments in which the alkaline earth metal salt is CaM, reaction with $H_2SO_4$ yields malonic acid and calcium sulfate (i.e., gypsum). Gypsum is highly insoluble (solubility at room temperature of less than 2.4 g/l) such that conditions can be readily optimized for high yield formation of gypsum in crystalline form of large size that can be easily separated from soluble malonic acid, for examples, via filtration or centrifugation. The inventors have discovered that such optimized conditions may include a molar ratio of $H_2SO_4$ to CaM of at least 1:1 to maximize protonation of the CaM, a temperature of below the temperature at which malonic acid decarboxylates to form acetic acid (i.e., approximately 80° C.), and a pH of between 0.5 and 3 to prevent formation of malonic acid salts. In some embodiments, the CaM may be re-slurried at a total suspended solids concentration (TSS) of 40% to achieve gypsum formation at a TSS of 25-30% when acidified with 25% v/v $H_2SO_4$. In some embodiments, formation of gypsum in crystalline form may be aided by addition of gypsum seed crystals during acidification. Gypsum in crystalline form can be isolated from soluble malonic acid based on size or weight or density via filtration or settling or centrifugation as disclosed herein. In some embodiments, separation of gypsum in crystalline form via filtration can be combined with removal of biomass as disclosed herein.

In some embodiments, a continuous draft tube baffled crystallizer may be employed for acidification and formation of gypsum in crystalline form. Crystalline gypsum may be separated in batch or continuously (e.g., using a continuous crystallizer with continuous output to a centrifuge). A continuous crystallization process is generally preferred over a batch or semi-batch crystallization process because the former simplifies filtration, washing, and dewatering of the crystalline form. It also allows for more precise control of the pH, which improves the yield of high quality, large gypsum crystals. Water may be added to the crystallizer to achieve the desired reaction volume. Further, the alkaline earth metal malonate salt slurry may be stirred in a separate vessel. In some embodiments, the feed tubes may be placed in the reactor next to the baffles and the feed rates may be such that the alkaline earth metal malonate salt and $H_2SO_4$ are fed at the same molar rate and the $H_2SO_4$ feed rate is adjusted to control the pH at 1.5.

In some embodiments, the acidification reaction may be performed using conditions that minimize malonic acid decarboxylation and acetic acid formation. Under acidic conditions, malonic acid begins to rapidly decompose at about 80° C.; therefore, it is preferable to perform the acidification reaction at a temperature of less than 80° C. In some embodiments, the acidification reaction may be performed at a temperature of between 20° C. and 80° C., between 30° C. and 80° C., or between 40° C. and 80° C.

In some embodiments, if desired, the resulting salt (e.g., gypsum) may be washed and filtered, on, for example, a horizontal vacuum belt filter or rotary drum filter to capture additional malonic acid an increase the overall unit operation yield.

Removal of Impurities from the Malonate Salt

In some embodiments of the described process, the major impurity contained in the solution after gypsum precipitation is sulfate resulting from the solubility of gypsum and any excess sulfuric acid which has been added. Sulfate may be removed by using barium carbonate to precipitate sulfate as barium sulfate, which has a solubility of 4 mg/L. Other anion exchange resins may be used but barium carbonate prevents more loss of desired product than other resins.

In some embodiments, the methods provided herein further comprise the step of removing impurities from the soluble malonic acid. Impurities may react with malonic acid and reduce final yields, or contribute to the bio-based malonic acid being of lower purity and having more limited industrial utility.

In embodiments in which the alkaline earth metal malonate salt is CaM and $H_2SO_4$ is used for acidification, a major impurity may be sulfate derived from solubilized gypsum and excess $H_2SO_4$. Sulfate can be removed via anion exchange resins. Alternatively, sulfate can be removed via addition of $BaCO_3$ to form barium sulfate ($BaSO_4$), conversion of the $BaSO_4$ to crystalline form by methods disclosed herein, and isolation of the $BaSO_4$ in crystalline form by methods disclosed herein. In embodiments in which $BaCO_3$ is used it is often preferable to use an at least 1 M solution to reduce dilution of the malonic acid.

In some embodiments, nanofiltration may be used to separate out certain salts, sugars, color forming bodies, and other organic compounds present in the soluble malonic acid solution prior to crystallizing malonic acid. In nanofiltration, the malonic acid solution resulting from the acidification step described above may be filtered through a membrane having pore sizes ranging from 0.0005 microns to 0.005 microns, equating to a molecular weight cut-off of about 100 Daltons to about 2,000 Daltons. Nanofiltration can be useful for removing divalent and multivalent ions, maltose and other disaccharides (e.g., sucrose), polysaccharides, and other complex molecules with a molecular weight greater than malonic acid.

As with the precipitation of gypsum, barium sulfate crystallization is involved in the separation of precipitated solids. In some embodiments, a preferred method is to use an overflow CSTR. It is carried out with a barium carbonate slurry and malonic acid solution as feeds. Depending on the crystal size, the precipitated solids may be filtered or centrifuged. Barium sulfate can be precipitated either in batch with the addition of solid barium carbonate or in a continuous crystallizer. Using a continuous crystallizer allows continuous output to a centrifuge for solids removal. Due to the relatively small concentration of sulfate present originally, a 1 M $BaCO_3$ slurry reduces the dilution of the output material to a minimum as well as to ease the stirring and pumping of the slurry. In some embodiments, a similar crystallizer as that described previously may be preferred for this step as well.

In some embodiments, cation and/or anion exchange chromatography may be used to remove specific salts and charged compounds present in the malonic acid solution.

Non-limiting examples of other impurities present in the malonic acid solution include color bodies, hydrophobic compounds, excess cations, volatile compounds (e.g., odorants), chloride ions, and uncatabolized carbohydrates. Many of these impurities can be removed by filtration, chromatography, steam stripping, and/or a combination of these unit operations.

Crystallizing Malonic Acid

The methods provided herein may further comprise the step of crystallizing the soluble malonic acid. For such conversion, the soluble malonic acid will typically reach its solubility limit. This can be accomplished by either concentrating the soluble malonic acid to above its solubility limit or by decreasing the solubility limit of malonic acid.

In some embodiments, soluble malonic acid solution may be concentrated by evaporation at temperatures below the decarboxylation temperature of malonic acid. Accordingly, in some embodiments, evaporation can be carried at temperatures no greater than 80° C. In some such embodiments, evaporation can be carried out at a temperature of 65° C. until a malonic acid concentration of greater than 70% (w/w) is reached, which is near the solubility limit of malonic acid at that temperature. In other embodiments, evaporation can be carried out at lower than atmospheric pressure (using, for example, a wiped film evaporator or falling film evaporator) to increase the rate of evaporation and/or decrease the rate of malonic acid decomposition to acetic acid.

Multiple crystallization schemes may be employed. For example, in some embodiments, multiple cycles of evaporation and cooling crystallization can be used to increase the yield of crystalline malonic acid obtained. The final mother liquor resulting from the last crystallization cycle can be sent through a malonic acid recovery/recycle step. Depending on the desired purity specification, the combined recovery yield can be as high as 99%. Further purification/crystallization schemes may be developed to produce greater purity malonic acid in crystalline form.

In some embodiments, activated carbon may be used to remove trace impurities including color and hydrophobic compounds. In some embodiments, cation exchange resin may be used to remove calcium left over from the gypsum precipitation as well as any other residual cationic species remaining in solution. This allows for the protonation of any deprotonated malonic acid which can decrease solubility, thus father increasing crystallization yields.

Using chromatography columns to elute the input solution through both activated carbon and cation exchange resin has been found to reduce final impurity concentrations further than in batch applications with the same amounts of material. In some embodiments, a flow rate of 3 BV/hour achieves an optimal resistance time for absorption. In some embodiments, the use of 1% granular activated carbon on a malonic acid weight basis has also been shown to sufficiently remove any color impurities that affect the final malonic acid crystal purity.

Evaporation

Evaporation is involved in isolating solid malonic acid as the final product. In various embodiments, water is evaporated to achieve a concentration of 76% wt/wt. For example, the solubility of malonic acid increases as the temperature of the solution is increased. At 65° C., 76% wt/wt is the solubility limit. Evaporation can be carried out under reduced pressure to increase the rate of evaporation and reduce the rate of decomposition of malonic acid. Since malonic acid is prone to decarboxylation at high temperatures, an efficient evaporation method at lower temperatures may be advantageous to reduce the yield loss. A wiped film evaporator or falling film evaporator can be incorporated to efficiently concentrate the solution at a reduced pressure.

Further Crystallization

In some embodiments, once the solution has reached the saturation limit of malonic acid at 65° C., malonic acid can be crystallized in a cooling crystallizer. In some embodiments, a final solution temperature of 20° C. allows for a recovery of greater than 50%. This stage of crystallization produces high grade product. Multiple crystallization schemes may be employed at this point.

In one embodiment, "Scheme 1," the method utilizes three cooling crystallization batches in series with the preceding crystallization liquor being evaporated to its saturation limit and sent to the next crystallizer. In this scheme, the resulting combined yield of three cooling crystallizers is 89%. The final liquor can then be sent through a malonic acid recovery/recycle step.

In another embodiment, "Scheme 2," the method incorporates a yield recovering evaporative crystallization following the initial cooling crystallization. Depending on the desired purity specification, the combined recovery yield may be as high as 99%. Further purification/crystallization schemes may be developed to produce greater purity product.

Advantages of the resultant crystals from embodiments of the method as described herein will generally be large and of high quality. They will be also be relatively free of cellular contamination, thus providing a source of malonic acid that can be put to many industrial uses.

Preparation of Diester Derivatives of Malonic Acid

The methods provided herein may further comprise the step of preparing diester derivatives of malonic acid from bio-based malonic acid. Diester derivatives of malonic acid may include, among others, diethyl malonate or dimethyl malonate. For such preparation, the improved distillation protocols disclosed herein may reduce residual diethyl carbonate levels in the resulting diester derivatives of malonic acid. The improved distillation protocols disclosed herein may further reduce or eliminate levels of impurities such as cyanoacetate and sodium cyanide in the resulting diester derivatives of malonic acid.

Bio-DEM or Bio-Dimethyl Carbonate Purified from Malonic Acid

In some embodiments, malonic acid may be combined with dialkyl carbonate (for example diethyl carbonate or dimethyl carbonate) and sulfuric acid and refluxed for a period of time. In some embodiments, the ratio of malonic acid:dialkyl carbonate:sulfuric acid may be 1:5:0.5. In some embodiments, the ratio of malonic acid:dialkyl carbonate: sulfuric acid may be 1:2.5:0.5. In some embodiments, the amount of malonic acid used in the reaction may be between 1 kg and 125 kg. In some embodiments, the mixture is added to a reactor capable of holding anywhere from 6 gallons to 300 gallons. In some embodiments, the mixture may be refluxed for 5 hours. In other embodiments, the mixture may be refluxed for 8 hours. In other embodiments, the mixture may be refluxed for between 5 and 8 hours. In some embodiments, the refluxing mixture may be at a temperature of 90° C. It some embodiments, after the period of heating, the mixture may be cooled and quenched with saturated sodium carbonate or saturated sodium bicarbonate solution. In some embodiments, in this step, the mixture may be cooled to 30° C. In some embodiments, in this step, the mixture may be cooled to 38° C. In some embodiments, in this step, the mixture may be cooled to a temperature between 30° C. and 38° C.

In some embodiments, the reaction may next comprise slowing or stopping of the mixing and allowing the liquid phases of the mixture to separate. In some embodiments, there will be a separate aqueous phase and organic phase. In some embodiments, the pH of the aqueous phase may be 7.0.

In some embodiments, the reaction may continue by separating and removing the aqueous phase. In some embodiments, the remaining organic phase may be further purified by simple distillation under vacuum at or near 20 torr. In some embodiments, the distillate may be further purified by slowly increasing the solution's temperature from room temperature to about 70° C., to remove impurities, and may further comprise increasing the solution's temperature to 95° C. In some embodiments, this slow increase of temperature may occur at 1° C. per minute. In some embodiments, the product distillate may then be collected. In some embodiments, the product distillate may contain greater than 97% diethyl malonate. In some embodiments, the product distillate may contain greater than 98% diethyl malonate. In some embodiments, the product distillate may contain greater than 99% diethyl malonate. In some embodiments, the product distillate may contain greater than 97% dimethyl malonate. In some embodiments, the product distillate may contain greater than 98% dimethyl malonate. In some embodiments, the product distillate may contain greater than 99% dimethyl malonate.

Further Purification of Bio-DEM or Bio-Dimethyl Malonate

In some embodiments, DEM or dimethyl malonate may be further purified. In some embodiments, this purification may comprise combining bio-DEM or bio-dimethyl malonate with an equivalent mass of deionized water. In some embodiments, this mixture may be heated to a temperature of 90° C. while mixing for 1 hour. In some embodiments, the mixture may then be cooled to room temperature, with no mixing, thus allowing the mixture to settle. In some embodiments, the aqueous phase may then be removed from the purification. In some embodiments, 5-10% of the weight of the material may be removed (in a lower-purity fraction) from the organic phase and the solution may be further purified by simple distillation under vacuum at or near 20 torr. In some embodiments, this may occur by slowly increasing the solution's temperature from room temperature to about 95° C. In some embodiments, a sample of the distillate product may be collected for analysis. In some embodiments, the simple distillation step may be repeated, after removing an additional 5-10% of the weight of the material. In some embodiments, the distillate product from the simple distillation may be further purified utilizing a fractionating column, such as a 5-stage Vigreux column, at or near 20 torr, by slowly increasing the solution's temperature to about 95° C. In some embodiments, this slow increase of temperature may occur at 1° C. per minute. In some embodiments, the product distillate may contain greater than 97% diethyl malonate. In some embodiments, the product distillate may contain greater than 98% diethyl malonate. In some embodiments, the product distillate may contain greater than 99% diethyl malonate. In some embodiments, the product distillate may contain greater than 97% dimethyl malonate. In some embodiments, the product distillate may contain greater than 98% dimethyl malonate. In some embodiments, the product distillate may contain greater than 99% dimethyl malonate.

The methods provided herein may decrease the concentration of chain terminators in the resulting diester derivatives of malonic acid. In some embodiments, this decrease in concentration may result in a faster curing time.

In some embodiments, the methods provided herein may decrease the levels of one or more impurities in the resulting diester derivatives of malonic acid. Impurities in diester derivatives of malonic acid may cause unintended effects, including a lack of control over the rate of polymerization, a termination of polymerization when malonate diester monomers are used for crosslinking, Michael Addition reactions or polymerization with diols to synthesize polyester polymers. In some embodiments, impurities such as diethyl sulfate (DES) can cause haziness due to salt formation with amines during polymerization and curing. By removing impurities or making a de novo preparation lacking the impurities, through the compositions containing diester derivatives of malonic acid disclosed herein, more control is held over cure speed and in the improvement of the hardness of resins and polymers in downstream applications. Non-limiting examples of impurities removed to a degree from malonic acid using the methods disclosed herein comprise diethyl sulfate (DES), cyanoacetic acid esters, cyanoacetate, other cyano-compounds, chloro compounds including chloroacetate and ethyl chloroacetate, 2-propanone, 1,1,3,3-tetrochloro, sodium cyanide, and acetic acid, (acetyloxy)-ethyl ester.

The use of the disclosed improved methods will avoid the synthesis of diester derivatives of malonic acid containing higher levels of impurities, and may increase final yields of diester derivatives of malonic acid and/or downstream products. In some embodiments, the use of the disclosed methods may result in the purification or synthesis of bio-based diester derivatives of malonic acid of higher purity and with broader industrial utility.

In some embodiments, the process for purifying diester derivatives of malonic acid can result in compositions for use in downstream polymerization, crosslinking, Michael Addition reactions, or other such applications, such as those described in U.S. Pat. Nos. 9,718,988 and 9,834,701.

In addition to the purification processes identified herein, direct enzymatic esterification to produce diethyl malonate may be achieved via introduction of O-acyltransferases into the organisms described herein. Table 1 provides a starting point for choices of 0-malonyl transferases, but fruits contain many O-acyltransferases, thus providing a wealth of suitable enzymes to introduce.

TABLE 1

Examples of O-malonyl Transferases

| Organism | Gene/NCBI identifier | Comment |
|---|---|---|
| Cucumis melo | CAA94432 | alcohol acyltransferase |
| Musa acuminata | AX025506 | alcohol acyltransferase |
| Actinidia deliciosa | AdATG | homologous to strawberry acyltransferases |
| Actinidia deliciosa | AdAT22 | homologous to strawberry acyltransferases |
| Actinidia deliciosa | AdAT24 | homologous to strawberry acyltransferases |
| Glycine max | GmIF7MaT | isoflavone 7-O-beta-D-glucoside |
| Salvia splendens | Ss5MaT1 | anthocyanin 5-O-glucoside |
| Dahlia variabilis | Dv3MaT | anthocyanidin 3-O-glucoside |
| Fragaria vesca | Aat1 | alcohol acyltransferase |
| Fragaria vesca | Aat2 | alcohol acyltransferase |
| Fragaria vesca | Aat3 | alcohol acyltransferase |
| Fragaria vesca | Aat4 | alcohol acyltransferase |
| Fragaria vesca | FvAat5T | alcohol acyltransferase |
| Fragaria vesca | FvAat6 | alcohol acyltransferase |

Compositions

Further provided herein are bio-based malonic acid compositions and bio-based diester derivatives of malonic acid. For determination of relative or absolute quantities of malonic acid and/or diester derivatives of malonic acid in any of the compositions described herein, any suitable analytical method may be used. For example, malonic acid and/or diester derivatives of malonic acid components of a composition may be quantified by chromatography such as liquid chromatography (e.g., HPLC). Area per area percent (area %) of elution peaks associated with malonic acid and/or diester derivatives of malonic acid and/or their byproducts can be measured and quantified using known techniques, or weight per weight percent (w/w % or wt %) of each malonic acid and/or byproducts in a composition may be determined using known techniques for mass assay following HPLC analysis (e.g., by using a standard malonic acid sample having a purity of greater than 99% (e.g., 99.95% pure) as a reference). Malonic acid having a purity of 99.95% derived synthetically using non-renewable carbon may be purchased from Sigma-Aldrich, St. Louis, Mo. Diester derivatives of malonic acid (diethyl malonate and dimethyl malonate) having a purity of 98% and derived synthetically using non-renewable carbon may be purchased from Sigma-Aldrich, St. Louis, Mo. For any of the compositions disclosed herein, quantities of malonic acid or diester derivatives of malonic acid are given as percentages refer to any of the wt %, area %, or vol %, unless specifically indicated otherwise.

In certain embodiments, provided herein are malonic acid compositions (e.g., malonic acid having a purity of about 90% or greater, e.g., about 90%, 92%, 95%, 99%, or 99.5%, more than 95%, more than 96%, more than 97%, more than 98%, more than 99%, more than 99.95%, or more than 99.99%, or greater based on the total composition, where % refers to weight percent, area percent, or volume percent) produced by crystallization of malonic acid from an aqueous solution of malonic acid.

In some variations, the malonic acid may be produced by engineered microorganisms grown in media containing a renewable carbon source. The malonic acid compositions described herein are differentiated from malonic acid derived from chloroacetic acid and cyanide by the presence of substantially lower amounts of impurities.

In certain embodiments, provided herein are compositions containing diester derivatives of malonic acid. In some embodiments, the composition contains diethyl malonate (e.g., diethyl malonate having a purity of about 90% or greater, e.g., about 90%, 92%, 95%, 97%, 99%, or 99.5%, more than 95%, more than 96%, more than 97%, more than 98%, more than 99%, more than 99.95%, or more than 99.99%, or greater based on the total composition, where % refers to weight percent, area percent, or volume percent) purified by the disclosed methods from malonic acid.

In certain embodiments, provided herein are compositions containing dimethyl malonate (e.g., dimethyl malonate having a purity of about 90% or greater, e.g., about 90%, 92%, 95%, 97%, 99%, or 99.5%, more than 95%, more than 96%, more than 97%, more than 98%, more than 99%, more than 99.95%, or more than 99.99%, or greater based on the total composition, where % refers to weight percent, area percent, or volume percent) purified by the disclosed methods from malonic acid.

In some embodiments, the methods provided herein result in diester derivatives of malonic acid containing diethyl malonate purity of at least 99%, less than 1.5% diethyl carbonate (DEC), less than 0.34% diethyl sulfate (DES), and less than 0.004% cyanoacetic acid.

In some embodiments, provided herein are compositions containing diester derivatives of malonic acid for use in polymerization reactions. In some such embodiments, the compositions contain diester derivatives of malonic acid with a low impurity level and use of these compositions may result in a less hazy polymer end-product. In some embodiments, provided herein are compositions containing diester derivatives of malonic acid for use as a blocking catalyst. In some embodiments, provided herein are compositions containing diester derivatives of malonic acid with a low impurity level and use of these compositions may result in a faster cure speed of resins and polymers. In some embodiments, provided herein are compositions containing diester derivatives of malonic acid with a low impurity level and use of these compositions may result in increased resin or polymer hardness.

Additional components of compositions of diester derivatives of malonic acid resulting from the methods disclosed herein may comprise succinate diesters and general plasticizers. These components may be beneficial, or may have no effect on the downstream uses of the compositions containing diester derivatives of malonic acid.

EXAMPLES

Example 1: Construction of recombinant nucleic acids encoding wild-type EHD3 and EHD3 mutants E124S, E124A, E124A/E308V, and E124V malonyl-CoA hydrolases and expression vectors for production of malonate in E. coli The present disclosure provides methods for producing malonate in an *E. coli* host, as well as *E. coli* host cells that produce malonate and express an EHD3 mutant enzyme, including but not limited to E124S, E124A, and E124V. This example describes the construction of protein coding sequences for EHD3 and the mutant EHD3 proteins useful in this disclosure, expression vectors containing those coding sequences, and host cells comprising those expression vectors. The nucleic acid encoding wild type *S. cerevisiae* EHD3 was amplified by PCR from Baker's yeast using primer pair A93/A94 (see Table 1 for primer sequences). Point mutation E124A was introduced using primer pairs A93/A96 and A95/A94, mutation E124V was introduced using primer pairs A93/A98 and A97/A94, and mutation E124S was introduced using primer pairs A93/A100 and A99/A94. The resulting nucleic acids were cloned into an *E. coli* expression vector containing the pSC101 origin of replication, a chloramphenicol resistance cassette, and a $P_{LacO1}$ promoter using standard techniques. The resulting vectors were transformed into an *E. coli* DH10b host and plated on Luria-Bertani (LB) agar plates containing 50 μg/ml chloramphenicol ($Cm^{50}$) and 2% w/v glucose. Individual colonies were then inoculated into 3 ml LB media in 48-well plates; following 6 hours growth, plasmids were isolated and the EHD3 protein-coding region sequenced. When sequencing plasmids derived from clones of EHD3 (E124A), it was discovered that a second, point mutation, E308V, stabilized the EHD3 (124A) clone; the presence of an uncharged valine residue likely stabilizes protein folding. The EHD3 (E124A, E308V) strain was also used for malonate production (see Example 2).

TABLE 1

PCR primers used for introduction of point mutations into EHD3 coding sequence

| Primer | PCR Primer Sequence (5'-3') | SEQ ID NO |
|---|---|---|
| A93 | CCAATATATAATAAAATATGGAGGAATGCG ATGCTCAGAAATACGCTAAAATGTGCCCAA | SEQ ID NO: 11 |
| A94 | TGCCTGGAGATCCTTACTCGAGTTGGATCC TTATTTCCATCTTAAGCCATCGTTAACTTC | SEQ ID NO: 12 |
| A95 | TTTTACTGATGCGTATTCTTTGAATTTTCA AATAGCA | SEQ ID NO: 13 |
| A96 | TCAAAGAATACGCATCAGTAAAAAATTTGA TGGA | SEQ ID NO: 14 |
| A97 | TTTTACTGATGTTATTCTTTGAATTTTCA AATAGCAACTT | SEQ ID NO: 15 |
| A98 | TCAAAGAATAAACATCAGTAAAAAATTTGA TGGACTTGG | SEQ ID NO: 16 |
| A99 | TTTTACTGATTCGTATTCTTTGAATTTTCA AATAGCAAC | SEQ ID NO: 17 |
| A100 | TCAAAGAATACGAATCAGTAAAAAATTTGA TGGACT | SEQ ID NO: 18 |

Example 2: In Vivo Production of Malonate in E. coli Using EHD3 Mutants E124S and E124A/E308V This example describes the host cells and culture conditions resulting in the in vivo production of malonate using a heterologous EHD3 malonyl-CoA hydrolase in an *E. coli* host cell. *E. coli* strain K12 was transformed with vectors containing wild-type EHD3, EHD3 (E124A), EHD2 (E124V), EHD3 (E124S), EHD3 (E124A, E308V) or an empty vector negative control. Transformants were streaked on LB agar plates ($Cm^{50}$, 2% glucose). Following overnight growth at 37° C., individual colonies were inoculated into 3 ml LB ($Cm^{50}$, 2% glucose) in a 48-well plate. Cultures were incubated on a plate shaker at 37° C. for 6 hours, at which point each culture was inoculated 1% v/v into M9 minimal medium supplemented with $Cm^{50}$ and a mixed carbon source (0.5% glycerol, 0.05% glucose, 0.2% lactose) in a 48-well plate. Cultures were incubated on a plate shaker at 30° C., and a 500 μL sample of the fermentation broth was removed for analysis after 48 hours incubation.

Samples were centrifuged (×6000 g, 1 min) and the supernatant analyzed for malonate quantification. Chemical standards were prepared in 20 μM of water. The separation of malonate was conducted on a Shimadzu Prominence XR UPLC connected to a refractive index detector and UV detector monitoring 210 nm. Product separation was performed on a Bio-Rad Fermentation Monitoring column. The UPLC was programmed to run isocratically using 5 mM $H_2SO_4$ as the eluant with a flow rate of 600 μL per minute. 10 μL were injected per sample, and the sample plate temperature was held at 4° C. Malonate standards began eluting at ~19.8 minutes. Addition of the standard to samples containing malonate demonstrated a proportional increase in malonate peak area, confirming malonate production. Malonate concentrations (mg/l) were calculated by comparison to a standard curve prepared from authentic malonate.

For cultures harboring the empty vector control, no peak was observed at the same retention time as the malonate standard, and the integrated peak area was below the detection limit of the instrument (i.e., no malonate production was observed). Malonate production was observed in samples harboring wild-type EHD3, EHD3 (E124A), EHD3 (E124V), EHD3 (E124S), and EHD3 (E124A, E308V); malonate concentrations are provided in Table 2 (mean±std dev; n=3). EHD3 (E124V) resulted in decreased production of malonate relative to the wild-type protein, likely due to both poor malonyl-CoA substrate binding and high promiscuous activity toward other, endogenous acyl-CoA molecules. Similarly, EHD3 (E124A) yielded only a minor increase in malonate production relative to wild-type EHD3. EHD3 mutant E124S resulted in a significant (p<0.05, t-test) increase in malonate production over wild-type EHD3, EHD3 (E124A), and EHD (E124V), demonstrating the importance of E124S in increasing malonyl-CoA substrate binding and malonate production.

TABLE 2

Production of malonate in E. coli using S. cerevisiae EHD3 malonyl-CoA hydrolases

| Strain | Malonate Concentration (mg/l) |
|---|---|
| Empty vector control | Not detected |
| Wild-type EHD3 | 6.0 ± 0.2 |

TABLE 2-continued

Production of malonate in E. coli using
S. cerevisiae EHD3 malonyl-CoA hydrolases

| Strain | Malonate Concentration (mg/l) |
| --- | --- |
| EHD3 (E124A) | 7.6 ± 0.7 |
| EHD3 (E124V) | 0.28 ± 0.03 |
| EHD3 (E124S) | 82.3 ± 7.8 |
| EHD3 (E124A/E308V) | 8.35 ± 2.5 |

Example 3: Construction of Additional EHD3 E124 Mutants and Expression Vectors for In Vivo Production of Malonate in E. coli Example 1 describes the construction of E. coli expression vectors for wild-type EHD3 and a subset of E124 mutations, specifically E124A, E124V, E124S, and E124A/E308V, and Example 2 describes their use to produce malonate in E. coli cells. This example describes construction of E. coli expression vectors for all EHD3 E124 point mutations, i.e., E124G, E124T, E124C, E124L, E124I, E124M, E124P, E124Y, E124W, E124D, E124N, E124Q, E124H, E124K, E124R, and E124F. These EHD3 mutants were constructed using an E. coli vector with pSC101 origin and PLacO1 origin of replication, as described in Example 1. The forward PCR primer comprises nucleic acid sequence (5'-aatttttactgatNNNtattctttgaattttcaaatagc-3')(SEQ ID NO: 19), where sequence "NNN" is the three nucleotides encoding the desired E124 amino acid point mutation; likewise, the reverse PCR primer comprises nucleic acid sequence (5'-ttcaaagaataaNNNatcagtaaaaaatttgatggacttg-3') (SEQ ID NO: 20), where sequence "NNN" is complementary to the three nucleotides encoding the desired E124 amino acid point mutation. The forward PCR primer was used in conjunction with PCR primer A94, and the reverse PCR primer was used in conjunction with PCR primer A93 (see Example 1) to produce two overlapping EHD3 gene fragments containing the desired point mutation. Amplification of the two EHD3 gene fragments with primers A93 and A94 yielded the full length EHD3 gene containing the desired point mutation. The expression vectors were constructed using standard cloning protocols and transformed into E. coli DH10b and were subsequently isolated as described in Example 1 and verified by sequencing.

Example 4: In Vivo Production of Malonate in Recombinant E. coli Using EHD3 E124 Mutants This example describes fermentation of a set of E. coli host cells, each member of the set containing one of the 19 possible EHD3 E124 amino acid substitutions and determination of malonate levels produced. Specific E124 point mutations should theoretically improve malonyl-CoA binding and malonate production relative to wild-type; in particular, point mutations E124T, E124N, E124Q, E124H, E124K, and E124R should improve malonate production, theoretically due to introducing amino acids containing functional groups that improve interaction with the terminal carboxylic acid moiety of malonate. Point mutations E124S, E124Q, and E124K have side-chains that are located in the EHD3 binding pocket in positions that should theoretically best coordinate malonate binding. Malonate production is performed as substantially described in Example 2.

Example 5: Construction of YciA Malonyl-CoA Hydrolase Expression Vectors for In Vivo Production of Malonate in E. coli This example describes the use of E. coli YciA for the production of malonate in E. coli in accordance with this disclosure. Wild type E. coli acyl-CoA YciA is PCR amplified from the host genome using primers A120 (5'-ccaatatataataaaatatggaggaatgcgatgtctacaacacataacgtccctc-3') (SEQ ID NO: 21) and A121 (5'-tgcctggagatccttactcgagttggatccttactcaacaggtaaggcgcgag-3') (SEQ ID NO: 22). The resulting nucleic acid is cloned behind the $P_{LacO1}$ promoter on an E. coli expression plasmid containing a pSC101 origin of replication and an ampicillin resistant gene. The control vector comprises an empty vector without the yciA gene insertion behind the $P_{LacO1}$ promoter. As described in Example 1, individual colonies are cultured, their plasmid isolated, and the coding region of the YciA gene insert sequenced.

Example 6: In Vivo Production of Malonate in Recombinant E. coli Using Heterologous YciA This example describes the host cells and culture conditions resulting in in vivo production of malonate using an expression vector encoding a heterologous YciA malonyl-CoA hydrolase as described in Example 5 in an E. coli host cell. Wild type E. coli strain K12 is transformed with vectors containing E. coli YciA; wild-type E. coli harboring an empty vector serves as a negative control. Malonate production is performed as described in Example 2.

Example 7: Construction of Engineered EHD3 Malonyl-CoA Hydrolase Expression Vectors for In Vivo Production of Malonate in Yeast The present disclosure also provides expression vectors, host cells, and methods for in vivo production of malonate in a yeast cell. Yeast cells can, in general, tolerate higher concentrations of organic acids in the fermentation broth and possess better-established industrial fermentation protocols than E. coli.

The yeast expression vectors described in this example were generated in part from use of the E. coli expression vectors described in Examples 1 and 3 as PCR templates for the EHD3 genes. The yeast expression vectors contain a 2-micron origin of replication, ura3 auxotrophic marker, and TEF promoter; the vectors also contain a puc origin of replication and an ampicillin or chloramphenicol resistance cassette for vector propagation in E. coli. The plasmids were transformed into either a S. cerevisiae BY4741 or BY4742 background, both derivatives of the S288C parental strain.

Additional mutations can be introduced into the EHD3 coding sequence to abrogate mitochondrial targeting. The basic amino acids R3, K7, K14, K18, and R22 in the EHD3 coding sequence are involved in mitochondrial targeting, and mutation of any one or more of them to A or V decreases mitochondrial EHD3 expression and increases cytosolic EHD3 expression. Mutations are introduced by PCR amplification of an EHD3 template with forward and reverse primers containing the desired point mutation. Mutations are introduced using primers matching the EHD3 gene with the exception that the nucleotide sequence at the position of the desired amino acid point mutations is altered to "gyt" (where y is either a cysteine or thymine nucleotide in a mixed population of oligonucleotide PCR primers). The gene fragments are first cloned into an E. coli expression vector harboring a pSC101 origin of replication, pLac01 promoter, and chloramphenicol resistance marker, and the vector sequences confirmed as described in Example 1; following isolation of the desired mutant, the EHD3 gene is amplified and cloned into a yeast expression vector.

Example 8: In Vivo Production of Malonate in Recombinant Yeast Using Engineered EHD3 Malonyl-CoA Hydrolase S. cerevisiae BY4742 host cells are transformed with a yeast expression vector prepared substantially as described in Example 7 harboring heterologous EHD3 or an empty vector negative control plasmid using standard protocols. Transformants are streaked on synthetic complete dropout medium (SD) agar plates lacking uracil and cultured at 30° C.; individual colonies are grown overnight in 3 mL SD media overnight at 30° C. and subsequently diluted 1% v/v into 3 ml of SD lacking uracil. Strains are cultured at 30° C. for 72 hours; 500 µl aliquots are sampled at 24, 48, and 72 hour timepoints for quantification of malonate production and $OD_{600}$. The TEF promoter is a constitutive promoter.

Example 9: Increasing Malonate Biosynthesis in Engineered Yeast Through Expression of Heterologous Acetyl-CoA Synthetase In addition to the methods, vectors, and host cells for expression of a heterologous malonyl-CoA hydrolase and in vivo production of malonate, as illustrated in Examples 1-8, this disclosure also provides methods and host cells for improved titer, yield, and/or productivity of malonate. In one aspect, malonate production is improved by increasing the biosynthesis of acetyl-CoA. This example describes heterologous expression of acetyl-CoA carboxylase enzymes in a recombinant S. cerevisiae host comprising a malonyl-CoA hydrolase pathway and resulting improvement in malonate production. The five acetyl-CoA carboxylase proteins illustrated are S. cerevisiae ACS1 and ACS2, E. coli AcsA, Salmonella enterica Acs, and Bacillus subtilis AcsA. All genes are PCR amplified from their respective hosts and cloned into a yeast expression vector harboring a 2-micron origin of replication, ura3 auxotrophic marker, and TEF promoter; the vectors also contain a puc origin of replication and ampicillin resistance cassette for vector propagation in E. coli.

Example 10: Increasing Malonate Biosynthesis in Engineered Yeast Through Expression of Heterologous Pyruvate Dehydrogenase While Example 9 describes increased acetyl-CoA biosynthesis through expression of heterologous acetyl-CoA carboxylases, this example describes increased acetyl-CoA biosynthesis through expression of heterologous pyruvate dehydrogenase enzymes. In specific, S. cerevisiae pyruvate dehydrogenase enzymes PDA1, PDB1, LAT1, LPD1, and PDX1 are heterologously expressed in recombinant S. cerevisiae comprising a malonyl-CoA hydrolase pathway. The genes are all PCR amplified from the S. cerevisiae chromosome and cloned into a yeast expression vector harboring a 2-micron origin of replication, ura3 auxotrophic marker, and TEF promoter; the vectors also contain a puc origin of replication and ampicillin resistance cassette for vector propagation in E. coli.

Example 11: Increasing Malonate Biosynthesis in E. coli and S. cerevisiae by Heterologous Expression of an Ethanol Catabolic Pathway This example describes a third route to increase acetyl-CoA biosynthesis: heterologous expression of an ethanol catabolic pathway. An ethanol catabolic pathway comprises two or three enzymes. An alcohol dehydrogenase and an acetaldehyde dehydrogenase (acylating), or an alcohol dehydrogenase, acetaldehyde dehydrogenase (non-acylating), and an acetyl-CoA synthetase. The alcohol dehydrogenase enzymes S. cerevisiae ADH2, E. coli AdhP, and H. sapiens ADH1A, H. sapiens ADH1B, and H. sapiens ADH1C are combinatorially cloned with an acetaldehyde dehydrogenase (acylating) or aldehyde dehydrogenase and acetyl-CoA synthetase. The acetaldehyde dehydrogenase (acylating) enzymes E. coli MhpF, E. coli AdhE, Pseudomonas sp CF600 DmpF, and Pseudomonas putida TodL are also all cloned combinatorially. In ethanol catabolic pathways utilizing an acetaldehyde dehydrogenase (non-acylating) S. cerevisiae ALD2, ALD3, ALD4, ALD5, and ALD6 are used. Acetyl-CoA synthetase enzymes used are S. cerevisiae ACS1 and ACS2, and E. coli Acs. All genes are PCR amplified from genomic DNA.

For E. coli host cells, the ethanol catabolic pathway is expressed from a vector backbone harboring p15a origin of replication, ampicillin resistance marker, and $P_{lacO1}$ promoter. All combinations of all two and three gene pathways are constructed as single operons. E. coli K12 is co-transformed with an EHD3 expression plasmid and an ethanol catabolic pathway plasmid and streaked on LB agar plates (Cm50, Cb50, 2% w/v glucose). Control strains harbor empty vector. Production cultures and analysis thereof are conducted as described in Example 2, with the notable exception of the addition of the second antibiotic used to maintain the second plasmid.

S. cerevisiae fermentations can be conducted using identical ethanol concentrations as the E. coli experiments. The yeast expression vectors harbor a 2-micron origin, ura3 auxotrophic marker, and CUP promoter, and all combinations of the ethanol catabolic pathways are constructed on this vector backbone; a plasmid absent an ethanol catabolic pathway serves as a negative control. An ethanol catabolic pathway plasmid is transformed into recombinant S. cerevisiae BY4742 comprising an engineered EHD3 malonyl-CoA hydrolase pathway on a yeast chromosome. All fermentations are conducted at 30° C. in SD media without uracil. Ethanol catabolic pathway expression is induced with 100 µM copper sulfate after 12 or 24 hours growth. 500 µl aliquots are sampled at 24, 48, and 72 hours for quantification of ethanol, acetaldehyde, acetate, and malonate concentrations; $OD_{600}$ measurements of cell density are also recorded at each timepoint. In addition to malonate titer, ethanol consumption is calculated.

Example 12: Increasing Malonate Biosynthesis in S. cerevisiae by Heterologous Expression of an ATP Citrate Lyase This example describes a fourth approach to increase acetyl-CoA biosynthesis and improve malonate production in recombinant S. cerevisiae. ATP citrate lyase (EC 2.3.3.8) catalyzes the formation of acetyl-CoA, oxaloacetate, and ADP in the cytosol from citrate. ATP citrate lyase enzymes from the oleaginous yeasts Candida curvata, Cryptococcus albidus, Lipomyces hpofer, Rhodospiridium toruloides, Rhodotorula glutanis, Trichosporon cutaneum, Yarrowia hpolytica, are PCR amplified from genomic DNA and cloned into a yeast expression vector behind a CUP promoter; the expression vector contains a 2-micron origin and leu2d auxotrophic marker. A plasmid absent an ATP citrate lyase enzyme serves as a negative control.

An ATP citrate lyase pathway plasmid is transformed into recombinant S. cerevisiae BY4742 comprising an engineered EHD3 malonyl-CoA hydrolase pathway on a yeast chromosome. All experiments are conducted at 30° C. in SD media without uracil. ATP citrate lyase pathway expression is induced with 100 μM copper sulfate after 12 or 24 hours growth. Some cultures are also supplemented with 0.5, 1, 2.5, or 5 g/l citrate to provide an additional demonstration of pathway activity. 500 μl aliquots are sampled at 24, 48, and 72 hours for quantification of citrate (where applicable) and malonate concentrations; $OD_{600}$ measurements of cell density are also recorded at each timepoint. In addition to malonate titer, citrate consumption can be calculated.

Example 13: Increasing Malonate Biosynthesis in Recombinant Yeast Through Modification of Host Cell Fatty Acid Storage This example describes a fifth approach to increase acetyl-CoA biosynthesis and improve malonate production in recombinant *S. cerevisiae*. Fatty acid biosynthesis pathways compete with malonate production for acetyl-CoA and malonyl-CoA, and altering host cell fatty acid anabolism can increase malonate production. The present disclosure provides host cells comprising genetic modifications of one or more nucleic acids encoding proteins affecting fatty acid storage and catabolism. In *Saccharomyces cerevisiae*, the proteins SNF2, IRA2, PRE9, PHO90, SPT21, PDX1, ANTI, FOX3, EHD3, PAS1, PAS3, ARE1, ARE2, DGA1, LRO1, ACL1, MAE1, GLC3, GLG1, GLG2, PAT1, and PEX11 are knocked out individually and combinatorially and the resulting strains cultured for malonate production. All *S. cerevisiae* strains constructed comprise an engineered EHD3 malonyl-CoA hydrolase pathway for production of malonate. Fermentations are performed as described in Example 8, and malonate is quantified as described in Example 2.

Example 14: Increasing Malonate Biosynthesis in Recombinant Yeast Through Increased Beta-Oxidase Activity This example describes a sixth approach to increase acetyl-CoA biosynthesis and improve malonate production in recombinant *S. cerevisiae*. In addition to decreasing host cell fatty acid anabolism, increasing host cell fatty acid catabolism can increase malonate production. The present disclosure provides host cells modified for increased expression of PAT1 and/or PEX11. PAT1 and PEX11 are PCR amplified from genomic *S. cerevisiae* DNA and cloned into a yeast expression vector behind a CUP promoter; the expression vector contains a 2-micron origin and leu2d auxotrophic marker. A plasmid without a beta-peroxidase enzyme serves as a negative control.

A beta-oxidase pathway plasmid is transformed into recombinant *S. cerevisiae* BY4742 comprising an engineered EHD3 malonyl-CoA hydrolase pathway on a yeast chromosome. The engineered malonyl-CoA hydrolase is integrated onto the chromosome using standard recombination methods. The resulting strain serves as a base to test subsequent modifications and their impact on malonate production. All experiments are conducted at 30° C. in SD media without uracil. Pathway expression is induced with 100 μM copper sulfate after 12 or 24 hours growth. Some cultures are also supplemented with 0.5, 1, 2.5, or 5 g/l palmitic acid to provide an additional demonstration of pathway activity. 500 μl aliquots are sampled at 24, 48, and 72 hours for quantification of palmitic acid (where applicable) and malonate concentrations; $OD_{600}$ measurements of cell density are also recorded at each timepoint. In addition to malonate titer, palmitic acid consumption can be calculated.

Example 15: Improving Malonate Biosynthesis in Engineered Yeast Through Increased Acetyl-CoA Carboxylase Activity In addition to the methods, vectors, and host cells for expression of a heterologous malonyl-CoA hydrolase and in vivo production of malonate, this disclosure also provides methods and host cells for improved titer, yield, and/or productivity of malonate. In one aspect, malonate production is improved by increasing the biosynthesis of malonyl-CoA. Malonyl-CoA is the penultimate intermediate in the biosynthesis of malonate from acetyl-CoA, and in *S. cerevisiae*, this reaction is catalyzed by acetyl-CoA carboxylase (ACC1). Malonyl-CoA biosynthesis is increased by overexpression of *S. cerevisiae* ACC1. Toward this end, the ACCT gene is cloned using standard methods behind the CUP promoter on an *S. cerevisiae* expression plasmid containing a 2-micron origin of replication and ura3 auxotrophic marker. The control vector comprises an empty vector. *S. cerevisiae* host strains are engineered with chromosomal deletions of ACC1 and SNF1 protein kinase responsible for ACC1 phosphoregulation; chromosomal deletions are constructed both independently and in combination. Host cells harboring expression plasmids or control plasmids are grown as described in Example 8 and malonate production quantified as described in Example 2.

Example 16: Improving Malonate Biosynthesis in Host Cells Through Supplementation of the Fermentation Broth with Cerulenin In this example, malonate production in a recombinant host cell expressing an EHD3-derived malonyl-CoA hydrolase is improved by supplementation of the fermentation broth with cerulenin. The malonate production plasmid A4, comprising *S. cerevisiae* EHD3 (E124S) under control of a $P_{LacO1}$ promoter, is transformed into an *E. coli* K12 host.

Individual colonies are inoculated into 3 ml LB medium ($Cm^{50}$, 2% w/v glucose) in 48-well plates and cultured for 6 hours at 37 degrees C. on a plate shaker (Lab Line Instruments). Strains are then subcultured 1% v/v into 3 mL of M9 minimal medium ($Cm^{50}$, 0.5% w/v glycerol, 0.05% w/v glucose, 0.2% w/v lactose) and cultured at 30 degrees C. on a plate shaker (Lab Line Instruments). Following 6 hours growth, one half of the cultures are supplemented with 10 mg/l cerulenin. After 48 hours growth, malonate concentration in the supernatant is measured as described in Example 2.

Example 17: Improving Malonate Biosynthesis in Engineered Yeast Through Supplementation of Fermentation Broth with Carbon Dioxide In this example, fermentation conditions are modified to increase the biosynthesis of malonyl-CoA. Enzymatic conversion of acetyl-CoA to malonyl-CoA by the enzyme acetyl-CoA carboxylase occurs in the presence of a stoichiometric amount of carbon dioxide, and supplementation of the growth media with carbon dioxide increases malonate production. Carbon dioxide is added to the growth media as either solid calcium carbonate or gaseous carbon dioxide.

Recombinant yeast cells harboring a malonyl-CoA biosynthetic pathway are grown in a defined minimal medium supplemented with between 0.1-10 g/l calcium carbonate. Control cultures are not supplemented with calcium carbon. Malonate production is quantified as described in Example 2 over the course of 48 hours growth.

Example 18: Improving Malonate Biosynthesis in Engineered Yeast Through Decreased Malonate Catabolism In this example, malonate production is increased by eliminating endogenous malonate catabolism in the host cell. *S. cerevisiae* contains multiple acyl-CoA synthetases, including FAA1, FAA2, FAA3, FAA4, LSC1, and LSC2; by deletion or modification of the nucleic acids on the host genome encoding these proteins, catabolism of malonate in the growth media can be decreased.

Malonyl-CoA knockout strains are constructed of each of the yeast acyl-CoA synthetases. The resulting strains are then cultured in a defined medium supplemented with 1-5 g/l sodium malonate. The malonate concentration in the fermentation broth is monitored over the course of 48 hours and quantified as described in Example 2. Strains with multiple knockouts can be constructed following similar procedures.

Example 19: Improving Malonate Biosynthesis in Engineered Yeast Through Improved Malonate Secretion from the Host Cell In this example, malonate production is improved by increasing secretion of malonate from the host cell. This is accomplished by overexpression of one or more of each of the *S. cerevisiae* pleiotropic resistant pumps, namely PDR5, PDR10, PDR11, PDR12, PDR15 and PDR18.

Example 20: Improving Malonate Biosynthesis in Engineered Yeast Through Decreased Succinate Dehydrogenase Competitive Inhibition by Malonate In this example, competitive inhibition of *S. cerevisiae* succinate dehydrogenase SDH1 is decreased, enabling higher titers of malonate to be achieved. First, the *S. cerevisiae* is genetically modified for deletion of the native, chromosomal copy of succinate dehydrogenase (SDH1) using standard methods. The resulting strain is grown anaerobically to facilitate growth in absence of SDH1 protein. The SDH1 deletion strain is subsequently transformed with a vector harboring a genetically modified SDH expression cassette containing an E300D, R331K, R331H, R442K, R442H mutation, or a combination of these mutations. These mutant SDH genes are cloned behind a constitutive TEF promoter on a yeast backbone harboring 2-micron origin and ura3 auxotrophic marker. Vectors are subsequently transformed into *S. cerevisiae* strain encoding malonyl-CoA hydrolase on the chromosome and the resulting strains grown in SD media lacking uracil. The transformed strains are cultured for malonate production as described in Example 8 and malonate is quantified as described in Example 2 to quantify the impact of these SDH mutations on malonate production.

Example 21: MdcY Malonate Transcription Factor Biosensor Using Exogenously Added Malonate Plasmid S14 was used to demonstrate biosensor response to exogenously added malonate in an *E. coli* host cell. S14 employs the malonate responsive transcription factor, MdcY (SEQ ID NO:3), and the MdcY-responsive promoter, $P_{MdcL}$ (SEQ ID NO:6) derived from *Acinetobacter calcoaceticus*. This biosensor of this disclosure was constructed using an *E. coli* vector backbone with ampicillin resistance marker and ColE1 origin of replication; the tetA tetracycline resistance gene was placed under control of the $P_{MdcL}$ promoter. Transformation of plasmid S14 into an *E. coli* host resulted in a strain expressing the tetA gene product following supplementation of the fermentation broth with malonate, and the strain was expected to exhibit a malonate-dependent increase in tetracycline resistance.

Nucleic acids encoding for MdcY and TetA gene products, $P_{MdcL}$ promoter, and the *E. coli* vector backbone were synthetically produced; the biosensor vectors were than constructed by PCR amplification of the nucleic acids and subsequent cloning into the *E. coli* vector backbone. The plasmids were transformed into chemically competent *E. coli* DH10b and the resulting clones plated on LB agar plates containing 50 μg/ml carbenicillin ($Cb^{50}$). Individual colonies were grown overnight in 3 ml LB medium supplemented with antibiotic and the sequences of the purified plasmid were verified.

*E. coli* strain K12 was co-transformed with plasmids S14 and individual colonies isolated from LB agar plates ($Cb^{50}$). Colonies were grown in 25 ml LB broth ($Cb^{50}$) until reaching an optical density at 600 nm ($OD_{600}$) of approximately 0.50, at which point in time cell stocks were prepared and stored at −80° C.; cell stocks were 0.5 ml cell culture and 0.5 ml of a 50% v/v glycerol solution.

All biosensor demonstrations were performed with malonate. An aliquot of biosensor cell stock was thawed and used to inoculate 50 ml of LB medium ($Cb^{50}$) in a 250 ml, baffled Erlenmeyer flask. Cultures were incubated for 2 hours at 37° C.; subsequently, 0.6 ml biosensor culture was added to 48-well plates prepared with 2.3 ml LB medium) ($Cb^{50}$) supplemented with tetracycline and malonate acid at the desired concentration (n=4). Plates were than grown at 30° C. on an orbital titer plate shaker. Following 12 hours incubation, 200 μl samples were taken for $OD_{600}$ measurement.

Figure 5:
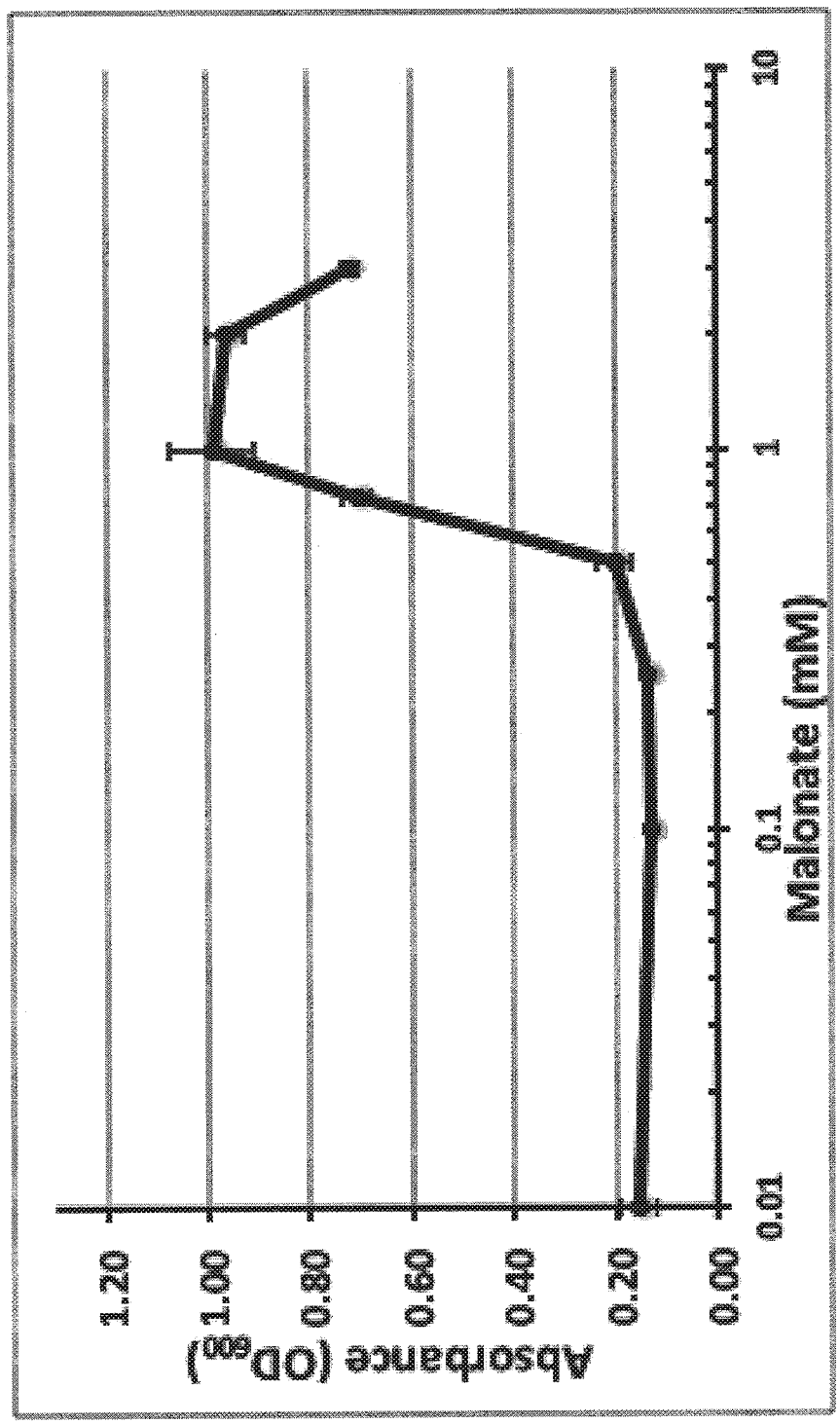
FIG. 5 shows a dose-response curve for an *E. coli* MdcY malonate biosensor according to embodiments of this disclosure that utilizes the promoter PMdcL. The X-axis is the concentration of exogenous malonate added to the fermentation broth; the Y-axis is the cell culture density (OD600) after 12 hours growth in medium with 25 µg/ml tetracycline. *E. coli* transformed with plasmid S14, comprising an MdcY transcription factor and a tetA gene under control of a PMdcL promoter, produced the tetracycline resistance protein TetA upon exogenous addition of malonate. The biosensor displayed malonate-dependent increases in tetracycline resistance as measured by the increase in OD600 with the increase in concentration exogenously added malonate as described in additional detail in Example 21.
Figure 6:
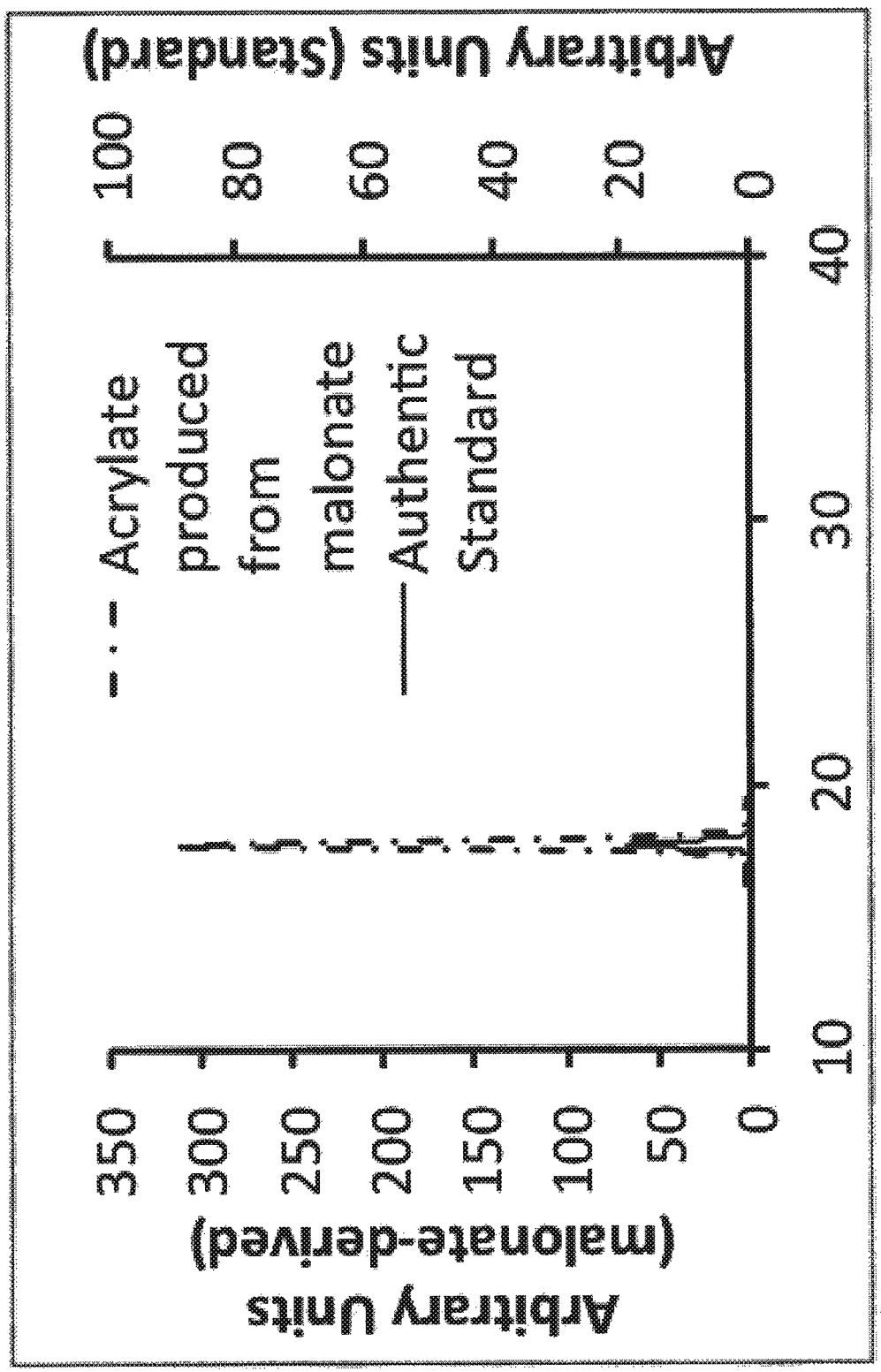
FIG. 6 is an HPLC chromatogram trace showing separation and detection of acrylic acid production from malonate according to embodiments of the methods of this disclosure as described in Example 28. The X-axis shows elution of acrylic acid at approximately 17.5 minutes, and the Y-axis shows arbitrary units derived from detection of acrylic acid via a UV detector monitoring 210 nm. Acrylic acid produced from malonate according to the methods of this disclosure (dashed line) exhibited the same retention time as an authentic acrylic acid standard (solid line).

Biosensor cultures harboring S14 displayed a dose-dependent response for malonate (FIG. 5). The dynamic range (the maximum difference in $OD_{600}$ values between the fully induced samples and those samples absent malonate supplementation) was 1.2 $OD_{600}$ units, indicating the MdcY-$P_{MdCL}$ based biosensor was highly responsive to exogenously added malonate. An increase in $OD_{600}$ was observed between 0.5-1 mM exogenously added malonate, providing a suitable range over which malonate can be quantified using this method.

Example 22. MdcY Malonate Transcription Factor Biosensor to Detect Biologically Produced Malonate in Fermentation Broth In this example, a malonate transcription factor biosensor was used to detect the production of malonate from a yeast strain engineered as described in other aspects of this disclosure.

Malonic acid was produced using a genetically engineered yeast strain as follows. *S. cerevisiae* BY4741 yeast cells harboring a vector for expression of malonyl-CoA hydrolase comprising a CYC1 terminator, an ampicillin resistance cassette, a PMB1 origin of replication, a CEN/ARS origin of replication, and a URA3 selection marker was used for fermentation. The FOPNG8-1 malonyl-CoA hydrolase (from *Bacillus thuringiensis* subsp. *finitimus* strain YBT-020; UniProt ID FOPNG8, with E91S mutation) and the F6AA82-2 malonyl-CoA hydrolase (from *Pseudomonas fulva* strain 12-X; UniProt ID F6AA82, with E95S and Q348A mutations) were each expressed from this plasmid under control of the TEF1 promoter. The culture medium described in Example 30 was used with 20 g/L glucose as a carbon source. Production was performed as follows. Two ml of culture medium in a 48-well plate was inoculated with 20 µl of a starter culture of the producer strain, in quadruplicate. The plate was covered with a breathable membrane, incubated on a plate shaker at 30° C., and sampled for HPLC and biosensor analysis of product accumulated after 142 h of growth. Cells and cell debris were removed from the culture media by centrifugation and filtered through 0.45 micron membrane prior to analysis by HPLC or biosensor.

*E. coli* cells harboring either plasmid pS14, encoding a tetracycline resistance gene (tetA) under expression control of the malonic acid-responsive $P_{mdcL}$ promoter, or plasmid pS27, encoding a lacZ gene under expression control of the malonic acid-responsive $P_{mdcL}$ promoter, were used as biosensor indicator strains. The vector pS27 was constructed in the same manner as described for pS14 in Example 21, with the lacZ gene, encoding a beta-galactosidase, inserted in place of the tetA gene. Biosensor strains were prepared as described in Example 21.

Yeast spent media obtained from 96-well production plates were added to 96-well plates containing 120 µl of biosensor cell culture. For the TetA (pS14) biosensor, 10 µl of tetracycline stock solution (to provide a range of 20-35 µg/ml) were added to each well. For both the TetA (pS14) and lacZ (pS27) biosensor, the remaining volume of each well was filled with LB medium (Cb$^{50}$) to a final volume of 600 µl. The plates were incubated at 30° C. on an orbital plate shaker. Samples (200 µl) were collected to 96 well plates after 2 h for S27 cultures and after 5-8 h for S14 cultures, and OD600 was measured. An ortho-nitrophenyl-β-galactoside (ONPG) assay was performed on samples from S27 (beta-galactosidase reporter) biosensor plates as follows. Cells were diluted 1:4 in 25 µl lysis buffer and subsequently 90 µl of ONPG stock solution (10 mg/ml in deionized water) were added to each well. Contents of each well were completely mixed and left at 30° C. for 4-16 hours. Optical densities were measured at 420 nm.

A dose-dependent response to malonate was observed. Specific malonic acid concentrations were also measured by HPLC, as described in Example 2, and quantified by comparison to a standard curve. Linear regression analyses between the quantifiable output of the biosensor, OD420 (for pS27) or OD600 (for pS14) and specific malonic acid concentrations measured by HPLC were calculated to have coefficients of determination ($R^2$) of 0.88492 plotting 37 OD420 samples and 0.89755 plotting 18 OD600 samples.

These very high coefficients of determination are indicative of the correlation between biosensor output and malonate concentration in the culture media. This aspect of this disclosure provides a tremendous advantage in both cost and time with regard to screening differential outputs in biological malonate production. Dilution of culture media used to challenge the biosensor can facilitate the extension of the dynamic response range of the sensor from zero to full solution saturation of malonate. The use of a plate-based screen enables the screening of 96 samples in a few minutes in comparison to a time requirement of 2-20 minutes or more per sample for HPLC analysis. The savings in capital investment and solvent usage and disposal engendered by limiting or replacing HPLC altogether are also substantial.

Example 23: Construction and Expression of Recombinant Plasmid Vectors Encoding Various Malonyl-CoA Hydrolases, and their Use in the Production of Malonate in Yeast Nucleic acids encoding various malonyl-CoA hydrolases provided by this disclosure [EHD3 (E124S), B9IZZ9-1, F0PNG8-1, H0NHL7, C3ALI3-1, Q81DR3-1, A4XS22-1, E2XN63-1, A5W8H3-1 and F6AA82-2] were amplified by PCR from plasmids using the primers listed in Table 4. The purified PCR products were cloned downstream of the TEF1 promoter and upstream of the CYC1 terminator in a shuttle vector containing an ampicillin resistance cassette, a PMB1 origin of replication, a CEN/ARS origin of replication and a URA3 selection marker. The resulting plasmids were transformed into *E. coli* competent host cells and selected on LB agar plates containing Cb$^{50}$. Following overnight incubation at 37° C., individual colonies were inoculated in 2 ml of LB-Cb$^{50}$ in a 48-well plate and grown for 5 h at 37° C. on a shaker before the plasmids were isolated and confirmed by sequencing.

TABLE 4

PCR primers

| Hydrolase | Primer | Sequence (5'-3') | SEQ ID NO |
|---|---|---|---|
| EHD3(E124S) | Y1-11_A13-R | ctaattacatgactcgaggtcgacggtatcgttatttc catcttaagccatcgttaacttc | SEQ ID NO: 23 |
| | Y1-11_A13-F | cattagaaagaaagcatagcaatctaatctaagttta aaacaatgactactcaacccccagctaaatg | SEQ ID NO: 24 |
| B9IZZ9-1 | Y0012 | gaaagcatagcaatctaatctaagtttaaaacaatga ccgaacaagtcttattctcagta | SEQ ID NO: 25 |
| | Y0013 | ctaattacatgactcgaggtcgacggtatcgttaagc gttcaacaaattgaaaaatctg | SEQ ID NO: 26 |
| F0PNG8-1 | Y0014 | gaaagcatagcaatctaatctaagtttaaaacaatga ccgaacatgtattattctcag | SEQ ID NO: 27 |
| | Y0015 | ctaattacatgactcgaggtcgacggtatcgttaagc gtttaacaaattgaaaaatc | SEQ ID NO: 28 |
| H0NHL7-1 | Y0016 | gaaagcatagcaatctaatctaagtttaaaacaatga ctgaacacgtgttgttctctg | SEQ ID NO: 29 |
| | Y0017 | ctaattacatgactcgaggtcgacggtatcgttaagc gtttaacaaattgaaaaatctg | SEQ ID NO: 30 |

TABLE 4-continued

PCR primers

| Hydrolase | Primer | Sequence (5'-3') | SEQ ID NO |
|---|---|---|---|
| C3ALI3-1 | YO018 | gaaagcatagcaatctaatctaagtttaaaacaatga gaagatacatcagaggtggt | SEQ ID NO: 31 |
| | YO019 | ctaattacatgactcgaggtcgacggtatcgttatgc agcgttcaacaaattgaaaa | SEQ ID NO: 32 |
| Q81DR3-1 | YO020 | gaaagcatagcaatctaatctaagtttaaaacaatga ccgaacaagtcttattctcag | SEQ ID NO: 33 |
| | YO021 | ctaattacatgactcgaggtcgacggtatcgttaagc gttcaacaaattgaaaaatct | SEQ ID NO: 34 |
| A4XS22-1 | YO024 | gaaagcatagcaatctaatctaagtttaaaacaatga acttacaatttgaagaaagacca | SEQ ID NO: 35 |
| | YO025 | ctaattacatgactcgaggtcgacggtatcgttacaa atcagctaaagggtgttcac | SEQ ID NO: 36 |
| E2XN63-1 | YO026 | gaaagcatagcaatctaatctaagtttaaaacaatga acttacactttgaagaattgac | SEQ ID NO: 37 |
| | YO027 | ctaattacatgactcgaggtcgacggtatcgttagta gtcagacaaatctgctaaag | SEQ ID NO: 38 |
| A5W8H3-1 | YO028 | gaaagcatagcaatctaatctaagtttaaaacaatga caatccactgtgaagtattaac | SEQ ID NO: 39 |
| | YO029 | ctaattacatgactcgaggtcgacggtatcgttaacc aacgtcagccaaagggtg | SEQ ID NO: 40 |
| F6AA82-2 | YO030 | gaaagcatagcaatctaatctaagtttaaaacaatga atgtcacctttgaagaaagag | SEQ ID NO: 41 |
| | YO031 | ctaattacatgactcgaggtcgacggtatcgttatgc caaatcagctaaagggtg | SEQ ID NO: 42 |

*S. cerevisiae* BY4741 yeast cells were used as host for the vectors for expression of the various malonyl-CoA hydrolases. The plasmid vectors were individually introduced into the yeast host cells using standard procedures. Transformants were selected on agar plates of the media described in Example 30, containing 2% glucose as the carbon source.

An individual colony for each transformant picked was inoculated into a 50 µl aliquot of SD-Ura medium in a 96-well plate. The plate was incubated on a shaker at 30° C. for approximately 4 h, and 25 µl were used to inoculate fermentation plates (2 ml of SD-Ura medium in 48-well plates). The fermentation plates were covered with a breathable membrane, incubated on a plate shaker at 30° C., and sampled for HPLC analysis of product accumulation after 140 h of fermentation. The relative concentrations of malonate in the fermentation media of yeast strains expressing various malonyl-CoA at this time point are shown in Table 26 (mean±S.D.; n=4). "None" refers to an empty vector control. No malonate was detected in samples consisting of medium not inoculated with yeast cells.

TABLE 5

| Hydrolase | Source organism | Uniprot ID | Mutation | Malonate Peak Area |
|---|---|---|---|---|
| None | N/A | N/A | N/A | 48,865 ± 9,345 |
| EHD3(E124S) | *S. cerevisiae* | P28817 | E124S | 94,721 ± 8,115 |
| B9IZZ9-1 | *Bacillus cereus* (strain Q1) | B9IZZ9 | E91S | 261,717 ± 38,012 |
| F0PNG8-1 | *Bacillus thuringiensis* subsp. *finitimus* (strain YBT-020) | F0PNG8 | E91S | 216,654 ± 31,145 |
| F6AA82-2 | *Pseudomonas aeruginosa* (strain ATCC 15692/PAO1/ 1C/PRS 101/LMG 12228) | Q9I5I5 | E95S, Q248A | 212,096 ± 29,338 |
| E2XN63-1 | *Pseudomonas fluorescens* WH6 | E2XN63 | E95S | 198,046 ± 35,084 |
| Q81DR3-1 | *Bacillus cereus* (strain ATCC 14579/DSM 31) | Q81DR3 | E91S | 193,665 ± 37,898 |
| Q63BK8-1 | *Bacillus cereus* (strain ZK/E33L) | Q63BK8 | E91S | 167,477 ± 8,110 |
| A5W8H3-1 | *Pseudomonas putida* (strain F1/ATCC 700007) | A5W8H3 | E95S | 52,047 ± 9,042 |

In additional examples, C3ALI3 from *Bacillus mycoides* and A4XS22 from *Pseudomonas medocina* (strain ymp) containing E101S and E95S mutations, respectively, were utilized as malonyl-CoA hydrolases. Because the media conditions were varied slightly by buffering to pH 4.0, F0PNG8-1 and Q9I5I5-1 were included for comparison. The results are shown in Table 6.

TABLE 6

Malonate accumulation after 144 h of fermentation. Mean ± S.D.; n = 6.

| Hydrolase | Source organism | Uniprot ID | Mutation | Malonate (mM) |
|---|---|---|---|---|
| F0PNG8-1 | *Bacillus thuringiensis* subsp. *finitimus* (strain YBT-020) | F0PNG8 | E91S | 11 ± 2 |
| Q9I5I5-1 | *Pseudomonas aeruginosa* (strain ATCC 15692/PAO1/1C/PRS 101/LMG 12228) | Q9I5I5 | E95S | 23 ± 2 |
| C3ALI3-1 | *Bacillus mycoides* | C3ALI3 | E101S | 10 ± 1 |
| A4XS22-1 | *Pseudomonas mendocina* (strain ymp) | A4XS22 | E95S | 7 ± 1 |

This example demonstrates, in accordance with this disclosure, malonate can be produced in a yeast host cell expressing a malonyl-CoA hydrolase derived from one of several different organisms. The E to S active site mutations common to all the mutant hydrolases used in this example can be utilized in other members of these enzyme classes to provide similar results.

Example 24: Construction and Expression of Recombinant Vectors Encoding Additional Malonyl-CoA Hydrolases, and Production of Malonate in Yeast In this example, FabD from *E. coli*, a malonyl CoA:ACP transacylase (EC 2.3.1.39) having one or more of the following amino acid changes at the indicated positions: C92, H201, N201, D117, E117, N117, Y117, G117, H117, Q11, D11, E11, N11, Y11, G11, H11, A93, V93, I93, F93, S93, G93 was employed as a malonyl-CoA hydrolase. The nucleic acid encoding *E. coli* FabD was PCR amplified from *E. coli* strain K12 using primer F1 (5'-ATGACGCAATTTG-CATTTGTGTTCCC-3') (SEQ ID NO: 43) and F2 (5'-TTAAAGCTCGAGCGCCGCT-3') (SEQ ID NO: 44). The amplified gene was then mutated using standard methods and inserted into a shuttle expression plasmid under the control of the TEF1 promoter and upstream of the CYC1 terminator. This vector contains an ampicillin resistance cassette, a PMB1 origin of replication, a CEN/ARS origin of replication, and a URA3 selection marker. The individual mutational combinations assayed are listed with the results below.

Individual colonies were inoculated into 1 ml of yeast fermentation media comprising 5 g/L ammonium sulfate, 1 g/L monopotassium phosphate, 0.5 g/L magnesium sulfate, 0.1 g/L sodium chloride, 0.1 g/L calcium chloride, 2 mg/L inositol, 0.5 mg/L boric acid, 0.4 mg/L calcium pentothenate, 0.4 mg/L niacin, 0.4 mg/L pyridoxine hydrochloride, 0.4 mg/L thiamine HCl, 0.4 mg/L zinc sulfate, 0.4 mg/L manganese sulfate, 0.2 mg/L p-aminobenzoic acid, 0.2 mg/L riboflavin, 0.2 mg/L sodium molybdate, 0.2 mg/L ferric chloride, 0.1 mg/L potassium iodide, 40 μg/L copper sulfate, 2 μg/L folic acid, 2 μg/L biotin, 10 mg/L adenine, 50 mg/L L-arginine HCl, 80 mg/L L-aspartic acid, 20 mg/L L-histidine HCl, 50 mg/L L-isoleucine, 100 mg/L L-leucine, 50 mg/L L-lysine HCl, 20 mg/L methionine, 50 mg/L L-phenylalanine, 100 mg/L L-threonine, 50 mg/L L-tryptophan, 50 mg/L L-tyrosine, and 140 mg/L L-valine (the base media) containing 2% glucose as a carbon source. The cultures were incubated on a shaker at 30° C. for 24 h, and 20 μl of these cultures were used to inoculate production cultures of 2 ml of the same media. The production cultures were covered with a breathable membrane, incubated with shaking at 30° C. and sampled for HPLC analysis of product accumulation after 96 h and 168 h of growth.

No malonate was detected in samples consisting of medium not inoculated with yeast cells. Wild type yeast produced less than 0.1 mM malonate following 168 h fermentation. Expressing any of the four FabD variants produced malonate at levels higher then cells not expressing these proteins. Malonate accumulation after 96 and 168 h of fermentation using various engineered FabD malonyl CoA-acyl carrier protein transacylase expressed in *S. cerevisiae* were as follows; FabD S92C/L93V/R117H 96 h=1.01 mM, 168 h=2.49 mM, FabD L93I/R117Y 96 h=1.47 mM, 168 h=2.48 mM, FabD L93S/R117G 96 h=1.11 mM, 168 h=2.89 mM, FabD L93I/R117Y 96 h=1.64 mM, 168 h=3.47 mM.

Example 25: Method for Fermentative Production of Bio-Based CaM by Recombinant P. *Kudriavzevii*, and Subsequent Purification of Bio-Based Malonic Acid In Example 25, a recombinant *P. kudriavzevii* strain was used to produce CaM according to methods of the present disclosure. A sterile fermentation tank was filled half full with a defined medium of 650 g/L glucose, dipotassium phosphate, urea, trace metals and vitamins. The medium had been previously sterilized via heat or filtration. An inoculum of 1% (v/v) yeast *Pichia kudriavzevii* was added. A 3M slurry of Ca(OH)2 was added as needed to maintain a pH of 5.0 throughout the fermentation. A fixed stir and airflow rate was initiated upon inoculation. Antifoam was added at the time of inoculation as well. An oxygen transfer rate of 50 mmol/L/hr was maintained. The fermentation was allowed to continue for 6 days (144 hours) at 30° C. After the fermentation broth was allowed to cool, it was centrifuged 3 times in a hydrocyclone. The result was a concentrated calcium malonate slurry that was then placed on a horizontal vacuum belt filter and washed with water. The resultant calcium malonate cake was diluted with water and placed in a gypsum reactive crystallizer. Sulfuric acid was added at 25% (v/v). This material was then again placed on a horizontal vacuum belt filter. The resultant gypsum cake was placed in a draft tube baffle crystallizer and barium carbonate was added. After crystallization the material was centrifuged to remove the barium sulfate. The material was polished by running it over an activated carbon cation exchange column. This material was placed under vacuum at 65° C. to remove the water. The crystals were diluted in water and put in a draft tube baffle crystallizer at 18° C. and then the water was removed in a vacuum evaporator at 65° C. This was repeated two more times. The result was a fine white crystalline powder.

Example 26: Method for Fermentative Production of Bio-Based CaM by Recombinant P. Kudriavzevii, and Subsequent Purification of Bio-Based Malonic Acid In Example 26, a recombinant *P. kudriavzevii* strain was used to produce CaM according to the methods of the present disclosure. A pre-sterilized fermentation tank was charged with 4,000 liters of sterile culture medium comprising glucose, a phosphate source, a nitrogen source, salts, and vitamins in amounts known to practitioners skilled in the art as sufficient for enabling *P. kudriavzevii* growth and malonic acid production. The fermenter was inoculated with recombinant *P. kudriavzevii* strain capable of producing malonic acid to a concentration of 0.26 OD600 nm. In this example, the fermentation involved two phases—an initial batch phase followed by a second fed-batch phase. When the majority of the glucose present in the initial batch phase was completely consumed in the batch phase, the fed-batch phase started and additional growth nutrients were pulsed into the fermentation tank. The culture was maintained at a temperature of 30° C. for the entirety of the run. The aeration rate was adjusted at the start of the fermentation to achieve an OTR of 57 mmol/l/hr; the aeration rate was not adjusted further during the remainder of the run. Fermentation broth pH was maintained at approximately 5.0 by addition of a 3M $Ca(OH)_2$ slurry; the addition of $Ca(OH)_2$ along with the production of malonic acid by *P. kudriavzevii* produced a visible CaM precipitate during the fermentation. The fermentation was complete when the fermentation vessel was completely filled and all glucose fed into the fermentation broth was consumed. At this point, the broth pH was gradually increased to 9.0 over the course of an hour through further addition of 3M $Ca(OH)_2$ slurry; since CaM solubility decreases with increasing pH, the pH increase to 9.0 precipitated additional solid CaM from the fermentation broth.

An approximately 10-ml sample was drawn from the fermenter and sub-aliquoted into 2-ml samples. One of the 2-ml samples was used to determine dry cell weight according to methods known to practitioners skilled in the art, with an extra step of HCl addition to dissolve the solid CaM prior to measuring the dry cell weight. Another 2-ml sample was used to determine the amount of CaM produced—the sample was acidified using HCl to dissolve the solid CaM, centrifuged to pellet the biomass, and then the supernatant was analyzed by HPLC to measure the concentration malonic acid. In this example, the fermentation broth had a total mass of 10,550 kg and contained 1,796 kg CaM (17% w/w) and 156 kg cells (1.48% w/w). This example demonstrated fermentation processes useful for producing an insoluble alkaline earth metal malonate salt, CaM. Additionally, by using a concentrated (3M) alkaline earth metal base, calcium hydroxide, the dilution of CaM in the final fermentation broth was minimized and CaM titers were high, about 170 g/l (equating to 99 g/l malonic acid), and greater than 95% of the total CaM in the fermentation broth was present as a solid, part of increasing overall purification yields.

Example 27: Method for Extraction of Bio-Based CaM from Fermentation Broth Through Centrifugation In Example 27, centrifugation was used to process fermentation containing CaM and cells and produce a heavy phase enriched in CaM and substantially free of cells. The fermentation broth used for this example was produced using the same methods described in Example 26. An Alfa Laval NX416 decanter centrifuge was used for this example. The centrifuge was set to obtain a 300×-g force and the inlet flow rate was adjusted to achieve a 10 second residence time. During processing, additional water was added to the fermenter to aid removal of residual CaM stuck on the fermenter sides. After CaM separation using the decanter centrifuge, the heavy phase was a 1,520 kg wet cake enriched in CaM (1027 kg of solid CaM; equating to 67.2% w/w) and substantially free of cells (30.4 kg of cells; equating to 2% w/w). The centrate, or light phase, had a total mass of 7040 kg and contained about 105 kg of fine CaM crystals (1.5% w/w) and 141 kg (2% w/w) of cells. Thus, the majority (82.3%) of the cells present in the original fermentation broth were found in the centrate, or light phase, following centrifugation. The purity of the solid CaM crystals isolated in the heavy phase was determined by HPLC and shown to have a purity of at least 98.25%. The overall CaM yield obtained for the centrifugation step was about 91%. Therefore, this example demonstrated the use of centrifugation as a means to efficiently separate high purity CaM crystals that are substantially free of cells from fermentation broth.

Example 28: Method for Increasing Bio-Based CaM Purity Through Washing and Centrifugation In Example 28, the CaM cake resulting from centrifugation of fermentation broth as described in Example 27 was resuspended in cold water and centrifuged at a high G-force to increase the CaM purity and decrease the amount of residual cells present. Impurities can affect the quality of the final malonic acid product and it is often useful to wash these impurities from the solid CaM prior to subsequent processing.

In this example, a wet cake enriched in CaM and substantially free of cells was separated from fermentation broth using a decanter centrifuge as described in Example 27. The wet cake had a total mass of 3,944 kg and was washed by addition of 2,424 kg cold water. This mixture was then centrifuged with an Alfa Laval NX416 decanter centrifuge operated at 3,000×-g with a 10 second residence time. The washed CaM from this first wash-decant step was 98.9% pure by HPLC analysis and was substantially free of cells (<1.75% w/w cells). The CaM slurry was then washed a second time by further addition of 3593 kg ice-cold water and centrifuging the mixture using the previously described decanter centrifuge operating conditions. The twice-washed CaM was determined to be 99.8% pure by HPCL and contained less than 1.56% w/w cells; this CaM was saved and used for further downstream processing. Thus, this example demonstrated that repeated washing of the wet CaM cake can be used to increase CaM purity and decrease the amount of residual cells present.

Example 29: Method for Acidification of Bio-Based CaM and Method for Removal of Gypsum Impurities Through Crystallization In Example 29, washed CaM (produced by the aforementioned steps in Examples 25-28) was acidified with a mineral acid, sulfuric acid, to solubilize the malonic acid in solution and simultaneously form an insoluble salt, calcium sulfate. First, a high shear mixer was used to ensure a homogenous CaM particle size distribution in a CaM slurry. Then, 20% (v/v) $H_2SO_4$ was added to the CaM slurry to form soluble malonic acid and insoluble calcium sulfate ($CaSO_4$, or gypsum). The reaction was carried out for one hour in a glass, jacketed stirred tank reactor by metered addition of both CaM and $H_2SO_4$ to the reaction vessel. The reaction temperature was maintained at 50° C. throughout the course of the gypsum crystallization period.

The solid gypsum was removed from the soluble malonic acid by centrifugation using a decanter centrifuge operated at a G-force of 3,000×-g. The centrate had a total mass of 4,969 kg and contained 461 kg malonic acid; no cells were measured in the centrate. The heavy phase was a wet gypsum cake with a total mass of 2005 kg and contained 1103 kg gypsum and about 902 kg water. A gypsum rinsing step followed to help capture the malonic acid present in the wet gypsum cake; 2,707 kg of cold water was added to the gypsum cake and the mixture was recentrifuged as described above and the centrate containing the malonic acid was collected. After the two wash steps, 7,758 kg of centrate containing 524 kg malonic acid was collected; thus, the malonic acid yield for the gypsum crystallization step was about 96%.

Example 30: Method for Removal of Sulfate Impurities During the Bio-Based Malonic Acid Purification Process In Example 30, a barium polishing step was used to remove a trace contaminant, sulfate, from the malonic acid solution resulting from Example 29. Because an excess of $H_2SO_4$ was added during the gypsum crystallization, sulfate ions were present in excess in solution with malonic acid. In this example, barium carbonate ($BaCO_3$), which has a very low solubility (ca. 4 mg/l at 25° C.), was used to remove excess sulfate from the solution in the form of $BaSO_4$. Specifically, 24 kg of $BaCO_3$ was added to the malonic acid solution from Example 29 and stirred at 25° C. for 30 minutes. The insoluble $BaSO_4$ was removed by centrifugation at 8,000×-g using a disc stack centrifuge. In this example, a 103 kg of wet cake containing the solid $BaSO_4$ was removed from the malonic acid solution. The centrate had a total mass of 7655 kg and contained 517 kg of malonic acid; thus, the malonic acid yield for the sulfate removal step was about 99%.

Example 31: Method for Polishing to Remove Trace Cation Contaminants from a Solution Containing Bio-Based Malonic Acid In Example 31, a cation exchange polishing step was used to remove trace cation contaminants from the malonic acid solution resulting from Example 30 and further clarify the malonic acid solution. DOWEX G26(H), a cation exchange resin, was used in this step. 362 l of resin was loaded into a column with a 0.6 m diameter. In this example, 7,655 kg of malonic acid solution resulting from Example 30 was flowed through the chromatography column at a feed rate of 18 l/min. This step produced 7,655 kg of malonic acid solution containing 517 kg of malonic acid; thus, a near quantitative malonic acid yield was obtained for this cation exchange step.

Example 32: Method for Nanofiltration and Diafiltration Polishing to Remove Trace Contaminants from a Solution Containing Bio-Based Malonic Acid In Example 32, a nanofiltration and diafiltration polishing step was used to remove trace contaminants from the malonic acid solution resulting from Example 31 and further clarify the malonic acid solution. Impurities, including glucose and other carbohydrates, color forming bodies, organic acids, and salts, are concentrated during crystallization as water is evaporated and the malonic acid is concentrated in the solution. These impurities can negatively affect the crystallization yield and/or the purity of the final malonic acid product, and reducing their occurrence in the malonic acid solution prior to crystallization can be desired. In this example, nanofiltration was implemented to remove colored impurities and other organic impurities. A GE Duracid NF8040F35 membrane with a 100-200 Da molecular weight cutoff was used. Nanofiltration was carried out at 50° C. with a feed rate of 265 l/min, a transmembrane pressure of 237.8-374.5 psi, and a minimum flux of 24 $l/m^2/hr$. This nanofiltration step produced a permeate with a total mass of 6,064 kg that contained 413.5 kg of malonic acid. The retentate had a total mass of 1,591 kg and contained 103.5 kg of malonic acid. The nanofiltration permeate had a visual reduction in color from a yellow color in the feed to a clear permeate product.

A diafiltration step was used to recover more of the malonic acid remaining in the nanofiltration permeate. The operating conditions were the same as described for the nanofiltration step. This diafiltration step produced a permeate with a total mass of 1,906 kg and contained 111 kg of malonic acid. The retentate had a total mass of 501 kg and contained 51 kg of malonic acid. The permeates from the nanofiltration and diafiltration steps were pooled and saved for future use. In this example, 90% of malonic acid was recovered due to the combination of both nanofiltration and diafiltration steps.

Example 33: Method for Purifying Pure Bio-Based Malonic Acid Crystals

Example 33 shows the crystallization of the final, purified malonic acid product from a portion of the malonic acid solution resulting from nanofiltration and diafiltration conducted in Example 32. In this example, the dilute malonic acid solution produced after the filtration steps described in the present disclosure was concentrated prior to crystallization. Table 7 shows the solubility of malonic acid in water at various temperatures.

TABLE 7

| Malonic acid solubility in water | |
|---|---|
| Temperature (° C.) | % (w/w) |
| 5 | 53.92 |
| 10 | 55.75 |
| 15 | 57.63 |
| 20 | 59.68 |
| 25 | 61.69 |
| 30 | 63.5 |
| 35 | 65.28 |
| 40 | 67.43 |
| 45 | 68.85 |
| 50 | 70.33 |
| 55 | 72.38 |

TABLE 7-continued

Malonic acid solubility in water

| Temperature (° C.) | % (w/w) |
|---|---|
| 60 | 74.29 |
| 65 | 75.96 |

Water was evaporated from the dilute malonic acid solution at 50° C. to produce a concentrated, 71% (w/w) malonic acid solution. In order to minimize malonic acid decomposition, evaporation was carried out at reduced pressure and at a temperature of 50° C. In this example, evaporation was carried out at 100 Torr, with a feed rate of 33.33 kg/min, and an evaporation rate of 30.59 kg/min. In total, 8,000 kg of malonic acid solution was fed into the evaporator; 7,343 kg of water was removed to produce a 71% (w/w) malonic acid solution (i.e., 466 kg of malonic acid in a total mass of 657 kg).

After evaporation of water, purified malonic acid was crystallized by cooling crystallization. In this example, the 657 kg of 71% w/w malonic acid at 50° C. was cooled to 20° C. at a rate of 0.5° C. per minute, resulting in production of 168 kg of crystallized malonic acid. About 298 kg of malonic acid remained dissolved in solution after the first crystallization cycle. The remaining malonic acid solution was taken through 5 more cycles of evaporation and crystallization to increase the yield of crystallized malonic acid. Table 8 shows how multiple rounds of evaporation and cooling crystallization were used to increase the yield of final, crystallized malonic acid product.

TABLE 8

Crystallization of malonic acid

| Crystallization Round | Volume (l) | Malonic acid crystals removed from solution (kg) | Malonic acid in solution (kg) | Water removed (kg) |
|---|---|---|---|---|
| 1 | 456.04 | 167.88 | 298.45 | — |
| 2 | 291.87 | 107.44 | 191.01 | 59.73 |
| 3 | 186.8 | 68.76 | 122.24 | 38.23 |
| 4 | 119.55 | 44.01 | 78.24 | 24.47 |
| 5 | 76.51 | 28.16 | 50.07 | 15.66 |
| 6 | 48.97 | 18.03 | 32.05 | 10.02 |

Lastly, to reduce their moisture content, the purified malonic acid crystals were dried. To prevent decarboxylation of malonic acid, a vacuum drying oven was used in this Example. Drying was carried out at 50° C. and 50 Torr for 24 hours. The final moisture content was measured at less than 0.5% w/w. The purity of the final malonic acid crystals was assayed by HPLC and determined to be greater than 99% pure.

Example 34: Determination of pH and Ca:Malonic Acid Molar Ratio Sufficient to Achieve Efficient Malonic Acid Purification In Example 34, the second carboxylic acid pKa for malonic acid was shown to decrease to about 3.15 when a malonic acid solution was titrated with calcium hydroxide. The decrease in the carboxylic acid pKa when using a calcium base for control of fermentation pH allows for fermentations to be run at less than neutral pH values without detrimental effects on cell growth or production from high concentrations of soluble malonic acid and/or calcium malonate. Running fermentations at lower than neutral pH can minimizing the risk of other, undesired microbes contaminating the fermentation. This example also demonstrated that the dihydrate salt of calcium malonate was formed following addition of calcium hydroxide to a malonic acid solution.

A mock fermentation broth was generated by dissolving 15 g (0.146 mols) malonic acid into 150 mL of DI water. In a step-wise fashion, calcium hydroxide was added to the solution and the pH and was measured; additionally, the occurrence of any insoluble salts was monitored following each addition (Table 9). After about pH 3, corresponding to about a 0.58:1 molar ratio of calcium to malonic acid, a salt precipitate was observed. After about pH 5.3, corresponding to about a 1:1 molar ratio of calcium to malonic acid, further addition of calcium hydroxide resulted in a marked increase in solution pH to about 8. To confirm these results, additional malonic acid was added to the system to obtain a 1:2 molar ratio of calcium to malonic acid. The pH of the solution dropped to about 2.8, but the precipitate remained undissolved. The precipitate was recovered and air-dried. The molar ratios of water, calcium, and malonic acid were then determined, confirming the salt to be calcium malonate dihydrate.

Thus, surprisingly use of calcium hydroxide (an alkaline earth metal base) resulted in an apparent shift in the pKa of the second malonic acid carboxylic acid to about 3.15, as compared to a pKa of about 5.7 when titrating with NaOH. This had the unexpected result of forming an insoluble calcium malonate salt at pH values where formation of calcium bis(hydrogen malonate) was expected (i.e., a 0.5:1 molar ratio of calcium to malonic acid). Thus, in order to achieve an efficient yield of malonic acid separation from the fermentation broth a molar ratio of calcium to malonic acid of about 1:1 and a pH of greater than about 3.15 is preferable.

TABLE 9

Calcium:Malonic Acid and Calcium Malonate Dihydrate Precipitate

| Calcium to malonic acid molar ratio | Solution pH | Calcium malonate dihydrate precipitate observed? |
|---|---|---|
| 0 | 1.8 | No |
| 0.31 | 2.6 | No |
| 0.58 | 3.15 | Yes |
| 0.740 | 3.19 | Yes |
| 0.92 | 3.45 | Yes |
| 1.01 | 5.3 | Yes |
| 1.03 | 8 | Yes |

Example 35: Separation of CaM from Fermentation Broth and Cells by Gravity Settling In Example 35, an alternative method to centrifugation, gravity settling, was used to separate CaM from fermentation broth and the majority of cells. Gravity settling is a useful method to separate out CaM because no specialized equipment is required.

First, 250 mL of well mixed fermentation broth (25° C.) comprising about 20 g/l biomass and 67 g/l CaM was poured into a graduated cylinder with internal diameter of 3.81 cm. Measurements of the height of the wet calcium malonate cake height were taken at regular intervals over a period of 225 minutes as the mixture separated. A large amount of CaM was observed to settle within the first minute, creating a 20 cm high, loosely packed cake. The CaM continued to separate from the broth and cells at a settling rate of 0.08 cm/min. After 150 minutes, the majority of the CaM had fallen to the bottom of the graduated cylinder. No cell layer was observed on top of the CaM and the supernatant was visibly cloudy with biomass, indicating that the majority of the cells remained suspended in the fermentation broth and were not carried through with the separated CaM.

Example 36: Effect of Centrifugal Force on CaM Separation Efficiency from Cells in Fermentation Broth In Example 36, centrifugal force was varied to demonstrate how this centrifuge operating parameter can be varied to achieve efficient separation of CaM from the cells present in the fermentation broth. Centrifugation is advantageous over settling in that the higher g-forces decrease processing times.

A 50 mL sample of fermentation broth containing about 165 g/l CaM and about 15 g/l cells was prepared. The broth was well mixed to ensure that a homogenous mixture of CaM and cells in solution. 50-mL samples were pipetted into 50-mL conical centrifuge tubes and centrifuged at g-forces of 100×-g and 500×-g for 20, 60, and 120 seconds. Following centrifugation, the volume of both the CaM and cell layers were determined based on the volume gradations on the centrifuge tube wall; the cell layer was distinguished from the CaM layer by its darker color. Subsequently, the supernatant was decanted, taking care to not disturb the pellet, and then centrifuged in a separate 50-mL centrifuge tube at a force of 2000×-g for 2 minutes. The volume of the CaM pellet was again measured and used to determine the percentage CaM yield.

For the 100×-g force samples, the CaM pellet volumes were all 18 mL for the 20, 60, and 120 second time periods. The cell pellet volumes were 0 mL (20 s), 0 mL (60 s), and <0.5 mL (120 s). When the supernatants were centrifuged at 2000×-g for 2 minutes, only the supernatant from the sample centrifuged at 100×-g for 20 seconds produced a CaM pellet (1.5 mL), equating to about a 92.5% yield of the solid CaM in this example. No CaM pellets were observed from the other two samples, demonstrating a near quantitative yield of the solid CaM.

For the 500×-g force samples, the calcium malonate dihydrate pellet volumes were all 18 mL for the 20, 60, and 120 second time periods. The cell pellet volumes were <0.1 mL (20 s), 0.5 mL (60 s), and 1 mL (120 s). When the supernatants were centrifuged at 2000×-g for 2 minutes, and no additional CaM was pelleted, indicating a near quantitative yield of the solid CaM was obtained at this g-force for all centrifugation times tested.

This example demonstrated that a near quantitative yield of calcium malonate dihydrate was obtained with minimum carry through of cells by adjusting the centrifugation G-force and time. The application of a G-force of 500×-g or higher resulted in undesirable cell carry through along with the CaM in the pellet.

Example 37: First Round Purification of Bio-Malonic Acid to Bio-Diethyl Malonate In Example 37, bio-based diester derivatives of bio-malonic acid were purified from the malonic acid as prepared per the disclosures in Examples 25-33.

A sample of one kg (9.61 mol) sample of bio-derived malonic acid was mixed with 5.67 kg diethyl carbonate (48.0 mol, 5 equivalents) and 0.50 kg sulfuric acid (98%, 4.8 mol, 0.5 equivalents), heated to 90° C. and reacted under reflux for 8 hours. The temperature was decreased to 30° C. and the reaction mixture quenched with 6.40 kg saturated sodium bicarbonate solution (96 g/L $NaHCO_3$, 6.9 mol, 1.5 equivalents). The aqueous phase was separated and the crude diethyl malonate mixture was purified by simple distillation under vacuum at 20 torr. The temperature was slowly ramped from room temperature to 70° C. to remove the light impurities and then to 95° C., at which temperature the diethyl malonate fraction was collected until distillation stopped. As indicated in Table 10, the first-round, purified diethyl malonate ("bio-DEM control") distillate was 97.89% pure by GC-FID (area %). The distillate composition included 1.64% diethyl carbonate, and 0.34% diethyl sulfate. 1.42 kg (8.88 mol) were collected, corresponding to a 92.5% total yield.

Example 38: Purification of Bio-DEM

In Example 38, bio-DEM was further purified. A sample of 1.25 kg (7.81 mol) bio-derived diethyl malonate that had been purified by simple distillation (a combination of the bio-DEM produced through the methods as described in Examples 37 and 39), containing 1.5% diethyl carbonate and 0.3% diethyl sulfate, was mixed with an equivalent mass of 1.25 kg of deionized water. The mixture was heated to 90° C. while mixing for 1 hour to hydrolyze diethyl sulfate. The mixture was cooled to room temperature and allowed to settle, and the aqueous phase was removed from the purification mixture. Gas chromatography (GC) analysis showed 0.01% (area %) diethyl sulfate, indicating that diethyl sulfate was hydrolyzed effectively. Diethyl malonate in the remaining organic phase was then purified by simple distillation at 20 torr. The temperature was slowly ramped up to 95° C., at which temperature diethyl malonate began to distill. Approximately 5% of the weight of the material was removed in a lower-purity fraction to ensure that all of the diethyl carbonate was removed before the core distillate product was collected. Analysis of the core distillate by GC with Flame Ionization Detector (GC-FID) showed no detectable diethyl sulfate and 0.30% diethyl carbonate. In second round of simple distillation, approximately 10% of the material fed to the distillation was collected in a lower-purity fraction before the core distillate was collected. GC analysis of the resulting core distillate product again showed 0.27% diethyl carbonate. The final distillation step utilized a 5 stage Vigreux column under the same pressure and temperature conditions, with approximately 5% of the material fed to the distillation removed as a lower-purity fraction before collection of the core distillate. The final distillate composition included 0.15% ethanol, 0.05% diethyl carbonate, and 99.80% diethyl malonate (area %). 1.05 kg (6.56 mol) were collected, corresponding to an 84% total yield.

In Examples 37 and 38, the neutralization protocol matched the total acid number (TAN) of petrochemical-sourced DEM (0.05 mg KOH/g). Table 10 shows the GC-MS analysis of the composition of the final, purified bio-DEM prepared per the disclosed method of Example 14, as compared with the bio-DEM control, which was prepared from a similar source of bio-malonic acid (per Examples 25-33) but purified using the method disclosed in Example 37.

TABLE 10

Components of Bio-DEM

| Component | Bio-DEM control | Bio-DEM | Notes re component |
|---|---|---|---|
| Diethyl malonate (DEM) | 97.89% | 99.80% | GC peak area |
| Diethyl Carbonate (DEC) | 1.64% | 0.04% | Process Solvent |
| EtOH | 0.10% | 0.15% | |
| Diethyl Sulfate (DES) | 0.34% | ND | By-product, now eliminated |
| Unknown Peak * | 0.03% | 0.01% | * GC-MS suggests a match to ethyl methyl malonate or possibly dimethyl malonate, this peak is also generally seen in petro-DEM |
| Total | 100.00% | 100.00% | |

Example 39: Large Scale Reaction of Bio-Malonic Acid to Bio-Diethyl Malonate A sample of 106.14 kg of malonic acid (1.02 kmol) was mixed with 301.185 kg of diethyl carbonate (2.55 kmol, 2.5 eq) and 49.89 kg of sulfuric acid (0.51 kmol, 0.50 eq) in a 300 gal reactor. The material was refluxed at 90° C. for 5 hours. The reaction mass was cooled to 38° C. and neutralized with 464.9 kg of saturated aqueous sodium carbonate solution. The pH of the aqueous phase was measured as 7.0. Mixing was stopped to allow the liquid phases to separate, and 602.8 kg of aqueous phase was drained from the reactor. The organic phase was then distilled at 20 torr. A low-boiling fraction weighing 28.57 kg was collected until the pot temperature was 95° C. The core product distillate was then collected. The product distillate weighed 90.71 kg. 3.17 kg of high-boiling residue remained in the reactor when distillation was stopped. As indicated in Table 11, the second round, improved purified diethyl malonate (bio-DEMa) distillate composition included 99.5% diethyl malonate, 0.38% diethyl carbonate, and 0.058% diethyl sulfate (measurements are area % of total ion count by GC-MS).

Table 11 shows GC-MSD analysis of a sample of the composition of bio-DEM (bio-DEMa) prepared per the disclosed method as compared with samples of petro-DEM, acquired from various commercial sources.

TABLE 11

Components of bio-DEM as compared with Petro-DEM

| Component | Bio-DEMa | Petro-DEM 1(AA) | Petro-DEM 2 (Parchem) |
|---|---|---|---|
| Diethyl malonate (DEM) | 99.533% | 99.817% | 99.768% |
| Diethyl Carbonate (DEC) | 0.382% | ND | ND |
| Diethyl sulfate | 0.058% | 0.001% | ND |
| Dimethyl malonate | 0.003% | 0.146% | 0.189% |
| Propanedioic methyl, ethyl ester | 0.024% | 0.022% | 0.030% |
| Ethylcyanoacetate | ND | 0.004% | 0.004% |
| Acetic acid, (acetyloxy)-ethyl ester | ND | 0.003% | 0.005% |
| Butanedioic acid diethyl ester | ND | 0.002% | 0.003% |
| Butanedioic acid diethyl ester isomer | ND | 0.001% | ND |
| 2-Propanone, 1,1,3,3-tetrochloro | ND | ND | 0.001% |
| Unknown Peak 1 | ND | 0.002% | ND |
| Unknown Peak 2 | ND | 0.003% | ND |

Example 40: Cure Kinetics Using Bio-Based Diester Derivatives of Malonic Acid Cure kinetics and gel point of Bio-DEM and Petro-DEM formulations were measured using oscillatory rheology. 2 mL of DEM was pre-mixed with 0.1 mL base catalyst in a 15 mL Cole Palmer polypropylene centrifuge tube using a vortex mixer for 15 sec. This was followed by adding 8 mL of ethyl acrylate followed by blending for 10 sec on the vortex mixer. All the operations were conducted at 25° C. 1 mL of this mixture was then immediately placed between disposable plates with diameter of 25 mm made from steel. The test was run at a frequency of 1 Hz, a strain of 0.01, and with a 0.5 mm gap between the plates. Sinusoidal stress was used, which was the basis for calculating the storage modulus (G') and the loss modulus (G"). As curing progresses, G' increases from a low value and G" (which is initially high when the mixture behaves as a liquid) starts to drop. The gel point is measured as the point where the two curves intersect (i.e. G' increases above G").

The results in Table 12 indicate that bio-DEM prepared by the improved processes for purification of diester derivatives of malonic acid as described herein has a faster gel-time compared to existing petro-DEM materials. This imparts a significant advantage when using bio-DEM in certain industrial applications where fast cure time is part of the process or product performance. The lower levels of impurities in the bio-DEM may contribute directly or indirectly to this result.

TABLE 12

| Cure Kinetics | |
|---|---|
| Sample | Gel Point |
| Bio-DEM | Short |
| Petro-DEM (control) | Medium |
| Petro-DEM (control) | Long |

```
SEQUENCES
Wild type Saccharomyces cerevisiae EHD3 3-hydroxypropionyl-CoA
hydrolase amino acid sequence.
                                                    SEQ ID NO: 1
    1- MLRNTLKCAQ  LSSKYGFKTT  TRTFMTTQPQ  LNVTDAPPVL

41- FTVQDTARVI  TLNRPKKLNA  LNAEMSESMF  KTLNEYAKSD

81- TTNLVILKSS  NRPRSFCAGG  DVATVAIFNF  NKEFAKSIKF

121- FTDEYSLNFQ  IATYLKPIVT  FMDGITMGGG  VGLSIHTPFR

161- IATENTKWAM  PEMDIGFFPD  VGSTFALPRI  VTLANSNSQM

201- ALYLCLTGEV  VTGADAYMLG  LASHYVSSEN  LDALQKRLGE

241- ISPPFNNDPQ  SAYFFGMVNE  SIDEFVSPLP  KDYVFKYSNE

281- KLNVIEACFN  LSKNGTIEDI  MNNLRQYEGS  AEGKAFAQEI

321- KTKLLTKSPS  SLQIALRLVQ  ENSRDHIESAI  KRDLYTAAN

361- MCMNQDSLVE  FSEATKHKLI  DKQRVPYPWT  KKEQLFVSQL

401- TSITSPKPSL  PMSLLRNTSN  VTWTQYPYHS  KYQLPTEQEI

441- AAYIEKRTND  DTGAKVTERE  VLNHFANVIP  SRRGKLGIQS

481- LCKIVCERKC  EEVNDGLRWK.                  -500

Wild type Haemophilus influenzae nucleic acid sequence encoding
YciA acyl-CoA hydrolase.
                                                    SEQ ID NO: 2
    1- ATGTTTTACA  CTGAAACTTA  TGATGTGATT  GTGATCGGTG

41- GTGGTCATGC  GGGTACAGAA  GCCGCACTTG  CACCAGCTCG

81- TATGGGATTT  AAAACCCTTT  TATTAACACA  TAATGTAGAT

121- ACTTTAGGGC  AAATGTCTTG  TAACCCTGCA  ATTGGTGGGA

161- TCGGTAAAGG  TCATTTAGTA  AAAGAAGTAG  ATGCAATGGG

201- CGGTTTAATG  GCGCATGCTG  CAGATAAAGC  AGGGATCCAA

241- TTTCGTACTT  TAAATAGCAG  TAAAGGCCCA  GCAGTGCGTG

281- CTACTCGAGC  TCAAGCTGAC  AGAGTTCTAT  ATCGTCAAGC

321- TGTTCGTACT  GCATTAGAAA  ATCAACCTAA  TTTAGATATT

361- TTCCAACAAG  AAGCGACCGA  TATTCTGATT  AAGCAAGATC

401- GAGTTACAGG  CGTTAGCACA  AAAATGGGAT  TAACTTTTCG
```

-continued

```
441- TGCTAAATCA GTGGTATTAA CTGCGGGTAC TTTCTTAGCT

481- GGTAAAATTC ATATTGGTTT GGAAAATTAT GAAGGTGGCC

521- GTGCAGGGGA TCCTGCTTCT GTAAATCTTT CACATCGATT

561- AAGAGATCTC GGATTACGTG TAGATCGCCT TAAAACAGGT

601- ACACCGCCGC GTATTGATGC ACGTACGATC AATTTTGATA

641- TTTTAGCTAA ACAACACGGT GATGCTGTTT TACCTGTGTT

681- TTCTTTTATG GGATCAGTTG ATGATCACCC TCAACAAATT

721- CCTTGTTATA TAACTCATAC CAATGAACAA ACCCATGAAG

761- TGATCCGTAA TAACTTGGAT CGCAGTCCAA TGTATACTGG

801- TGTGATTGAA GGGATCGGTC CACGTTATTG CCCATCCATT

841- GAAGATAAAG TGATGCGTTT CTCGGATCGT AATTCACATC

881- AAATTTATTT AGAACCAGAA GGCTTAACCA GTAATGAAGT

921- GTATCCAAAC GGGATCTCTA CCAGTTTACC GTTTGACGTG

961- CAAATGGGCA TTGTGAATTC TATGAAAGGT TTAGAAAACG.  -1000
```

*Acinetobacter calcoaceticus* MdcY malonate-binding transcription factor amino acid sequence.
SEQ ID NO: 3

```
  1- MNSIAELPLS IQISKKLEDD IIYGFYLPGT KLDEQELCER

41- YGASRTPIRE ALKLLAAEGL VEIRPRRGAI IPTINPLTLC

81- EMFEVMAELE AMCGRLAARR IQPEEKLELQ RLHQLCQDYL

121- NQNDSENYYE ANRLFHFAIY QASHNAFLIE QACTLHKRLH

161- PYRRLQLRVN NRMNNSFTEH NEILEAIFAG NEQQAEALLK

201- AHVVIQGQKF TDFISTIESL QPKS              -224
```

*Rhizobium leguminosarum* MatR malonate-binding transcription factor amino acid sequence.
SEQ ID NO: 4

```
  1- MRKVKRMSEN VGRWLRDEIE NSILSNEFSP GERLDETVLA

41- TRFGVSRTPV REALMQLDAI GLIEIRPRRG AIVIDPGPHR

81- VYEMFEVMAE LEGLAGSLAA RRLDKTSREA ITATHGRCEK

121- SAAAGDSDAY YYDNEEFHKA IYAAGRSDFL EEQCLQLHRR

161- LRPDRRLQLR VRNRLSTSFL EHCAIVDAIF AGDGDEARRL

201- LRGHVGIQGE RFSDLVASMA AR.              -222
```

*Klebsiella pneumoniae* MauR malonate-binding transcription factor amino acid sequence.
SEQ ID NO: 5

```
  1- MKDDINQEIT FRKLSVFMMF MAKGNIARTA EAMKLSSVSV

41- HRALHTLEEG VGCPLFVHKG RNLLPLQAAW TLLEYCQDVI

81- SLMNRGLEAT RKVAGVGQGR LRIGTLYSLT LETVPRIIMG

121- MKLRRPELEL DLTMGSNQML LDMLEDDALD AILIATNEGE

161- FNNTAFDVVP LFEDDIFLAA PATERLDASR LADLRDYADR

201- KFVSLAEGFA TYAGFREAFH IAGFEPEIVT RVNDIFSMIS

241- LVQAGVGFAL LPGRMKKVYE KDVQLLKLAE PYQMRQLISI

281- VYSHHRERDA DLLALAAEGR MYARSINR.        -308
```

MdcY regulated P$_{MdcL}$ promoter from *Acinetobacter calcoaceticus*.

-continued

```
                                                      SEQ ID NO: 6
  1- AAAAAAATTG TATACAATTT ATGTTTATTT GAGTACAAAG
 41- CATTGTACAC TGAATACAGA TAGGCTATAA CTATACC.         -77
```

EHD3 EC 3.1.2.4 malonyl-CoA hydrolase consensus sequence.
```
                                                      SEQ ID NO: 7
  1- ---------- ------MOBU UOB+AQ+UBB +----+----

41- +GFOBBOB-- --+------+B UOUUU----- ----------

81- ---------- AQON+++UUU VOFUOQJUAR OOULNRPBKL

121- NALNUJMUJU OFBULNEYUK SJUUNOOOOB SUNQPRUOCA

161- GGDVAUOAO+ NOJBBF--BB UOJFFBUX₁YS ONFQOATYOK

201- POOOOMJGIT MGGGVGOUOH UPFROATENT BWAMPEMDIG

241- FFPDVGUUFA OPBOOUOANU BUQOAOYLCO TGJOOUGJJA

281- YOOGOASHYO UBJNOJJLJB RLGEOBPUJ+ OJ+-+++UQU

321- JJFFJOONJU OJEFUUP-OP BJYBFBYUNJ BLJVIJBCFJ

361- OUBOUUOBJO OBBLJJO-++ -YJGUJJABJ FABJOBJBLO

401- UKSPUSOQOA OBOOBJNUBJ BOJUAOBBDL OTAUNMCON-

441- +++QJUOOEF UJAUBBKLOJ KQBOPYPWBB B+JJOUOUQO

481- UUOOUPBPUO POULOBNUUN OTWBJYPBBO BYQLPUJUJO

521- BQYOBBBJNB N---+G-++O BOUBBJOOBB FUNONJUBBJ

561- KOGOJUOOBO OOJBBCUJJJ A+GGOBWB++ -+------.    -598
```

*Bacillus* EC 3.1.2.4 malonyl-CoA hydrolase consensus sequence.
```
                                                      SEQ ID NO: 8
  1- MTEBVLFSOU JNGVAUITLN RPKALNSLSY JMLQPIGQKL

41- KEWEBJJBIA OIVLKGAGUK GFCAGGDIKT LYEARSNEOA

81- LQBAEBFFJE X₁YJIDTYOYQ YBKPIIACLD GIVMGGGVGL

121- TNGABYRIVT JBTKWAMPEM NIGFFPDVGA AYFLNBAPGY

161- UGBYVALUAU OLKAUDVLFI NAADYFMUUJ ULPBFLUJOJ

201- UONWBBJJJV BUBLKJOOBU FAUUUUOJUJ LUUOOEJONU

241- HFAFJUOEJI IBSLEBJQUU FAOBUBJULL SKSPOSLKVT

281- LKQFOJGBJK SOEJCFATDL OLAKNFMRHJ DFFEGVRSOV

321- ODKDQNPNYK YBQOUDVUJJ JVNBFFNLLN A.           -351
```

*Pseudomonas* EC 3.1.2.4 malonyl-CoA hydrolase consensus sequence.
```
                                                      SEQ ID NO: 9
  1- MNOBFEJBUU OBGARIGOAU LDAJBULNAL ULPMIJOLGJ

41- BOBAWABJPG OOCVOLRGNG AKAFCAGGJV BBLOJACBJB

81- PGJOPPLAAB FFAJX₁YRLJB BOHUYPKPOO CWGHGBVOGG

121- GMGLOQGAUO RIVTPUURLA MPEOUIGLYP DVGASWFLUR

161- OPGBLGLFOG LUGABONABD AODLJLADRF OBJBQQJJLO

201- JJLOQONWQE QUJOQLBSLO BAJJBBABJJ OPJAQOLPRR

241- QBODJOLDOA JOAUAWBAOJ AOBJBJDPLO ABAABBOBJG

281- CPOUABOVWJ QOBRARBLSL AJOFBMEYUO SLNCCRHPJF

321- UEGVRARLOD BDBQPBWBWP JOAQOPJAOO JAHFJBOWJG

361- BBPOAJOU++.                                    -370
```

General bacterial EC 3.1.2.4 malonyl-CoA hydrolase consensus sequence.

```
                                                -continued
                                                                SEQ ID NO: 10
  1- ---------- +--------- ---+------ M+M--TEHOO

41- FUOSENGOAS IULNRPBALN SLUYDMOQPO GQBOBEWENJ

81- EROALOOLB- GAGTBGFCAG GJOBUOYJAR SNEPG+ALQH

121- AERFFEJX₁YE OJTYOYQYKK POOACLDGIO MGGGVGLTNG

161- AKYBOOTERU BWAMPEMNIG FFPDVGAAYF LNBA------

201- PGYLGRYOAL UASIOKASDV OFONAAJYFM TSJSLPAFOT

241- EOESONWHKE DJOHTHLLKE +-+VORTFAT APNLJSEOAP

281- ----SLEEON SHFAF---DT OEEIW+AOHS OE--KJQSSF

321- ALKTKETOLS KUPOULBOTL KQFIDGRDKU OEJCFATJLV

361- OAKNFMBB-- --EJFFEGOB SVOODBJQNP NYBYKQOSDO

401- SJED------ ---------O NRFFNLONAG +H--PLADL+

441  ------++-- ---------- ---------- ----------

481  ---------- ---------- -----.                 -505

Artificial Sequence
                                                SEQ ID NO: 11
 1-  ccaatatata ataaaatatg gaggaatgcg atgctcagaa 41-  atacgctaaa atgtgcccaa.                        -60

Artificial Sequence
                                                SEQ ID NO: 12
 1-  tgcctggaga tccttactcg agttggatcc ttatttccat 41-  cttaagccat cgttaacttc.                        -60

Artificial Sequence
                                                SEQ ID NO: 13
 1-  ttttactgat gcgtattctt tgaattttca aatagca.     -37

Artificial Sequence
                                                SEQ ID NO: 14
 1-  tcaaagaata cgcatcagta aaaaatttga tgga.        -34

Artificial Sequence
                                                SEQ ID NO: 15
 1-  ttttactgat gtttattctt tgaattttca aatagcaact 41-  t.                                            -41

Artificial Sequence
                                                SEQ ID NO: 16
 1-  tcaaagaata aacatcagta aaaaatttga tggacttgg.   -39

Artificial Sequence
                                                SEQ ID NO: 17
 1-  ttttactgat tcgtattctt tgaattttca aatagcaac.   -39

Artificial Sequence
                                                SEQ ID NO: 18
 1-  tcaaagaata cgaatcagta aaaaatttga tggact.      -36

Artificial Sequence
                                                SEQ ID NO: 19
 1-  aattttttac tgatnnntat tctttgaatt ttcaaatagc.  -40

Artificial Sequence
                                                SEQ ID NO: 20
 1-  ttcaaagaat aannnatcag taaaaaattt gatggacttg.  -40

Artificial Sequence
                                                SEQ ID NO: 21
 1-  ccaatatata ataaaatatg gaggaatgcg atgtctacaa 41-  cacataacgt ccctc.                             -55
```

```
Artificial Sequence                              SEQ ID NO: 22
 1-  tgcctggaga tccttactcg agttggatcc ttactcaaca
41-  ggtaaggcgc gag.                             -53
Artificial Sequence                              SEQ ID NO: 23
 1-  ctaattacat gactcgaggt cgacggtatc gttatttcca
     Tcttaagcca tcgttaactt c.                    -61
Artificial Sequence                              SEQ ID NO: 24
 1-  cattagaaag aaagcatagc aatctaatct aagtttaaaa
41-  caatgactac tcaaccccag ctaaatg.              -67
Artificial Sequence                              SEQ ID NO: 25
 1-  gaaagcatag caatctaatc taagtttaaa acaatgaccg
41-  aacaagtctt attctcagta.                      -60
Artificial Sequence                              SEQ ID NO: 26
 1-  ctaattacat gactcgaggt cgacggtatc gttaagcgtt
41-  caacaaattg aaaaatctg.                       -59
Artificial Sequence                              SEQ ID NO: 27
 1-  gaaagcatag caatctaatc taagtttaaa acaatgaccg
41-  aacatgtatt attctcag.                        -58
Artificial Sequence                              SEQ ID NO: 28
 1-  ctaattacat gactcgaggt cgacggtatc gttaagcgtt
41-  taacaaattg aaaaatc.                         -57
Artificial Sequence                              SEQ ID NO: 29
 1-  gaaagcatag caatctaatc taagtttaaa acaatgactg
41-  aacacgtctt gttctctg.                        -58
Artificial Sequence                              SEQ ID NO: 30
 1-  ctaattacat gactcgaggt cgacggtatc gttaagcgtt
41-  taacaaattg aaaaatctg.                       -59
Artificial Sequence                              SEQ ID NO: 31
 1-  gaaagcatag caatctaatc taagtttaaa acaatgagaa
41-  gatacatcag aggtggt.                         -57
Artificial Sequence                              SEQ ID NO: 32
 1-  ctaattacat gactcgaggt cgacggtatc gttatgcagc
41-  gttcaacaaa ttgaaaa.                         -57
Artificial Sequence                              SEQ ID NO: 33
 1-  gaaagcatag caatctaatc taagtttaaa acaatgaccg
41-  aacaagtctt attctcag.                        -58
Artificial Sequence                              SEQ ID NO: 34
 1-  ctaattacat gactcgaggt cgacggtatc gttaagcgtt
41-  caacaaattg aaaaatct.                        -58
```

-continued

```
Artificial Sequence
                                            SEQ ID NO: 35
  1- gaaagcatag caatctaatc taagtttaaa acaatgaact
 41- tacaatttga agaaagacca.                  -60
Artificial Sequence
                                            SEQ ID NO: 36
  1- ctaattacat gactcgaggt cgacggtatc gttacaaatc
 41- agctaaaggg tgttcac.                     -57
Artificial Sequence
                                            SEQ ID NO: 37
  1- gaaagcatag caatctaatc taagtttaaa acaatgaact
 41- tacactttga agaattgac.                   -59
Artificial Sequence
                                            SEQ ID NO: 38
  1- ctaattacat gactcgaggt cgacggtatc gttagtagtc
 41- agacaaatct gctaaag.                     -57
Artificial Sequence
                                            SEQ ID NO: 39
  1- gaaagcatag caatctaatc taagtttaaa acaatgacaa
 41- tccactgtga agtattaac.                   -59
Artificial Sequence
                                            SEQ ID NO: 40
  1- ctaattacat gactcgaggt cgacggtatc gttaaccaac
 41- gtcagccaaa gggtg.                       -55
Artificial Sequence
                                            SEQ ID NO: 41
  1- gaaagcatag caatctaatc taagtttaaa acaatgaatg
 41- tcacctttga agaaagag.                    -58
Artificial Sequence
                                            SEQ ID NO: 42
  1- ctaattacat gactcgaggt cgacggtatc gttatgccaa
 41- atcagctaaa gggtg.                       -55
Artificial Sequence
                                            SEQ ID NO: 43
  1- atgacgcaat ttgcatttgt gttccc.           -26
Artificial Sequence
                                            SEQ ID NO: 44
  1- ttaaagctcg agcgccgct.                   -19
```

---

What is claimed:

1. A method for isolating a dialkyl malonate from a fermentation broth, comprising:
   separating calcium malonate crystals of at least 10 microns in diameter from the fermentation broth by centrifugation;
   obtaining dissolved malonic acid from the calcium malonate crystals by adding sulfuric acid to the calcium malonate crystals from the fermentation broth;
   crystallizing the dissolved malonic acid in a malonic acid crystallizer;
   refluxing the crystalline malonic acid with a dialkyl carbonate and sulfuric acid to generate the dialkyl malonate; and
   isolating the dialkyl malonate via distillation.

2. The method of claim 1, wherein the centrifugation is done using a hydrocyclone apparatus.

3. The method of claim 1, wherein the centrifugation is done using a decanter centrifuge.

4. The method of claim 1, further comprising introducing seed crystals into the fermentation broth.

5. The method of claim 4, wherein the seed crystals are introduced before the step of separating calcium malonate crystals.

6. The method of claim 4, wherein the seed crystals are calcium malonate seed crystals.

7. The method of claim 6, wherein the calcium malonate seed crystals are introduced at a concentration of at least 6 g/l.

8. The method of claim 1 wherein the pH of the fermentation broth is maintained at around 5.0.

9. The method of claim 1, further comprising fermenting a malonate-producing microorganism.

10. The method of claim 9, wherein the malonate-producing microorganism is a yeast selected from *Saccharomyces* and *Pichia*.

11. The method of claim 9, wherein the malonate-producing microorganism is *Pichia kudriazevii*.

12. The method of claim 1, wherein the fermentation broth comprises succinate at a concentration below 11 g/l.

13. The method of claim 1, wherein the centrifugation is carried out in two centrifugation steps.

14. The method of claim 13, wherein two centrifugation steps comprise:
   a) centrifugation of the fermentation broth at high g-force;
   b) resuspension of solids to a concentration of 5-25%; and
   c) centrifugation of the solids at a lower g-force.

15. The method of claim 14, wherein the lower g-force centrifugation is carried out in a hydrocyclone apparatus.

16. The method of claim 1, wherein the ratio of malonic acid to dialkyl carbonate to sulfuric acid in the refluxing step is between 1:5:0.5 and 1:2.5:0.5.

17. The method of claim 1, wherein the distillation is performed at or near 20 torr.

18. The method of claim 1, wherein the refluxing is performed for 1 to 8 hours.

19. The method of claim 1, further comprising refluxing the dialkyl malonate in deionized water after distillation.

20. The method of claim 19, wherein the ratio of deionized water to the dialkyl malonate is 1:1.

21. The method of claim 1, wherein the distillation is performed more than once.

22. The method of claim 1, wherein the distillation is performed in a fractionating column.

* * * * *